US012685839B2

(12) United States Patent
Blanchard

(10) Patent No.: US 12,685,839 B2
(45) Date of Patent: Jul. 21, 2026

(54) MAGNETIC ELEMENT-EQUIPPED NEEDLE ASSEMBLIES

(71) Applicant: C. R. Bard, Inc., Franklin Lakes, NJ (US)

(72) Inventor: Daniel B. Blanchard, Bountiful, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1532 days.

(21) Appl. No.: 16/653,594

(22) Filed: Oct. 15, 2019

(65) Prior Publication Data

US 2020/0054858 A1     Feb. 20, 2020

Related U.S. Application Data

(60) Division of application No. 14/054,700, filed on Oct. 15, 2013, now Pat. No. 10,449,330, which is a
(Continued)

(51) Int. Cl.
*A61B 34/20* (2016.01)
*A61B 5/06* (2006.01)
(Continued)

(52) U.S. Cl.
CPC ......... *A61M 25/0127* (2013.01); *A61B 5/062* (2013.01); *A61B 5/283* (2021.01);
(Continued)

(58) Field of Classification Search
CPC .. A61M 25/0127; A61B 5/062; A61B 8/0833; A61B 8/0841; A61B 34/20;
(Continued)

(56) References Cited

U.S. PATENT DOCUMENTS 2,619,515 A     11/1952  Doane
2,646,086 A      7/1953  Smith
(Continued)

FOREIGN PATENT DOCUMENTS

AU          642647 B2     10/1993
AU          706052 B2      6/1999
(Continued)

OTHER PUBLICATIONS

JP 2008196593 machine translation (Year: 2008).*
(Continued)

*Primary Examiner* — Alexei Bykhovski
(74) *Attorney, Agent, or Firm* — Rutan & Tucker LLP

(57) ABSTRACT

A guidance system for assisting with the insertion of a needle into a patient is disclosed. The guidance system utilizes ultrasound imaging or other suitable imaging technology. The guidance system can include an imaging device including a probe for producing an image of an internal body target, such as a vessel. One or more sensors can be included with the probe. The sensors sense a detectable characteristic related to the needle, such as a magnetic field of a magnet included with the needle. The system can include a processor that uses data relating to the sensed characteristic to determine a 3-D position of the needle, and a display for depicting the position of the needle. A needle assembly including a hub, cannula, and magnetic element is also disclosed, in which a magnetic axis of the magnetic element can be configured to be coaxially or otherwise aligned with the cannula axis.

9 Claims, 55 Drawing Sheets

Related U.S. Application Data continuation-in-part of application No. 14/040,205, filed on Sep. 27, 2013, now Pat. No. 10,524,691, and a continuation-in-part of application No. 13/118,138, filed on May 27, 2011, now Pat. No. 9,456,766, which is a continuation-in-part of application No. 13/118,033, filed on May 27, 2011, now Pat. No. 9,554,716, and a continuation-in-part of application No. 12/323,273, filed on Nov. 25, 2008, now Pat. No. 8,388,541.

(60) Provisional application No. 61/774,512, filed on Mar. 7, 2013, provisional application No. 61/715,769, filed on Oct. 18, 2012, provisional application No. 61/709,877, filed on Oct. 4, 2012, provisional application No. 61/707,782, filed on Sep. 28, 2012, provisional application No. 61/349,771, filed on May 28, 2010, provisional application No. 61/095,921, filed on Sep. 10, 2008, provisional application No. 61/095,451, filed on Sep. 9, 2008, provisional application No. 61/091,233, filed on Aug. 22, 2008, provisional application No. 61/045,944, filed on Apr. 17, 2008, provisional application No. 60/990,242, filed on Nov. 26, 2007.

(51) Int. Cl.

| | |
|---|---|
| *A61B 5/283* | (2021.01) |
| *A61B 8/08* | (2006.01) |
| *A61M 25/01* | (2006.01) |
| *A61B 90/00* | (2016.01) |

(52) U.S. Cl.
CPC .......... *A61B 8/0833* (2013.01); *A61B 8/0841* (2013.01); *A61B 34/20* (2016.02); *A61B 5/064* (2013.01); *A61B 2034/2051* (2016.02); *A61B 2090/378* (2016.02); *A61B 2090/3954* (2016.02)

(58) Field of Classification Search
CPC . A61B 5/064; A61B 5/283; A61B 2034/2051; A61B 2090/378; A61B 2090/3954
See application file for complete search history.

(56) References Cited

U.S. PATENT DOCUMENTS

| | | | |
|---|---|---|---|
| 3,133,244 | A | 5/1964 | Wojtulewicz |
| 3,297,020 | A | 1/1967 | Mathiesen |
| 3,625,200 | A | 12/1971 | Muller |
| 3,674,014 | A | 7/1972 | Tillander |
| 3,794,041 | A | 2/1974 | Frei et al. |
| 3,795,855 | A | 3/1974 | Browning |
| 3,817,241 | A | 6/1974 | Grausz |
| 3,847,157 | A | 11/1974 | Caillouette et al. |
| 3,868,565 | A | 2/1975 | Kuipers |
| 3,896,373 | A | 7/1975 | Zelby |
| 3,902,501 | A | 9/1975 | Citron et al. |
| 3,986,373 | A | 10/1976 | Goodlaxson |
| 3,995,623 | A | 12/1976 | Blake et al. |
| 4,003,369 | A | 1/1977 | Heilman et al. |
| 4,063,561 | A | 12/1977 | McKenna |
| 4,072,146 | A | 2/1978 | Howes |
| 4,092,867 | A | 6/1978 | Matzuk |
| 4,114,601 | A | 9/1978 | Abels |
| 4,149,535 | A | 4/1979 | Volder |
| 4,161,943 | A | 7/1979 | Nogier |
| 4,173,228 | A | 11/1979 | Van Steenwyk et al. |
| 4,175,566 | A | 11/1979 | Millar |
| 4,181,120 | A | 1/1980 | Kunii et al. |
| 4,224,949 | A | 9/1980 | Scott et al. |
| 4,244,362 | A | 1/1981 | Anderson |
| 4,289,139 | A | 9/1981 | Enjoji et al. |

| | | | |
|---|---|---|---|
| 4,317,078 | A | 2/1982 | Weed et al. |
| 4,327,722 | A | 5/1982 | Groshong et al. |
| 4,327,723 | A | 5/1982 | Frankhouser |
| 4,362,166 | A | 12/1982 | Furler et al. |
| 4,365,639 | A | 12/1982 | Goldreyer |
| 4,380,237 | A | 4/1983 | Newbower |
| 4,407,294 | A | 10/1983 | Vilkomerson |
| 4,417,886 | A | 11/1983 | Frankhouser et al. |
| 4,429,693 | A | 2/1984 | Blake et al. |
| 4,431,005 | A | 2/1984 | McCormick |
| 4,431,214 | A | 2/1984 | Buffington |
| 4,445,501 | A | 5/1984 | Bresler |
| 4,459,854 | A | 7/1984 | Richardson et al. |
| 4,469,106 | A | 9/1984 | Harui |
| 4,483,343 | A | 11/1984 | Beyer et al. |
| 4,491,137 | A | 1/1985 | Jingu |
| 4,565,201 | A | 1/1986 | Lass |
| 4,572,198 | A | 2/1986 | Codrington |
| 4,577,634 | A | 3/1986 | Gessman |
| 4,582,067 | A | 4/1986 | Silverstein et al. |
| 4,587,975 | A | 5/1986 | Salo et al. |
| 4,588,394 | A | 5/1986 | Schulte et al. |
| 4,593,687 | A | 6/1986 | Gray |
| 4,595,012 | A | 6/1986 | Webler et al. |
| 4,601,706 | A | 7/1986 | Aillon |
| 4,608,989 | A | 9/1986 | Drue |
| 4,608,992 | A | 9/1986 | Hakim et al. |
| 4,619,247 | A | 10/1986 | Inoue et al. |
| 4,622,644 | A | 11/1986 | Hansen |
| 4,644,960 | A | 2/1987 | Johans |
| 4,652,820 | A | 3/1987 | Maresca |
| 4,660,571 | A | 4/1987 | Hess et al. |
| 4,665,925 | A | 5/1987 | Millar |
| 4,667,230 | A | 5/1987 | Arakawa et al. |
| 4,674,518 | A | 6/1987 | Salo |
| 4,676,249 | A | 6/1987 | Arenas et al. |
| 4,681,106 | A | 7/1987 | Kensey et al. |
| 4,681,117 | A | 7/1987 | Brodman et al. |
| 4,688,578 | A | 8/1987 | Takano et al. |
| 4,692,148 | A | 9/1987 | Kantrowitz et al. |
| 4,697,595 | A | 10/1987 | Breyer et al. |
| 4,700,997 | A | 10/1987 | Strand |
| 4,706,681 | A | 11/1987 | Breyer et al. |
| 4,710,708 | A | 12/1987 | Rorden et al. |
| 4,733,669 | A | 3/1988 | Segal |
| 4,737,794 | A | 4/1988 | Jones |
| 4,741,356 | A | 5/1988 | Letzo et al. |
| 4,742,356 | A | 5/1988 | Kuipers |
| 4,753,247 | A | 6/1988 | Kirsner |
| 4,770,185 | A | 9/1988 | Silverstein et al. |
| 4,771,788 | A | 9/1988 | Millar |
| 4,781,685 | A | 11/1988 | Lehmann et al. |
| 4,784,646 | A | 11/1988 | Feingold |
| 4,787,070 | A | 11/1988 | Suzuki et al. |
| 4,787,396 | A | 11/1988 | Pidorenko |
| 4,790,809 | A | 12/1988 | Kuntz |
| 4,793,361 | A | 12/1988 | DuFault |
| 4,794,930 | A | 1/1989 | Machida et al. |
| 4,796,632 | A | 1/1989 | Boyd et al. |
| 4,798,588 | A | 1/1989 | Aillon |
| 4,798,598 | A | 1/1989 | Bonello et al. |
| 4,809,681 | A | 3/1989 | Kantrowitz et al. |
| 4,809,713 | A | 3/1989 | Grayzel |
| 4,813,729 | A | 3/1989 | Speckhart |
| 4,821,731 | A | 4/1989 | Martinelli et al. |
| 4,834,709 | A | 5/1989 | Banning et al. |
| 4,836,214 | A | 6/1989 | Sramek |
| 4,840,182 | A | 6/1989 | Carlson |
| 4,840,622 | A | 6/1989 | Hardy |
| 4,841,977 | A | 6/1989 | Griffith et al. |
| 4,849,692 | A | 7/1989 | Blood |
| 4,850,358 | A | 7/1989 | Millar |
| 4,852,580 | A | 8/1989 | Wood |
| 4,856,317 | A | 8/1989 | Pidorenko et al. |
| 4,856,529 | A | 8/1989 | Segal |
| 4,860,757 | A | 8/1989 | Lynch et al. |
| 4,867,169 | A | 9/1989 | Machida et al. |
| 4,869,263 | A | 9/1989 | Segal et al. |
| 4,869,718 | A | 9/1989 | Brader |

(56) References Cited

U.S. PATENT DOCUMENTS

| | | |
|---|---|---|
| 4,873,987 A | 10/1989 | Djordjevich et al. |
| 4,887,606 A | 12/1989 | Yock et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,917,669 A | 4/1990 | Bonaldo |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,110 A | 9/1990 | Vogel et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,989,610 A | 2/1991 | Patton et al. |
| 4,995,396 A | 2/1991 | Inaba et al. |
| 4,998,916 A | 3/1991 | Hammerslag et al. |
| 5,004,456 A | 4/1991 | Botterbusch et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,055,813 A | 10/1991 | Johnson |
| 5,057,095 A | 10/1991 | Fabian |
| 5,058,583 A | 10/1991 | Geddes et al. |
| 5,058,595 A | 10/1991 | Kern |
| 5,067,489 A | 11/1991 | Lind |
| 5,076,278 A | 12/1991 | Vilkomerson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| 5,125,410 A | 6/1992 | Misono et al. |
| 5,134,370 A | 7/1992 | Jefferts et al. |
| 5,144,955 A | 9/1992 | O'Hara |
| 5,146,151 A | 9/1992 | Korn |
| 5,148,809 A | 9/1992 | Biegeleisen-Knight et al. |
| 5,156,151 A | 10/1992 | Imran |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,174,299 A | 12/1992 | Nelson |
| 5,181,513 A | 1/1993 | Touboul et al. |
| 5,184,601 A | 2/1993 | Putman |
| 5,184,627 A | 2/1993 | de Toledo |
| 5,190,045 A | 3/1993 | Frazin |
| 5,202,985 A | 4/1993 | Goyal |
| 5,205,830 A | 4/1993 | Dassa et al. |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer |
| 5,217,026 A | 6/1993 | Stoy et al. |
| 5,220,924 A | 6/1993 | Frazin |
| 5,233,994 A | 8/1993 | Shmulewitz |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,246,426 A | 9/1993 | Lewis et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,269,306 A | 12/1993 | Warnking et al. |
| 5,269,759 A | 12/1993 | Hernandez et al. |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,293 A | 6/1994 | Dorne |
| 5,325,860 A | 7/1994 | Seward et al. |
| 5,325,873 A | 7/1994 | Hirschi et al. |
| 5,330,496 A | 7/1994 | Alferness |
| 5,331,491 A | 7/1994 | Hayakawa et al. |
| 5,331,966 A | 7/1994 | Bennett et al. |
| 5,333,614 A | 8/1994 | Feiring |
| 5,337,678 A | 8/1994 | Grout |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,365,935 A | 11/1994 | Righter et al. |
| 5,366,443 A | 11/1994 | Eggers et al. |
| 5,368,048 A | 11/1994 | Stoy et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,385,146 A | 1/1995 | Goldreyer |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,411,485 A | 5/1995 | Tennican et al. |
| 5,413,107 A | 5/1995 | Oakley et al. |
| 5,417,208 A | 5/1995 | Winkler |
| 5,417,701 A | 5/1995 | Holmes |
| 5,422,478 A | 6/1995 | Wlodarczyk et al. |
| 5,423,334 A | 6/1995 | Jordan |
| 5,423,877 A | 6/1995 | Mackey |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |

(56)                References Cited

U.S. PATENT DOCUMENTS

| | | |
|---|---|---|
| 5,437,276 A | 8/1995 | Takada |
| 5,437,277 A | 8/1995 | Dumoulin et al. |
| 5,438,873 A | 8/1995 | Wlodarczyk et al. |
| 5,441,052 A | 8/1995 | Miyajima |
| 5,443,066 A | 8/1995 | Dumoulin et al. |
| 5,443,489 A | 8/1995 | Ben-Haim |
| 5,445,150 A | 8/1995 | Dumoulin et al. |
| 5,445,166 A | 8/1995 | Taylor |
| 5,450,846 A | 9/1995 | Goldreyer |
| 5,453,575 A | 9/1995 | O'Donnell et al. |
| 5,453,576 A | 9/1995 | Krivitski |
| 5,456,256 A | 10/1995 | Schneider et al. |
| 5,456,718 A | 10/1995 | Szymaitis |
| 5,464,016 A | 11/1995 | Nicholas et al. |
| 5,474,065 A | 12/1995 | Meathrel et al. |
| 5,476,090 A | 12/1995 | Kishi |
| 5,480,409 A | 1/1996 | Riza |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,011 A | 3/1996 | Desai |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,160 A | 5/1996 | Schulz et al. |
| 5,515,853 A | 5/1996 | Smith et al. |
| 5,517,989 A | 5/1996 | Frisbie et al. |
| 5,522,878 A | 6/1996 | Montecalvo et al. |
| 5,522,880 A | 6/1996 | Barone et al. |
| 5,526,812 A | 6/1996 | Dumoulin et al. |
| 5,531,664 A | 7/1996 | Adachi et al. |
| 5,536,248 A | 7/1996 | Weaver et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,555,618 A | 9/1996 | Winkler |
| 5,558,091 A | 9/1996 | Acker et al. |
| 5,568,809 A | 10/1996 | Ben-Haim |
| D375,450 S | 11/1996 | Bidwell et al. |
| 5,570,671 A | 11/1996 | Hickey |
| 5,575,291 A | 11/1996 | Hayakawa et al. |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,603,333 A | 2/1997 | Konings |
| 5,606,981 A | 3/1997 | Tartacower et al. |
| 5,610,967 A | 3/1997 | Moorman et al. |
| 5,617,866 A | 4/1997 | Marian, Jr. |
| 5,622,169 A | 4/1997 | Golden et al. |
| 5,622,170 A | 4/1997 | Schulz |
| 5,622,184 A | 4/1997 | Ashby et al. |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,638,819 A | 6/1997 | Manwaring et al. |
| 5,640,967 A | 6/1997 | Fine et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |
| 5,665,103 A | 9/1997 | Lafontaine et al. |
| 5,665,477 A | 9/1997 | Meathrel et al. |
| 5,666,473 A | 9/1997 | Wallace |
| 5,666,958 A | 9/1997 | Rothenberg et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,682,890 A | 11/1997 | Kormos et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,701,898 A | 12/1997 | Adam et al. |
| 5,702,433 A | 12/1997 | Taylor et al. |
| 5,711,299 A | 1/1998 | Manwaring et al. |
| 5,713,362 A | 2/1998 | Vilkomerson |
| 5,713,363 A | 2/1998 | Seward et al. |
| 5,713,858 A | 2/1998 | Heruth et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,776,064 A | 7/1998 | Kalfas et al. |
| 5,776,080 A | 7/1998 | Thome et al. |
| 5,779,638 A | 7/1998 | Vesely et al. |
| 5,782,767 A | 7/1998 | Pretlow, III |
| 5,782,773 A | 7/1998 | Kuo et al. |
| 5,785,657 A | 7/1998 | Breyer et al. |
| 5,792,055 A | 8/1998 | McKinnon |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| RE35,924 E | 10/1998 | Winkler |
| 5,817,022 A | 10/1998 | Vesely |
| 5,817,024 A | 10/1998 | Ogle et al. |
| 5,820,549 A | 10/1998 | Marian, Jr. |
| 5,820,560 A | 10/1998 | Sinderby et al. |
| 5,824,031 A | 10/1998 | Cookston et al. |
| 5,827,192 A | 10/1998 | Gopakumaran et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |

(56)            References Cited

U.S. PATENT DOCUMENTS

| | | | |
|---|---|---|---|
| 5,835,561 | A | 11/1998 | Moorman et al. |
| 5,836,882 | A | 11/1998 | Frazin |
| 5,836,990 | A | 11/1998 | Li |
| 5,840,024 | A | 11/1998 | Taniguchi et al. |
| 5,840,025 | A | 11/1998 | Ben-Haim |
| 5,840,030 | A | 11/1998 | Ferek-Petric et al. |
| 5,840,031 | A | 11/1998 | Crowley |
| 5,842,986 | A | 12/1998 | Avrin et al. |
| 5,842,998 | A | 12/1998 | Gopakumaran et al. |
| 5,843,076 | A | 12/1998 | Webster, Jr. et al. |
| 5,843,153 | A | 12/1998 | Johnston et al. |
| 5,844,140 | A | 12/1998 | Seale |
| 5,846,198 | A | 12/1998 | Killmann |
| 5,851,218 | A | 12/1998 | Lev |
| 5,855,553 | A | 1/1999 | Tajima et al. |
| 5,859,893 | A | 1/1999 | Moorman et al. |
| 5,865,748 | A | 2/1999 | Co et al. |
| 5,868,673 | A | 2/1999 | Vesely |
| 5,873,822 | A | 2/1999 | Ferre et al. |
| 5,876,328 | A | 3/1999 | Fox et al. |
| 5,879,297 | A | 3/1999 | Haynor et al. |
| 5,893,363 | A | 4/1999 | Little et al. |
| 5,897,495 | A | 4/1999 | Aida et al. |
| 5,899,860 | A | 5/1999 | Pfeiffer et al. |
| 5,902,238 | A | 5/1999 | Golden et al. |
| 5,907,487 | A | 5/1999 | Rosenberg et al. |
| 5,908,385 | A | 6/1999 | Chechelski et al. |
| 5,908,387 | A | 6/1999 | LeFree et al. |
| 5,910,113 | A | 6/1999 | Pruter |
| 5,910,120 | A | 6/1999 | Kim et al. |
| 5,913,820 | A | 6/1999 | Bladen et al. |
| 5,913,830 | A | 6/1999 | Miles |
| 5,919,141 | A | 7/1999 | Money et al. |
| 5,919,170 | A | 7/1999 | Woessner |
| 5,928,145 | A | 7/1999 | Ocali et al. |
| 5,929,607 | A | 7/1999 | Rosenberg et al. |
| 5,931,788 | A | 8/1999 | Keen et al. |
| 5,931,818 | A | 8/1999 | Werp et al. |
| 5,931,863 | A | 8/1999 | Griffin, III et al. |
| 5,935,160 | A | 8/1999 | Auricchio et al. |
| 5,941,858 | A | 8/1999 | Johnson |
| 5,941,889 | A | 8/1999 | Cermak |
| 5,941,904 | A | 8/1999 | Johnston et al. |
| 5,944,022 | A | 8/1999 | Nardella et al. |
| 5,944,023 | A | 8/1999 | Johnson et al. |
| 5,951,472 | A | 9/1999 | Van Vaals et al. |
| 5,951,598 | A | 9/1999 | Bishay et al. |
| 5,953,683 | A | 9/1999 | Hansen et al. |
| 5,957,857 | A | 9/1999 | Hartley |
| 5,961,923 | A | 10/1999 | Nova et al. |
| 5,967,978 | A | 10/1999 | Littmann et al. |
| 5,967,980 | A | 10/1999 | Ferre et al. |
| 5,967,984 | A | 10/1999 | Chu et al. |
| 5,967,991 | A | 10/1999 | Gardineer et al. |
| 5,969,722 | A | 10/1999 | Palm |
| 5,970,119 | A | 10/1999 | Hofmann |
| 5,971,933 | A | 10/1999 | Gopakumaran et al. |
| 5,971,983 | A | 10/1999 | Lesh |
| 5,978,705 | A | 11/1999 | KenKnight et al. |
| 5,983,126 | A | 11/1999 | Wittkampf |
| 5,984,908 | A | 11/1999 | Davis et al. |
| 5,991,693 | A | 11/1999 | Zalewski |
| 5,997,473 | A | 12/1999 | Taniguchi et al. |
| 5,997,481 | A | 12/1999 | Adams et al. |
| 6,004,270 | A | 12/1999 | Urbano et al. |
| 6,006,123 | A | 12/1999 | Nguyen et al. |
| 6,011,988 | A | 1/2000 | Lynch et al. |
| 6,014,473 | A | 1/2000 | Hossack et al. |
| 6,014,580 | A | 1/2000 | Blume et al. |
| 6,015,414 | A | 1/2000 | Werp et al. |
| 6,017,496 | A | 1/2000 | Nova et al. |
| 6,019,724 | A | 2/2000 | Gronningsaeter et al. |
| 6,019,725 | A | 2/2000 | Vesely et al. |
| 6,022,342 | A | 2/2000 | Mukherjee |
| 6,023,638 | A | 2/2000 | Swanson |
| 6,026,312 | A | 2/2000 | Shemwell et al. |
| 6,031,765 | A | 2/2000 | Lee et al. |
| 6,032,070 | A | 2/2000 | Flock et al. |
| 6,039,694 | A | 3/2000 | Larson et al. |
| 6,050,718 | A | 4/2000 | Schena et al. |
| 6,052,610 | A | 4/2000 | Koch |
| 6,052,618 | A | 4/2000 | Dahlke et al. |
| D424,693 | S | 5/2000 | Pruter |
| 6,058,323 | A | 5/2000 | Lemelson |
| 6,059,718 | A | 5/2000 | Taniguchi et al. |
| 6,060,970 | A | 5/2000 | Bell |
| 6,063,032 | A | 5/2000 | Grunwald |
| 6,064,905 | A | 5/2000 | Webster, Jr. et al. |
| 6,066,094 | A | 5/2000 | Ben-Haim |
| 6,068,599 | A | 5/2000 | Saito et al. |
| 6,073,043 | A | 6/2000 | Schneider |
| 6,074,367 | A | 6/2000 | Hubbell |
| 6,075,442 | A | 6/2000 | Welch |
| 6,076,007 | A | 6/2000 | England et al. |
| 6,081,737 | A | 6/2000 | Shah |
| 6,082,366 | A | 7/2000 | Andra et al. |
| 6,083,170 | A | 7/2000 | Ben-Haim |
| 6,099,524 | A | 8/2000 | Lipson et al. |
| 6,100,026 | A | 8/2000 | Nova et al. |
| 6,102,044 | A | 8/2000 | Naidyhorski |
| 6,102,862 | A | 8/2000 | Grunwald et al. |
| 6,107,699 | A | 8/2000 | Swanson |
| 6,112,111 | A | 8/2000 | Glantz |
| 6,112,115 | A | 8/2000 | Feldman et al. |
| 6,113,504 | A | 9/2000 | Kuesters |
| 6,115,624 | A | 9/2000 | Lewis et al. |
| 6,120,445 | A | 9/2000 | Grunwald |
| 6,122,538 | A | 9/2000 | Sliwa, Jr. et al. |
| 6,128,174 | A | 10/2000 | Ritter et al. |
| 6,129,668 | A | 10/2000 | Haynor et al. |
| 6,129,724 | A | 10/2000 | Fleischman et al. |
| 6,132,378 | A | 10/2000 | Marino |
| 6,132,379 | A | 10/2000 | Patacsil et al. |
| 6,135,961 | A | 10/2000 | Pflugrath et al. |
| 6,136,274 | A | 10/2000 | Nova et al. |
| 6,138,681 | A | 10/2000 | Chen et al. |
| 6,139,496 | A | 10/2000 | Chen et al. |
| 6,139,502 | A | 10/2000 | Fredriksen |
| 6,139,540 | A | 10/2000 | Rost et al. |
| 6,144,300 | A | 11/2000 | Dames |
| 6,148,823 | A | 11/2000 | Hastings |
| 6,152,933 | A | 11/2000 | Werp et al. |
| 6,157,853 | A | 12/2000 | Blume et al. |
| 6,165,144 | A | 12/2000 | Talish et al. |
| 6,165,977 | A | 12/2000 | Mochly-Rosen |
| 6,166,496 | A | 12/2000 | Lys et al. |
| 6,166,806 | A | 12/2000 | Tjin |
| 6,167,765 | B1 | 1/2001 | Weitzel |
| 6,172,499 | B1 | 1/2001 | Ashe |
| 6,173,199 | B1 | 1/2001 | Gabriel |
| 6,173,715 | B1 | 1/2001 | Sinanan et al. |
| 6,175,756 | B1 | 1/2001 | Ferre et al. |
| 6,176,829 | B1 | 1/2001 | Vilkomerson |
| 6,187,744 | B1 | 2/2001 | Rooney |
| 6,190,370 | B1 | 2/2001 | Tsui |
| 6,191,136 | B1 | 2/2001 | Marban |
| 6,193,743 | B1 | 2/2001 | Brayton et al. |
| 6,197,001 | B1 | 3/2001 | Wilson et al. |
| 6,200,305 | B1 | 3/2001 | Berthiaume et al. |
| 6,203,499 | B1 | 3/2001 | Imling et al. |
| 6,208,884 | B1 | 3/2001 | Kumar et al. |
| 6,211,626 | B1 | 4/2001 | Lys et al. |
| 6,211,666 | B1 | 4/2001 | Acker |
| 6,212,426 | B1 | 4/2001 | Swanson |
| 6,212,430 | B1 | 4/2001 | Kung |
| 6,216,027 | B1 | 4/2001 | Willis et al. |
| 6,216,028 | B1 | 4/2001 | Haynor et al. |
| 6,216,029 | B1 | 4/2001 | Paltieli |
| 6,217,517 | B1 | 4/2001 | Grunwald |
| 6,223,087 | B1 | 4/2001 | Williams |
| 6,226,547 | B1 | 5/2001 | Lockhart et al. |
| 6,230,042 | B1 | 5/2001 | Slettenmark |
| 6,230,046 | B1 | 5/2001 | Crane et al. |
| 6,231,518 | B1 | 5/2001 | Grabek et al. |

(56)                References Cited

U.S. PATENT DOCUMENTS

| 6,233,476 | B1 | 5/2001 | Strommer et al. |
| 6,233,994 | B1 | 5/2001 | Roy et al. |
| 6,236,883 | B1 | 5/2001 | Ciaccio et al. |
| 6,238,344 | B1 | 5/2001 | Gamelsky et al. |
| 6,241,673 | B1 | 6/2001 | Williams |
| 6,245,018 | B1 | 6/2001 | Lee |
| 6,246,231 | B1 | 6/2001 | Ashe |
| 6,246,898 | B1 | 6/2001 | Vesely et al. |
| 6,248,072 | B1 | 6/2001 | Murkin |
| 6,248,074 | B1 | 6/2001 | Ohno et al. |
| 6,248,075 | B1 | 6/2001 | McGee et al. |
| 6,249,234 | B1 | 6/2001 | Ely et al. |
| 6,253,770 | B1 | 7/2001 | Acker et al. |
| 6,254,543 | B1 | 7/2001 | Grunwald et al. |
| 6,258,035 | B1 | 7/2001 | Hoeksel et al. |
| 6,259,938 | B1 | 7/2001 | Zarychta et al. |
| 6,259,941 | B1 | 7/2001 | Chia et al. |
| 6,261,231 | B1 | 7/2001 | Damphousse et al. |
| 6,263,230 | B1 | 7/2001 | Haynor et al. |
| 6,266,550 | B1 | 7/2001 | Selmon et al. |
| 6,266,551 | B1 | 7/2001 | Osadchy et al. |
| 6,266,552 | B1 | 7/2001 | Slettenmark |
| 6,266,563 | B1 | 7/2001 | KenKnight et al. |
| 6,270,493 | B1 | 8/2001 | Lalonde et al. |
| 6,271,833 | B1 | 8/2001 | Rosenberg et al. |
| 6,272,371 | B1 | 8/2001 | Shlomo |
| 6,272,374 | B1 | 8/2001 | Flock et al. |
| 6,275,258 | B1 | 8/2001 | Chim |
| 6,275,724 | B1 | 8/2001 | Dickinson et al. |
| 6,277,077 | B1 | 8/2001 | Brisken et al. |
| 6,284,459 | B1 | 9/2001 | Nova et al. |
| 6,285,898 | B1 | 9/2001 | Ben-Haim |
| 6,287,259 | B1 | 9/2001 | Grunwald |
| 6,287,260 | B1 | 9/2001 | Hascoet et al. |
| 6,288,704 | B1 | 9/2001 | Flack et al. |
| 6,292,678 | B1 | 9/2001 | Hall et al. |
| 6,292,680 | B1 | 9/2001 | Somogyi et al. |
| 6,292,901 | B1 | 9/2001 | Fys et al. |
| 6,293,955 | B1 | 9/2001 | Houser et al. |
| 6,296,604 | B1 | 10/2001 | Garibaldi et al. |
| 6,298,261 | B1 | 10/2001 | Rex |
| 6,304,768 | B1 | 10/2001 | Blume et al. |
| 6,306,097 | B1 | 10/2001 | Park et al. |
| 6,306,105 | B1 | 10/2001 | Rooney et al. |
| 6,310,532 | B1 | 10/2001 | Santa Cruz et al. |
| 6,311,082 | B1 | 10/2001 | Creighton, IV et al. |
| 6,315,709 | B1 | 11/2001 | Garibaldi et al. |
| 6,315,727 | B1 | 11/2001 | Coleman et al. |
| 6,319,668 | B1 | 11/2001 | Nova et al. |
| 6,323,769 | B1 | 11/2001 | Dames |
| 6,323,770 | B1 | 11/2001 | Dames |
| 6,324,416 | B1 | 11/2001 | Seibert |
| 6,325,540 | B1 | 12/2001 | Lounsberry et al. |
| 6,325,762 | B1 | 12/2001 | Tjin |
| 6,329,139 | B1 | 12/2001 | Nova et al. |
| 6,329,916 | B1 | 12/2001 | Dames |
| 6,330,467 | B1 | 12/2001 | Creighton, IV et al. |
| 6,332,089 | B1 | 12/2001 | Acker et al. |
| 6,332,874 | B1 | 12/2001 | Eliasen et al. |
| 6,340,588 | B1 | 1/2002 | Nova et al. |
| 6,340,868 | B1 | 1/2002 | Lys et al. |
| 6,341,231 | B1 | 1/2002 | Ferre et al. |
| 6,346,081 | B1 | 2/2002 | Vilkomerson |
| 6,348,911 | B1 | 2/2002 | Rosenberg et al. |
| 6,350,160 | B1 | 2/2002 | Feuersanger et al. |
| 6,352,363 | B1 | 3/2002 | Munger et al. |
| 6,354,999 | B1 | 3/2002 | Dgany et al. |
| 6,355,026 | B1 | 3/2002 | Mick |
| 6,356,791 | B1 | 3/2002 | Westlund et al. |
| 6,360,123 | B1 | 3/2002 | Kimchi et al. |
| 6,361,499 | B1 | 3/2002 | Bates et al. |
| 6,364,823 | B1 | 4/2002 | Garibaldi et al. |
| 6,364,839 | B1 | 4/2002 | Little et al. |
| 6,366,804 | B1 | 4/2002 | Mejia |
| 6,368,141 | B1 | 4/2002 | VanAntwerp et al. |
| 6,368,285 | B1 | 4/2002 | Osadchy et al. |
| 6,369,564 | B1 * | 4/2002 | Khalfin ............... G01B 3/1084 |
|  |  |  | 324/207.17 |
| 6,370,411 | B1 | 4/2002 | Osadchy et al. |
| 6,373,240 | B1 | 4/2002 | Govari |
| 6,373,388 | B1 | 4/2002 | Dames |
| 6,374,134 | B1 | 4/2002 | Bladen et al. |
| 6,374,670 | B1 | 4/2002 | Spelman et al. |
| 6,375,606 | B1 | 4/2002 | Garibaldi et al. |
| 6,375,615 | B1 | 4/2002 | Flaherty et al. |
| 6,375,639 | B1 | 4/2002 | Duplessie et al. |
| 6,377,857 | B1 | 4/2002 | Brayton et al. |
| 6,379,302 | B1 | 4/2002 | Kessman et al. |
| 6,379,303 | B1 | 4/2002 | Seitz et al. |
| 6,379,307 | B1 | 4/2002 | Filly et al. |
| 6,381,485 | B1 | 4/2002 | Hunter et al. |
| 6,385,472 | B1 | 5/2002 | Hall et al. |
| 6,385,476 | B1 | 5/2002 | Osadchy et al. |
| 6,398,736 | B1 | 6/2002 | Seward |
| 6,398,738 | B1 | 6/2002 | Millar |
| 6,401,723 | B1 | 6/2002 | Garibaldi et al. |
| 6,406,422 | B1 | 6/2002 | Landesberg |
| 6,406,442 | B1 | 6/2002 | McFann et al. |
| 6,412,978 | B1 | 7/2002 | Watanabe et al. |
| 6,412,980 | B1 | 7/2002 | Lounsberry et al. |
| 6,417,839 | B1 | 7/2002 | Odell |
| 6,418,332 | B1 | 7/2002 | Mastrototaro et al. |
| 6,418,335 | B2 | 7/2002 | Avrin et al. |
| 6,423,002 | B1 | 7/2002 | Hossack |
| 6,423,050 | B1 | 7/2002 | Twardowski |
| 6,427,079 | B1 | 7/2002 | Schneider et al. |
| 6,428,551 | B1 | 8/2002 | Hall et al. |
| 6,430,315 | B1 | 8/2002 | Makram-Ebeid |
| 6,432,069 | B1 | 8/2002 | Godo et al. |
| 6,436,043 | B2 | 8/2002 | Bonnefous |
| 6,438,411 | B1 | 8/2002 | Guttman et al. |
| 6,442,416 | B1 | 8/2002 | Schultz |
| 6,445,943 | B1 | 9/2002 | Ferre et al. |
| 6,456,874 | B1 | 9/2002 | Hafer et al. |
| 6,459,919 | B1 | 10/2002 | Lys et al. |
| 6,463,121 | B1 | 10/2002 | Milnes |
| 6,466,815 | B1 | 10/2002 | Saito et al. |
| 6,471,656 | B1 | 10/2002 | Shalman et al. |
| 6,471,658 | B1 | 10/2002 | Daniels et al. |
| 6,471,700 | B1 | 10/2002 | Burbank et al. |
| 6,473,167 | B1 | 10/2002 | Odell |
| 6,474,341 | B1 | 11/2002 | Hunter et al. |
| 6,475,152 | B1 | 11/2002 | Kelly, Jr. et al. |
| 6,475,223 | B1 | 11/2002 | Werp et al. |
| 6,477,402 | B1 | 11/2002 | Lynch et al. |
| 6,484,118 | B1 | 11/2002 | Govari |
| 6,487,916 | B1 | 12/2002 | Gomm et al. |
| 6,491,671 | B1 | 12/2002 | Larson, III et al. |
| 6,493,573 | B1 | 12/2002 | Martinelli et al. |
| 6,494,832 | B1 | 12/2002 | Feldman et al. |
| 6,496,715 | B1 | 12/2002 | Lee et al. |
| 6,498,942 | B1 | 12/2002 | Esenaliev et al. |
| 6,498,944 | B1 | 12/2002 | Ben-Haim et al. |
| 6,500,141 | B1 | 12/2002 | Irion et al. |
| 6,503,205 | B2 | 1/2003 | Manor et al. |
| 6,505,062 | B1 | 1/2003 | Ritter et al. |
| 6,506,159 | B2 | 1/2003 | Hascoet et al. |
| 6,507,751 | B2 | 1/2003 | Blume et al. |
| 6,508,769 | B2 | 1/2003 | Bonnefous |
| 6,508,802 | B1 | 1/2003 | Rosengart et al. |
| 6,511,413 | B2 | 1/2003 | Landesberg |
| 6,512,958 | B1 | 1/2003 | Swoyer et al. |
| 6,514,202 | B2 | 2/2003 | Grunwald |
| 6,514,226 | B1 | 2/2003 | Levin et al. |
| 6,514,249 | B1 | 2/2003 | Maguire et al. |
| 6,515,657 | B1 | 2/2003 | Zanelli |
| 6,516,212 | B1 | 2/2003 | Bladen et al. |
| 6,516,231 | B1 | 2/2003 | Flammang |
| 6,516,807 | B1 | 2/2003 | Panescu et al. |
| 6,517,520 | B2 | 2/2003 | Chang et al. |
| 6,522,906 | B1 | 2/2003 | Salisbury, Jr. et al. |
| 6,522,907 | B1 | 2/2003 | Bladen et al. |
| 6,522,909 | B1 | 2/2003 | Garibaldi et al. |
| 6,524,249 | B2 | 2/2003 | Moehring et al. |

(56)         References Cited

U.S. PATENT DOCUMENTS

| | | |
|---|---|---|
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,529,766 B1 | 3/2003 | Guendel |
| 6,534,982 B1 | 3/2003 | Jakab |
| 6,535,625 B1 | 3/2003 | Chang et al. |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,699 B1 | 4/2003 | Smith |
| 6,542,766 B2 | 4/2003 | Hall et al. |
| 6,544,251 B1 | 4/2003 | Crawford |
| 6,545,678 B1 | 4/2003 | Ohazama |
| 6,546,270 B1 | 4/2003 | Goldin et al. |
| 6,546,279 B1 | 4/2003 | Bova et al. |
| 6,546,787 B1 | 4/2003 | Schiller et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,569,103 B2 | 5/2003 | Hoeksel et al. |
| 6,569,160 B1 | 5/2003 | Goldin et al. |
| 6,569,862 B1 | 5/2003 | Marban |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,589,181 B2 | 7/2003 | Grunwald et al. |
| 6,592,520 B1 | 7/2003 | Peszynski et al. |
| 6,592,565 B2 | 7/2003 | Twardowski |
| 6,593,754 B1 | 7/2003 | Steber et al. |
| 6,593,884 B1 | 7/2003 | Gilboa et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,616,610 B2 | 9/2003 | Steininger et al. |
| 6,618,612 B1 | 9/2003 | Acker et al. |
| 6,623,431 B1 | 9/2003 | Sakuma et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,641,538 B2 | 11/2003 | Nakaya et al. |
| 6,645,148 B2 | 11/2003 | Nguyen-Dinh et al. |
| 6,647,135 B2 | 11/2003 | Bonnefous |
| 6,648,875 B2 | 11/2003 | Simpson et al. |
| 6,649,914 B1 | 11/2003 | Moorman et al. |
| 6,652,505 B1 | 11/2003 | Tsugita |
| 6,652,506 B2 | 11/2003 | Bowe et al. |
| 6,654,643 B1 | 11/2003 | Schmid |
| 6,660,024 B1 | 12/2003 | Flaherty et al. |
| 6,662,034 B2 | 12/2003 | Segner et al. |
| 6,663,661 B2 | 12/2003 | Boneau |
| 6,666,828 B2 | 12/2003 | Greco et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo et al. |
| 6,687,386 B1 | 2/2004 | Ito et al. |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |
| 6,711,431 B2 | 3/2004 | Sarin et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,458 B1 | 5/2004 | Steins et al. |
| 6,733,473 B1 | 5/2004 | Reifart et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito |
| 6,749,569 B1 | 6/2004 | Pellegretti |
| 6,754,596 B2 | 6/2004 | Ashe |
| 6,754,608 B2 | 6/2004 | Svanerudh et al. |
| 6,755,789 B2 | 6/2004 | Stringer et al. |
| 6,755,816 B2 | 6/2004 | Ritter et al. |
| 6,755,822 B2 | 6/2004 | Reu et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,785,571 B2 | 8/2004 | Glossop |
| 6,786,219 B2 | 9/2004 | Garibaldi et al. |
| 6,786,870 B2 | 9/2004 | Miyaki et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,815,651 B2 | 11/2004 | Odell |
| 6,816,266 B2 | 11/2004 | Varshneya et al. |
| 6,817,364 B2 | 11/2004 | Garibaldi et al. |
| 6,834,201 B2 | 12/2004 | Gillies et al. |
| 6,844,713 B2 | 1/2005 | Steber et al. |
| 6,845,142 B2 | 1/2005 | Hishi |
| 6,850,788 B2 | 2/2005 | Ai-Ali |
| 6,856,823 B2 | 2/2005 | Ashe |
| 6,857,196 B2 | 2/2005 | Dalrymple |
| 6,860,422 B2 | 3/2005 | Hull et al. |
| 6,862,467 B2 | 3/2005 | Moore et al. |
| 6,869,390 B2 | 3/2005 | Elliott et al. |
| 6,875,179 B2 | 4/2005 | Ferguson et al. |
| 6,879,160 B2 | 4/2005 | Jakab |
| 6,887,206 B2 | 5/2005 | Hoeksel et al. |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,905,469 B2 | 6/2005 | Hascoet et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |
| 6,926,674 B2 | 8/2005 | Tenerz et al. |
| 6,934,575 B2 | 8/2005 | Ferre et al. |
| 6,936,010 B2 | 8/2005 | Fang et al. |
| 6,939,313 B2 | 9/2005 | Saadat et al. |
| 6,940,379 B2 | 9/2005 | Creighton |
| 6,941,166 B2 | 9/2005 | MacAdam et al. |
| 6,945,938 B2 | 9/2005 | Grunwald |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,975,197 B2 | 12/2005 | Creighton, IV |
| 6,976,962 B2 | 12/2005 | Bullis |
| 6,976,987 B2 | 12/2005 | Flores |

(56)             References Cited

U.S. PATENT DOCUMENTS

| | | | |
|---|---|---|---|
| 6,979,294 | B1 | 12/2005 | Selzer et al. |
| 6,980,843 | B2 | 12/2005 | Eng et al. |
| 6,980,852 | B2 | 12/2005 | Jersey-Willuhn et al. |
| 6,980,921 | B2 | 12/2005 | Anderson et al. |
| 6,986,739 | B2 | 1/2006 | Warren et al. |
| 6,986,744 | B1 | 1/2006 | Krivitski |
| 6,999,821 | B2 | 2/2006 | Jenney et al. |
| 7,001,355 | B2 | 2/2006 | Nunomura et al. |
| 7,008,418 | B2 | 3/2006 | Hall et al. |
| 7,010,338 | B2 | 3/2006 | Ritter et al. |
| 7,015,393 | B2 | 3/2006 | Weiner et al. |
| 7,017,584 | B2 | 3/2006 | Garibaldi et al. |
| 7,019,610 | B2 | 3/2006 | Creighton, IV et al. |
| 7,020,512 | B2 | 3/2006 | Ritter et al. |
| D518,574 | S | 4/2006 | Chaggares |
| 7,022,075 | B2 | 4/2006 | Grunwald et al. |
| 7,022,082 | B2 | 4/2006 | Sonek |
| 7,026,927 | B2 | 4/2006 | Wright et al. |
| 7,027,634 | B2 | 4/2006 | Odell |
| 7,028,387 | B1 | 4/2006 | Huynh et al. |
| 7,029,446 | B2 | 4/2006 | Wendelken et al. |
| 7,033,603 | B2 | 4/2006 | Nelson et al. |
| D520,139 | S | 5/2006 | Chaggares |
| D520,140 | S | 5/2006 | Chaggares |
| 7,038,398 | B1 | 5/2006 | Lys et al. |
| 7,038,657 | B2 | 5/2006 | Rosenberg et al. |
| 7,043,293 | B1 | 5/2006 | Baura |
| 7,048,733 | B2 | 5/2006 | Hartley et al. |
| 7,054,228 | B1 | 5/2006 | Hickling |
| 7,059,878 | B1 | 6/2006 | Hendrixson |
| 7,065,403 | B1 | 6/2006 | Mouchawar et al. |
| 7,066,914 | B2 | 6/2006 | Andersen |
| 7,066,924 | B1 | 6/2006 | Garibaldi et al. |
| 7,069,072 | B2 | 6/2006 | Jansen et al. |
| D525,363 | S | 7/2006 | Chaggares |
| 7,070,565 | B2 | 7/2006 | Vaezy et al. |
| 7,072,704 | B2 | 7/2006 | Bucholz |
| 7,074,187 | B2 | 7/2006 | Selzer et al. |
| 7,082,325 | B2 | 7/2006 | Hashimshony et al. |
| 7,090,639 | B2 | 8/2006 | Govari |
| 7,096,059 | B2 | 8/2006 | Geddes et al. |
| 7,096,148 | B2 | 8/2006 | Anderson et al. |
| 7,096,870 | B2 | 8/2006 | Lamprich et al. |
| 7,098,907 | B2 | 8/2006 | Houston et al. |
| 7,103,205 | B2 | 9/2006 | Wang et al. |
| 7,104,980 | B1 | 9/2006 | Laherty et al. |
| 7,106,043 | B1 | 9/2006 | Da Silva et al. |
| 7,106,431 | B2 | 9/2006 | Odell |
| 7,106,479 | B2 | 9/2006 | Roy et al. |
| 7,107,105 | B2 | 9/2006 | Bjorklund et al. |
| 7,112,197 | B2 | 9/2006 | Hartley et al. |
| 7,128,734 | B1 | 10/2006 | Wilson et al. |
| 7,132,804 | B2 | 11/2006 | Lys et al. |
| 7,137,976 | B2 | 11/2006 | Ritter et al. |
| 7,141,019 | B2 | 11/2006 | Pearlman |
| 7,141,812 | B2 | 11/2006 | Appleby et al. |
| 7,142,905 | B2 | 11/2006 | Slayton et al. |
| 7,148,970 | B2 | 12/2006 | de Boer |
| 7,153,291 | B2 | 12/2006 | Bierman |
| 7,161,453 | B2 | 1/2007 | Creighton, IV |
| 7,162,291 | B1 | 1/2007 | Nachaliel |
| 7,167,738 | B2 | 1/2007 | Schweikard et al. |
| 7,169,107 | B2 | 1/2007 | Jersey-Willuhn et al. |
| 7,169,109 | B2 | 1/2007 | Jansen et al. |
| 7,174,201 | B2 | 2/2007 | Govari et al. |
| 7,175,646 | B2 | 2/2007 | Brenneman et al. |
| 7,180,252 | B2 | 2/2007 | Lys et al. |
| 7,184,820 | B2 | 2/2007 | Jersey-Willuhn et al. |
| 7,189,198 | B2 | 3/2007 | Harburn et al. |
| 7,189,205 | B2 | 3/2007 | McMorrow et al. |
| 7,189,208 | B1 | 3/2007 | Beatty et al. |
| 7,190,819 | B2 | 3/2007 | Viswanathan |
| 7,194,295 | B2 | 3/2007 | Vilsmeier |
| 7,204,798 | B2 | 4/2007 | Zdeblick et al. |
| 7,206,064 | B2 | 4/2007 | Rogers et al. |
| 7,207,941 | B2 | 4/2007 | Sharf |
| 7,211,082 | B2 | 5/2007 | Hall et al. |
| 7,214,191 | B2 | 5/2007 | Stringer et al. |
| 7,215,326 | B2 | 5/2007 | Rosenberg |
| 7,221,104 | B2 | 5/2007 | Lys et al. |
| 7,223,256 | B2 | 5/2007 | Bierman |
| 7,229,400 | B2 | 6/2007 | Elliott et al. |
| 7,231,243 | B2 | 6/2007 | Tearney et al. |
| 7,236,157 | B2 | 6/2007 | Schena et al. |
| 7,236,816 | B2 | 6/2007 | Kumar et al. |
| 7,236,820 | B2 | 6/2007 | Mabary et al. |
| 7,237,313 | B2 | 7/2007 | Skujins et al. |
| 7,238,169 | B2 | 7/2007 | Takagi et al. |
| 7,241,267 | B2 | 7/2007 | Furia |
| 7,244,234 | B2 | 7/2007 | Ridley et al. |
| 7,248,032 | B1 | 7/2007 | Hular et al. |
| 7,248,914 | B2 | 7/2007 | Hastings et al. |
| 7,252,633 | B2 | 8/2007 | Obata et al. |
| 7,260,428 | B2 | 8/2007 | Virtanen |
| 7,261,691 | B1 | 8/2007 | Asomani |
| 7,264,584 | B2 | 9/2007 | Ritter et al. |
| 7,270,662 | B2 | 9/2007 | Visram et al. |
| 7,276,044 | B2 | 10/2007 | Ferry et al. |
| 7,286,034 | B2 | 10/2007 | Creighton |
| 7,291,146 | B2 | 11/2007 | Steinke et al. |
| 7,297,140 | B2 | 11/2007 | Orlu et al. |
| 7,299,085 | B2 | 11/2007 | Bergelson et al. |
| 7,300,430 | B2 | 11/2007 | Wilson et al. |
| 7,302,288 | B1 | 11/2007 | Schellenberg |
| 7,308,296 | B2 | 12/2007 | Fys et al. |
| 7,310,150 | B2 | 12/2007 | Guillermo et al. |
| 7,311,702 | B2 | 12/2007 | Tallarida et al. |
| 7,321,228 | B2 | 1/2008 | Govari |
| 7,326,241 | B2 | 2/2008 | Jang |
| 7,327,872 | B2 | 2/2008 | Vaillant et al. |
| 7,331,462 | B2 | 2/2008 | Steppe |
| 7,342,058 | B2 | 3/2008 | Peppmoller et al. |
| 7,344,554 | B2 | 3/2008 | Kuyava et al. |
| 7,349,732 | B1 | 3/2008 | Kil et al. |
| 7,355,716 | B2 | 4/2008 | de Boer et al. |
| 7,359,554 | B2 | 4/2008 | Klingensmith et al. |
| 7,360,427 | B2 | 4/2008 | Drinkwater et al. |
| 7,366,376 | B2 | 4/2008 | Shishkov et al. |
| 7,366,562 | B2 | 4/2008 | Dukesherer et al. |
| 7,366,563 | B2 | 4/2008 | Kleen et al. |
| 7,373,271 | B1 | 5/2008 | Schneider |
| 7,381,204 | B2 | 6/2008 | Wilson et al. |
| 7,382,949 | B2 | 6/2008 | Bouma et al. |
| 7,384,407 | B2 | 6/2008 | Rodriguez et al. |
| 7,413,562 | B2 | 8/2008 | Ferguson et al. |
| 7,418,169 | B2 | 8/2008 | Tearney et al. |
| 7,447,408 | B2 | 11/2008 | Bouma et al. |
| 7,452,331 | B1 | 11/2008 | Pruter |
| 7,452,358 | B2 | 11/2008 | Stern et al. |
| 7,454,244 | B2 | 11/2008 | Kassab et al. |
| D585,556 | S | 1/2009 | Kosaku |
| 7,479,141 | B2 | 1/2009 | Kleen et al. |
| 7,507,114 | B2 | 3/2009 | Kent et al. |
| 7,519,424 | B2 | 4/2009 | Dennis et al. |
| 7,529,584 | B2 | 5/2009 | Laske et al. |
| 7,534,209 | B2 | 5/2009 | Abend et al. |
| 7,534,223 | B2 | 5/2009 | Boutilette et al. |
| 7,538,859 | B2 | 5/2009 | Tearney et al. |
| 7,543,239 | B2 | 6/2009 | Viswanathan et al. |
| 7,546,158 | B2 | 6/2009 | Allison et al. |
| 7,547,282 | B2 | 6/2009 | Lo et al. |
| 7,551,293 | B2 | 6/2009 | Yelin et al. |
| D603,050 | S | 10/2009 | Chen |
| 7,599,730 | B2 | 10/2009 | Hunter et al. |
| 7,606,615 | B2 | 10/2009 | Makower et al. |
| 7,613,478 | B2 | 11/2009 | Jabri et al. |
| 7,616,992 | B2 | 11/2009 | Dennis et al. |
| 7,627,376 | B2 | 12/2009 | Dennis et al. |
| 7,635,336 | B1 | 12/2009 | Pruter |
| 7,637,163 | B2 | 12/2009 | Fetzer et al. |
| 7,637,870 | B2 | 12/2009 | Flaherty et al. |
| 7,640,053 | B2 | 12/2009 | Verin |
| 7,651,469 | B2 | 1/2010 | Osborne et al. |
| 7,652,080 | B2 | 1/2010 | Peppmoller et al. |

(56) References Cited

U.S. PATENT DOCUMENTS

| 7,660,623 B2 | 2/2010 | Hunter et al. |
| 7,665,893 B2 | 2/2010 | Buchalter |
| 7,666,191 B2 | 2/2010 | Orban, III et al. |
| 7,668,583 B2 | 2/2010 | Fegert et al. |
| 7,681,579 B2 | 3/2010 | Schwartz |
| 7,691,061 B2 | 4/2010 | Hirota |
| 7,697,972 B2 | 4/2010 | Verard et al. |
| 7,699,779 B2 | 4/2010 | Sasaki et al. |
| 7,699,782 B2 | 4/2010 | Angelsen et al. |
| 7,699,829 B2 | 4/2010 | Harris et al. |
| 7,715,925 B2 | 5/2010 | Hafer et al. |
| 7,727,153 B2 | 6/2010 | Fritz et al. |
| 7,727,192 B2 | 6/2010 | Tokumoto et al. |
| 7,729,743 B2 | 6/2010 | Sabczynski et al. |
| 7,751,865 B2 | 7/2010 | Jascob et al. |
| 7,766,839 B2 | 8/2010 | Rogers et al. |
| 7,771,437 B2 | 8/2010 | Hogg et al. |
| 7,774,051 B2 | 8/2010 | Voth |
| 7,774,055 B1 | 8/2010 | Min |
| 7,794,407 B2 | 9/2010 | Rothenberg |
| 7,798,970 B2 | 9/2010 | Lo et al. |
| 7,819,810 B2 | 10/2010 | Stringer et al. |
| 7,822,464 B2 | 10/2010 | Maschke et al. |
| 7,828,528 B2 | 11/2010 | Estes et al. |
| 7,831,294 B2 | 11/2010 | Viswanathan |
| 7,831,449 B2 | 11/2010 | Mng et al. |
| 7,833,168 B2 | 11/2010 | Taylor et al. |
| 7,833,214 B2 | 11/2010 | Wilson et al. |
| 7,840,252 B2 | 11/2010 | Strommer et al. |
| D629,526 S | 12/2010 | Ladwig et al. |
| D629,527 S | 12/2010 | Crunkilton |
| 7,846,157 B2 | 12/2010 | Kozel |
| 7,850,613 B2 | 12/2010 | Stribling |
| D630,756 S | 1/2011 | Kitayama |
| D630,757 S | 1/2011 | Kitayama |
| 7,869,854 B2 | 1/2011 | Shachar et al. |
| 7,869,865 B2 | 1/2011 | Govari et al. |
| 7,873,402 B2 | 1/2011 | Shachar |
| 7,887,516 B2 | 2/2011 | Young |
| 7,905,837 B2 | 3/2011 | Suzuki |
| 7,909,815 B2 | 3/2011 | Whitmore, III et al. |
| 7,925,327 B2 | 4/2011 | Weese |
| 7,927,278 B2 | 4/2011 | Selzer et al. |
| 7,931,596 B2 | 4/2011 | Rachlin et al. |
| 7,947,040 B2 | 5/2011 | Davies et al. |
| 7,969,142 B2 | 6/2011 | Krueger et al. |
| 7,976,469 B2 | 7/2011 | Bonde et al. |
| 7,976,518 B2 | 7/2011 | Shaughnessy et al. |
| 7,981,038 B2 | 7/2011 | Kanade et al. |
| 7,988,633 B2 | 8/2011 | Hossack et al. |
| 8,016,814 B2 | 9/2011 | Blakstvedt et al. |
| 8,046,052 B2 | 10/2011 | Verard et al. |
| 8,055,327 B2 | 11/2011 | Strommer et al. |
| 8,057,394 B2 | 11/2011 | Dala-Krishna |
| 8,060,185 B2 | 11/2011 | Hunter et al. |
| 8,075,488 B2 | 12/2011 | Burton |
| 8,078,274 B2 | 12/2011 | Kassab |
| 8,078,279 B2 | 12/2011 | Dennis et al. |
| 8,082,025 B2 | 12/2011 | Amitai et al. |
| 8,082,032 B2 | 12/2011 | Kassab et al. |
| 8,088,072 B2 | 1/2012 | Munrow et al. |
| 8,090,427 B2 | 1/2012 | Eck et al. |
| 8,090,430 B2 | 1/2012 | Makower et al. |
| 8,099,161 B2 | 1/2012 | Kassab |
| 8,105,239 B2 | 1/2012 | Specht |
| 8,105,338 B2 | 1/2012 | Anderson et al. |
| 8,114,143 B2 | 2/2012 | Kassab et al. |
| 8,118,743 B2 | 2/2012 | Park et al. |
| 8,123,691 B2 | 2/2012 | Mine et al. |
| 8,133,698 B2 | 3/2012 | Silver |
| 8,142,417 B2 | 3/2012 | Pajunk et al. |
| 8,150,522 B2 | 4/2012 | Echauz et al. |
| 8,152,724 B2 | 4/2012 | Ridley et al. |
| 8,155,732 B2 | 4/2012 | Scholz et al. |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,204,582 B2 | 6/2012 | Zantos et al. |
| 8,211,023 B2 | 7/2012 | Swan et al. |
| 8,214,018 B2 | 7/2012 | Markowitz et al. |
| 8,221,402 B2 | 7/2012 | Francischelli et al. |
| 8,226,540 B2 | 7/2012 | Chi |
| 8,228,347 B2 | 7/2012 | Beasley et al. |
| 8,240,211 B2 | 8/2012 | Zeitner et al. |
| 8,241,274 B2 | 8/2012 | Keogh et al. |
| 8,244,339 B2 | 8/2012 | Shen et al. |
| 8,255,035 B2 | 8/2012 | Cao et al. |
| 8,260,395 B2 | 9/2012 | Markowitz et al. |
| 8,262,577 B2 | 9/2012 | Munrow et al. |
| 8,298,147 B2 | 10/2012 | Huennekens et al. |
| 8,298,149 B2 | 10/2012 | Hastings et al. |
| 8,303,502 B2 | 11/2012 | Washburn et al. |
| 8,303,505 B2 | 11/2012 | Webler et al. |
| 8,323,202 B2 | 12/2012 | Roschak et al. |
| 8,326,419 B2 | 12/2012 | Rosenberg et al. |
| 8,326,651 B2 | 12/2012 | McLaren et al. |
| 8,328,727 B2 | 12/2012 | Miele et al. |
| 8,340,751 B2 | 12/2012 | Markowitz et al. |
| 8,346,343 B2 | 1/2013 | Kimura et al. |
| 8,369,922 B2 | 2/2013 | Paul et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,400,164 B2 | 3/2013 | Osadchy et al. |
| 8,401,616 B2 | 3/2013 | Verard et al. |
| 8,409,103 B2 | 4/2013 | Grunwald et al. |
| 8,412,313 B2 | 4/2013 | Amitai et al. |
| 8,425,425 B2 | 4/2013 | Hagy et al. |
| 8,437,833 B2 | 5/2013 | Silverstein |
| 8,439,873 B1 | 5/2013 | Donovan |
| 8,442,621 B2 | 5/2013 | Gorek et al. |
| 8,447,384 B2 | 5/2013 | Xu et al. |
| 8,449,465 B2 | 5/2013 | Nair et al. |
| D684,265 S | 6/2013 | Cadera |
| 8,456,182 B2 | 6/2013 | Bar-Tal et al. |
| 8,478,382 B2 | 7/2013 | Burnside et al. |
| 8,478,388 B2 | 7/2013 | Nguyen et al. |
| 8,485,980 B2 | 7/2013 | Sinderby et al. |
| 8,494,608 B2 | 7/2013 | Markowitz et al. |
| 8,496,592 B2 | 7/2013 | Ridley et al. |
| 8,504,139 B2 | 8/2013 | Jacobsen et al. |
| 8,512,256 B2 | 8/2013 | Rothenberg |
| 8,521,122 B2 | 8/2013 | Scott et al. |
| 8,527,036 B2 | 9/2013 | Jalde et al. |
| 8,529,433 B2 | 9/2013 | Kawano et al. |
| 8,538,509 B2 | 9/2013 | Harlev et al. |
| 8,545,255 B2 | 10/2013 | Litzler et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,597,193 B2 | 12/2013 | Grunwald et al. |
| 8,620,412 B2 | 12/2013 | Griffiths et al. |
| 8,622,913 B2 | 1/2014 | Dentinger et al. |
| 8,644,907 B2 | 2/2014 | Hartmann et al. |
| 8,663,116 B2 | 3/2014 | Hamilton, Jr. |
| 8,676,295 B2 | 3/2014 | Cunningham et al. |
| 8,684,737 B1 | 4/2014 | Jordan |
| 8,690,776 B2 | 4/2014 | Razzaque et al. |
| 8,700,137 B2 | 4/2014 | Albert |
| 8,706,457 B2 | 4/2014 | Hart et al. |
| 8,715,195 B2 | 5/2014 | Ziv |
| 8,721,655 B2 | 5/2014 | Viswanathan et al. |
| 8,727,988 B2 | 5/2014 | Flaherty et al. |
| 8,734,357 B2 | 5/2014 | Taylor |
| 8,734,440 B2 | 5/2014 | Wu |
| 8,744,211 B2 | 6/2014 | Owen |
| 8,754,865 B2 | 6/2014 | Merritt et al. |
| 8,761,862 B2 | 6/2014 | Ridley et al. |
| 8,764,663 B2 | 7/2014 | Smok et al. |
| 8,774,907 B2 | 7/2014 | Rothenberg |
| 8,781,555 B2 | 7/2014 | Burnside et al. |
| 8,784,336 B2 | 7/2014 | Bown et al. |
| 8,790,263 B2 | 7/2014 | Randall et al. |
| 8,801,693 B2 | 8/2014 | He et al. |

(56) References Cited

U.S. PATENT DOCUMENTS

| | | |
|---|---|---|
| 8,849,382 B2 | 9/2014 | Cox et al. |
| 8,858,455 B2 | 10/2014 | Rothenberg |
| 8,934,961 B2 | 1/2015 | Lakin et al. |
| 8,939,908 B2 | 1/2015 | Suzuki et al. |
| 8,942,784 B2 | 1/2015 | Neidert et al. |
| 8,965,490 B2 | 2/2015 | Lee et al. |
| 8,971,994 B2 | 3/2015 | Burnside et al. |
| 9,014,794 B2 | 4/2015 | Brodnick et al. |
| 9,022,940 B2 | 5/2015 | Meier |
| 9,033,889 B2 | 5/2015 | Hamilton, Jr. |
| 9,125,578 B2 | 9/2015 | Grunwald |
| 9,138,290 B2 | 9/2015 | Hadjicostis |
| 9,179,860 B2 | 11/2015 | Markowitz et al. |
| 9,198,600 B2 | 12/2015 | Grunwald et al. |
| 9,204,858 B2 | 12/2015 | Pelissier et al. |
| 9,220,477 B2 | 12/2015 | Jrabe et al. |
| 9,295,447 B2 | 3/2016 | Shah |
| 9,320,493 B2 | 4/2016 | Visveshwara |
| 9,339,206 B2 | 5/2016 | Grunwald |
| 9,357,980 B2 | 6/2016 | Toji et al. |
| 9,364,171 B2 | 6/2016 | Harris et al. |
| 9,415,188 B2 | 8/2016 | He et al. |
| 9,427,207 B2 | 8/2016 | Sheldon et al. |
| 9,445,780 B2 | 9/2016 | Hossack et al. |
| 9,456,766 B2 | 10/2016 | Cox et al. |
| 9,456,804 B2 | 10/2016 | Tamada |
| 9,459,087 B2 | 10/2016 | Dunbar et al. |
| 9,468,413 B2 | 10/2016 | Hall et al. |
| 9,492,097 B2 | 11/2016 | Wilkes et al. |
| 9,521,961 B2 | 12/2016 | Silverstein et al. |
| 9,526,440 B2 | 12/2016 | Bumside et al. |
| 9,532,724 B2 | 1/2017 | Grunwald |
| 9,554,716 B2 | 1/2017 | Burnside et al. |
| 9,582,876 B2 | 2/2017 | Specht |
| 9,610,061 B2 | 4/2017 | Ebbini et al. |
| 9,636,031 B2 | 5/2017 | Cox |
| 9,642,986 B2 | 5/2017 | Beasley |
| 9,649,037 B2 | 5/2017 | Lowe et al. |
| 9,649,048 B2 | 5/2017 | Cox et al. |
| 9,681,823 B2 | 6/2017 | Messerly et al. |
| 9,702,969 B2 | 7/2017 | Hope Simpson et al. |
| 9,715,757 B2 | 7/2017 | Ng et al. |
| 9,717,415 B2 | 8/2017 | Cohen et al. |
| 9,731,066 B2 | 8/2017 | Liu et al. |
| 9,814,433 B2 | 11/2017 | Benishti et al. |
| 9,814,531 B2 | 11/2017 | Yagi et al. |
| 9,833,169 B2 | 12/2017 | Rothenberg |
| 9,839,372 B2 | 12/2017 | Bukhman et al. |
| 9,861,337 B2 | 1/2018 | Patwardhan et al. |
| 9,895,138 B2 | 2/2018 | Sasaki |
| 9,901,714 B2 | 2/2018 | Lemon et al. |
| 9,907,513 B2 | 3/2018 | Silverstein |
| 9,913,605 B2 | 3/2018 | Harris et al. |
| 9,949,720 B2 | 4/2018 | Southard et al. |
| 9,950,139 B2 | 4/2018 | Blanchard et al. |
| 9,999,371 B2 | 6/2018 | Messerly et al. |
| 10,004,875 B2 | 6/2018 | Bown et al. |
| 10,032,552 B2 | 7/2018 | Ma et al. |
| 10,043,272 B2 | 8/2018 | Forzoni et al. |
| 10,046,139 B2 | 8/2018 | Powers et al. |
| 10,105,121 B2 | 10/2018 | Burnside et al. |
| 10,165,962 B2 | 1/2019 | Messerly et al. |
| 10,231,643 B2 | 3/2019 | Grunwald |
| 10,231,753 B2 | 3/2019 | Burnside et al. |
| 10,238,418 B2 | 3/2019 | Cox et al. |
| 10,249,424 B2 | 4/2019 | Ma et al. |
| 10,271,762 B2 | 4/2019 | Grunwald |
| 10,349,857 B2 | 7/2019 | Grunwald |
| 10,349,890 B2 | 7/2019 | Misener et al. |
| 10,449,330 B2 | 10/2019 | Newman et al. |
| 10,524,691 B2 | 1/2020 | Newman et al. |
| 10,524,694 B2 | 1/2020 | Hunter |
| 10,602,958 B2 | 3/2020 | Silverstein et al. |
| 10,751,509 B2 | 8/2020 | Misener |
| 10,849,695 B2 | 12/2020 | Cox et al. |
| 10,966,630 B2 | 4/2021 | Messerly et al. |
| 11,027,101 B2 | 6/2021 | Lemon et al. |
| 11,103,213 B2 | 8/2021 | Burnside et al. |
| 2001/0014774 A1 | 8/2001 | Grunwald |
| 2001/0027332 A1 | 10/2001 | Grunwald et al. |
| 2002/0010392 A1 | 1/2002 | Desai |
| 2002/0016549 A1 | 2/2002 | Mejia |
| 2002/0019447 A1 | 2/2002 | Renn et al. |
| 2002/0022777 A1 | 2/2002 | Crieghton et al. |
| 2002/0032391 A1 | 3/2002 | McFann et al. |
| 2002/0045810 A1 | 4/2002 | Ben-Haim |
| 2002/0049488 A1 | 4/2002 | Boneau |
| 2002/0055680 A1 | 5/2002 | Miele et al. |
| 2002/0082559 A1 | 6/2002 | Chang et al. |
| 2002/0113555 A1 | 8/2002 | Lys et al. |
| 2002/0123679 A1 | 9/2002 | Dominguez |
| 2002/0128554 A1 | 9/2002 | Seward |
| 2002/0129952 A1 | 9/2002 | Matsudate et al. |
| 2002/0133079 A1 | 9/2002 | Sandhu |
| 2002/0138007 A1 | 9/2002 | Nguyen-Dinh et al. |
| 2002/0156363 A1 | 10/2002 | Hunter et al. |
| 2002/0156376 A1 | 10/2002 | Wang et al. |
| 2002/0165448 A1 | 11/2002 | Ben-Haim et al. |
| 2002/0165534 A1 | 11/2002 | Hayzelden et al. |
| 2002/0165537 A1 | 11/2002 | Kelley et al. |
| 2002/0173721 A1 | 11/2002 | Grunwald et al. |
| 2002/0193756 A1 | 12/2002 | Prindle |
| 2002/0198568 A1 | 12/2002 | Hafer et al. |
| 2003/0009132 A1 | 1/2003 | Schwartz et al. |
| 2003/0011359 A1 | 1/2003 | Ashe |
| 2003/0013959 A1 | 1/2003 | Grunwald et al. |
| 2003/0013966 A1 | 1/2003 | Barnes et al. |
| 2003/0013986 A1 | 1/2003 | Saadat |
| 2003/0018251 A1 | 1/2003 | Solomon |
| 2003/0036696 A1 | 2/2003 | Willis et al. |
| 2003/0040671 A1 | 2/2003 | Somogyi et al. |
| 2003/0040743 A1 | 2/2003 | Cosman et al. |
| 2003/0047126 A1 | 3/2003 | Tomaschko |
| 2003/0072805 A1 | 4/2003 | Miyazawa et al. |
| 2003/0073901 A1 | 4/2003 | Simon et al. |
| 2003/0076281 A1 | 4/2003 | Morgan et al. |
| 2003/0083698 A1 | 5/2003 | Whitehurst et al. |
| 2003/0088195 A1 | 5/2003 | Vardi et al. |
| 2003/0092993 A1 | 5/2003 | Grunwald |
| 2003/0100849 A1 | 5/2003 | Jang |
| 2003/0114742 A1 | 6/2003 | Lewkowicz et al. |
| 2003/0114777 A1 | 6/2003 | Griffin et al. |
| 2003/0120150 A1 | 6/2003 | Govari |
| 2003/0120154 A1 | 6/2003 | Sauer et al. |
| 2003/0139661 A1 | 7/2003 | Kimchy et al. |
| 2003/0149328 A1 | 8/2003 | Elliott et al. |
| 2003/0149368 A1 | 8/2003 | Hennemann et al. |
| 2003/0152290 A1 | 8/2003 | Odell |
| 2003/0160721 A1 | 8/2003 | Gilboa et al. |
| 2003/0162414 A1 | 8/2003 | Schulz et al. |
| 2003/0163037 A1 | 8/2003 | Bladen et al. |
| 2003/0163142 A1 | 8/2003 | Paltieli et al. |
| 2003/0171691 A1 | 9/2003 | Casscells et al. |
| 2003/0173953 A1 | 9/2003 | Ashe |
| 2003/0181892 A1 | 9/2003 | Pajunk et al. |
| 2003/0184544 A1 | 10/2003 | Prudent |
| 2003/0191392 A1 | 10/2003 | Haldeman |
| 2003/0191460 A1 | 10/2003 | Hobbs et al. |
| 2003/0195420 A1 | 10/2003 | Mendlein et al. |
| 2003/0199746 A1 | 10/2003 | Fuimaono et al. |
| 2003/0208142 A1 | 11/2003 | Boudewijn et al. |
| 2003/0216639 A1 | 11/2003 | Gilboa et al. |
| 2003/0216723 A1 | 11/2003 | Shinmura et al. |
| 2003/0220557 A1 | 11/2003 | Cleary et al. |
| 2003/0220578 A1 | 11/2003 | Ho et al. |
| 2003/0229298 A1 | 12/2003 | Wami et al. |
| 2003/0233042 A1 | 12/2003 | Ashe |
| 2003/0236445 A1 | 12/2003 | Couvillon |
| 2004/0010189 A1 | 1/2004 | van Sloun et al. |
| 2004/0015070 A1 | 1/2004 | Liang et al. |
| 2004/0024301 A1 | 2/2004 | Hockett et al. |
| 2004/0030319 A1 | 2/2004 | Korkor et al. |
| 2004/0054278 A1 | 3/2004 | Kimchy et al. |
| 2004/0059217 A1 | 3/2004 | Kessman et al. |

(56)  References Cited

U.S. PATENT DOCUMENTS

| | | |
|---|---|---|
| 2004/0059237 A1 | 3/2004 | Narayan et al. |
| 2004/0082916 A1 | 4/2004 | Jenkins |
| 2004/0087877 A1 | 5/2004 | Besz et al. |
| 2004/0088136 A1 | 5/2004 | Ashe |
| 2004/0092962 A1 | 5/2004 | Thornton et al. |
| 2004/0097803 A1 | 5/2004 | Panescu |
| 2004/0097804 A1 | 5/2004 | Sobe |
| 2004/0097805 A1 | 5/2004 | Verard et al. |
| 2004/0097806 A1 | 5/2004 | Hunter et al. |
| 2004/0116809 A1 | 6/2004 | Chow et al. |
| 2004/0127805 A1 | 7/2004 | MacAdam et al. |
| 2004/0131998 A1 | 7/2004 | Marom et al. |
| 2004/0133111 A1 | 7/2004 | Szczech et al. |
| 2004/0133130 A1 | 7/2004 | Ferry et al. |
| 2004/0135069 A1 | 7/2004 | Odell |
| 2004/0138557 A1 | 7/2004 | Le et al. |
| 2004/0138564 A1 | 7/2004 | Hwang et al. |
| 2004/0138569 A1 | 7/2004 | Grunwald et al. |
| 2004/0138570 A1 | 7/2004 | Nita et al. |
| 2004/0143183 A1 | 7/2004 | Toyoda et al. |
| 2004/0147837 A1 | 7/2004 | Macaulay et al. |
| 2004/0150963 A1 | 8/2004 | Holmberg et al. |
| 2004/0152972 A1 | 8/2004 | Hunter |
| 2004/0155609 A1 | 8/2004 | Lys et al. |
| 2004/0158140 A1 | 8/2004 | Fuimaono et al. |
| 2004/0162487 A1 | 8/2004 | Klingenbeck-Regn et al. |
| 2004/0171924 A1 | 9/2004 | Mire et al. |
| 2004/0176688 A1 | 9/2004 | Haldeman |
| 2004/0186461 A1 | 9/2004 | DiMatteo |
| 2004/0199069 A1 | 10/2004 | Connelly et al. |
| 2004/0210289 A1 | 10/2004 | Wang et al. |
| 2004/0225233 A1 | 11/2004 | Frankowski et al. |
| 2004/0230131 A1 | 11/2004 | Kassab et al. |
| 2004/0230271 A1 | 11/2004 | Wang et al. |
| 2004/0234453 A1 | 11/2004 | Smith |
| 2004/0243018 A1 | 12/2004 | Organ et al. |
| 2004/0243116 A1 | 12/2004 | Joye et al. |
| 2004/0243118 A1 | 12/2004 | Ayers et al. |
| 2004/0253365 A1 | 12/2004 | Warren et al. |
| 2004/0254470 A1 | 12/2004 | Drinkwater et al. |
| 2004/0254495 A1 | 12/2004 | Mabary et al. |
| 2004/0260174 A1 | 12/2004 | Keene |
| 2004/0267086 A1 | 12/2004 | Anstadt et al. |
| 2005/0004450 A1 | 1/2005 | Ben-Haim et al. |
| 2005/0021019 A1 | 1/2005 | Hashimshony et al. |
| 2005/0033150 A1 | 2/2005 | Takahashi et al. |
| 2005/0033232 A1 | 2/2005 | Kriesel |
| 2005/0038355 A1 | 2/2005 | Gellman et al. |
| 2005/0043640 A1 | 2/2005 | Chang |
| 2005/0049486 A1 | 3/2005 | Urquhart et al. |
| 2005/0049504 A1 | 3/2005 | Lo et al. |
| 2005/0049510 A1 | 3/2005 | Haldeman et al. |
| 2005/0063194 A1 | 3/2005 | Lys et al. |
| 2005/0070788 A1 | 3/2005 | Wilson et al. |
| 2005/0075561 A1 | 4/2005 | Golden |
| 2005/0085715 A1 | 4/2005 | Dukesherer et al. |
| 2005/0085716 A1 | 4/2005 | Hamm et al. |
| 2005/0085718 A1 | 4/2005 | Shahidi |
| 2005/0085720 A1 | 4/2005 | Jascob et al. |
| 2005/0090746 A1 | 4/2005 | Ohtake |
| 2005/0096543 A1 | 5/2005 | Jackson et al. |
| 2005/0101868 A1 | 5/2005 | Ridley et al. |
| 2005/0101869 A1 | 5/2005 | Burba et al. |
| 2005/0105081 A1 | 5/2005 | Odell |
| 2005/0105101 A1 | 5/2005 | Duling et al. |
| 2005/0112135 A1 | 5/2005 | Cormier et al. |
| 2005/0113669 A1 | 5/2005 | Helfer et al. |
| 2005/0113676 A1 | 5/2005 | Weiner et al. |
| 2005/0113700 A1 | 5/2005 | Yanagihara et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0143689 A1 | 6/2005 | Ramsey |
| 2005/0148836 A1 | 7/2005 | Kleen et al. |
| 2005/0148902 A1 | 7/2005 | Minar et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0182454 A1 | 8/2005 | Gharib et al. |
| 2005/0197674 A1 | 9/2005 | McCabe et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0240102 A1 | 10/2005 | Rachlin et al. |
| 2005/0245811 A1 | 11/2005 | Scheffler |
| 2005/0256398 A1 | 11/2005 | Hastings et al. |
| 2005/0256451 A1 | 11/2005 | Adams et al. |
| 2005/0256521 A1 | 11/2005 | Kozel |
| 2005/0256541 A1 | 11/2005 | Stypulkowski |
| 2005/0267365 A1 | 12/2005 | Sokulin et al. |
| 2005/0283210 A1 | 12/2005 | Blischak et al. |
| 2005/0283216 A1 | 12/2005 | Pyles |
| 2005/0288586 A1 | 12/2005 | Ferek-Petric |
| 2005/0288695 A1 | 12/2005 | Jenson et al. |
| 2006/0009759 A1 | 1/2006 | Chrisitian et al. |
| 2006/0015003 A1 | 1/2006 | Moaddes et al. |
| 2006/0015039 A1 | 1/2006 | Cassidy et al. |
| 2006/0025677 A1 | 2/2006 | Verard et al. |
| 2006/0025697 A1 | 2/2006 | Kurzweil et al. |
| 2006/0058633 A1 | 3/2006 | Hoshino et al. |
| 2006/0058654 A1 | 3/2006 | Di Marco et al. |
| 2006/0065275 A1 | 3/2006 | Lamprich et al. |
| 2006/0068074 A1 | 3/2006 | Stefandl |
| 2006/0079781 A1 | 4/2006 | Germond-Rouet et al. |
| 2006/0084867 A1 | 4/2006 | Tremblay et al. |
| 2006/0106306 A1 | 5/2006 | Essner et al. |
| 2006/0116571 A1 | 6/2006 | Maschke et al. |
| 2006/0116576 A1 | 6/2006 | McGee et al. |
| 2006/0116578 A1 | 6/2006 | Grunwald et al. |
| 2006/0122514 A1 | 6/2006 | Byrd et al. |
| 2006/0142656 A1 | 6/2006 | Malackowski et al. |
| 2006/0149134 A1 | 7/2006 | Soper et al. |
| 2006/0173251 A1 | 8/2006 | Govari et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184029 A1 | 8/2006 | Haim et al. |
| 2006/0184074 A1 | 8/2006 | Vaezy et al. |
| 2006/0206037 A1 | 9/2006 | Braxton |
| 2006/0210130 A1 | 9/2006 | Germond-Rouet et al. |
| 2006/0211944 A1 | 9/2006 | Mauge et al. |
| 2006/0217655 A1 | 9/2006 | Vitullo et al. |
| 2006/0217755 A1 | 9/2006 | Eversull et al. |
| 2006/0224188 A1 | 10/2006 | Libbus et al. |
| 2006/0241397 A1 | 10/2006 | Govari et al. |
| 2006/0241432 A1 | 10/2006 | Herline et al. |
| 2006/0247746 A1 | 11/2006 | Danek et al. |
| 2006/0253029 A1 | 11/2006 | Altmann et al. |
| 2006/0253115 A1 | 11/2006 | Avitall et al. |
| 2006/0258895 A1 | 11/2006 | Maschke |
| 2006/0276867 A1 | 12/2006 | Viswanathan |
| 2006/0287595 A1 | 12/2006 | Maschke |
| 2007/0010753 A1 | 1/2007 | MacAdam |
| 2007/0013540 A1 | 1/2007 | Altmann et al. |
| 2007/0015960 A1 | 1/2007 | Gornert et al. |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0016131 A1 | 1/2007 | Munger et al. |

(56)  References Cited

U.S. PATENT DOCUMENTS

| | | |
|---|---|---|
| 2007/0032746 A1 | 2/2007 | Sell |
| 2007/0038113 A1 | 2/2007 | Donuki et al. |
| 2007/0049817 A1 | 3/2007 | Preiss et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0055294 A1 | 3/2007 | Giap |
| 2007/0060992 A1 | 3/2007 | Pappone |
| 2007/0062544 A1 | 3/2007 | Rauk Bergstrom et al. |
| 2007/0066888 A1 | 3/2007 | Maschke |
| 2007/0073155 A1 | 3/2007 | Park et al. |
| 2007/0078343 A1 | 4/2007 | Kawashima et al. |
| 2007/0087038 A1 | 4/2007 | Richardson et al. |
| 2007/0093710 A1 | 4/2007 | Maschke |
| 2007/0100236 A1 | 5/2007 | McMorrow et al. |
| 2007/0100285 A1 | 5/2007 | Griffin et al. |
| 2007/0112282 A1 | 5/2007 | Skujins et al. |
| 2007/0123805 A1 | 5/2007 | Shireman et al. |
| 2007/0129770 A1 | 6/2007 | Younis |
| 2007/0135803 A1* | 6/2007 | Belson ............... A61B 1/00154 |
| | | 606/1 |
| 2007/0135886 A1 | 6/2007 | Maschke |
| 2007/0156205 A1 | 7/2007 | Larson et al. |
| 2007/0161853 A1 | 7/2007 | Yagi et al. |
| 2007/0161914 A1 | 7/2007 | Zdeblick et al. |
| 2007/0161915 A1 | 7/2007 | Desai |
| 2007/0167738 A1 | 7/2007 | Timinger et al. |
| 2007/0167743 A1 | 7/2007 | Honda et al. |
| 2007/0167762 A1 | 7/2007 | Kim et al. |
| 2007/0167769 A1 | 7/2007 | Ikuma et al. |
| 2007/0167801 A1 | 7/2007 | Webler et al. |
| 2007/0167997 A1 | 7/2007 | Forsberg et al. |
| 2007/0197891 A1 | 8/2007 | Shachar et al. |
| 2007/0197905 A1 | 8/2007 | Timinger et al. |
| 2007/0197926 A1 | 8/2007 | Danehorn et al. |
| 2007/0199848 A1 | 8/2007 | Ellswood et al. |
| 2007/0208255 A1 | 9/2007 | Ridley et al. |
| 2007/0219453 A1 | 9/2007 | Kremliovsky et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232896 A1 | 10/2007 | Gilboa et al. |
| 2007/0238984 A1 | 10/2007 | Maschke et al. |
| 2007/0239004 A1 | 10/2007 | Kakee et al. |
| 2007/0239018 A1 | 10/2007 | Fetzer et al. |
| 2007/0244387 A1 | 10/2007 | Rodriguez Ponce et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0250150 A1 | 10/2007 | Pal et al. |
| 2007/0255270 A1 | 11/2007 | Carney |
| 2007/0265526 A1 | 11/2007 | Govari et al. |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2007/0299353 A1 | 12/2007 | Harlev et al. |
| 2008/0004652 A1 | 1/2008 | Abboud et al. |
| 2008/0008745 A1 | 1/2008 | Stinchcomb et al. |
| 2008/0009720 A1 | 1/2008 | Schefelker et al. |
| 2008/0015442 A1 | 1/2008 | Watson et al. |
| 2008/0021283 A1 | 1/2008 | Kuranda |
| 2008/0021322 A1 | 1/2008 | Stone et al. |
| 2008/0027320 A1 | 1/2008 | Bolorforosh et al. |
| 2008/0033282 A1 | 2/2008 | Bar-Tal et al. |
| 2008/0033283 A1 | 2/2008 | Dellaca et al. |
| 2008/0033316 A1 | 2/2008 | Kassab et al. |
| 2008/0033350 A1 | 2/2008 | Wilson et al. |
| 2008/0033759 A1 | 2/2008 | Finlay |
| 2008/0045908 A1 | 2/2008 | Gould et al. |
| 2008/0051626 A1 | 2/2008 | Sato et al. |
| 2008/0077158 A1 | 3/2008 | Haider et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0114095 A1 | 5/2008 | Peppmoller et al. |
| 2008/0119697 A1 | 5/2008 | Vadodaria et al. |
| 2008/0125772 A1 | 5/2008 | Stone et al. |
| 2008/0137927 A1 | 6/2008 | Altmann et al. |
| 2008/0139944 A1 | 6/2008 | Weymer et al. |
| 2008/0146915 A1 | 6/2008 | McMorrow |
| 2008/0146925 A1 | 6/2008 | Byrd et al. |
| 2008/0146939 A1 | 6/2008 | McMorrow et al. |
| 2008/0146940 A1 | 6/2008 | Jenkins et al. |
| 2008/0146941 A1 | 6/2008 | Dala-Krishna |
| 2008/0146942 A1 | 6/2008 | Dala-Krishna |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0174304 A1 | 7/2008 | Anderson |
| 2008/0183075 A1 | 7/2008 | Govari et al. |
| 2008/0188830 A1 | 8/2008 | Rosenblatt et al. |
| 2008/0190438 A1 | 8/2008 | Harlev et al. |
| 2008/0195169 A1 | 8/2008 | Pinter et al. |
| 2008/0200754 A1 | 8/2008 | Buchalter |
| 2008/0200801 A1 | 8/2008 | Wildes et al. |
| 2008/0200913 A1 | 8/2008 | Viswanathan |
| 2008/0228082 A1 | 9/2008 | Scheirer et al. |
| 2008/0236598 A1 | 10/2008 | Gobel |
| 2008/0255404 A1 | 10/2008 | Nogawa et al. |
| 2008/0255446 A1 | 10/2008 | Akins |
| 2008/0255475 A1 | 10/2008 | Kondrosky et al. |
| 2008/0262338 A1 | 10/2008 | Paitel et al. |
| 2008/0269581 A1 | 10/2008 | Wood et al. |
| 2008/0269611 A1 | 10/2008 | Pedrizzetti et al. |
| 2008/0275465 A1 | 11/2008 | Paul et al. |
| 2008/0275765 A1 | 11/2008 | Kuchar |
| 2008/0288038 A1 | 11/2008 | Paul et al. |
| 2008/0294041 A1 | 11/2008 | Kassab |
| 2008/0319350 A1 | 12/2008 | Wallace et al. |
| 2009/0005674 A1 | 1/2009 | Saadat et al. |
| 2009/0005675 A1 | 1/2009 | Grunwald et al. |
| 2009/0005679 A1 | 1/2009 | Dala-Krishna |
| 2009/0012399 A1 | 1/2009 | Sunagawa et al. |
| 2009/0018497 A1 | 1/2009 | Birchard et al. |
| 2009/0024018 A1 | 1/2009 | Boyden et al. |
| 2009/0030380 A1 | 1/2009 | Binmoeller |
| 2009/0043205 A1 | 2/2009 | Pelissier et al. |
| 2009/0062646 A1 | 3/2009 | Creighton, IV et al. |
| 2009/0062684 A1 | 3/2009 | Gregersen et al. |
| 2009/0062772 A1 | 3/2009 | Wakeford et al. |
| 2009/0080738 A1 | 3/2009 | Zur et al. |
| 2009/0082661 A1 | 3/2009 | Saladin et al. |
| 2009/0084382 A1 | 4/2009 | Jalde et al. |
| 2009/0099468 A1 | 4/2009 | Thiagalingam et al. |
| 2009/0101577 A1 | 4/2009 | Fulkerson et al. |
| 2009/0115406 A1 | 5/2009 | Anderson et al. |
| 2009/0118612 A1 | 5/2009 | Grunwald et al. |
| 2009/0118637 A1 | 5/2009 | Kassab et al. |
| 2009/0118706 A1 | 5/2009 | Schweikert et al. |
| 2009/0124901 A1 | 5/2009 | Fink et al. |
| 2009/0143672 A1 | 6/2009 | Harms et al. |
| 2009/0143736 A1 | 6/2009 | Mittermeyer et al. |
| 2009/0156926 A1 | 6/2009 | Messerly et al. |
| 2009/0163810 A1 | 6/2009 | Kanade et al. |
| 2009/0171217 A1 | 7/2009 | Kim et al. |
| 2009/0177083 A1 | 7/2009 | Matsumura |
| 2009/0177090 A1 | 7/2009 | Grunwald et al. |
| 2009/0182224 A1 | 7/2009 | Shmarak et al. |
| 2009/0203989 A1 | 8/2009 | Burnside et al. |
| 2009/0204113 A1 | 8/2009 | MacAdam et al. |
| 2009/0209872 A1 | 8/2009 | Pop |
| 2009/0209950 A1 | 8/2009 | Starksen |
| 2009/0221908 A1 | 9/2009 | Glossop |
| 2009/0227952 A1 | 9/2009 | Blakstvedt et al. |
| 2009/0234328 A1 | 9/2009 | Cox et al. |
| 2009/0247835 A1 | 10/2009 | Voipio |
| 2009/0253976 A1 | 10/2009 | Harlev et al. |
| 2009/0258171 A1 | 10/2009 | Jang |
| 2009/0259124 A1 | 10/2009 | Rothenberg |
| 2009/0262982 A1 | 10/2009 | Markowitz et al. |
| 2009/0269949 A1 | 10/2009 | Schmidgall et al. |

(56)                    References Cited

U.S. PATENT DOCUMENTS

| | | |
|---|---|---|
| 2009/0270729 A1 | 10/2009 | Corbucci et al. |
| 2009/0270746 A1 | 10/2009 | Min |
| 2009/0275828 A1 | 11/2009 | Shachar et al. |
| 2009/0281419 A1 | 11/2009 | Troesken et al. |
| 2009/0297441 A1 | 12/2009 | Canham et al. |
| 2009/0312629 A1 | 12/2009 | Razzaque et al. |
| 2010/0004543 A1 | 1/2010 | Ahlund et al. |
| 2010/0004547 A1 | 1/2010 | Scholz et al. |
| 2010/0010355 A1 | 1/2010 | Kassab |
| 2010/0010444 A1 | 1/2010 | Bettuchi |
| 2010/0010612 A1 | 1/2010 | Gelbart et al. |
| 2010/0016726 A1 | 1/2010 | Meier |
| 2010/0036227 A1 | 2/2010 | Cox et al. |
| 2010/0036238 A1* | 2/2010 | Neidert .................... A61B 5/06 |
| | | 600/424 |
| 2010/0036284 A1 | 2/2010 | Laynes et al. |
| 2010/0041973 A1 | 2/2010 | Vu et al. |
| 2010/0041984 A1 | 2/2010 | Shapland et al. |
| 2010/0049062 A1 | 2/2010 | Ziv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0063401 A1 | 3/2010 | Nishina et al. |
| 2010/0076305 A1 | 3/2010 | Maier-Hein et al. |
| 2010/0076328 A1 | 3/2010 | Matsumura et al. |
| 2010/0081934 A1 | 4/2010 | Soltani et al. |
| 2010/0083719 A1 | 4/2010 | Peppmoller et al. |
| 2010/0094116 A1 | 4/2010 | Silverstein |
| 2010/0106011 A1 | 4/2010 | Byrd et al. |
| 2010/0113917 A1 | 5/2010 | Anderson |
| 2010/0114573 A1 | 5/2010 | Huang et al. |
| 2010/0117659 A1 | 5/2010 | Osadchy et al. |
| 2010/0130858 A1 | 5/2010 | Arai et al. |
| 2010/0143119 A1 | 6/2010 | Kooijman et al. |
| 2010/0152596 A1 | 6/2010 | Griffiths et al. |
| 2010/0152604 A1 | 6/2010 | Kaula et al. |
| 2010/0160772 A1 | 6/2010 | Gardeski et al. |
| 2010/0168557 A1 | 7/2010 | Deno et al. |
| 2010/0168767 A1 | 7/2010 | Yassinzadeh et al. |
| 2010/0185097 A1 | 7/2010 | Hall |
| 2010/0198048 A1 | 8/2010 | Togawa |
| 2010/0198346 A1 | 8/2010 | Keogh et al. |
| 2010/0204569 A1 | 8/2010 | Burnside et al. |
| 2010/0204614 A1 | 8/2010 | Lindquist et al. |
| 2010/0210938 A1 | 8/2010 | Verard et al. |
| 2010/0210939 A1 | 8/2010 | Hartmann et al. |
| 2010/0210950 A1 | 8/2010 | Dunbar et al. |
| 2010/0217116 A1 | 8/2010 | Eck et al. |
| 2010/0222664 A1 | 9/2010 | Lemon et al. |
| 2010/0222786 A1 | 9/2010 | Kassab |
| 2010/0234724 A1 | 9/2010 | Jacobsen et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0268059 A1 | 10/2010 | Ryu et al. |
| 2010/0273895 A1 | 10/2010 | Stinchcomb et al. |
| 2010/0274150 A1 | 10/2010 | Harlev et al. |
| 2010/0291521 A1 | 11/2010 | Simon |
| 2010/0298702 A1 | 11/2010 | Rogers et al. |
| 2010/0298704 A1 | 11/2010 | Pelissier et al. |
| 2010/0298705 A1 | 11/2010 | Pelissier et al. |
| 2010/0298712 A1 | 11/2010 | Pelissier et al. |
| 2010/0312086 A9 | 12/2010 | Beatty et al. |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0002518 A1 | 1/2011 | Ziv-Ari et al. |
| 2011/0015496 A1 | 1/2011 | Sherman et al. |
| 2011/0015527 A1 | 1/2011 | Heasty et al. |
| 2011/0015533 A1 | 1/2011 | Cox et al. |
| 2011/0034823 A1 | 2/2011 | Gelbart et al. |
| 2011/0034940 A1 | 2/2011 | Payner |
| 2011/0040212 A1 | 2/2011 | Dietz et al. |
| 2011/0052694 A1 | 3/2011 | Stinchcomb et al. |
| 2011/0087105 A1 | 4/2011 | Ridley et al. |
| 2011/0087106 A1 | 4/2011 | Ridley et al. |
| 2011/0087107 A1 | 4/2011 | Lindekugel et al. |
| 2011/0106101 A1 | 5/2011 | Tortonese et al. |
| 2011/0112396 A1 | 5/2011 | Shachar et al. |
| 2011/0136242 A1 | 6/2011 | Marx et al. |
| 2011/0137156 A1 | 6/2011 | Razzaque et al. |
| 2011/0196235 A1 | 8/2011 | Dunbar et al. |
| 2011/0196248 A1 | 8/2011 | Grunwald |
| 2011/0196255 A1 | 8/2011 | Kassab |
| 2011/0224564 A1 | 9/2011 | Moon et al. |
| 2011/0237935 A1 | 9/2011 | Kalpin et al. |
| 2011/0245659 A1 | 10/2011 | Ma et al. |
| 2011/0263164 A1 | 10/2011 | Lenhert et al. |
| 2011/0282187 A1 | 11/2011 | Harlev et al. |
| 2011/0282188 A1 | 11/2011 | Burnside et al. |
| 2011/0282285 A1 | 11/2011 | Blanchard et al. |
| 2011/0282686 A1 | 11/2011 | Venon et al. |
| 2011/0295108 A1 | 12/2011 | Cox et al. |
| 2011/0306859 A1 | 12/2011 | Saldivar et al. |
| 2011/0306867 A1 | 12/2011 | Gopinathan et al. |
| 2011/0313293 A1 | 12/2011 | Lindekugel et al. |
| 2012/0004564 A1 | 1/2012 | Dobak, III |
| 2012/0016316 A1 | 1/2012 | Zhuang et al. |
| 2012/0035460 A1 | 2/2012 | Stangenes et al. |
| 2012/0035539 A1 | 2/2012 | Tegg |
| 2012/0046562 A1 | 2/2012 | Powers et al. |
| 2012/0059249 A1 | 3/2012 | Verard et al. |
| 2012/0059270 A1 | 3/2012 | Grunwald |
| 2012/0059271 A1 | 3/2012 | Amitai et al. |
| 2012/0071751 A1 | 3/2012 | Sra et al. |
| 2012/0071759 A1 | 3/2012 | Hagy et al. |
| 2012/0071782 A1 | 3/2012 | Patil et al. |
| 2012/0078342 A1 | 3/2012 | Vollkron et al. |
| 2012/0095319 A1 | 4/2012 | Kondrosky et al. |
| 2012/0108950 A1 | 5/2012 | He et al. |
| 2012/0115007 A1 | 5/2012 | Felder et al. |
| 2012/0136242 A1 | 5/2012 | Qi et al. |
| 2012/0143029 A1 | 6/2012 | Silverstein et al. |
| 2012/0143078 A1 | 6/2012 | Kassab et al. |
| 2012/0172727 A1 | 7/2012 | Hastings et al. |
| 2012/0197132 A1 | 8/2012 | O'Connor |
| 2012/0220854 A1 | 8/2012 | Messerly et al. |
| 2012/0220874 A1 | 8/2012 | Hancock et al. |
| 2012/0265084 A1 | 10/2012 | Stewart et al. |
| 2012/0283582 A1 | 11/2012 | Mahapatra et al. |
| 2012/0296200 A1 | 11/2012 | Shachar et al. |
| 2012/0296213 A1 | 11/2012 | Mauldin, Jr. et al. |
| 2012/0310052 A1 | 12/2012 | Mahapatra et al. |
| 2012/0310066 A1 | 12/2012 | Shachar et al. |
| 2012/0310660 A1 | 12/2012 | Liu et al. |
| 2012/0316440 A1 | 12/2012 | Munrow et al. |
| 2013/0006100 A1 | 1/2013 | Shachar et al. |
| 2013/0006102 A1 | 1/2013 | Wilkes et al. |
| 2013/0018248 A1 | 1/2013 | Hurezan |
| 2013/0018602 A1* | 1/2013 | Ong ......................... F17D 5/02 |
| | | 702/45 |
| 2013/0035590 A1 | 2/2013 | Ma et al. |
| 2013/0041250 A1 | 2/2013 | Pelissier et al. |
| 2013/0041254 A1 | 2/2013 | Hagy et al. |
| 2013/0041269 A1 | 2/2013 | Stahmann et al. |
| 2013/0060116 A1 | 3/2013 | Messerly et al. |
| 2013/0079628 A1 | 3/2013 | Groszmann et al. |
| 2013/0085416 A1 | 4/2013 | Mest |
| 2013/0090938 A1 | 4/2013 | Fishman et al. |
| 2013/0102889 A1 | 4/2013 | Southard et al. |
| 2013/0102890 A1 | 4/2013 | Dib |
| 2013/0102967 A1 | 4/2013 | Hanlon et al. |
| 2013/0123597 A1 | 5/2013 | Rothenberg |
| 2013/0131502 A1 | 5/2013 | Blaivas et al. |
| 2013/0131503 A1 | 5/2013 | Schneider et al. |
| 2013/0150724 A1 | 6/2013 | Blaivas et al. |
| 2013/0169272 A1 | 7/2013 | Eichler et al. |
| 2013/0213147 A1 | 8/2013 | Rice et al. |
| 2013/0217999 A1 | 8/2013 | Burnside et al. |
| 2013/0223702 A1 | 8/2013 | Holsing et al. |
| 2013/0245434 A1 | 9/2013 | Messerly et al. |
| 2013/0281787 A1* | 10/2013 | Avneri ............. A61B 17/12109 |
| | | 604/528 |

(56)　　　　References Cited

U.S. PATENT DOCUMENTS

| | | |
|---|---|---|
| 2013/0281837 A1 | 10/2013 | Ridley et al. |
| 2013/0289417 A1 | 10/2013 | Grunwald et al. |
| 2013/0296691 A1* | 11/2013 | Ashe .................. A61B 5/6848 |
| | | 600/424 |
| 2013/0296693 A1 | 11/2013 | Wenzel et al. |
| 2013/0303878 A1 | 11/2013 | Nevo et al. |
| 2013/0303896 A1 | 11/2013 | Kalpin et al. |
| 2013/0303945 A1 | 11/2013 | Blumenkranz et al. |
| 2013/0317338 A1 | 11/2013 | Silverstein |
| 2013/0324841 A1 | 12/2013 | Kamen et al. |
| 2013/0338503 A1 | 12/2013 | Cohen et al. |
| 2013/0338517 A1 | 12/2013 | Rothenberg |
| 2013/0345555 A1 | 12/2013 | Kanade et al. |
| 2014/0005530 A1 | 1/2014 | Liu et al. |
| 2014/0031674 A1 | 1/2014 | Newman et al. |
| 2014/0046261 A1 | 2/2014 | Newman et al. |
| 2014/0066798 A1 | 3/2014 | Albert |
| 2014/0073976 A1 | 3/2014 | Fonte et al. |
| 2014/0089836 A1 | 3/2014 | Damani et al. |
| 2014/0094694 A1 | 4/2014 | Moctezuma de la Barrera |
| 2014/0094768 A1 | 4/2014 | Stangenes et al. |
| 2014/0107475 A1 | 4/2014 | Cox et al. |
| 2014/0128712 A1 | 5/2014 | Banet et al. |
| 2014/0163356 A2 | 6/2014 | Burnside et al. |
| 2014/0180074 A1 | 6/2014 | Green et al. |
| 2014/0180098 A1 | 6/2014 | Flaherty et al. |
| 2014/0187917 A1 | 7/2014 | Clark et al. |
| 2014/0187990 A1 | 7/2014 | Banet et al. |
| 2014/0188133 A1 | 7/2014 | Misener |
| 2014/0221862 A1 | 8/2014 | Tambe |
| 2014/0228689 A1 | 8/2014 | Ishikawa et al. |
| 2014/0243659 A1 | 8/2014 | Rothenberg |
| 2014/0249428 A1 | 9/2014 | Ingold, Jr. et al. |
| 2014/0249505 A1 | 9/2014 | Bukhman |
| 2014/0253270 A1 | 9/2014 | Nicholls et al. |
| 2014/0257080 A1 | 9/2014 | Dunbar et al. |
| 2014/0275957 A1 | 9/2014 | Fupotti |
| 2014/0275990 A1 | 9/2014 | Hagy et al. |
| 2014/0276010 A1 | 9/2014 | Anderson |
| 2014/0276059 A1 | 9/2014 | Sheehan |
| 2014/0276081 A1 | 9/2014 | Tegels |
| 2014/0303492 A1 | 10/2014 | Burnside et al. |
| 2014/0309624 A1 | 10/2014 | Bown et al. |
| 2014/0343398 A1 | 11/2014 | He et al. |
| 2014/0343431 A1 | 11/2014 | Vajinepalli et al. |
| 2015/0005621 A1 | 1/2015 | Liu |
| 2015/0011887 A1 | 1/2015 | Ahn et al. |
| 2015/0018701 A1 | 1/2015 | Cox et al. |
| 2015/0025365 A1 | 1/2015 | Esguerra Wilczynski et al. |
| 2015/0025402 A1 | 1/2015 | Rothenberg |
| 2015/0051489 A1 | 2/2015 | Caluser et al. |
| 2015/0065916 A1 | 3/2015 | Maguire et al. |
| 2015/0073279 A1 | 3/2015 | Cai et al. |
| 2015/0073285 A1 | 3/2015 | Albert et al. |
| 2015/0080716 A1 | 3/2015 | Powers et al. |
| 2015/0173723 A1 | 6/2015 | Bates et al. |
| 2015/0209008 A1 | 7/2015 | Ridley et al. |
| 2015/0209113 A1 | 7/2015 | Burkholz et al. |
| 2015/0209526 A1 | 7/2015 | Matsubara et al. |
| 2015/0216445 A1 | 8/2015 | Carmeli et al. |
| 2015/0216446 A1 | 8/2015 | Bukhman et al. |
| 2015/0223775 A1 | 8/2015 | Hamilton, Jr. |
| 2015/0245809 A1 | 9/2015 | Hagy et al. |
| 2015/0245872 A1 | 9/2015 | Hagy et al. |
| 2015/0246247 A1 | 9/2015 | Binnekamp et al. |
| 2015/0282734 A1 | 10/2015 | Schweikert et al. |
| 2015/0289781 A1 | 10/2015 | Grunwald et al. |
| 2015/0297097 A1 | 10/2015 | Matsubara et al. |
| 2015/0297114 A1 | 10/2015 | Cox et al. |
| 2015/0317810 A1 | 11/2015 | Grunwald et al. |
| 2015/0335310 A1 | 11/2015 | Bernstein et al. |
| 2015/0335383 A9 | 11/2015 | Cohen |
| 2016/0000399 A1 | 1/2016 | Halmann et al. |
| 2016/0067449 A1 | 3/2016 | Misener et al. |
| 2016/0120607 A1 | 5/2016 | Sorotzkin et al. |

| | | |
|---|---|---|
| 2016/0166232 A1 | 6/2016 | Merritt |
| 2016/0202053 A1 | 7/2016 | Walker et al. |
| 2016/0278869 A1 | 9/2016 | Grunwald |
| 2016/0296208 A1 | 10/2016 | Sethuraman et al. |
| 2016/0331344 A1 | 11/2016 | Hadzic |
| 2016/0374589 A1 | 12/2016 | Misener et al. |
| 2016/0374644 A1 | 12/2016 | Mauldin, Jr. et al. |
| 2017/0000367 A1 | 1/2017 | Grunwald |
| 2017/0020561 A1 | 1/2017 | Cox et al. |
| 2017/0079548 A1 | 3/2017 | Silverstein et al. |
| 2017/0079552 A1 | 3/2017 | Grunwald |
| 2017/0079615 A1 | 3/2017 | Burnside et al. |
| 2017/0079681 A1 | 3/2017 | Burnside et al. |
| 2017/0086782 A1 | 3/2017 | Hagy et al. |
| 2017/0151022 A1 | 6/2017 | Jascob et al. |
| 2017/0151027 A1 | 6/2017 | Walker et al. |
| 2017/0215762 A1 | 8/2017 | Burnside et al. |
| 2017/0231700 A1 | 8/2017 | Cox et al. |
| 2017/0238996 A1 | 8/2017 | Frame et al. |
| 2017/0281029 A1 | 10/2017 | Messerly et al. |
| 2017/0347914 A1 | 12/2017 | Isaacson et al. |
| 2017/0348510 A1 | 12/2017 | Shevgoor et al. |
| 2017/0348511 A1 | 12/2017 | Burkholz et al. |
| 2017/0367678 A1 | 12/2017 | Sirtori et al. |
| 2018/0042577 A1 | 2/2018 | Perrey et al. |
| 2018/0070856 A1 | 3/2018 | Grunwald |
| 2018/0103869 A1 | 4/2018 | Bukhman et al. |
| 2018/0116551 A1 | 5/2018 | Newman et al. |
| 2018/0116723 A1 | 5/2018 | Hettrick et al. |
| 2018/0116744 A1 | 5/2018 | Taya |
| 2018/0125450 A1 | 5/2018 | Blackbourne et al. |
| 2018/0145443 A1 | 5/2018 | Andreason et al. |
| 2018/0161012 A1 | 6/2018 | Bang et al. |
| 2018/0161502 A1 | 6/2018 | Nanan et al. |
| 2018/0169389 A1 | 6/2018 | Lemon et al. |
| 2018/0199914 A1 | 7/2018 | Ramachandran et al. |
| 2018/0214119 A1 | 8/2018 | Mehrmohammadi et al. |
| 2018/0220995 A1 | 8/2018 | Pelissier et al. |
| 2018/0296122 A1 | 10/2018 | Messerly et al. |
| 2018/0304043 A1 | 10/2018 | Bown et al. |
| 2018/0310955 A1 | 11/2018 | Lindekugel et al. |
| 2018/0325604 A1 | 11/2018 | Atarot et al. |
| 2018/0333559 A1 | 11/2018 | Makey |
| 2019/0069877 A1 | 3/2019 | Burnside et al. |
| 2019/0099108 A1 | 4/2019 | Messerly et al. |
| 2019/0216423 A1 | 7/2019 | Ko et al. |
| 2019/0246945 A1 | 8/2019 | Grunwald |
| 2019/0261886 A1 | 8/2019 | King et al. |
| 2019/0290208 A1 | 9/2019 | Toth et al. |
| 2019/0320982 A1 | 10/2019 | Misener et al. |
| 2020/0054858 A1 | 2/2020 | Newman et al. |
| 2020/0119488 A1 | 4/2020 | Stats et al. |
| 2020/0138332 A1 | 5/2020 | Newman et al. |
| 2020/0237255 A1 | 7/2020 | Silverstein et al. |
| 2020/0237403 A1 | 7/2020 | Southard et al. |
| 2020/0246588 A1 | 8/2020 | Akins et al. |
| 2020/0345983 A1 | 11/2020 | Misener |
| 2021/0077201 A1 | 3/2021 | Cox et al. |
| 2021/0082860 A1 | 3/2021 | Audette et al. |
| 2021/0401456 A1 | 12/2021 | Cox et al. |
| 2022/0096800 A1 | 3/2022 | Tran et al. |
| 2022/0347433 A1 | 11/2022 | Davis et al. |
| 2023/0233262 A9 | 7/2023 | Cox et al. |

FOREIGN PATENT DOCUMENTS

| | | | |
|---|---|---|---|
| AU | 1860597 | B2 | 6/1999 |
| AU | 20009592 | | 9/2000 |
| AU | 20015250 | | 6/2001 |
| AU | 768362 | B2 | 12/2003 |
| AU | 2001229024 | B2 | 9/2005 |
| AU | 2001283703 | B2 | 5/2006 |
| AU | 2006904933 | | 9/2006 |
| AU | 2006202149 | B2 | 3/2009 |
| AU | 2006283022 | B2 | 2/2012 |
| CA | 1197745 | A | 12/1985 |
| CA | 2420676 | C | 7/2010 |
| CA | 2619909 | C | 1/2014 |
| CN | 2031655 | U | 2/1989 |

(56)                    References Cited

FOREIGN PATENT DOCUMENTS

| | | | |
|---|---|---|---|
| CN | 1672649 A | 9/2005 |
| CN | 1913833 A | 2/2007 |
| CN | 101854853 A | 10/2010 |
| CN | 102209490 A | 10/2011 |
| CN | 102802514 A | 11/2012 |
| CN | 102821679 A | 12/2012 |
| CN | 103037761 A | 4/2013 |
| CN | 103037762 A | 4/2013 |
| CN | 103118591 A | 5/2013 |
| CN | 103189009 A | 7/2013 |
| CN | 104013425 A | 9/2014 |
| DE | 4319033 C1 | 6/1994 |
| EP | 0153021 A1 | 8/1985 |
| EP | 0362821 A1 | 4/1990 |
| EP | 0399536 A1 | 11/1990 |
| EP | 0359697 B1 | 11/1994 |
| EP | 0823261 A2 | 2/1998 |
| EP | 0928976 A2 | 7/1999 |
| EP | 1025805 A1 | 8/2000 |
| EP | 1015967 B1 | 4/2002 |
| EP | 1311226 A1 | 5/2003 |
| EP | 1504713 A1 | 2/2005 |
| EP | 1117331 B1 | 5/2005 |
| EP | 1117332 B1 | 8/2005 |
| EP | 1118019 B1 | 5/2006 |
| EP | 1717601 A2 | 11/2006 |
| EP | 1887940 A2 | 2/2008 |
| EP | 1932477 A1 | 6/2008 |
| EP | 2337491 A1 | 6/2011 |
| EP | 2440122 A1 | 4/2012 |
| EP | 2464407 A2 | 6/2012 |
| EP | 2482719 A1 | 8/2012 |
| EP | 2531098 A1 | 12/2012 |
| EP | 2575610 A1 | 4/2013 |
| EP | 2575611 A1 | 4/2013 |
| EP | 2603145 A2 | 6/2013 |
| EP | 2605699 A2 | 6/2013 |
| EP | 2474268 B1 | 7/2013 |
| EP | 2618727 A1 | 7/2013 |
| EP | 2632360 A1 | 9/2013 |
| EP | 2219526 B1 | 3/2014 |
| EP | 2712547 A1 | 4/2014 |
| EP | 2313143 B1 | 9/2014 |
| EP | 2913000 A2 | 9/2015 |
| EP | 2992825 B1 | 5/2017 |
| EP | 2170162 B1 | 8/2017 |
| EP | 2265175 B1 | 8/2017 |
| FR | 2545349 B1 | 9/1986 |
| JP | 01097440 | 4/1989 |
| JP | 03173542 A | 7/1991 |
| JP | 9-503054 | 3/1997 |
| JP | 09-094298 A | 4/1997 |
| JP | 10043310 | 2/1998 |
| JP | 10290839 A | 11/1998 |
| JP | H114829 | * | 1/1999 |
| JP | 11128237 A | 5/1999 |
| JP | 2001-145630 A | 5/2001 |
| JP | 2001161683 A | 6/2001 |
| JP | 2001-514533 A | 9/2001 |
| JP | 2001-524339 A | 12/2001 |
| JP | 2001340334 A | 12/2001 |
| JP | 2002520893 A | 7/2002 |
| JP | 2002-224069 A | 8/2002 |
| JP | 2002-529133 A | 9/2002 |
| JP | 2002-541947 A | 12/2002 |
| JP | 2003-010138 A | 1/2003 |
| JP | 2003501127 A | 1/2003 |
| JP | 2003061752 A | 3/2003 |
| JP | 2003299654 A | 10/2003 |
| JP | 2003334191 A | 11/2003 |
| JP | 2004505748 T | 2/2004 |
| JP | 2004515298 A | 5/2004 |
| JP | 2006508744 A | 3/2006 |
| JP | 2006-338526 A | 12/2006 |
| JP | 2007-000226 A | 1/2007 |
| JP | 2007-068989 A | 3/2007 |
| JP | 2007-105450 A | 4/2007 |
| JP | 2007-313122 A | 12/2007 |
| JP | 4090741 B2 | 5/2008 |
| JP | 2008196593 A | * | 8/2008 |
| JP | 2009/271123 A | 11/2009 |
| JP | 5010604 B2 | 8/2012 |
| JP | 2012-529929 A | 11/2012 |
| JP | 2013-518676 A | 5/2013 |
| JP | 2013-526959 A | 6/2013 |
| JP | 2013-526961 A | 6/2013 |
| KR | 20100047436 A | 5/2010 |
| RU | 2009101949 A | 7/2010 |
| WO | 1980002376 A1 | 11/1980 |
| WO | 1991012836 A1 | 9/1991 |
| WO | 1992003090 A1 | 3/1992 |
| WO | 1994003159 A1 | 2/1994 |
| WO | 1994004938 A1 | 3/1994 |
| WO | 1996005768 A1 | 2/1996 |
| WO | 1996007352 A1 | 3/1996 |
| WO | 1996041119 A1 | 12/1996 |
| WO | 1997/22395 A1 | 6/1997 |
| WO | 1997029683 A1 | 8/1997 |
| WO | 1997043989 A1 | 11/1997 |
| WO | 97/48438 A2 | 12/1997 |
| WO | 1998025159 A2 | 6/1998 |
| WO | 98/29032 A1 | 7/1998 |
| WO | 1998035611 A1 | 8/1998 |
| WO | 1999016495 A1 | 4/1999 |
| WO | 1999027837 A2 | 6/1999 |
| WO | 1999049407 A1 | 9/1999 |
| WO | 2000019906 A1 | 4/2000 |
| WO | 2000027281 A1 | 5/2000 |
| WO | 2000040155 A1 | 7/2000 |
| WO | 2000063658 A2 | 10/2000 |
| WO | 2000074775 A1 | 12/2000 |
| WO | 2001013792 A1 | 3/2001 |
| WO | 2001039683 A1 | 6/2001 |
| WO | 2001076479 A1 | 10/2001 |
| WO | 02/07794 A2 | 1/2002 |
| WO | 2002015973 A1 | 2/2002 |
| WO | 2002019905 A1 | 3/2002 |
| WO | 2002025277 A1 | 3/2002 |
| WO | 2002085442 A1 | 10/2002 |
| WO | 2003061752 A1 | 7/2003 |
| WO | 2003077759 A1 | 9/2003 |
| WO | 03/088833 A1 | 10/2003 |
| WO | 2003091495 A1 | 11/2003 |
| WO | 2004002303 A1 | 1/2004 |
| WO | 2004049970 A2 | 6/2004 |
| WO | 2005033524 A1 | 4/2005 |
| WO | 2005033574 A1 | 4/2005 |
| WO | 2005/089851 A1 | 9/2005 |
| WO | 2005117690 A1 | 12/2005 |
| WO | 2005117733 A2 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2006111056 A1 | 10/2006 |
| WO | 2007002541 A2 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2007144894 A1 | 12/2007 |
| WO | 2008005480 A1 | 1/2008 |
| WO | 2008024596 A2 | 2/2008 |
| WO | 2008028253 A1 | 3/2008 |
| WO | 2008083111 A1 | 7/2008 |
| WO | 2008097767 A2 | 8/2008 |
| WO | 2008118992 A1 | 10/2008 |
| WO | 2008126074 A2 | 10/2008 |
| WO | 2008129326 A1 | 10/2008 |
| WO | 2008131017 A2 | 10/2008 |
| WO | 2008136008 A2 | 11/2008 |

(56) References Cited

FOREIGN PATENT DOCUMENTS

| | | |
|---|---|---|
| WO | 2009000439 A1 | 12/2008 |
| WO | 2009002514 A2 | 12/2008 |
| WO | 2009003138 A1 | 12/2008 |
| WO | 2009009064 A1 | 1/2009 |
| WO | 2009057774 A1 | 5/2009 |
| WO | 2009063166 A1 | 5/2009 |
| WO | 2009067654 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |
| WO | 2009137262 A2 | 11/2009 |
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010029906 A1 | 3/2010 |
| WO | 2010030820 A1 | 3/2010 |
| WO | 2010132857 A1 | 11/2010 |
| WO | 2010132985 A1 | 11/2010 |
| WO | 2010/144922 A1 | 12/2010 |
| WO | 2010143196 A1 | 12/2010 |
| WO | 2011019760 A2 | 2/2011 |
| WO | 2011041450 A1 | 4/2011 |
| WO | 2011044421 A1 | 4/2011 |
| WO | 2011057289 A2 | 5/2011 |
| WO | 2011064209 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2011150376 A1 | 12/2011 |
| WO | 2012021542 A2 | 2/2012 |
| WO | 2012024577 A2 | 2/2012 |
| WO | 2012039866 A1 | 3/2012 |
| WO | 2012040487 A1 | 3/2012 |
| WO | 2012058461 A1 | 5/2012 |
| WO | 2012083245 A1 | 6/2012 |
| WO | 2012088535 A1 | 6/2012 |
| WO | 2012110955 A1 | 8/2012 |
| WO | 2012173697 A1 | 12/2012 |
| WO | 2013006713 A2 | 1/2013 |
| WO | 2013006817 A1 | 1/2013 |
| WO | 2013034175 A1 | 3/2013 |
| WO | 2014042329 A1 | 3/2014 |
| WO | 2014052894 A2 | 4/2014 |
| WO | 2014062728 A1 | 4/2014 |
| WO | 2014072238 A1 | 5/2014 |
| WO | 2014137977 A1 | 9/2014 |
| WO | 2014138652 A1 | 9/2014 |
| WO | 2014138918 A1 | 9/2014 |
| WO | 2015/055797 A1 | 4/2015 |
| WO | 2015048514 A1 | 4/2015 |
| WO | 2015073962 A1 | 5/2015 |
| WO | 2015/120256 A2 | 8/2015 |
| WO | 2016/210325 A1 | 12/2016 |
| WO | 2017079732 A1 | 5/2017 |
| WO | 2017096487 A1 | 6/2017 |
| WO | 2017214428 A1 | 12/2017 |
| WO | 2018/112252 A1 | 6/2018 |
| WO | 2018134726 A1 | 7/2018 |
| WO | 2020/160315 A1 | 8/2020 |
| WO | 2022232325 A1 | 11/2022 |

OTHER PUBLICATIONS

JP H114829 machine translation (Year: 1999).*
CN 201180052587.5 filed Apr. 28, 2013 Office Action dated Feb. 24, 2016.

CN 201180052587.5 filed Apr. 28, 2013 Second Office Action dated Aug. 19, 2015.
CN 201180068309.9 filed Aug. 22, 2013 First Office Action dated Oct. 16, 2014.
CN 201180068309.9 filed Aug. 22, 2013 Second Office Action dated May 6, 2015.
CN 201180068309.9 filed Aug. 22, 2013 Third Office Action dated Sep. 2, 2015.
CN 201280033189.3 filed Jan. 3, 2014 First Office Action dated Apr. 3, 2014.
CN 201280033189.3 filed Jan. 3, 2014 Second Office Action dated Sep. 14, 2015.
CN 201380051172.5 filed Mar. 30, 2015 Office Action dated Jan. 16, 2018.
CN 201380051172.5 filed Mar. 30, 2015 Office Action dated Jul. 30, 2018.
CN 201380051172.5 filed Mar. 30, 2015 Office Action dated May 2, 2017.
CN 201380065663.5 filed Jun. 15, 2015 Office Action dated Mar. 15, 2017.
CN 201380065663.5 filed Jun. 15, 2015 Office Action dated Oct. 10, 2017.
CN 201410009216.4 filed Jan. 8, 2014 Office Action dated Jun. 15, 2016.
CN 201410009216.4 filed Jan. 8, 2014 Second Office Action dated Sep. 25, 2015.
CN 201480010988.8 filed Aug. 27, 2015 Office Action dated Aug. 17, 2018.
CN 201480010988.8 filed Aug. 27, 2015 Office Action dated Dec. 13, 2017.
CN 201510144728.6 filed Apr. 17, 2015 Office Action dated Aug. 29, 2017.
CN 201510144728.6 filed Apr. 17, 2015 Office Action dated Jan. 23, 2017.
CN 201580007645.0 filed Aug. 8, 2016 Office Action dated Sep. 12, 2018.
CN 201610127217.8 filed Mar. 7, 2016 Office Action dated Dec. 28, 2017.
CN 201610127217.8 filed Mar. 7, 2016 Office Action dated Jun. 11, 2018.
CN 201610127217.8 filed Mar. 7, 2016 Office Action dated Nov. 19, 2018.
CN 201610166569.4 filed Dec. 23, 2010, Office Action dated Nov. 1, 2017.
CO 15110530 filed May 14, 2015 Office Action dated May 8, 2017.
CO 15110530 filed May 14, 2015 Office Action dated Nov. 25, 2016.
Colley, Peter S et al, ECG-Guided Placement of Sorenson CVP Catheters via Arm Veins, Anesthesia and Analgesia, pp. 953-956, vol. 63, 1984.
Collier, PE et al, Cardiac Tamponade from Central Venous Catheters, Am J Surg, pp. 212-214, vol. 176 No. 2, Aug. 1998.
ComboWire@ Pressure/Flow Guide Wire Ref 9500 Series, Instructions for Use, Apr. 2011.
Corsten, et al., "Central Placement Catheter Placement Using the ECG-Guided Cavafix-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Cullinane, DC et al, The Futility of Chest Roentgenograms Following Routine Central Venous Line Changes, Am J Surg, pp. 283-285, vol. 176 No 3, Sep. 1998.
Curet, Myriam J. et al., University and Practice-based Physicians Input on the Content of a Surgical Curriculum, The American Journal of Surgery® vol. 178 Jul. 1999, 78-84.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.
DELTEC Cath-Finder® Tracking System Operation Manual, 1994.
Egelhof, Petra, Effects of Somatostatin on Portal Blood Flow and Portal Vein Pressure in Patients with Portal Hypertension due to

(56)         References Cited

OTHER PUBLICATIONS

Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No 9, Sep. 1989 (Abstract only).
Enrique Company-Bosch, "ECG Front-End Design is Simplified with MicroConverter." Analog Dialogue 37-11, (dated Nov. 2003).
EP 08855396.1 filed Jun. 15, 2010 European Search Report dated Jul. 31, 2012.
EP 08855396.1 filed Jun. 15, 2010 Intent to Grant dated Jul. 5, 2013.
EP 09707467.8 supplemental European search report dated Jun. 18, 2013.
EP 09743249.6 filed Oct. 18, 2010 Extended European Search Report dated Jan. 13, 2016.
EP 09743249.6 filed Oct. 18, 2010 Intention to Grant dated Mar. 2, 2017.
EP 09808901.4 filed Aug. 21, 2009 European Search Report dated May 23, 2012.
EP 09808901.4 filed Aug. 21, 2009 Examination Report dated May 10, 2013.
EP 09813632.8 filed Apr. 5, 2011 European Search Report dated Jul. 4, 2012.
EP 09813632.8 filed Apr. 5, 2011 Office Action dated Apr. 30, 2013.
EP 09813632.8 filed Apr. 5, 2011 Summons to Attend Oral Proceedings dated Apr. 16, 2014.
EP 10 808 660.4 filed Feb. 15, 2012 Extended European Search Report dated Mar. 4, 2014.
EP 10786978.6 filed Dec. 19, 2011 Extended European Search Report dated Mar. 7, 2014.
EP 10786978.6 filed Dec. 19, 2011 Office Action dated Aug. 11, 2017.
U.S. Appl. No. 13/469,932, filed May 11, 2012 Final Office Action dated Apr. 7, 2016.
U.S. Appl. No. 13/665,420, filed Oct. 31, 2012 Final Office Action dated Apr. 8, 2016.
U.S. Appl. No. 13/665,420, filed Oct. 31, 2012 Non-Final Office Action dated Jan. 6, 2014.
U.S. Appl. No. 13/665,420, filed Oct. 31, 2012 Non-Final Office Action dated Jul. 9, 2015.
U.S. Appl. No. 13/665,420, filed Oct. 31, 2012 Non-Final Office Action dated Mar. 15, 2017.
U.S. Appl. No. 13/665,420, filed Oct. 31, 2012 Non-Final Office Action dated Oct. 9, 2014.
U.S. Appl. No. 13/665,420, filed Oct. 31, 2012 Notice of Allowance dated Feb. 7, 2018.
U.S. Appl. No. 13/737,806, filed Jan. 9, 2013 Notice of Allowance dated Oct. 31, 2013.
U.S. Appl. No. 13/858,782, filed Apr. 8, 2013 Notice of Allowance dated Oct. 9, 2014.
U.S. Appl. No. 13/887,166, filed May 3, 2013 Advisory Action dated Aug. 27, 2014.
U.S. Appl. No. 13/887,166, filed May 3, 2013 Appeal Decision dated Aug. 17, 2017.
U.S. Appl. No. 13/887,166, filed May 3, 2013 Examiner's Answer dated Jul. 16, 2015.
U.S. Appl. No. 13/887,166, filed May 3, 2013 Final Office Action dated Jun. 23, 2014.
U.S. Appl. No. 13/887,166, filed May 3, 2013 Non-Final Office Action dated Jan. 7, 2014.
U.S. Appl. No. 13/887,166, filed May 3, 2013 Notice of Allowance dated Nov. 6, 2017.
U.S. Appl. No. 13/890,158, filed May 8, 2013 Advisory Action dated Feb. 13, 2018.
U.S. Appl. No. 13/890,158, filed May 8, 2013 Advisory Action dated Jul. 26, 2016.
U.S. Appl. No. 13/890,158, filed May 8, 2013 Final Office Action dated Nov. 21, 2017.
U.S. Appl. No. 13/890,158, filed May 8, 2013 Non-Final Office Action dated Apr. 7, 2017.
U.S. Appl. No. 13/890,158, filed May 8, 2013 Non-Final Office Action dated Aug. 15, 2014.
U.S. Appl. No. 13/890,158, filed May 8, 2013 Non-Final Office Action dated Jul. 9, 2015.
U.S. Appl. No. 13/890,158, filed May 8, 2013 Notice of Allowance dated May 30, 2018.
U.S. Appl. No. 13/969,265, filed Aug. 16, 2013 Non-Final Office Action dated Dec. 19, 2013.
U.S. Appl. No. 13/969,265, filed Aug. 16, 2013 Notice of Allowance dated Jun. 23, 2014.
U.S. Appl. No. 14/040,205, filed Sep. 27, 2013 Advisory Action dated Dec. 15, 2016.
U.S. Appl. No. 14/040,205, filed Sep. 27, 2013 Board Decision dated May 1, 2019.
U.S. Appl. No. 14/040,205, filed Sep. 27, 2013 Examiner's Answer dated Jul. 20, 2017.
U.S. Appl. No. 14/040,205, filed Sep. 27, 2013 Final Office Action dated Oct. 19, 2016.
U.S. Appl. No. 14/040,205, filed Sep. 27, 2013 Non-Final Office Action dated Mar. 10, 2016.
U.S. Appl. No. 14/040,205, filed Sep. 27, 2013 Notice of Allowance dated Aug. 21, 2019.
U.S. Appl. No. 14/054,700, filed Oct. 15, 2013 Advisory Action dated Dec. 15, 2016.
U.S. Appl. No. 14/054,700, filed Oct. 15, 2013 Board Decision dated May 1, 2019.
U.S. Appl. No. 14/054,700, filed Oct. 15, 2013 Examiner's Answer dated Jul. 3, 2017.
U.S. Appl. No. 14/054,700, filed Oct. 15, 2013 Final Office Action dated Oct. 19, 2016.
U.S. Appl. No. 14/054,700, filed Oct. 15, 2013 Notice of Allowance dated Jun. 6, 2019.
U.S. Appl. No. 14/141,046, filed Dec. 26, 2013 Advisory Action dated Aug. 4, 2016.
U.S. Appl. No. 14/141,046, filed Dec. 26, 2013 Examiner's Answer dated Oct. 15, 2018.
U.S. Appl. No. 14/141,046, filed Dec. 26, 2013 Final Office Action dated Dec. 11, 2017.
U.S. Appl. No. 14/141,046, filed Dec. 26, 2013 Final Office Action dated May 11, 2016.
U.S. Appl. No. 14/141,046, filed Dec. 26, 2013 Non-Final Office Action dated Apr. 7, 2017.
U.S. Appl. No. 14/141,046, filed Dec. 26, 2013 Non-Final Office Action dated Feb. 11, 2015.
U.S. Appl. No. 14/141,046, filed Dec. 26, 2013 Non-Final Office Action dated Jun. 20, 2014.
U.S. Appl. No. 14/141,046, filed Dec. 26, 2013 Non-Final Office Action dated Nov. 5, 2015.
U.S. Appl. No. 14/201,300, filed Mar. 7, 2014 Advisory Action dated Jul. 18, 2016.
U.S. Appl. No. 14/201,300, filed Mar. 7, 2014 Advisory Action dated Mar. 2, 2017.
U.S. Appl. No. 14/201,300, filed Mar. 7, 2014 Board Decision dated Apr. 12, 2019.
U.S. Appl. No. 14/201,300, filed Mar. 7, 2014 Board Decision dated Jul. 23, 2019.
U.S. Appl. No. 14/201,300, filed Mar. 7, 2014 Examiner's Answer dated Apr. 19, 2018.
U.S. Appl. No. 14/201,300, filed Mar. 7, 2014 Final Office Action dated Dec. 19, 2016.
U.S. Appl. No. 14/201,300, filed Mar. 7, 2014 Final Office Action dated Jul. 10, 2017.
EP 20154593.6 filed Jan. 30, 2020 Extended European Search Report dated Jun. 2, 2020.
U.S. Appl. No. 14/996,247, filed Jan. 15, 2016 Non-Final Office Action dated Sep. 1, 2020.
U.S. Appl. No. 15/418,475, filed Jan. 27, 2017 Non-Final Office Action dated Sep. 1, 2020.
U.S. Appl. No. 15/585,051, filed May 2, 2017 Notice of Allowance dated Jul. 31, 2020.

(56)                    References Cited

OTHER PUBLICATIONS

U.S. Appl. No. 15/836,741, filed Jan. 8, 2017 Notice of Allowance dated Sep. 10, 2020.
U.S. Appl. No. 15/900,623, filed Feb. 20, 2018 Advisory Action dated Aug. 7, 2020.
U.S. Appl. No. 16/017,695, filed Jun. 25, 2018 Non-Final Office Action dated Jul. 20, 2020.
U.S. Appl. No. 16/457,606, filed Jun. 28, 2017 Non-Final Office Action dated Sep. 15, 2020.
Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.
Liu , Ji-Bin et al, Catheter-Based Intraluminical Sonography, J Ultrasound Med, pp. 145-160, vol. 23, 2004.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.
Lum, Phillip, A New Formula-Based Measurement Guide for Optimal Positioning of Central Venous Catheters, JAVA, vol. 9, No. 2, pp. 80-85, 2004.
Lynch, RE et al, A Procedure for Placing Pediatric Femoral Venous Catheter Tips near the Right Atrium, Pediatr Emerg Care, pp. 130-132, vol. 18 No. 2, Apr. 2002.
Madan, et al. "Right Atrial Electrocardiogramique for the Placement of Central Venous Catheters for Chemotherapy or Intravenous Nutrition." British Journal of Surgery, vol. B1, pp. 1604-1605, 1994.
Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, CHEST, 2003.
Markovich, Mary B., Central Venous Catheter Tip Placement: Determination of Posterior Malposition-A Case Study, JAVA, vol. 11, No. 2, pp. 85-89, 2006.
Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.
Mcdonnall, "Intra-Atrial Electrocardiogramatheter Placement." Literature review prepared for Bard Access Systems, Oct. 2007.
Mcgee et al., "Accurate Placement of Central Venous Catheters: A Prospective, Randomize, Multicenter Trail." Critical Care Medicine, vol. 21 No. 8, Aug. 1993.
MedGraphics, CardioPerfect® Resting/Stress ECG System, 3 pages, 2001.
Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.
Michenfelder, John et al, Air Embolism During Neurosurgery. A New Method of Treatment, Anesthesia and Analgesia. Current Researches, pp. 390-395, vol. 45, No. 4, Jul.-Aug. 1966.
MICROBIRD™ Miniaturized DC Magnetic Sensors for Intra-body Navigation and Localization, Specifications, 2005.
MICRONIX CathRite™ Cardiac Access Device Brochure. Jun. 2004.
Micronix Pty Ltd "CathRite" Guiding Styled Core Manufacturing, Jun. 15, 2006.
Moureau, Nancy L. et al., "Electrocardiogram (EKG) Guided Peripherally Inserted Central Catheter Placement and Tip Position: Results of a Trial to Replace Radiological Confirmation," Journal of the Association for Vascular Access, pp. 8-14, vol. 15, No. 1, 2010.
Murthy, Vrudhula et al, Analysis of Power Spectral Densities of Electrocardiograms, Mathematical Biosciences, pp. 41-51, vol. 12 No. 1-2, Oct. 1971.
MX/a/2012/013672 filed Nov. 23, 2012 First Office Action dated Aug. 10, 2015.
MX/a/2012/013858 filed Nov. 28, 2012 First Office Action dated Sep. 26, 2014.

MX/a/2012/013858 filed Nov. 28, 2012 Second Office Action dated Jun. 10, 2015.
MX/a/2013/001317 filed Jan. 31, 2013 First Office Action dated Nov. 26, 2015.
MX/a/2015/004864 filed Apr. 16, 2015 Office Action dated Apr. 24, 2018.
MX/a/2015/004864 filed Apr. 16, 2015 Office Action dated Dec. 18, 2017.
Nadroo, AM et al, Changes in Upper Extremity Position Cause Migration of Peripherally Inserted Central Catheters in Neonates, Pediatrics, pp. 131-136, vol. 110, Jul. 2002.
Nakatani, K et al, Accurate Placement of Central Venous Catheters—ECG-guided method vs Patient Height Method, MASUI, pp. 34-38, vol. 51 No. 1, Jan. 2002.
Nazarian, GK et al, Changes in Tunneled Catheter Tip Position when a patient is Upright, J Vasc Interv Radiol, pp. 437-441, vol. 8 No. 3, May-Jun. 1997.
NEUROMETER® CPT, Clinical Applications. Neurotron , Inc. website: www.neurotron.com/CLINAPS.html, last accessed Oct. 23, 2006.
NEUROMETER® CPT, Frequently Asked Questions. Neurotron , Inc. website: www.neurotron.com/CPTFAQ/html, last accessed Oct. 23, 2006.
NEUROMETER® CPT, Products Page. Neurotron , Inc. website: www.neurotron.com/products.html, last accessed Oct. 23, 2006.
NEUROMETER® Electrodiagnostic Neuroselective Sensory Nerve Evaluation: Charts, Tables, Documents & Downloads. Neurotron , Inc. website: www.neurotron.com/downloads.html, last accessed Oct. 23, 2006.
NOT Resource Center. Magnetic Permeability. Oct. 18, 2014. Last accessed Mar. 23, 2018. <URL:https://web.archive.org/web/20141018213902/https://www.nde-ed.org/EducationResources/CommunityCollege/Materials/Physical_Chemical/Permeability.htm>.
Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
Palesty, JA et al, Routine Chest Radiographs Following Central Venous Recatherization over a Wire are not Justified, Am J Surg, pp. 618-621, vol. 176 No. 6, Dec. 1998.
Paliotti, Roberta P. et al, Intravascular Doppler Technique for Monitoring Renal Venous Blood Flow in Man, J Nephrol, pp. 57-62, 2003.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Pawlik, et al., "Central Venous Catheter Placement: Comparison of the Intravascular Guidewire and the Fluid Column Electrocardiograms." European Journal of Anaesthesiology, vol. 41, pp. 594-599, 2004.
PCT/US13/62409 filed Sep. 27, 2013 International Search Report and Written Opinion dated Feb. 24, 2014.
PCT/US2006/033079 filed Aug. 24, 2006 International Preliminary Report on Patentability dated Feb. 26, 2008.
PCT/US2006/033079 filed Aug. 24, 2006 Search Report dated Dec. 19, 2006.
PCT/US2006/033079 filed Aug. 24, 2006 Written Opinion dated Dec. 19, 2006.
PCT/US2008/060502 filed Apr. 16, 2008 International Search Report and Written Opinion dated Oct. 16, 2008.
PCT/US2008/084751 filed Nov. 25, 2008 International Preliminary Report on Patentability dated Jun. 1, 2010.
PCT/US2008/084751 filed Nov. 25, 2008 Search Report dated May 20, 2009.
PCT/US2008/084751 filed Nov. 25, 2008 Written Opinion dated May 20, 2009.
PCT/US2009/033116 filed Feb. 4, 2009 International Preliminary Report on Patentability dated Aug. 10, 2010.
PCT/US2009/033116 filed Feb. 4, 2009 Search Report dated Mar. 13, 2009.
PCT/US2009/033116 filed Feb. 4, 2009 Written Opinion dated Mar. 13, 2009.

(56) References Cited

OTHER PUBLICATIONS

PCT/US2009/041051 filed Apr. 17, 2009 International Preliminary Report on Patentability dated Apr. 8, 2014.

U.S. Appl. No. 12/893,916, filed Sep. 29, 2010 Advisory Action dated Jun. 2, 2016.

U.S. Appl. No. 12/893,916, filed Sep. 29, 2010 Final Office Action dated Jan. 15, 2015.

U.S. Appl. No. 12/893,916, filed Sep. 29, 2010 Final Office Action dated Jun. 18, 2014.

U.S. Appl. No. 12/893,916, filed Sep. 29, 2010 Final Office Action dated Mar. 25, 2016.

U.S. Appl. No. 12/893,916, filed Sep. 29, 2010 Non-Final Office Action dated Aug. 31, 2016.

U.S. Appl. No. 12/893,916, filed Sep. 29, 2010 Non-Final Office Action dated Dec. 24, 2013.

U.S. Appl. No. 12/893,916, filed Sep. 29, 2010 Non-Final Office Action dated Sep. 10, 2015.

U.S. Appl. No. 12/893,916, filed Sep. 29, 2010 Non-Final Office Action dated Sep. 25, 2014.

U.S. Appl. No. 12/900,750, filed Oct. 8, 2010 Non-Final Office Action dated Jun. 3, 2013.

U.S. Appl. No. 13/019,939, filed Feb. 2, 2011 Final Office Action dated Apr. 2, 2014.

U.S. Appl. No. 13/019,939, filed Feb. 2, 2011 Non-Final Office Action dated February 9. 2015.

U.S. Appl. No. 13/019,939, filed Feb. 2, 2011 Non-Final Office Action dated Oct. 11, 2013.

U.S. Appl. No. 13/118,033, filed May 27, 2011 Final Office Action dated Apr. 1, 2016.

U.S. Appl. No. 13/118,033, filed May 27, 2011 Non-Final Office Action dated Aug. 1, 2013.

U.S. Appl. No. 13/118,033, filed May 27, 2011 Non-Final Office Action dated Feb. 3, 2015.

U.S. Appl. No. 13/118,033, filed May 27, 2011 Non-Final Office Action dated Jul. 8, 2015.

U.S. Appl. No. 13/118,033, filed May 27, 2011 Non-Final Office Action dated May 22, 2014.

U.S. Appl. No. 13/118,033, filed May 27, 2011 Notice of Allowance dated Sep. 2, 2016.

U.S. Appl. No. 13/118,138, filed May 27, 2011 Final Office Action dated Apr. 1, 2016.

U.S. Appl. No. 13/118,138, filed May 27, 2011 Final Office Action dated Apr. 3, 2013.

U.S. Appl. No. 13/118,138, filed May 27, 2011 Non-Final Office Action dated Jul. 15, 2015.

U.S. Appl. No. 13/118,138, filed May 27, 2011 Non-Final Office Action dated Oct. 3, 2012.

U.S. Appl. No. 13/118,138, filed May 27, 2011 Non-Final Office Action dated Oct. 9, 2014.

U.S. Appl. No. 13/213,622, filed Aug. 19, 2011 Final Office Action dated Feb. 19, 2013.

U.S. Appl. No. 13/213,622, filed Aug. 19, 2011 Non-Final Office Action dated Jul. 31, 2012.

U.S. Appl. No. 13/213,622, filed Aug. 19, 2011 Non-Final Office Action dated May 22, 2014.

U.S. Appl. No. 13/240,171, filed Sep. 22, 2011 Advisory Action dated Aug. 18, 2015.

U.S. Appl. No. 13/240,171, filed Sep. 22, 2011 Advisory Action dated Jul. 22, 2016.

U.S. Appl. No. 13/240,171, filed Sep. 22, 2011 Final Office Action dated Jun. 10, 2015.

U.S. Appl. No. 13/240,171, filed Sep. 22, 2011 Final Office Action dated May 6, 2016.

U.S. Appl. No. 13/240,171, filed Sep. 22, 2011 Non-Final Office Action dated Dec. 1, 2015.

U.S. Appl. No. 13/240,171, filed Sep. 22, 2011 Non-Final Office Action dated Dec. 26, 2014.

U.S. Appl. No. 13/283,395, filed Oct. 27, 2011 Advisory Action dated Jan. 28, 2014.

U.S. Appl. No. 13/283,395, filed Oct. 27, 2011 Final Office Action dated Nov. 14, 2013.

U.S. Appl. No. 13/283,395, filed Oct. 27, 2011 Non-Final Office Action dated Apr. 23, 2013.

U.S. Appl. No. 13/336,919, filed Dec. 23, 2011 Advisory Action dated May 23, 2013.

U.S. Appl. No. 13/336,919, filed Dec. 23, 2011 Final Office Action dated Dec. 19, 2014.

U.S. Appl. No. 13/336,919, filed Dec. 23, 2011 Final Office Action dated Mar. 1, 2013.

U.S. Appl. No. 13/336,919, filed Dec. 23, 2011 Non-Final Office Action dated Dec. 27, 2013.

U.S. Appl. No. 13/336,919, filed Dec. 23, 2011 Non-Final Office Action dated Jul. 9, 2015.

U.S. Appl. No. 13/336,919, filed Dec. 23, 2011 Non-Final Office Action dated Oct. 16, 2012.

U.S. Appl. No. 13/336,919, filed Dec. 23, 2011 Notice of Allowance dated Jul. 26, 2016.

U.S. Appl. No. 13/337,987, filed Dec. 27, 2011 Examiner's Answer dated Jul. 2, 2014.

U.S. Appl. No. 13/337,987, filed Dec. 27, 2011 Final Office Action dated Sep. 19, 2013.

U.S. Appl. No. 13/337,987, filed Dec. 27, 2011 Non-Final Office Action dated Mar. 15, 2013.

U.S. Appl. No. 13/469,932, filed May 11, 2012 Advisory Action dated Jun. 27, 2016.

U.S. Appl. No. 13/469,932, filed May 11, 2012 Non-Final Office Action dated Jan. 3, 2014.

U.S. Appl. No. 13/469,932, filed May 11, 2012 Non-Final Office Action dated Jul. 31, 2014.

U.S. Appl. No. 13/469,932, filed May 11, 2012 Non-Final Office Action dated Sep. 4, 2015.

U.S. Appl. No. 13/469,932, filed May 11, 2012 Notice of Allowance dated Jan. 31, 2017.

PCT/US2019/055716 filed Oct. 10, 2019 International Search Report and Written Opinion dated Feb. 4, 2020.

U.S. Appl. No. 14/141,046, filed Dec. 26, 2013 Board Decision dated Nov. 26, 2019.

U.S. Appl. No. 14/201,300, filed Mar. 7, 2014 Final Office Action dated Mar. 9, 2020.

U.S. Appl. No. 14/201,300, filed Mar. 7, 2014 Non-Final Office Action dated Nov. 27, 2019.

U.S. Appl. No. 14/996,247, filed Jan. 15, 2016 Advisory Action dated Feb. 20, 2020.

U.S. Appl. No. 14/996,247, filed Jan. 15, 2016 Final Office Action dated Dec. 11, 2019.

U.S. Appl. No. 15/365,698, filed Nov. 30, 2016 Notice of Allowance dated Nov. 4, 2019.

U.S. Appl. No. 15/418,475, filed Jan. 27, 2017 Final Office Action dated Apr. 2, 2020.

U.S. Appl. No. 15/418,475, filed Jan. 27, 2017 Non-Final Office Action dated Oct. 18, 2019.

U.S. Appl. No. 15/816,932, filed Nov. 17, 2017 Final Office Action dated Feb. 28, 2020.

U.S. Appl. No. 15/836,741, filed Jan. 8, 2017 Restriction Requirement dated Mar. 3, 2020.

U.S. Appl. No. 15/900,623, filed Feb. 20, 2018 Non-Final Office Action dated Dec. 30, 2019.

PCT/US2022/026606 filed Apr. 27, 2022, International Search Report and Written Opinion dated Jul. 21, 2022.

U.S. Appl. No. 16/011,380, filed Jun. 18, 2018 Final Office Action dated Jul. 21, 2022.

U.S. Appl. No. 16/734,011, filed Jan. 3, 2020, Restriction Requirement dated Jul. 20, 2022.

U.S. Appl. No. 16/777,685, filed Jan. 30, 2020 Final Office Action dated Jul. 12, 2022.

EP 11827551.0 filed Feb. 7, 2013 Office Action dated Mar. 13, 2020.

U.S. Appl. No. 14/201,300, filed Mar. 7, 2014 Notice of Allowance dated May 8, 2020.

U.S. Appl. No. 15/418,475, filed Jan. 27, 2017 Advisory Action dated May 28, 2020.

U.S. Appl. No. 15/585,051, filed May 2, 2017 Board Decision dated Apr. 21, 2020.

(56)		References Cited

OTHER PUBLICATIONS

U.S. Appl. No. 15/625,842, filed Jun. 16, 2017 Non-Final Office Action dated Mar. 18, 2020.
U.S. Appl. No. 15/816,932, filed Nov. 17, 2017 Advisory Action dated Jun. 18, 2020.
U.S. Appl. No. 15/836,741, filed Jan. 8, 2017 Non-Final Office Action dated Jun. 12, 2020.
U.S. Appl. No. 15/900,623, filed Feb. 20, 2018 Final Office Action dated Jun. 12, 2020.
EP 10786978.6 filed Dec. 19, 2011 Office Action dated Jan. 16, 2019.
EP 10821193.9 filed Mar. 27, 2012 Partial European Search Report dated Oct. 9, 2015.
EP 11 818 828.3 filed Mar. 18, 2013 Extended European Search Report dated Dec. 10, 2014.
EP 11740309.7 filed Aug. 23, 2012 Extended European Search Report dated Aug. 3, 2015.
EP 11787515.3 filed Dec. 12, 2012 partial European search report dated Jun. 23, 2015.
EP 11787515.3 filed Dec. 12, 2012 partial European search report dated Oct. 27, 2015.
EP 11787527.8 filed Dec. 19, 2012 Extended European Search Report dated Oct. 9, 2015.
EP 11787527.8 filed Dec. 19, 2012 partial European search report dated May 26, 2015.
EP 11827551.0 filed Feb. 7, 2013 Extended European Search Report dated Sep. 19, 2017.
EP 11837113.7 filed May 28, 2013 Extended European Search Report dated Apr. 24, 2014.
EP 11850625.2 filed Jul. 22, 2013 Extended European Search Report dated Jun. 21, 2017.
EP 11850625.2 filed Jul. 22, 2013 Office Action dated Feb. 25, 2019.
EP 11850625.2 filed Jul. 22, 2013 Office Action dated Sep. 24, 2018.
EP 12177438.4 filed Jul. 23, 2012 Communication dated Jan. 13, 2014.
EP 12177438.4 filed Jul. 23, 2012 European Search Report dated Dec. 4, 2012.
EP 12177438.4 filed Jul. 23, 2012 European Search Report dated Jun. 7, 2015.
EP 12177438.4 filed Jul. 23, 2012 Examination Report dated Dec. 5, 2014.
EP 12177438.4 filed Jul. 23, 2012 extended European Search Report dated Mar. 25, 2013.
EP 12807886.2 filed Jan. 15, 2014 Extended European Search Report dated Februry 6, 2015.
EP 13194818.4 filed Nov. 28, 2013 extended European search report dated Feb. 28, 2014.
EP 13840356.3 filed Apr. 27, 2015 Extended European Search Report dated Mar. 22, 2017.
EP 13840356.3 filed Apr. 27, 2015 Partial European Search Report dated Oct. 19, 2016.
EP 13846380.7 filed May 15, 2015 Extended European Search Report dated Sep. 30, 2016.
EP 13846380.7 filed May 15, 2015 Partial European Search Report dated Sep. 30, 2016.
EP 14151268.1 filed Jan. 15, 2014 European Search Report dated Feb. 21, 2014.
EP 14197137.4 filed Dec. 10, 2014 Extended European Search Report dated Nov. 4, 2015.
EP 14197137.4 filed Dec. 10, 2014 Office Action dated Apr. 5, 2018.
EP 14197137.4 filed Dec. 10, 2014 Office Action dated, Sep. 20, 2017.
EP 14197137.4 filed Dec. 10, 2014, Office Action dated Nov. 21, 2018.
EP 14197137.4 filed Dec. 10, 2014, Partial European Search Report dated May 29, 2015.
EP 14761249.3 Filed Sep. 3, 2015 Extended European Search Report dated Sep. 19, 2016.
EP 14761249.3 Filed Sep. 3, 2015 Office Action dated Sep. 28, 2017.

EP 15179061.5 filed Jul. 30, 2015 Extended European Search Report dated Jan. 14, 2016.
EP 15179061.5 filed Jul. 30, 2015 Partial European Search Report dated Jan. 17, 2018.
EP 15746326.6 filed Jul. 1, 2016 Extended European Search Report dated Jun. 9, 2017.
EP 15746326.6 filed Jul. 1, 2016 Office Action dated Jan. 29, 2019.
EP 17157118.5 filed Feb. 21, 2017 Extended European Search Report Jun. 8, 2017.
EP 17186624.7 filed Aug. 17, 2017 Extended European Search Report dated Jan. 17, 2018.
EP 17186624.7 filed Aug. 17, 2017 Partial European Search Report dated Jan. 17, 2018.
EP14197136.6 filed Dec. 10, 2014 Extended European Search Report dated May 26, 2015.
EP14197136.6 filed Dec. 10, 2014 Office Action dated Nov. 21, 2018.
Fearon, William F et al, Evaluating Intermediate Coronary Lesions in the Cardiac Catheterization Laboratory, vol. 4, No. 1, 7 pages, Reviews in Cardiovascular Medicine, 2003.
Felleiter P et al, Use of Electrocardiogramacement Control of Central Venous Catheters in Austria, Acta Med Austriaca, pp. 109-113, vol. 26 No 3, 1999 (Abstract only).
Forauer, AR et al, Change in Peripherally Inserted Central Catheter Tip Location with Abduction and Adduction of the Upper Extremity, J Vasc Interv Radiol, pp. 1315-1318, vol. 11 No. 10, Nov.-Dec. 2000.
Frassinelli, P et al, Utility of Chest Radiographs after Guidewire Exchanges of Central Venous Catheters, Crit Care Med, pp. 611-615, vol. 26 No. 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
GB Application 0800474.9 filed Aug. 24, 2006 Office Action dated Mar. 17, 2010.
Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).
Gebhard, et al., "The accuracy of Electrocardiogram-Controlled Central Line Placement." The International Anesthesia Research Society, vol. 104, No. 1 Jan. 2007.
Gjendemsjo, Anders, et al., Energy and Power, The Connexions Project, Version 1.2, Feb. 20, 2004.
Gladwin, MT et al, Cannulation of the Internal Jugular Vein: is postpocedural chest radiography always necessary?, Crit Care Med, 33 pages, Oct. 2000.
Gonzales, et al. "Peripherally Inserted Central Catheter Placement in Swine Using Magnet Detection." Journal of Intravenous Nursing, vol. 22, No. 3, May/Jun. 1999.
Greenall, M.J. et al, Cardiac Tamponade and Central Venous Catheters, British Medical Journal, pp. 595-597, Jun. 14, 1975.
Guillory, "Basic Principles of Technologies for Catheter Localization." C.R. Bard internal paper, Oct. 20, 2004.
Guth, AA, Routine Chest X-rays after Insertion of Implantable Long-Term Venous Catheters: Necessary or Not?, Am Surg, pp. 26-29, vol. 67 No. 1, Jan. 2001 (Abstract only).
Hamza, N. et al. "Interference reduction in ECG signal acquisition: Ground electrode removal." 2013 International Conference on Computer Medical Applications (ICCMA), Jan. 2013.
Hill, Bradley et al, Abstract of article discussing VasaNova VPS as guide for placement of PICCs. 2009.
Hill, Bradley, Identifying the Caval-Atrial Junction Using Smart-Catheter Technology presentation, 22nd Annual Scientific Meeting of the AVA in Savannah, Georgia, Sep. 13, 2008.
Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.

(56)          References Cited

OTHER PUBLICATIONS

Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.

Honeywell, "1, 2 and 3 Axis Magnetic Sensors HMC1051/HMC1052L/HMC1053" dated Jan. 2010.

Iacopino, Domenico Gerardo et al., Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.

Jeon, Yunseok et al., "Transesophageal Echocardiographic Evaluation of ECG-guided Central Venous Catheter Placement," Canadian Journal of Anesthesia, vol. 53, No. 10, Oct. 1, 2006, pp. 978-983.

Joosting, Jean-Pierre, "Dual-interface RFID-compatible EEPROM enables remote access to electronic device parameters," EE Times, Mar. 8, 2010.

JP 2008-528151 filed Aug. 24, 2006 Notice of Grant dated May 6, 2012.

JP 2010-504220 filed Sep. 3, 2009 Final Office Action dated Apr. 18, 2013.

JP 2010-504220 filed Sep. 3, 2009 Office Action dated Apr. 1, 2014.

JP 2010-504220 filed Sep. 3, 2009 Office Action dated Apr. 18, 2013.

JP 2010-504220 filed Sep. 3, 2009 Office Action dated May 21, 2012.

JP 2010-535117 filed May 26, 2011 First Office Action dated Aug. 5, 2013.

JP 2012-515222 filed Dec. 9, 2011 Office Action dated Feb. 23, 2015.

JP 2012-515222 filed Dec. 9, 2011 Office Action dated Mar. 24, 2014.

JP 2012-552060 filed Aug. 1, 2012 Office Action dated Nov. 12, 2014.

JP 2012-552060 filed Aug. 1, 2012 Second Office Action dated Nov. 6, 2015.

JP 2013-512046 filed Nov. 26, 2012 First Office Action dated Mar. 23, 2015.

JP 2013-512046 filed Nov. 26, 2012 Office Action dated Dec. 8, 2015.

JP 2013-512046 filed Nov. 26, 2012 Office Action dated May 16, 2016.

JP 2013-512051 filed Nov. 26, 2012 First Office Action dated Mar. 23, 2015.

JP 2013-524999 filed Jan. 22, 2013 First Office Action dated Jun. 1, 2015.

JP 2013-530322 filed Mar. 18, 2013, Office Action dated Jul. 6, 2018.

JP 2013-530322 filed Mar. 18, 2013, Office Action dated Mar. 2, 2017.

JP 2013-530322 filed Mar. 18, 2013, Office Action dated Nov. 6, 2017.

UP 2014-519081 filed Dec. 27, 2013 First Office Action dated Apr. 26, 2016.

JP 2015-534770 filed Mar. 26, 2015 Office Action dated Feb. 21, 2018.

JP 2015-534770 filed Mar. 26, 2015 Office Action dated Jun. 12, 2017.

JP2013-530322 filed Mar. 18, 2013, Office Action dated May 2, 2016.

JP2013-530322 filed Mar. 18, 2013, First Office Action dated Jul. 31, 2015.

Kim, Ko et al, Positioning Internal Jugular Venous Catheters using the Right Third Intercostal Space in Children, Acta Anaesthesiol Scand, pp. 1284-1286, vol. 47 No. 10, Nov. 2003.

Kjelstrup T et al, Positioning of Central Venous Catheters using ECG, Tidssk Nor Laegeforen, pp. 599-601, vol. 111 No. 5, Feb. 1999 (Abstract only).

Kofler, Julia, et al., Epinephrine application via an endotracheal airway and via the Combitube in esophageal position, Critical Care Medicine: May 2000, vol. 28: Issue 5, pp. 1445-1449.

Konings, MK, et al., Development of an intravascular impedance catheter for detection of fatty lesions in arteries, IEEE Trans Med Imaging Aug. 1997; 16(4):439-46.

Kowalski, CM et al, Migration of Central Venous Catheters: Implications for Initial Catheter Tip Positioning, J Vasc Interv Radiol, pp. 443-447, vol. 8 No. 3, May-Jun. 1997.

KR 10-2012-7000866 filed Jan. 11, 2012 First Office Action dated Jun. 16, 2016.

KR 10-2012-7000866 filed Jan. 11, 2012 Second Office Action dated Nov. 3, 2016.

KR 10-2013-7006933 filed Mar. 19, 2013 Office Action dated Aug. 7, 2017.

KR 10-2014-7002789 filed Feb. 3, 2014 Office Action dated Feb. 22, 2019.

KR 10-2014-7002789 filed Feb. 3, 2014 Office Action dated Jun. 21, 2018.

Leowenthal, MR et al, The Peripherally Inserted Central Catheter (Picc): A Prospective Study of its Natural History after Fossa Insertion, Anaesth Intensive Care, pp. 21-24; vol. 30 No. 1, Feb. 2002.

U.S. Appl. No. 14/996,247, filed Jan. 15, 2016 Notice of Allowance dated Dec. 4, 2020.

U.S. Appl. No. 15/625,842, filed Jun. 16, 2017 Final Office Action dated Nov. 5, 2020.

U.S. Appl. No. 15/625,842, filed, Jun. 16, 2017 Notice of Allowance dated Dec. 11, 2020.

U.S. Appl. No. 15/816,932, filed Nov. 17, 2017 Corrected Notice of Allowance dated Nov. 16, 2020.

U.S. Appl. No. 15/816,932, filed Nov. 17, 2017 Notice of Allowance dated Oct. 29, 2020.

U.S. Appl. No. 16/017,695, filed Jun. 25, 2018 Final Office Action dated Dec. 18, 2020.

U.S. Appl. No. 16/457,606, filed Jun. 28, 2017 Final Office Action dated Dec. 21, 2020.

U.S. Appl. No. 16/598,952, filed Oct. 10, 2019 Notice of Allowance dated Dec. 23, 2020.

U.S. Appl. No. 14/201,300, filed Mar. 7, 2014 Final Office Action dated May 5, 2016.

U.S. Appl. No. 14/201,300, filed Mar. 7, 2014 Non-Final Office Action dated Aug. 24, 2016.

U.S. Appl. No. 14/201,300, filed Mar. 7, 2014 Non-Final Office Action dated Jan. 6, 2016.

U.S. Appl. No. 14/201,300, filed Mar. 7, 2014 Non-Final Office Action dated Mar. 30, 2017.

U.S. Appl. No. 14/270,241, filed May 5, 2014 Non-Final Office Action dated Apr. 23, 2015.

U.S. Appl. No. 14/270,241, filed May 5, 2014 Notice of Allowance dated Oct. 7, 2015.

U.S. Appl. No. 14/309,511, filed Jun. 19, 2014 Non-Final Office Action, dated Sep. 24, 2015.

U.S. Appl. No. 14/309,511, filed Jun. 19, 2014 Notice of Allowance, dated Jul. 26, 2016.

U.S. Appl. No. 14/317,501, filed Jun. 27, 2014 Advisory Action dated Sep. 16, 2015.

U.S. Appl. No. 14/317,501, filed Jun. 27, 2014 Decision on Appeal dated Nov. 17, 2017.

U.S. Appl. No. 14/317,501, filed Jun. 27, 2014 Examiner's Answer dated Jun. 30, 2016.

U.S. Appl. No. 14/317,501, filed Jun. 27, 2014 Final Office Action dated Jul. 1, 2015.

U.S. Appl. No. 14/317,501, filed Jun. 27, 2014 Non-Final Office Action dated Mar. 3, 2015.

U.S. Appl. No. 14/317,501, filed Jun. 27, 2014 Non-Final Office Action dated Sep. 12, 2014.

U.S. Appl. No. 14/317,501, filed Jun. 27, 2014 Notice of Allowance dated Feb. 9, 2018.

U.S. Appl. No. 14/449,061, filed Jul. 31, 2014 Final Office Action dated Nov. 6, 2015.

U.S. Appl. No. 14/449,061, filed Jul. 31, 2014 Non-Final Office Action dated Apr. 27, 2015.

(56) References Cited

OTHER PUBLICATIONS

U.S. Appl. No. 14/449,061, filed Jul. 31, 2014 Notice of Allowance dated Apr. 13, 2016.
U.S. Appl. No. 14/498,887, filed Sep. 26, 2014 Advisory Action dated Aug. 22, 2016.
U.S. Appl. No. 14/498,887, filed Sep. 26, 2014 Final Office Action dated Jun. 15, 2016.
U.S. Appl. No. 14/498,887, filed Sep. 26, 2014 Non-Final Office Action dated Feb. 19, 2016.
U.S. Appl. No. 14/506,552, filed Oct. 3, 2014 Non-Final Office Action dated Oct. 1, 2015.
U.S. Appl. No. 14/548,151, filed Nov. 19, 2014 Advisory Action dated Aug. 1, 2017.
U.S. Appl. No. 14/548,151, filed Nov. 19, 2014 Advisory Action dated Jul. 22, 2016.
U.S. Appl. No. 14/548,151, filed Nov. 19, 2014 Final Office Action dated Apr. 19, 2017.
U.S. Appl. No. 14/548,151, filed Nov. 19, 2014 Non-Final Office Action dated Jun. 5, 2015.
U.S. Appl. No. 14/548,151, filed Nov. 19, 2014 Non-Final Office Action dated Sep. 21, 2017.
U.S. Appl. No. 14/548,151, filed Nov. 19, 2014 Non-Final Office Action dated Sep. 28, 2016.
U.S. Appl. No. 14/615,932, filed Feb. 6, 2015 Non-Final Office dated Dec. 29, 2016.
U.S. Appl. No. 14/788,305, filed Jun. 30, 2015 Advisory Action dated Oct. 19, 2018.
U.S. Appl. No. 14/788,305, filed Jun. 30, 2015 Final Office Action dated Jul. 27, 2018.
U.S. Appl. No. 14/788,305, filed Jun. 30, 2015 Non-Final Office Action dated Jan. 10, 2018.
U.S. Appl. No. 14/788,305, filed Jun. 30, 2015 Notice of Allowance dated Nov. 15, 2018.
U.S. Appl. No. 14/788,305, filed Jun. 30, 2015 Restriction Requirement dated Aug. 25, 2017.
U.S. Appl. No. 14/846,496, filed Sep. 4, 2015 Non-Final Office Action dated Nov. 25, 2016.
U.S. Appl. No. 14/996,247, filed Jan. 15, 2016 Non-Final Office Action dated Jul. 18, 2019.
U.S. Appl. No. 14/996,247, filed Jan. 15, 2016 Restriction Requirement dated Mar. 22, 2019.
U.S. Appl. No. 15/160,958, filed May 20, 2016 Advisory Action dated Jul. 10, 2017.
U.S. Appl. No. 15/160,958, filed May 20, 2016 Final Office Action dated Apr. 21, 2017.
U.S. Appl. No. 15/160,958, filed May 20, 2016 Non-Final Office Action dated Dec. 15, 2016.
U.S. Appl. No. 15/160,958, filed May 20, 2016 Notice of Allowance dated Jul. 26, 2017.
U.S. Appl. No. 15/192,561, filed Jun. 24, 2016 Final Office Action dated Nov. 1, 2018.
U.S. Appl. No. 15/192,561, filed Jun. 24, 2016 Non-Final Office Action dated Apr. 6, 2018.
U.S. Appl. No. 15/266,977, filed Sep. 15, 2016 Non-Final Office Action dated Oct. 30, 2018.
U.S. Appl. No. 15/284,355, filed Oct. 3, 2016 Advisory Action dated Aug. 13, 2018.
U.S. Appl. No. 15/284,355, filed Oct. 3, 2016 Final Office Action dated May 24, 2018.
U.S. Appl. No. 15/284,355, filed Oct. 3, 2016 Non-Final Office Action dated Apr. 24, 2018.
U.S. Appl. No. 15/284,355, filed Oct. 3, 2016 Non-Final Office Action dated Nov. 17, 2017.
U.S. Appl. No. 15/284,355, filed Oct. 3, 2016 Notice of Allowance dated Feb. 21, 2019.
U.S. Appl. No. 15/365,698, filed Nov. 30, 2016 Final Office Action dated Jul. 12, 2018.
PCT/US2021/052066 filed Sep. 24, 2021 International Search Report and Written Opinion dated Jan. 10, 2022.

U.S. Appl. No. 16/011,380, filed Jun. 18, 2018 Non-Final Office Action dated Dec. 24, 2021.
U.S. Appl. No. 16/017,695, filed Jun. 25, 2018 Notice of Allowance dated Nov. 2, 2021.
U.S. Appl. No. 16/164,592, filed Oct. 18, 2018 Notice of Allowability dated Jun. 23, 2021.
U.S. Appl. No. 16/394,861, filed Apr. 25, 2019 Final Office Action dated Jan. 31, 2022.
U.S. Appl. No. 16/394,861, filed Apr. 25, 2019 Non-Final Office Action dated Aug. 5, 2021.
U.S. Appl. No. 16/777,685, filed Jan. 30, 2020 Non-Final Office Action dated Jan. 18, 2022.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
Chang, Thomas C. et al., Are Routine Ch Ladiographs Necessary After Image-Guided Placement of Internal Jugular Central Venous Access Devices?, AJR Feb. 1998;170:335-337.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.
Cheng, KI et al., A Novel Approach of Intravenous Electrocardiogramique in Correct Position the Long-Term Central Venous Catheter, Kaohsiung J Med Sci, pp. 241-247, vol. 16 No. 5, May 2000 (Abstract only).
Cheung, P., et al., The Effect of a Disposable Probe Cover on Pulse Oximetry, Anaesth Intensive Care 2002; 30: 211-214.
Chu, et al., "Accurate Central Venous Port—A Catheter Placement: Intravenous Electrocardiogramand Surface Landmark Techniques Compared by Using Transesophageal Echocardiography." The International Anesthesia Research Society, vol. 98, pp. 910-914, 2004.
Claasz, Antonia et al, A Study of the Relationship of the Superior Vena Cava to the Bony Landmarks of the Sternum In the Supine Adult: Implications for Magnetic Guidance Systems, Journal, vol. 12 No.3, JAVA, Jul. 24, 2007.
Clifford, et al. "Assessment of Hepatic Motion Secondary to Respiration for Computer Assisted Interventions." Computer Aided Surgery, vol. 7, pp. 291-299, 2002.
CN 200880012117.4 filed Apr. 16, 2008 First Office Action dated Dec. 23, 2011.
CN 200880012117.4 filed Apr. 16, 2008 Fourth Office Action dated Sep. 4, 2013.
CN 200880012117.4 filed Apr. 16, 2008 Second Office Action dated Oct. 8, 2012.
CN 200880012117.4 filed Apr. 16, 2008 Third Office Action dated Apr. 27, 2013.
CN 200880125528.4 filed Nov. 25, 2008 First Office Action dated Jun. 5, 2012.
CN 200880125528.4 filed Nov. 25, 2008 Second Office Action dated Mar. 6, 2013.
CN 200880125528.4 filed Nov. 25, 2008 Third Office Action dated Jul. 1, 2013.
Cn 200980123021.X filed Dec. 17, 2010 First Office Action dated Nov. 19, 2012.
CN 200980123021 X filed Dec. 17, 2010 Second Office Action dated Aug. 13, 2013.
Cn 200980123021.X filed Dec. 17, 2010 Third Office Action dated Apr. 22, 2014.
CN 200980144663.8 filed May 9, 2011 Decision of Re-Examination dated Feb. 21, 2017.
CN 200980144663.8 filed May 9, 2011 Fifth Office Action dated May 26, 2015.
CN 200980144663.8 filed May 9, 2011 First Office Action dated Dec. 5, 2012.
CN 200980144663.8 filed May 9, 2011 Fourth Office Action dated Nov. 15, 2014.

(56) References Cited

OTHER PUBLICATIONS

CN 200980144663.8 filed May 9, 2011 Notice of Reexamination dated Aug. 5, 2016.
CN 200980144663.8 filed May 9, 2011 Second Office Action dated Aug. 22, 2013.
CN 200980144663.8 filed May 9, 2011 Third Office Action dated May 4, 2014.
CN 201080035659.0 filed Feb. 10, 2012 First Office Action dated Jan. 26, 2014.
CN 201080035659.0 filed Feb. 10, 2012 Second Office Action dated Oct. 9, 2014.
CN 201080035659.0 filed Feb. 10, 2012 Third Office Action dated Mar. 19, 2015.
CN 201080053838.7 filed May 28, 2012 First Office Action dated Jan. 6, 2014.
CN 201080053838.7 filed May 28, 2012 Fourth Office Action dated Jun. 2, 2015.
CN 201080053838.7 filed May 28, 2012 Second Office Action dated Jun. 17, 2014.
CN 201080053838.7 filed May 28, 2012 Third Office Action dated Dec. 4, 2014.
CN 201180016462.7 filed Sep. 27, 2012 First Office Action dated Mar. 21, 2014.
CN 201180016462.7 filed Sep. 27, 2012 Second Office Action dated Dec. 9, 2014.
CN 201180016462.7 filed Sep. 27, 2012 Third Office Action dated Jun. 10, 2015.
CN 201180037065.8 filed Jan. 28, 2013 First Office Action dated Sep. 28, 2014.
CN 201180037065.8 filed Jan. 28, 2013 Fourth Office Action dated May 5, 2016.
CN 201180037065.8 filed Jan. 28, 2013 Notice of Grant dated Aug. 30, 2016.
CN 201180037065.8 filed Jan. 28, 2013 Second Office Action dated Jun. 2, 2015.
CN 201180037065.8 filed Jan. 28, 2013 Third Office Action dated Nov. 24, 2015.
CN 201180037068.1 filed Jan. 28, 2013 First Office Action dated Apr. 20, 2015.
CN 201180037068.1 filed Jan. 28, 2013 First Office Action dated Sep. 9, 2014.
CN 201180037068.1 filed Jan. 28, 2013 Third Office Action dated Oct. 19, 2015.
CN 201180040151.4 filed Feb. 19, 2013 First Office Action dated Oct. 28, 2014.
CN 201180040151.4 filed Feb. 19, 2013 Office Action dated Dec. 10, 2015.
CN 201180040151.4 filed Feb. 19, 2013 Second Office Action dated Jun. 19, 2015.
CN 201180043512.0 filed Mar. 8, 2013 First Office Action dated Jul. 31, 2014.
CN 201180043512.0 filed Mar. 8, 2013 Second Office Action dated Apr. 14, 2015.
CN 201180052587.5 filed Apr. 28, 2013 First Office Action dated Jan. 26, 2015.
PCT/US2009/041051 filed Apr. 17, 2009 Search Report dated Jul. 28, 2009.
PCT/US2009/041051 filed Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.

PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/038391 filed May 27, 2011 International Preliminary Report on Patentability and Written Opinion dated Dec. 4, 2012.
PCT/US2011/038391 filed May 27, 2011 International Search Report dated Sep. 21, 2011.
PCT/US2011/038415 filed May 27, 2011 International Preliminary Report on Patentability dated Dec. 13, 2012.
PCT/US2011/038415 filed May 27, 2011 International Search Report dated Sep. 28, 2011.
PCT/US2011/038415 filed May 27, 2011 Written Opinion dated Sep. 28, 2011.
PCT/US2011/047127 filed Aug. 9, 2011 International Preliminary Report on Patentability dated Apr. 18, 2013.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/048403 filed Aug. 19, 2011 International Preliminary Report on Patentability dated Jul. 30, 2013.
PCT/US2011/048403 filed Aug. 19, 2011 International Search Report dated Dec. 15, 2011.
PCT/US2011/048403 filed Aug. 19, 2011 Written Opinion dated Dec. 15, 2011.
PCT/US2011/052793 filed Sep. 22, 2011 International Preliminary Report on Patentability dated Apr. 4, 2013.
PCT/US2011/052793 filed Sep. 22, 2011 International Search Report dated Jan. 6, 2012.
PCT/US2011/052793 filed Sep. 22, 2011 Written Opinion dated Jan. 6, 2012.
PCT/US2011/058138 filed Oct. 27, 2011 International Preliminary Report on Patentability dated May 10, 2013.
PCT/US2011/058138 filed Oct. 27, 2011 International Search Report dated Feb. 7, 2012.
PCT/US2011/058138 filed Oct. 27, 2011 Written Opinion dated Feb. 7, 2012.
PCT/US2011/067268 filed Dec. 23, 2011 International Preliminary Report on Patentability dated Jul. 4, 2013.
PCT/US2011/067268 filed Dec. 23, 2011 International Search Report and Written Opinion dated Apr. 27, 2012.
PCT/US2012/045814 filed Jul. 6, 2012 International Search Report and Written Opinion dated Oct. 1, 2012.
PCT/US2013/065121 filed Oct. 15, 2013 International Search Report and Written Opinion dated Jan. 16, 2014.
PCT/US2014/022019 filed Mar. 7, 2014 International Search Report and Written Opinion dated Jun. 11, 2014.
PCT/US2015/014795 filed Feb. 6, 2015 International Search Report and Written Opinion dated May 14, 2015.
PCT/US2016/039356 filed Jun. 24, 2016 International Search Report and Written Opinion dated Sep. 16, 2016.

(56) References Cited

OTHER PUBLICATIONS

PCT/US2017/066503 filed Dec. 14, 2017 International Search Report and Written Opinion dated Feb. 20, 2018.
Pennington, C.R., Right Atrial Thrombus: a Complication of Total Parenteral Nutrition, British Medical Journal, pp. 446-447, vol. 295, Aug. 15, 1987.
Petersen, J. et al, Silicone Venous Access Devices Positioned with their Tip High in the Superior Vena Cava are More Likely to Malfunction, Am J Surg, pp. 38-41, vol. 178 No. 1, Jul. 1999.
Pittiruti, et al, "The intracavitary ECG method for positioning the tip of central venous catheters: results of an Italian multicenter study," J Vasc Access, pp. 1-9, Nov. 21, 2011.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Pittiruti, et al. "The electrocardiogramethod for positioning the tip of central venous catheters" JAVA, pp. 1-12, Feb. 12, 2011.
PCT/US2020/066186 filed Dec. 18, 2020 International Search Report dated Mar. 23, 2021.
U.S. Appl. No. 14/141,046, filed Dec. 26, 2013 Notice of Allowance dated May 12, 2021.
U.S. Appl. No. 15/842,685, filed Dec. 14, 2017 Non-Final Office Action dated Mar. 31, 2021.
U.S. Appl. No. 16/017,695, filed Jun. 25, 2018 Non-Final Office Action dated May 21, 2021.
U.S. Appl. No. 16/164,592, filed Oct. 18, 2018 Notice of Allowance dated Jun. 8, 2021.
U.S. Appl. No. 15/418,475, filed Jan. 27, 2017 Notice of Allowance dated Jan. 28, 2021.
U.S. Appl. No. 15/842,685, filed Dec. 14, 2017 Non-Final Office Action dated Jan. 7, 2021.
U.S. Appl. No. 15/900,623, filed Feb. 20, 2018 Notice of Allowance dated Mar. 4, 2021.
U.S. Appl. No. 16/017,695, filed Jun. 25, 2018 Advisory Action dated Feb. 23, 2021.
U.S. Appl. No. 16/164,592, filed Oct. 18, 2018 Non-Final Office Action dated Feb. 19, 2021.
U.S. Appl. No. 16/457,606, filed Jun. 28, 2017 Notice of Allowance dated Mar. 17, 2021.
U.S. Appl. No. 16/598,952, filed Oct. 10, 2019 Supplemental Notice of Allowance dated Feb. 24, 2021.
U.S. Appl. No. 16/598,952, filed Oct. 10, 2019 Supplemental Notice of Allowance dated Jan. 25, 2021.
U.S. Appl. No. 16/598,952, filed Oct. 10, 2019 Supplemental Notice of Allowance dated Jan. 29, 2021.
EP 211857735 filed Jul. 16, 2021 Extended European Search Report dated Nov. 5, 2021.
U.S. Appl. No. 16/394,861, filed Apr. 25, 2019 Notice of Allowance dated Apr. 11, 2022.
U.S. Appl. No. 16/830,040, filed Mar. 25, 2020 Non-Final Office Action dated May 5, 2022.
U.S. Appl. No. 17/127,587, filed Dec. 18, 2020 Non-Final Office Action dated May 11, 2022.
Polos, PG et al, Tips for Monitoring the Position of a Central Venous Catheter—How Placement can go awry—even when the anatomy is normal, J Crit Illn, pp. 660-674, vol. 8 No. 6, Jun. 1993 (Abstract only).
Pop, Gheorghe A. et al., Catheter-based impedance measurements in the right atrium for continuously monitoring hematocrit and esti-mating blood viscosity changes; an in vivo feasibility study in swine, Biosensors and Bioelectronics 19 (2004) 1685-1693.
Popp, M. B. et al., Accuracy of implanted port placement with the use of the electromagnetic CathTrack® catheter locator system, The Journal of Vascular Access 2005; 6: 9-12.
Randolph AG et al., Ultrasound guidance for placement of central venous catheters: a meta-analysis of the literature, Critcal Care Medicine, pp. 2053-2058, vol. 24, Dec. 1996.

Reece, A et al, Posititioning Long Lines: Contrast Versus Plain Radiography, Arch Dis Child Fetal Neonatal Ed, pp. 129-130, vol. 84 No. 2, Mar. 2001.
Reynolds, N et al, Assessment of Distal Tip Position of Long Term Central Venous Feeding Catheters using Transesophageal Echocardiol-ogy, JPEN J Parenter Enteral Nutr, pp. 39-41, vol. 25 No. 1, Jan.-Feb. 2001.
RU 2011150917 filed Dec. 15, 2011 First Office Action dated Apr. 24, 2014.
RU 2011150917 filed Dec. 15, 2011 Second Office Action dated Aug. 28, 2014.
RU 2013158008 filed Dec. 26, 2013 First Office Action dated May 27, 2016.
RU 2015110633 filed Mar. 26, 2015 Office Action dated Oct. 25, 2018.
RU 2015111669 filed Apr. 1, 2015 Office Action dated Jan. 25, 2018.
RU 2015111669 filed Apr. 1, 2015 Office Action dated May 18, 2018.
RU 2015111669 filed Apr. 1, 2015 Office Action dated Sep. 5, 2017.
Ruschulte, Heiner et al, Prevention of Central Venous Catheter related infections with chlorhex idine gluconate Impregnated wound dressings: A randomized controlled trial, presented as an abstract at the Annual meeting of the European Society of Anaesthesiologists (ESA) in Madrid, Spain in Jun. 2006, 12 pages, Annals of Hema-tology, Jul. 14, 2008.
Rutherford, J. S. et al., Depth of Central Venous Catheterization: An Audit of Practice in a Cardiac Surgical Unit, Anaesth Intens Care 1994; 22: 267-271.
Sacolick, et al. "Electromagnetically Tracked Placement of a Periph-erally Inserted Central Catheter." SPIE Medical Imaging, 2004 Proceedings.
Salem, et al. "A New Peripherally Implanted Subcutaneous Perma-nent Central Venous Access Device for Patients Requiring Chemo-therapy." Journal of Clinical Oncology, vol. 11, No. 11, pp. 2181-2185, Nov. 1993.
Savary, D et al, Intra-atrial Monitoring to Add Insertion of a Central Venous Line in Pre-Hospital Emergency Care Journal Europeen des Urgences, pp. 75-78, vol. 17 No. 2, 2004.
Schafer et al. "Incorrect placement of a vena cava catheter and its prevention by intra-atrial ECG." Anaesthesist. Jan. 1988;37(1):49-51.
Schummer, et al. "Central Venous Catheters—The inability of 'intra-atrial ECG' to prove adequate positioning." British Journal of Anaesthesia, vol. 93, No. 2, pp. 193-198, 2004.
Schummer, W et al, ECG-guided Central Venous Catheter Position-ing: Does it detect the Pericardial Reflection rather than the Right Atrium?, Eur J Anaesthesiol, pp. 600-605, vol. 21 No 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—the Inability of "Intra-Atrial ECG" to prove Adequate Positioning, Br J Anaesth, pp. 193-198, vol. 93 No. 2, Aug. 2004.
Schuster, M. et al., The carina as a landmark in central venous catheter placement, British Journal of Anaesthesia 85 (2): 192-4 (2000).
Siela, Debra, Using Chest Radiography in the Intensive Care Unit, Crit Care Nurse Aug. 1, 2002 vol. 22 No. 4, pp. 18-27.
Simon, et al., "Central Venous Catheter Placement in Children: Evaluation of Electrocardiogramaing J-Wire." Paediatric Anaesthe-sia vol. 9, pp. 501-504, 1999.
Smith, Brigham, et al., Intravenous electrocardiogramce for place-ment of peripherally inserted central catheters, Journal of Electrocardiol-ogy 43 (2010) 274-278.
Stark, DD et al., Radiographic Assessment of Venous Catheter Position in Children: Value of the Lateral View, Pediatric Radiology, pp. 76-80, vol. 14 No. 2, 1984.
Starkhammar et al. "Cath-Finder Catheter Tracking System: A New Device for Positioning of Central Venous Catheters. Early Experi-ence from Implantation of Brachial portal Systems." Acta Anaesthesiol Scandinavia, vol. 34, No. 4 pp. 296-300, May 1990.

(56) References Cited

OTHER PUBLICATIONS

Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.

Starr, David S et al, EKG Guided Placement of Subclavian CVP Catheters Using J-Wire, pp. 673-676, Ann. Surg, Dec. 1986.

Stas, M et al, Peroperative Intravasal Electrographic Control of Catheter Tip Position in Access Ports Placed by Venous Cut-Down Technique, EJSO, pp. 316-320, vol. 27, 2001.

STEREOTAXIS Magetic Navigation System with Navigant™ User Interface, 2005 Brochure.

STEREOTAXIS, Expanding the Possibilites of Interventional Medicine: Remote Navigation and Automation, pp. 1-8, Apr. 2011.

Tepa@ Health Innovation PC based ECG System Introduction and Technical Specifications, EKG Master USB, 2 pages, Nov. 2003.

Thakor, N. V., et al. "Ground-Free ECG Recording with Two Electrodes." IEEE Transactions on Biomedical Engineering, vol. BME-27, No. 12, Dec. 1980.

The FloWire Doppler Guide Wire located <http://www.volcanocorp.com/products/flowire-doppler-guide-wire.php>, 2011.

TRAXAL Technologies, Tracking Technology website overview: www.traxal.com/rd/rd_classroom_trackingtechnology.htm, last accessed Dec. 1, 2006.

UAB Health Systems, Arrhythmias, retrieved from http://www.health,uab.edu/14564/ on Nov. 15, 2007, 12 pages.

U.S. Appl. No. 11/466,602, filed Aug. 23, 2006 Advisory Action dated Jun. 22, 2009.

U.S. Appl. No. 11/466,602, filed Aug. 23, 2006 Appeal Board Decision dated Sep. 17, 2012.

U.S. Appl. No. 11/466,602, filed Aug. 23, 2006 Final Office Action dated Apr. 8, 2010.

U.S. Appl. No. 11/466,602, filed Aug. 23, 2006 Final Office Action dated Jan. 30, 2009.

U.S. Appl. No. 11/466,602, filed Aug. 23, 2006 Final Office Action dated Oct. 28, 2013.

U.S. Appl. No. 11/466,602, filed Aug. 23, 2006 Non-Final Office Action dated Mar. 28, 2013.

U.S. Appl. No. 11/466,602, filed Aug. 23, 2006 Non-Final Office Action dated Sep. 25, 2009.

U.S. Appl. No. 11/466,602, filed Aug. 23, 2006 Notice of Allowance dated Dec. 3, 2012.

U.S. Appl. No. 11/466,602, filed Aug. 23, 2006 Notice of Allowance dated Mar. 14, 2014.

U.S. Appl. No. 11/552,094, filed Oct. 23, 2006 Notice of Allowability dated Apr. 2, 2010.

U.S. Appl. No. 11/552,094, filed Oct. 23, 2006 Non-Final Office Action dated Apr. 27, 2009.

U.S. Appl. No. 16/734,011, filed Jan. 3, 2020, Non-Final Office Action dated Oct. 28, 2022.

U.S. Appl. No. 16/830,040, filed Mar. 25, 2020 Notice of Allowance dated Sep. 29, 2022.

U.S. Appl. No. 17/105,221, filed Nov. 25, 2020 Non-Final Office Action dated Oct. 6, 2022.

U.S. Appl. No. 17/127,587, filed Dec. 18, 2020 Final Office Action dated Sep. 21, 2022.

U.S. Appl. No. 15/365,698, filed Nov. 30, 2016 Non-Final Office Action dated Apr. 18, 2019.

U.S. Appl. No. 15/365,698, filed Nov. 30, 2016 Non-Final Office Action dated Dec. 14, 2017.

U.S. Appl. No. 15/365,734, filed Nov. 30, 2016 Non-Final Office Action dated Feb. 23, 2018.

U.S. Appl. No. 15/365,734, filed Nov. 30, 2016 Notice of Allowance dated Jun. 4, 2018.

U.S. Appl. No. 15/365,752, filed Nov. 30, 2016 Final Office Action dated Jul. 12, 2018.

U.S. Appl. No. 15/365,752, filed Nov. 30, 2016 Non-Final Office Action dated Dec. 13, 2017.

U.S. Appl. No. 15/365,752, filed Nov. 30, 2016 Notice of Allowance dated Nov. 6, 2018.

U.S. Appl. No. 15/365,872, filed Nov. 30, 2016 Non-Final Office Action dated Aug. 27, 2018.

U.S. Appl. No. 15/365,872, filed Nov. 30, 2016 Notice of Allowance dated Dec. 21, 2018.

U.S. Appl. No. 15/365,872, filed Nov. 30, 2016 Restriction Requirement dated Apr. 5, 2018.

U.S. Appl. No. 15/418,475, filed Jan. 27, 2017 Restriction Requirement dated Jul. 23, 2019.

U.S. Appl. No. 15/585,051, filed May 2, 2017 Examiner's Answer dated May 2, 2019.

U.S. Appl. No. 15/585,051, filed May 2, 2017 Final Office Action dated Feb. 28, 2018.

U.S. Appl. No. 15/585,051, filed May 2, 2017 Final Office Action dated Mar. 15, 2018.

U.S. Appl. No. 15/585,051, filed May 2, 2017 Non-Final Office Action dated Jul. 14, 2017.

U.S. Appl. No. 15/816,932, filed Nov. 17, 2017 Non-Final Office Action dated Aug. 22, 2019.

U.S. Appl. No. 15/900,623, filed Feb. 20, 2018 Final Office Action dated Sep. 20, 2018.

U.S. Appl. No. 15/900,623, filed Feb. 20, 2018 Non-Final Office Action dated Jul. 16, 2019.

U.S. Appl. No. 15/900,623, filed Feb. 20, 2018 Non-Final Office Action dated May 3, 2018.

U.S. Appl. No. 29/428,649, filed Aug. 1, 2012 Notice of Allowance dated Jul. 5, 2013.

Valdivieso, J.R. Perez, et al., Evaluation of a formula for optimal positioning of a central venous catheter inserted through the right internal jugular vein, Rev. Esp. Anestesiol. Reanim. 2003; 50: 77-79.

VasoNova Inc, Vascular navigation system for accurate placement of PICCs, Start-Up Emerging Medical Ventures, pp. 44-45, vol. 14 No. 7, Jul.-Aug. 2009.

Vesely, Thomas M. et al., Central Venous Catheter Tip Position: A Continuing Controversy, J Vasc Intery Radiol 2003; 14:527-534.

VIASYS Health Care Inc. Cortrak© Fact Sheet, 2005.

VIASYS Healthcare MedSystems, Navigator® Benefits, 2008.

VIASYS Healthcare MedSystems, Navigator® Research in Cost Justification, 2008.

VIASYS MedSystems, Cortrak™ Systems Brochure, 2005.

Volcano ComboMap Features and Benefits/Technical Specifications, 2 pages, 2011.

Watters, et al. "Use of Electrocardiogram to Position Right Atrial Catheters During Surgery." Annals of Surgery, vol. 225, No. 2, pp. 165-171, 1997.

Welch Allyn Cardioperfect® PC-Based Resting ECG, 2003.

Wilson, R. G. et al, Right Atrial Electrocardiogram Placement of Central Venous Catheters, The Lancet, pp. 462-463, Feb. 27, 1988.

Wong, Jeffrey J. et al., Azygos Tip Placement for Hemodialysis Catheters in Patients with Superior Vena Cava Occlusion, Cardiovasc Intervent Radiol (2006) 29:143-146.

Worley, Seth J. "Use of a Real-Time Three-Dimensional Magenetic Navigation System for Radiofrequency Ablation of Accessory Pathways." PACE, vol. 21 pp. 1636-1643, Aug. 1998.

Yilmazlar A et al, Complications of 1303 Central Venous Cannulations, J R Soc Med, pp. 319-321, vol. 90 No. 6, Jun. 1997 (Abstract only).

Yoon, SZ et al, Usefulness of the Carina as a Radiographic Landmark for Central Venous Catheter Placement in Paediatric Patients, Br J Anaesth, Jul. 2005.

Yoshida, Teruhisa et al, Detection of Concealed Left Sided Accessory Atrioventricular Pathway by P Wave Signal Averaged Electrocardiogram, J Am Coll Cardiol, pp. 55-62, 1999.

Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.

Zachariou, Zacharias et al., Intra-atrial ECG recording: a new and safe method for implantation of Broviac catheters in children, Pediatr Surg Int (1994) 9: 457-458.

Zaidi, Naveed A., et al. "Room temperature magnetic order in an organic magnet derived from polyaniline." 2004, Polymer, vol. 45, pp. 5683-5689.

(56)                    References Cited

OTHER PUBLICATIONS

"ASCENSION to Launch New 3D Guidance™ Tracker at TCT 2006." Press Releases from Ascension website: www.ascension-tech.com/news/press_101106.php, last accessed Dec. 1, 2006.

Acuson—The Value of Vision, AcuNav Diagnostic Ultrasound Catheter, 2000.

Advertising flyer for GAVECELT—The Italian Group for Long Term Venous Access Devices, for program on International Meeting on PICC's, Midline Catheters and Long Term Venous Access Devices in Catholic University, Rome, Italy on December 3, 4, 5, 2008.

Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.

Allan, P.L. et al, Role of Ultrsound in the Assessment of Chronic Venous Insufficiency, Ultrasound Quarterly, vol. 17, No. 1, pp. 3-10, 2001.

Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.

Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.

Arai, J et al, Detection of Peripherally Inserted Central Catheter Occlusion by in-line Pressure Monitoring, Paediatr Anaesth, pp. 621-624, vol. 12 No. 7, Sep. 2002.

Arrow International, Inc., The Arrow-Johans RAECG Adapter-Making Proper Central Venous Catheter Placement More Reliable (Modle No. EG-04900), Technical Report 1987, USA.

Aslamy, et al. "MRI of Central Venous Anatomy: Implications for Central Venous Catheter Insertion." American College of Chest Physicians, Jun. 8, 2009.

AU 2006283022 filed Aug. 24, 2006 Office Action dated Dec. 22, 2010.

AU 2008329807 exam requested Aug. 13, 2012 Examination Report No. 1 dated Feb. 15, 2013.

AU 2008329807 exam requested Aug. 13, 2012 Notice of Acceptance dated Feb. 14, 2014.

AU 2010300677 filed Mar. 12, 2012 First Examination Report dated Mar. 9, 2014.

AU 2011289513 filed Jan. 21, 2013 Examiner's Report dated Jul. 5, 2013.

AU 2012202293 filed Apr. 19, 2012 Examination Report No. 1 dated Apr. 24, 2013.

AU 2012278809 filed Nov. 12, 2013 Notice of Acceptance dated Sep. 13, 2016.

AU 2013201648 filed Mar. 19, 2013 Examiner's Report dated Mar. 5, 2014.

AU 2013201648 filed Mar. 19, 2013 Examiner's Report dated Oct. 14, 2013.

AU 2013202824 filed Apr. 6, 2013 First Examiner's Report dated Mar. 10, 2014.

AU 2013204243 filed Apr. 12, 2013 Examiner's Report dated Jun. 5, 2013.

AURORA® System Technical Specifications, Oct. 2003.

AZoMaterials. Nickel-Based Super Alloy Inconel 625—Properties and Applications by United Performance Alloys. Oct. 27, 2015. Last accessed Mar. 23, 2018. <URL:https://web.archive.org/web/20151027202821/https://www.azom.com/article.aspx?ArticleID=4461>.

B. Braun Website, "The Optimal Position of the Central Venous Catheter." http://www.cvcpartner.com/index.cfm18F1BDEA1310466194960A39F4E90968 (2009).

B. Braun, Certofix Central Venous Catheter for Placement Using the Seldinger Technique with Simultaneous ECG Lead Option, Feb. 2010.

Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.

Bankier, Alexander A., Azygos Arch Cannulation by Central Venous Catheters: Radiographic Detection of Malposition and Subsequent Complications, Journal of Thoracic Imaging 12:64-69 (1997).

Barber, JM et al, A Nurse led Peripherally Inserted Central Catheter Line Insertion Service is Effective with Radiological Support, Clin Radiol, pp. 352-354, vol. 57 No. 5, May 2002.

Bard Access Systems, Sherlock Tip Location System, 5 pages, 2006.

Bard Access Systems, Site Rite Vascular Acess Ultrasound System, 4 pages, 2005.

Benchimol, Alberto at al, Right Atrium and Superior Vena Cava Flow Velocity in Man Measured with the Doppler- Catheter Flowmeter-Telemetry System, The Amer Journal of Medicine, pp. 303-309, vol. 48, Mar. 1970.

Benzadon, M. N. et al: "Comparison of the Amplitude of the p. Wave from Intracardiac Electrocardiogram Obtained by Means of a Central Venous Catheter Filled With Saline Solution to That Obtained Via Esophageal Electrocardiogram", American Journal of Cardiology, Cahners Publishing Co., Newton, MA, US, vol. 98, No. 7, Oct. 1, 2006 (Oct. 1, 2006), pp. 978-981.

BioAdvance Lumen Vu, Greenhouse Fund Feb. 2004 Recipient, www.bioadvance.com <http://www.bioadvance.com>, 2005.

Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.

Buehrle, Douglas, PICC Placement in Humans using Electromagnetic Detection, <http://www.corpakmedsystems.com/supplement_material/supplementpages/navigator/navarticle.html>, 2008.

C.R. Bard, CathTrack™ Catheter Location System at www.bardaccess.com <http://www.bardaccess.com>, last accessed Apr. 28, 2011.

C.R. Bard, Inc., Bard Electrophysiology Product Catalogue, Bard Catheters, pp. 74-75 (2002), USA.

CA 2,619,909 filed Aug. 24, 2006 Examiner's Report dated Oct. 26, 2012.

CA 2,721,715 filed Apr. 17, 2009 Examiner's Report dated Aug. 18, 2015.

CA 2,721,715 filed Apr. 17, 2009 Examiner's Report dated Oct. 25, 2016.

CA 2800810 filed Nov. 26, 2012 Office Action dated Mar. 13, 2018.

CA 2800810 filed Nov. 26, 2012 Office Action dated Mar. 30, 2017.

CA 2800813 filed Nov. 26, 2012 Office Action dated Mar. 5, 2018.

Cadman, A et al, To Clot or Not to Clot? That is the question in Central Venous Catheters, Clinical Radiology, pp. 349-355, vol. 59 No. 4, Apr. 2004.

Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.

Cardella, John F et al., Interventinal Radiologic Placement of Peripherally Inserted Central Catheters, Journal of Vascular and Interventional Radiology 1993; 4:653-660.

Carlon, R et al, Secondary Migration of a Central Venous Catheter - A Case Report, Minerva Anestesiol, pp. 927-931, vol. 69 No 12, Dec. 2003.

Caruso, LJ et al, A Better Landmark for Positioning a Central Venous Catheter, J Clinical Monitoring and Computing, pp. 331-334, vol. 17 No. 6, Aug. 2002.

Cavatorta, et al., "Central Venous Catheter Placement in Hemodialysis: Evaluation of Electrocardiogramaing a Guidewire." The Journal of Vascular Access, vol. 2, pp. 45-50, 2001.

Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.

U.S. Appl. No. 16/011,380, filed Jun. 18, 2018 Notice of Allowance dated May 17, 2023.

U.S. Appl. No. 16/734,011, filed Jan. 3, 2020, Final Office Action dated May 18, 2023.

(56)  References Cited

OTHER PUBLICATIONS

U.S. Appl. No. 17/105,221, filed Nov. 25, 2020 Notice of Allowance dated Jun. 2, 2023.

U.S. Appl. No. 17/317,591, filed May 11, 2021 Non-Final Office Action dated Jun. 20, 2023.

U.S. Appl. No. 17/484,868, filed Sep. 24, 2021 Final Office Action dated Aug. 1, 2023.

U.S. Appl. No. 11/552,094, filed Oct. 23, 2006 Notice of Allowance dated May 20, 2010.

U.S. Appl. No. 12/104,253, filed Apr. 16, 2008 Final Office Action dated Jul. 27, 2011.

U.S. Appl. No. 12/104,253, filed Apr. 16, 2008 Non-Final Office Action dated Nov. 29, 2010.

U.S. Appl. No. 12/323,273, filed Nov. 25, 2008 Non-Final Office Action dated Jun. 8, 2012.

U.S. Appl. No. 12/369,625, filed Feb. 11, 2009 Final Office Action dated Feb. 23, 2012.

U.S. Appl. No. 12/369,625, filed Feb. 11, 2009 Notice of Allowance dated Oct. 5, 2012.

U.S. Appl. No. 12/369,625, filed Feb. 11, 2009 Notice of Panel Decision dated Aug. 1, 2012.

U.S. Appl. No. 12/369,625, filed Feb. 11, 2009 Non-Final Office Action dated Jul. 20, 2011.

U.S. Appl. No. 12/426,175, filed Apr. 17, 2009 Advisory Action dated Nov. 26, 2013.

U.S. Appl. No. 12/426,175, filed Apr. 17, 2009 Decision on Appeal dated Nov. 7, 2016.

U.S. Appl. No. 12/426,175, filed Apr. 17, 2009 Examiner's Answer dated Oct. 7, 2014.

U.S. Appl. No. 12/426,175, filed Apr. 17, 2009 Final Office Action dated Aug. 2, 2013.

U.S. Appl. No. 12/426,175, filed Apr. 17, 2009 Final Office Action dated Jan. 31, 2014.

U.S. Appl. No. 12/426,175, filed Apr. 17, 2009 Non-Final Office Action dated Dec. 3, 2012.

U.S. Appl. No. 12/426,175, filed Apr. 17, 2009 Notice of Allowance dated Dec. 13, 2016.

U.S. Appl. No. 12/427,244, filed Apr. 21, 2009 Non-Final Office Action dated Jan. 19, 2012.

U.S. Appl. No. 12/545,762, filed Aug. 21, 2009 Final Office Action dated Apr. 10, 2017.

U.S. Appl. No. 12/545,762, filed Aug. 21, 2009 Final Office Action dated Mar. 7, 2013.

U.S. Appl. No. 12/545,762, filed Aug. 21, 2009 Non-Final Office Action dated Aug. 1, 2012.

U.S. Appl. No. 12/545,762, filed Aug. 21, 2009 Non-Final Office Action dated Dec. 13, 2013.

U.S. Appl. No. 12/545,762, filed Aug. 21, 2009 Non-Final Office Action dated Feb. 16, 2016.

U.S. Appl. No. 12/545,762, filed Aug. 21, 2009 Non-Final Office Action dated Nov. 7, 2014.

U.S. Appl. No. 12/545,762, filed Aug. 21, 2009 Non-Final Office Action dated Sep. 11, 2015.

U.S. Appl. No. 12/545,762, filed Aug. 21, 2009 Non-Final Office Action dated Sep. 26, 2016.

U.S. Appl. No. 12/545,762, filed Aug. 21, 2009 Notice of Panel Decision dated Jul. 14, 2017.

U.S. Appl. No. 12/557,401, filed Sep. 10, 2009 Non-Final Office Action dated Apr. 24, 2012.

U.S. Appl. No. 12/557,401, filed Sep. 10, 2009 Non-Final Office Action dated Jan. 6, 2014.

U.S. Appl. No. 12/575,456, filed Oct. 7, 2009 Non-Final Office Action dated Oct. 5, 2012.

U.S. Appl. No. 12/715,556, filed Mar. 2, 2010 Final Office Action dated Oct. 2, 2013.

U.S. Appl. No. 12/715,556, filed Mar. 2, 2010 Non-Final Office Action dated Sep. 13, 2012.

U.S. Appl. No. 12/815,331, filed Jun. 14, 2010 Advisory Action dated Mar. 5, 2015.

U.S. Appl. No. 12/815,331, filed Jun. 14, 2010 Advisory Action dated Oct. 4, 2013.

U.S. Appl. No. 12/815,331, filed Jun. 14, 2010 Final Office Action dated Dec. 23, 2014.

U.S. Appl. No. 12/815,331, filed Jun. 14, 2010 Final Office Action dated Jul. 26, 2013.

U.S. Appl. No. 12/815,331, filed Jun. 14, 2010 Final Office Action dated Nov. 4, 2015.

U.S. Appl. No. 12/815,331, filed Jun. 14, 2010 Non-Final Office Action dated Jan. 22, 2013.

U.S. Appl. No. 12/815,331, filed Jun. 14, 2010 Non-Final Office Action dated Jul. 2, 2014.

U.S. Appl. No. 12/815,331, filed Jun. 14, 2010 Non-Final Office Action dated Jun. 1, 2015.

U.S. Appl. No. 12/854,083, filed Aug. 10, 2010 Advisory Action dated Sep. 8, 2014.

U.S. Appl. No. 12/854,083, filed Aug. 10, 2010 Final Office Action dated Aug. 15, 2013.

U.S. Appl. No. 12/854,083, filed Aug. 10, 2010 Final Office Action dated Aug. 21, 2015.

U.S. Appl. No. 12/854,083, filed Aug. 10, 2010 Final Office Action dated Jul. 1, 2014.

U.S. Appl. No. 12/854,083, filed Aug. 10, 2010 Non-Final Office Action dated Feb. 1, 2016.

U.S. Appl. No. 12/854,083, filed Aug. 10, 2010 Non-Final Office Action dated Jan. 29, 2013.

U.S. Appl. No. 12/854,083, filed Aug. 10, 2010 Non-Final Office Action dated Jan. 29, 2014.

U.S. Appl. No. 12/854,083, filed Aug. 10, 2010 Non-Final Office Action dated Mar. 16, 2015.

U.S. Appl. No. 12/878,915, filed Sep. 9, 2010 Final Office Action dated Sep. 26, 2012.

U.S. Appl. No. 12/878,915, filed Sep. 9, 2010 Non-Final Office Action dated Mar. 15, 2012.

U.S. Appl. No. 12/878,915, filed Sep. 9, 2010 Notice of Allowance dated Jan. 8, 2013.

U.S. Appl. No. 12/893,916, filed Sep. 29, 2010 Advisory Action dated Aug. 15, 2014.

PCT/US2020/015947 filed Jan. 30, 2020 International Search Report and Written Opinion dated Jun. 11, 2020.

U.S. Appl. No. 16/011,380, filed Jun. 18, 2018 Notice of Allowance dated Apr. 3, 2023.

U.S. Appl. No. 16/777,685, filed Jan. 30, 2020 Examiner's Answer dated Apr. 11, 2023.

U.S. Appl. No. 17/127,587, filed Dec. 18, 2020 Non-Final Office Action dated Apr. 7, 2023.

U.S. Appl. No. 17/240,894, filed Apr. 26, 2021 Notice of Allowance dated Dec. 13, 2022.

U.S. Appl. No. 17/317,591, filed May 11, 2021, Restriction Requirement dated Feb. 24, 2023.

U.S. Appl. No. 17/484,868, filed Sep. 24, 2021 Non-Final Office Action dated Jan. 20, 2023.

U.S. Appl. No. 17/317,591, filed May 11, 2021 Final Office Action dated Nov. 28, 2023.

EP 24175400.1 filed May 13, 2022 Extended European Search Report dated Jul. 23, 2024.

U.S. Appl. No. 17/127,587, filed Dec. 18, 2020 Examiner's Answer dated Jul. 5, 2024.

U.S. Appl. No. 17/317,591, filed May 11, 2021 Non-Final Office Action dated Jun. 18, 2024.

U.S. Appl. No. 17/484,868, filed Sep. 24, 2021 Non-Final Office Action dated Jul. 1, 2024.

U.S. Appl. No. 16/734,011, filed Jan. 3, 2020 Notice of Allowance dated Jan. 16, 2025.

U.S. Appl. No. 16/777,685, filed Jan. 30, 2020 Non-Final Office Action dated Mar. 3, 2025.

U.S. Appl. No. 17/389,191, filed Jul. 29, 2021 Restriction Requirement dated Feb. 6, 2025.

U.S. Appl. No. 17/471,034, filed Sep. 9, 2021 Restriction Requirement dated Feb. 6, 2025.

U.S. Appl. No. 16/206,890, filed Nov. 30, 2018 Non-Final Office Action dated May 20, 2025.

(56) References Cited

OTHER PUBLICATIONS

U.S. Appl. No. 17/389,191, filed Jul. 29, 2021 Non-Final Office Action dated May 22, 2025.
U.S. Appl. No. 17/484,868, filed Sep. 24, 2021 Examiner's Answer dated Apr. 11, 2025.
U.S. Appl. No. 17/731,169, filed Apr. 27, 2022 Non-Final Office Action dated Jul. 3, 2025.

\* cited by examiner

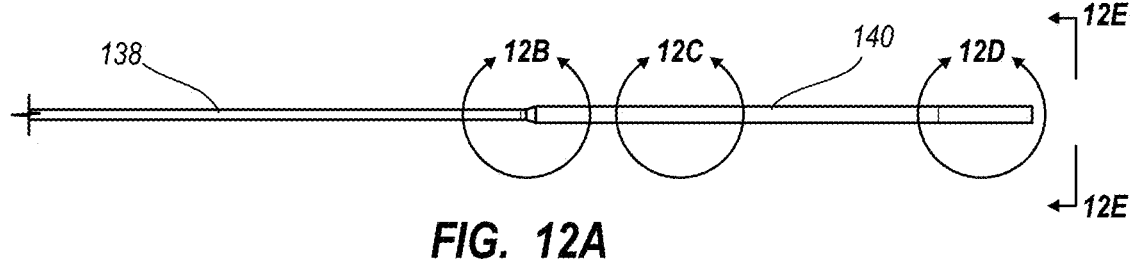
FIG. 12A
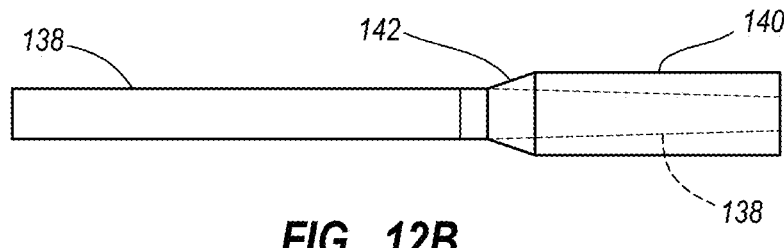
FIG. 12B
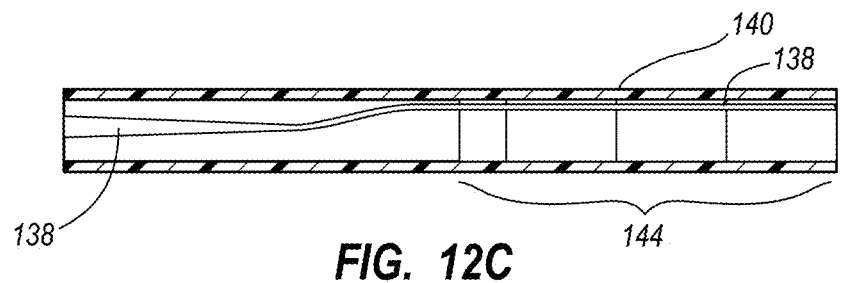
FIG. 12C
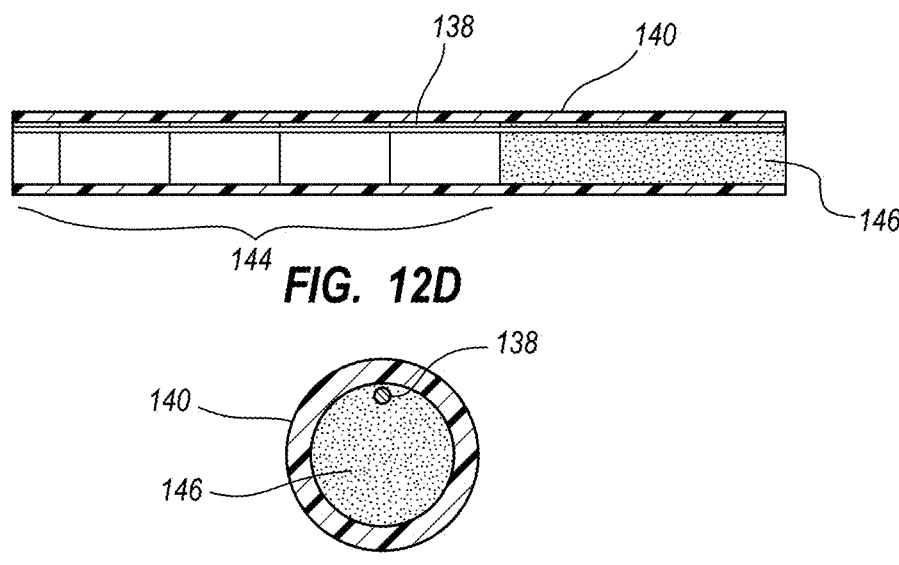
FIG. 12D
FIG. 12E

1314

1314A

1314

*1360*

*1360*

*1360*

*1360*

*1360*

*1360*

*1360*

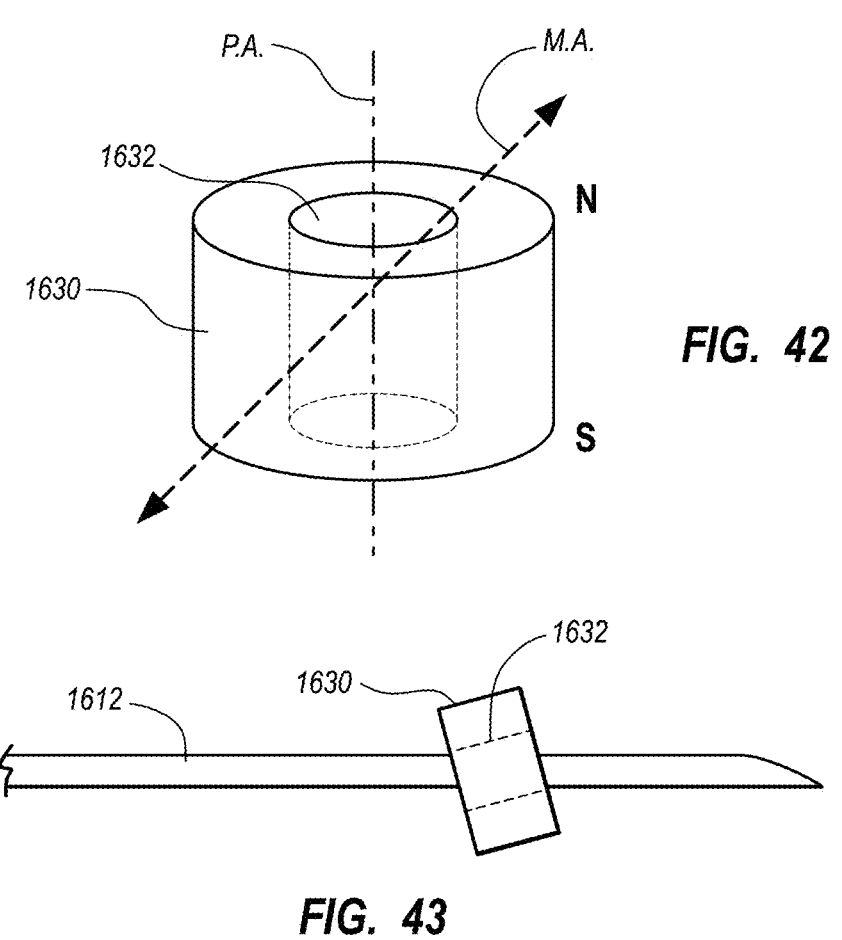
*FIG. 42*
*FIG. 43*
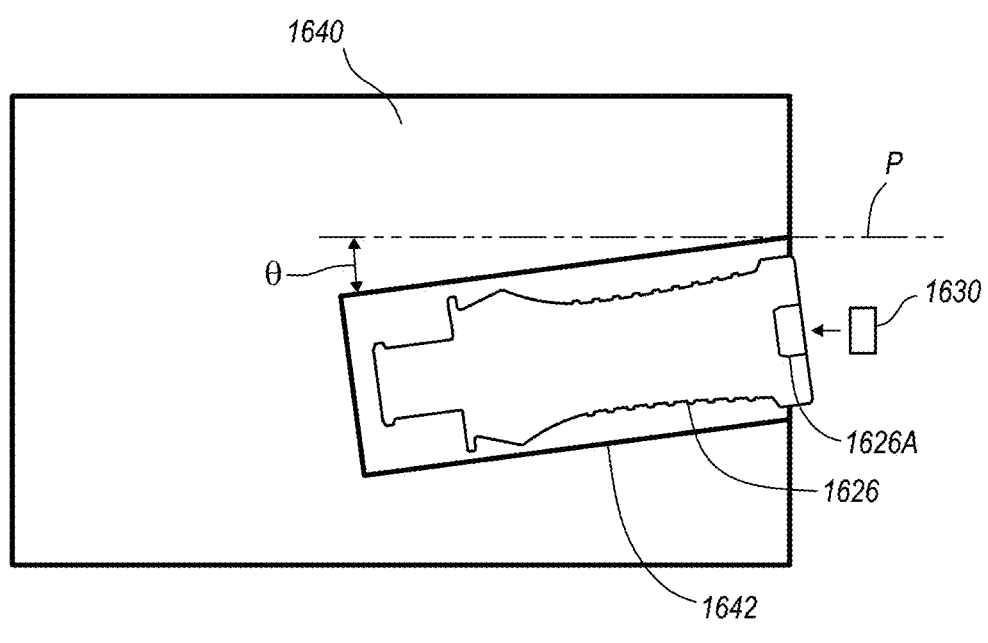
*FIG. 44*

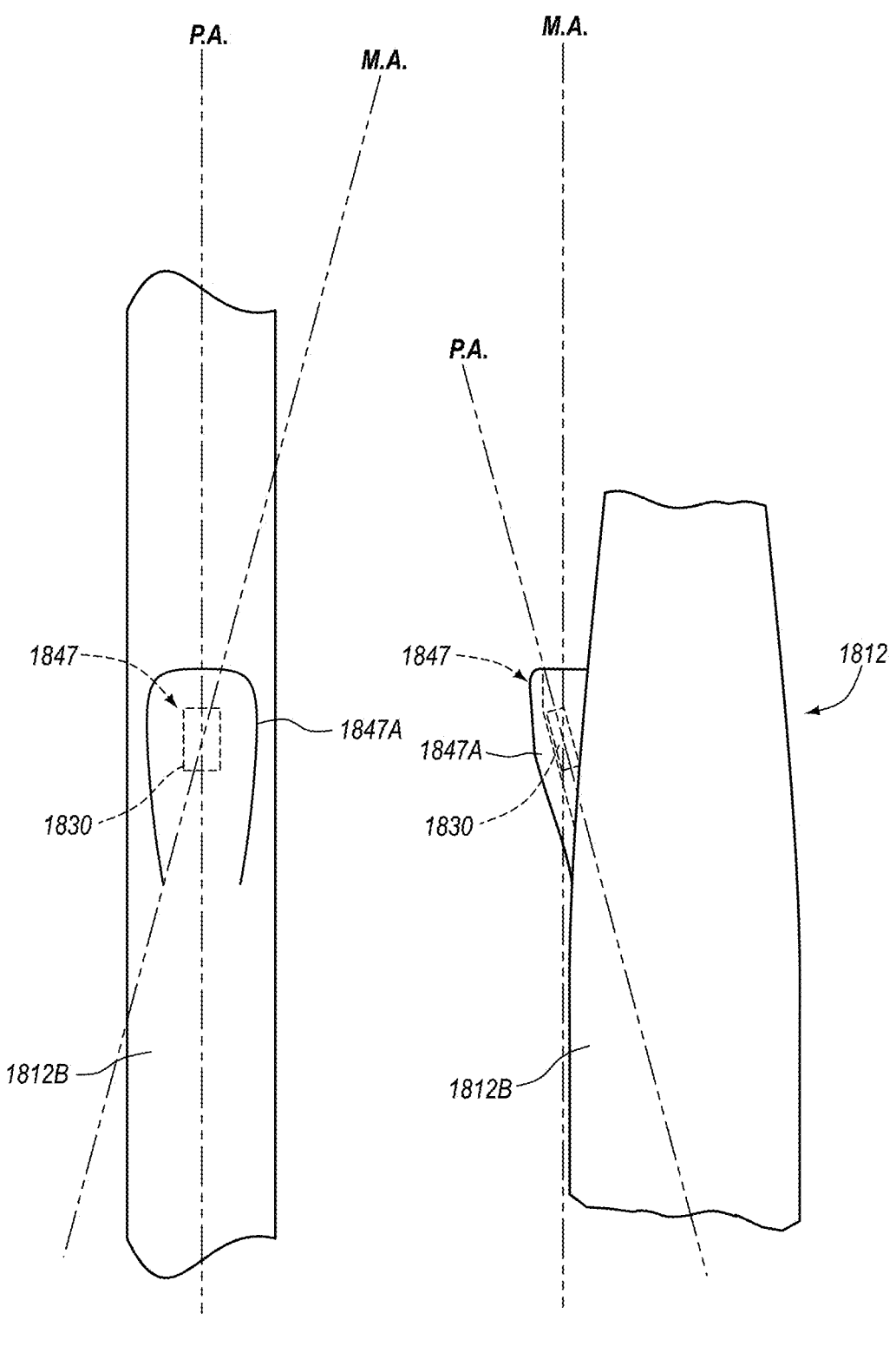
*FIG. 61A*              *FIG. 61B*

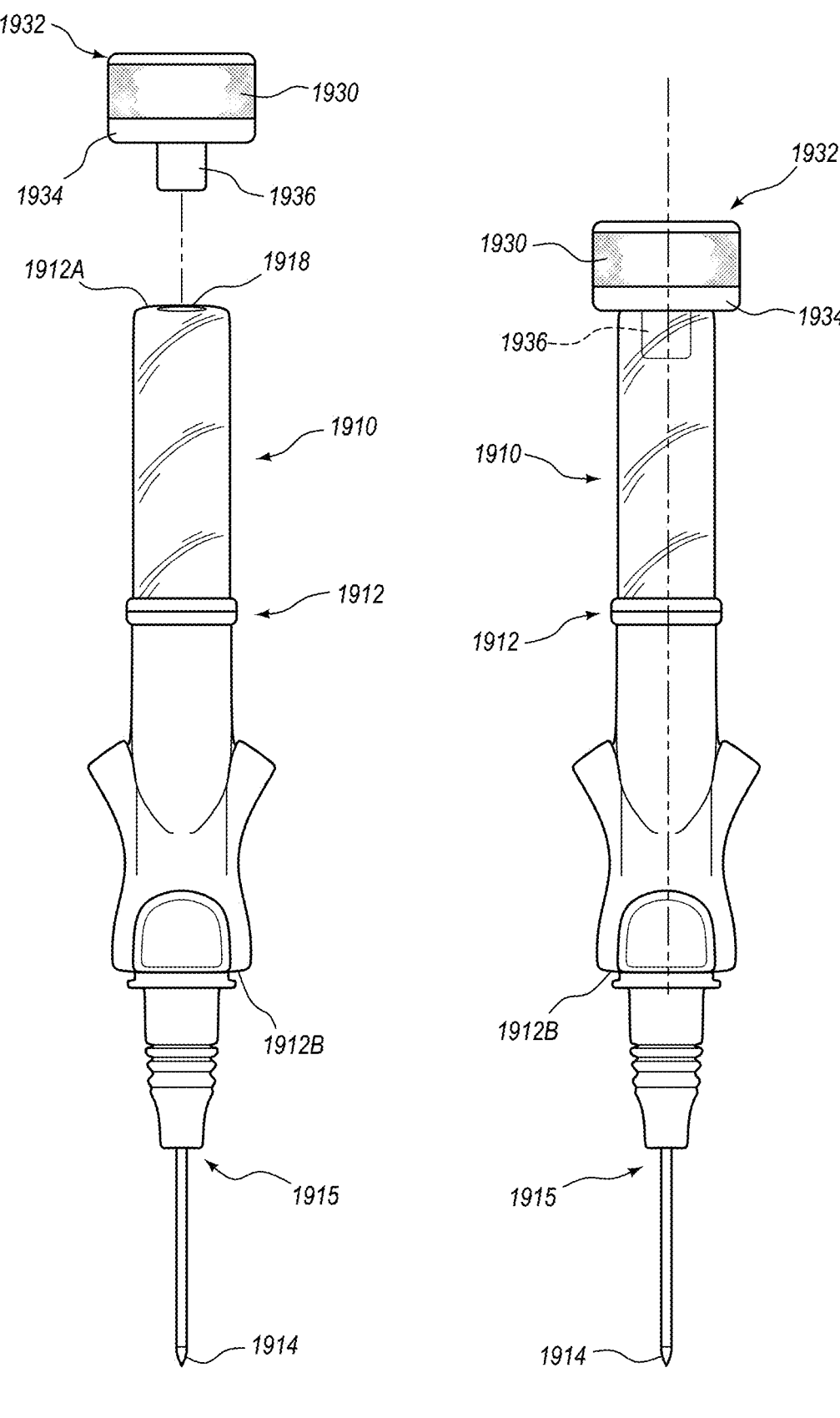
*FIG. 71A*                    *FIG. 71B*

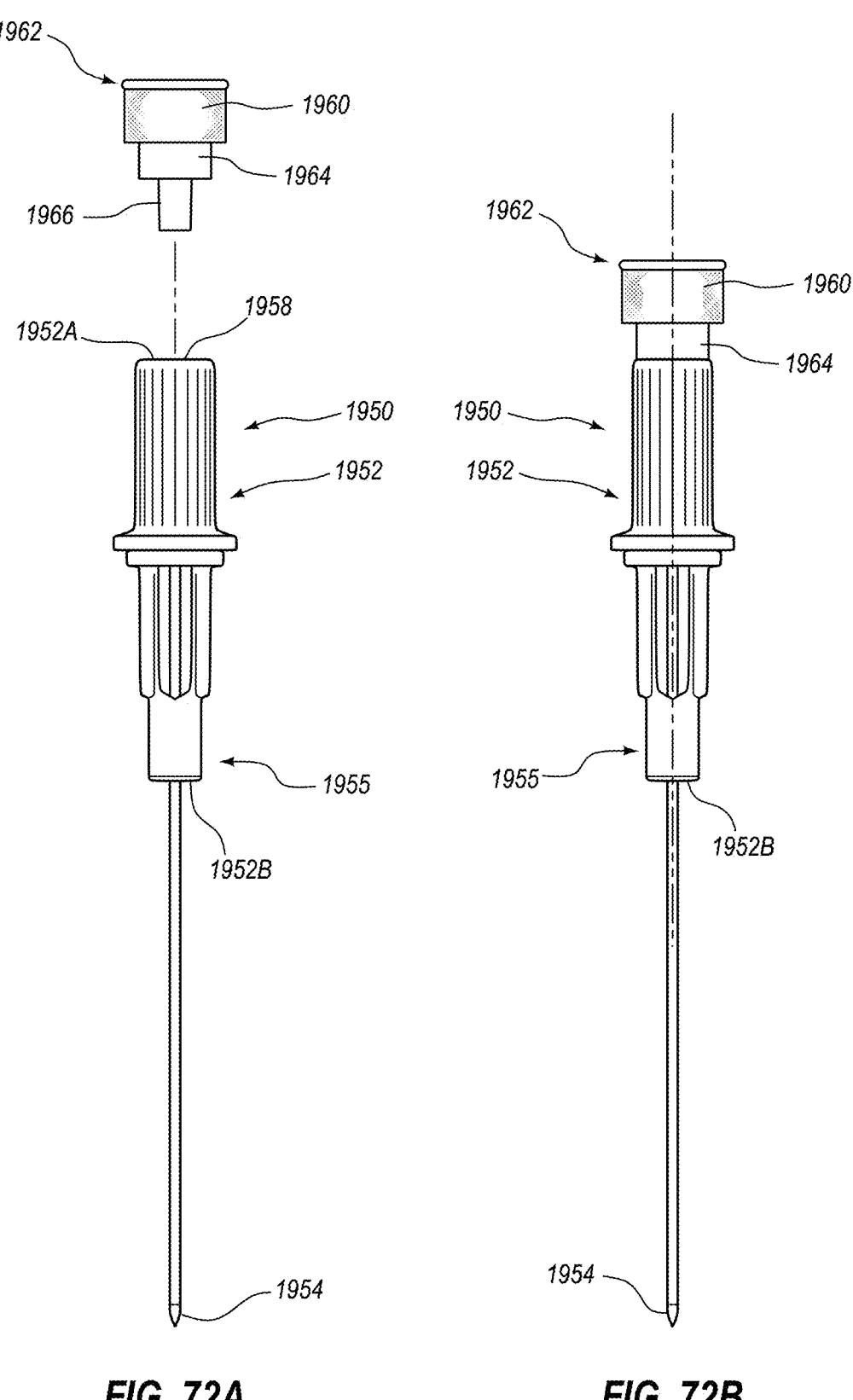
*FIG. 72A*                    *FIG. 72B*

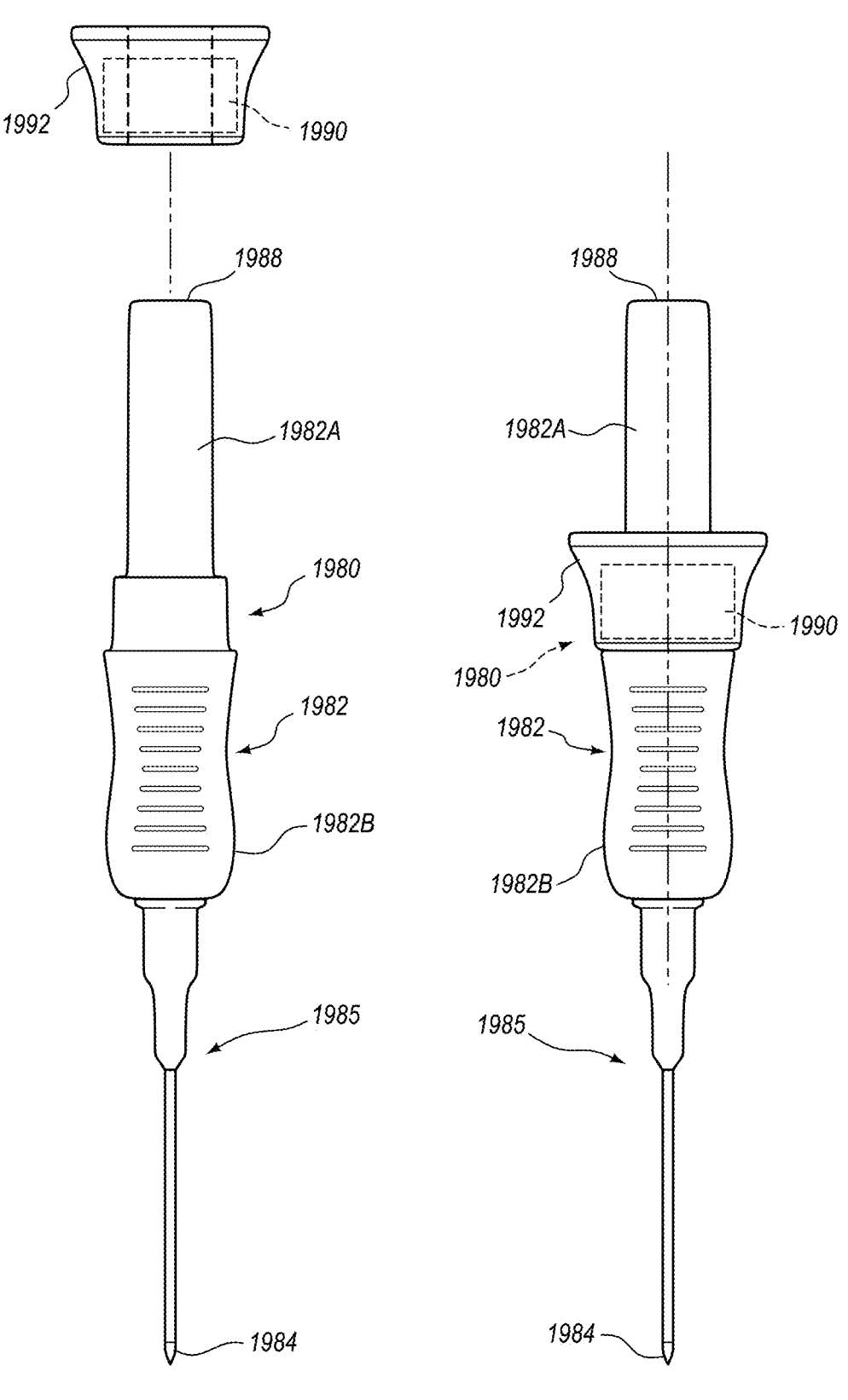
*FIG. 73A*          *FIG. 73B*

MAGNETIC ELEMENT-EQUIPPED NEEDLE ASSEMBLIES

CROSS-REFERENCE TO RELATED APPLICATIONS

This application is a division of U.S. patent application Ser. No. 14/054,700, filed Oct. 15, 2013, now U.S. Pat. No. 10,449,330, which claims the benefit of U.S. Provisional Application No. 61/715,769, filed Oct. 18, 2012, and which is a continuation-in-part of U.S. patent application Ser. No. 14/040,205, now U.S. Pat. No. 9,456,766, filed Sep. 27, 2013, which claims the benefit of the following three provisional applications: 1) U.S. Provisional Application No. 61/774,512, filed Mar. 7, 2013, 2) U.S. Provisional Application No. 61/709,877, filed Oct. 4, 2012, and 3) U.S. Provisional Application No. 61/707,782, filed Sep. 28, 2012, and which is a continuation-in-part of U.S. patent application Ser. No. 13/118,138, filed May 27, 2011, now U.S. Pat. No. 9,456,766, which is a continuation-in-part of U.S. patent application Ser. No. 13/118,033, filed May 27, 2011, now U.S. Pat. No. 9,554,716, which claims the benefit of U.S. Provisional Application No. 61/349,771, filed May 28, 2010, and which is a continuation-in-part of U.S. patent application Ser. No. 12/323,273, filed Nov. 25, 2008, now U.S. Pat. No. 8,388,541, which claims the benefit of the following five provisional applications: 1) U.S. Provisional Application No. 61/095,921, filed Sep. 10, 2008, 2) U.S. Provisional Application No. 61/095,451, filed Sep. 9, 2008, 3) U.S. Provisional Application No. 61/091,233, filed Aug. 22, 2008, 4) U.S. Provisional Application No. 61/045,944, filed Apr. 17, 2008, and 5) U.S. Provisional Application No. 60/990,242, filed Nov. 26, 2007. Each of the aforementioned applications is incorporated by reference in its entirety into this application.

BRIEF SUMMARY

Briefly summarized, embodiments of the present invention are directed to an integrated catheter placement system configured for accurately placing a catheter within the vasculature of a patient. The integrated system employs at least two modalities for improving catheter placement accuracy: 1) ultrasound-assisted guidance for introducing the catheter into the patient's vasculature; and 2) a tip location system ("TLS"), or magnetically-based (e.g., via permanent magnet(s) or electromagnet(s)) tracking of the catheter tip during its advancement through the vasculature to detect and facilitate correction of any tip malposition during such advancement.

In one embodiment, the integrated system comprises a system console including a control processor, a tip location sensor for temporary placement on a portion of a body of the patient, and an ultrasound probe. The tip location sensor senses a magnetic field of a stylet disposed in a lumen of the catheter when the catheter is disposed in the vasculature. The ultrasound probe ultrasonically images a portion of the vasculature prior to introduction of the catheter into the vasculature. In addition, the ultrasound probe includes user input controls for controlling use of the ultrasound probe in an ultrasound mode and use of the tip location sensor in a tip location mode.

In another embodiment, a third modality, i.e., ECG signal-based catheter tip guidance, is included in the system to enable guidance of the catheter tip to a desired position with respect to a node of the patient's heart from which the ECG signals originate.

In addition, embodiments of the present disclosure are also directed to a guidance system for assisting with the insertion of a needle or other medical component into the body of a patient. The guidance system utilizes ultrasound imaging or other suitable imaging technology.

In one embodiment, the guidance system comprises an imaging device including a probe for producing an image of an internal body portion target, such as a subcutaneous vessel, for instance. One or more sensors are included with the probe. The sensors sense a detectable characteristic related to the needle, such as a magnetic field of a magnet included with the needle.

The system includes a processor that uses data relating to the detectable characteristic sensed by the sensors to determine a position and/or orientation of the needle in three spatial dimensions. The system includes a display for depicting the position and/or orientation of the needle together with the image of the target.

In addition to magnet-based detection, other modalities for detecting the medical component are disclosed, including optically-based and electromagnetic signal-based systems.

In one embodiment, a stylet including one or more magnetic elements is removably inserted into the needle to enable tracking of the needle via detection of the magnetic elements by a sensor included with the ultrasound probe. In one embodiment, the sensor is a ring sensor disposed about a portion of the ultrasound probe. In another embodiment, the stylet can additionally include a strain sensor that detects bending of the needle during insertion into the patient. Feedback from the strain sensor can be input into the system and accounted for in order to more accurately depict needle location on the display.

In yet another embodiment, the magnetic element is configured as a donut-shaped passive magnet defining a hole through which the cannula of the needle passes. In yet another embodiment, a needle assembly including a hub, cannula, and magnetic element is also disclosed, wherein a magnetic axis of the magnetic element is configured to be coaxially aligned with the needle cannula. Fixtures and devices for aligning such a magnetic element are also disclosed. In yet other embodiments, various structures are disclosed for at least temporarily attaching a magnetic element to a needle assembly or other medical device.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 12A-12E are various views of portions of the stylet of FIG. 11;

FIG. 42 is a perspective view showing various aspects of a magnetic element according to one embodiment;

FIG. 43 is a side view of a needle cannula and magnetic element according to one embodiment;

FIG. 44 is a top view of a jig, needle hub, and magnetic element according to one embodiment;

US 12,685,839 B2

5

Figure 53A:
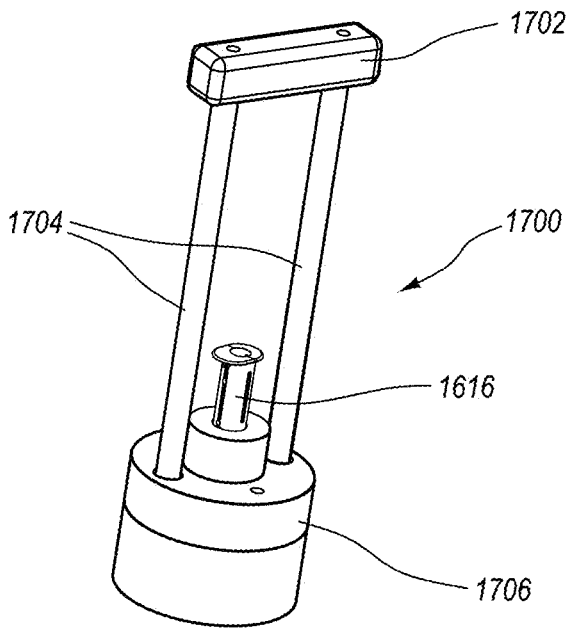
FIGS. 53A and 53B shows a fixture of the alignment coil assembly of FIGS. 52A and 52B.
Figure 53B:
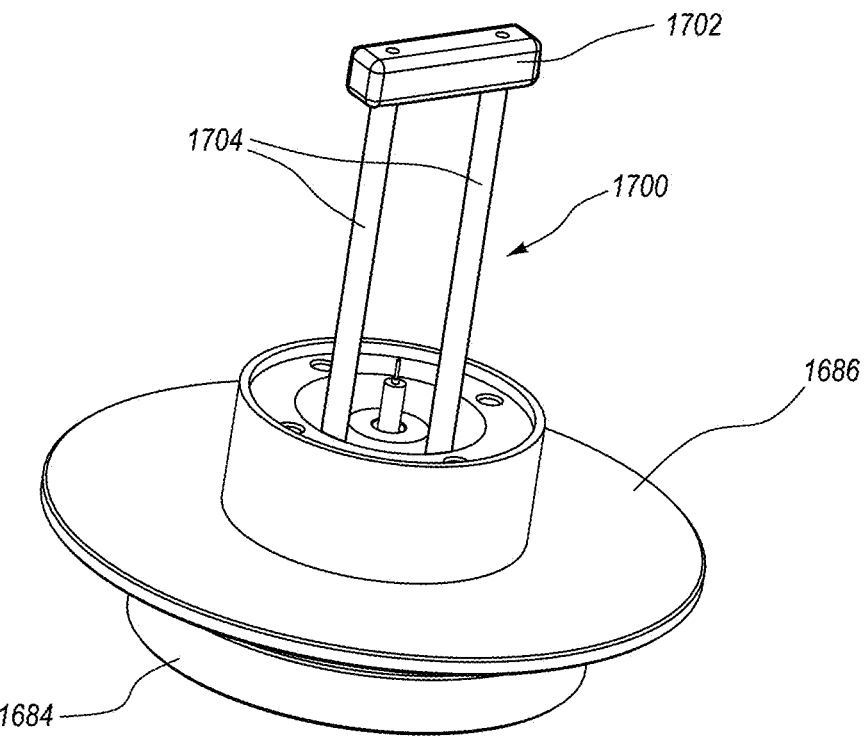
Figure 54A:
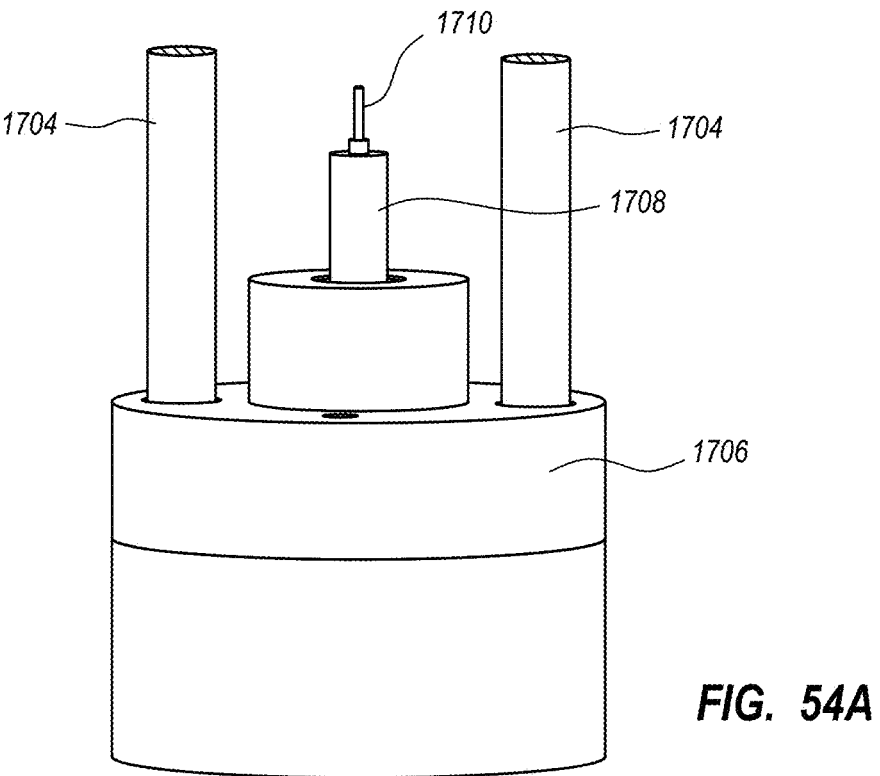
Figure 54B:
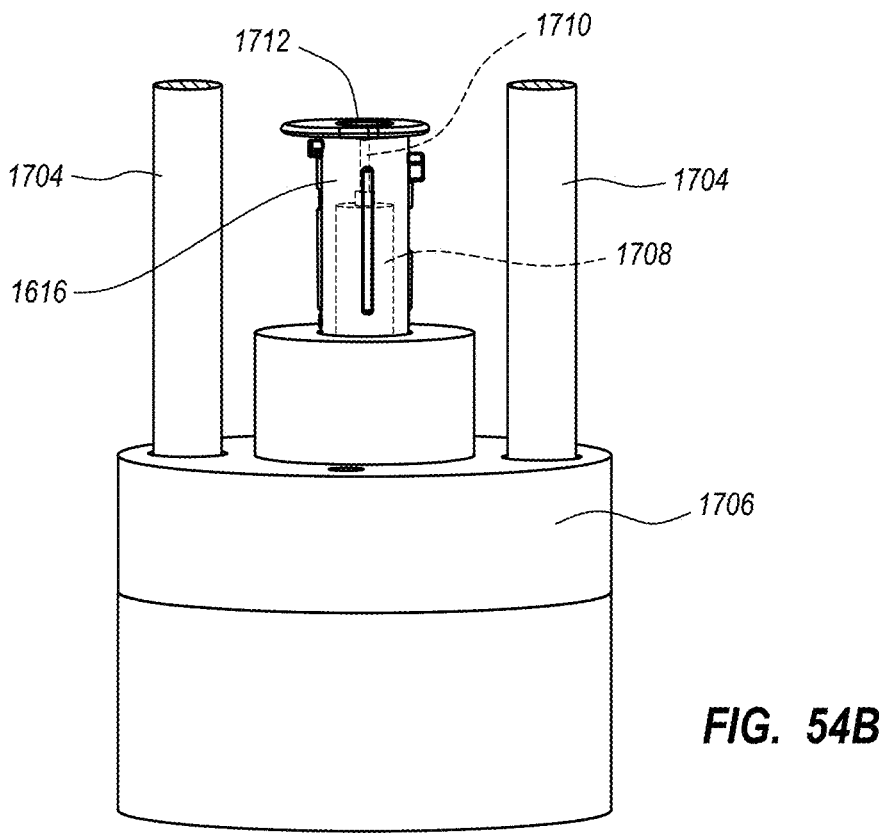
Figure 54C:
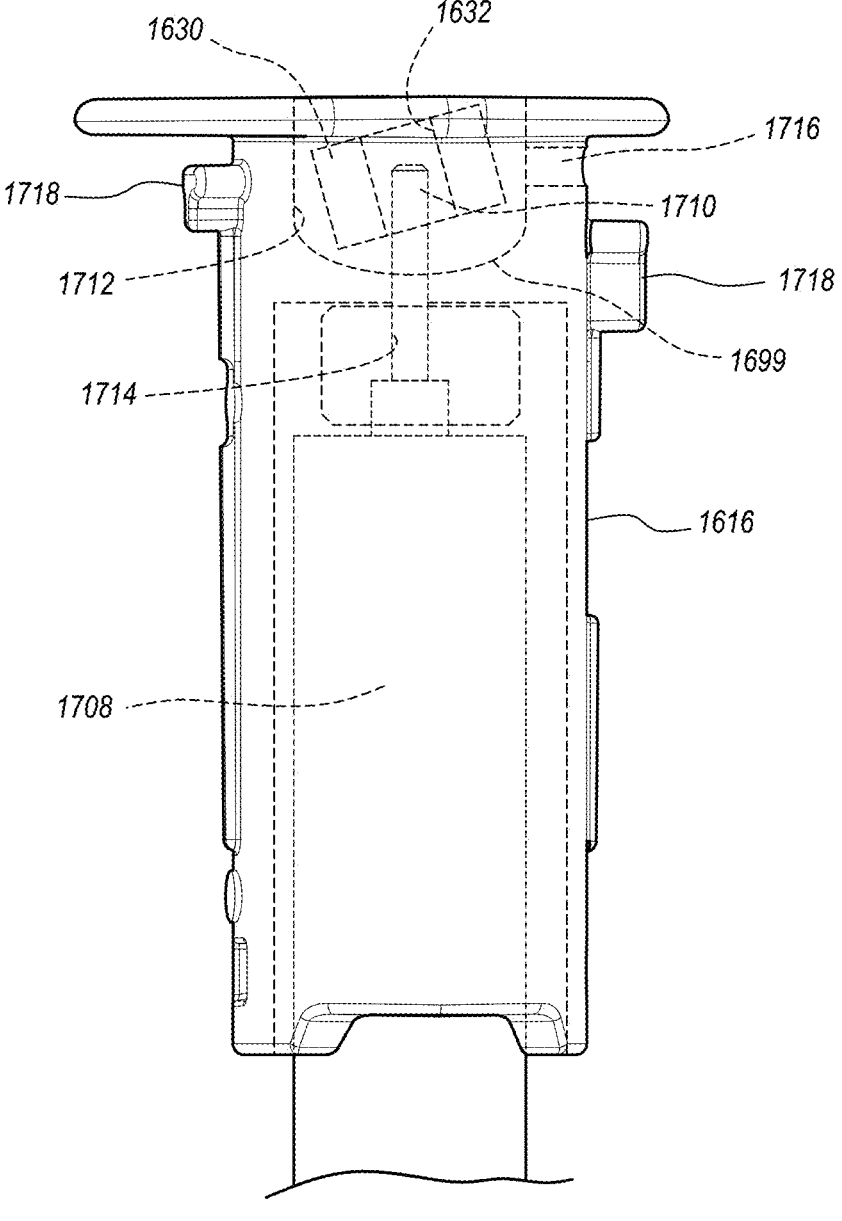
Figure 55A:
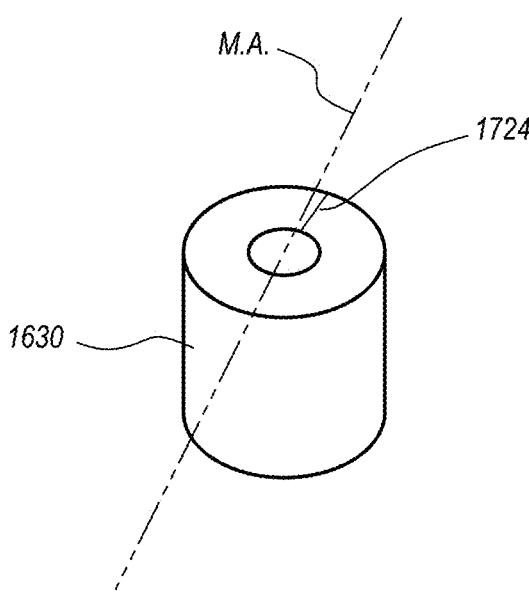
Figure 55B:
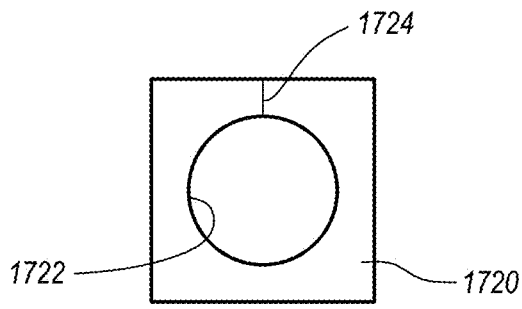
Figure 55C:
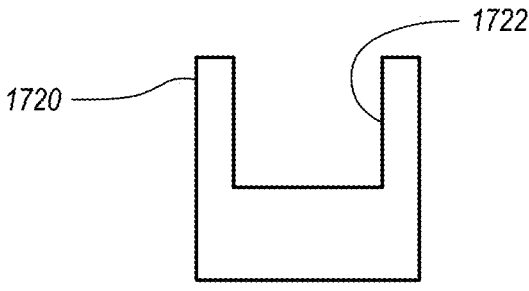
Figure 56:
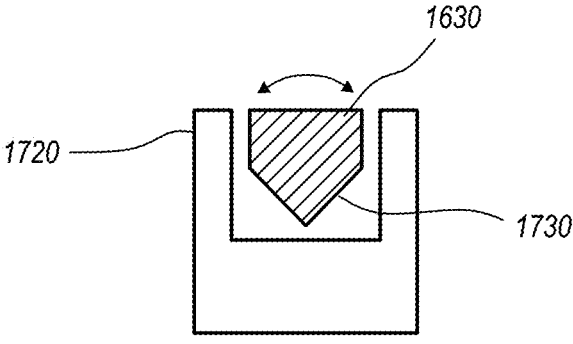
Figure 57:
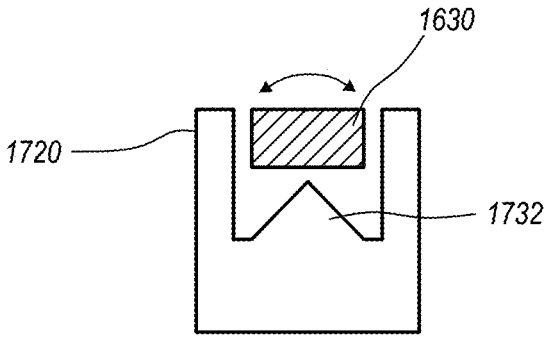
Figure 58:
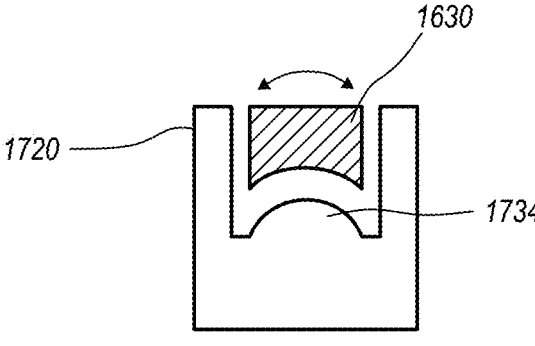
Figure 59:
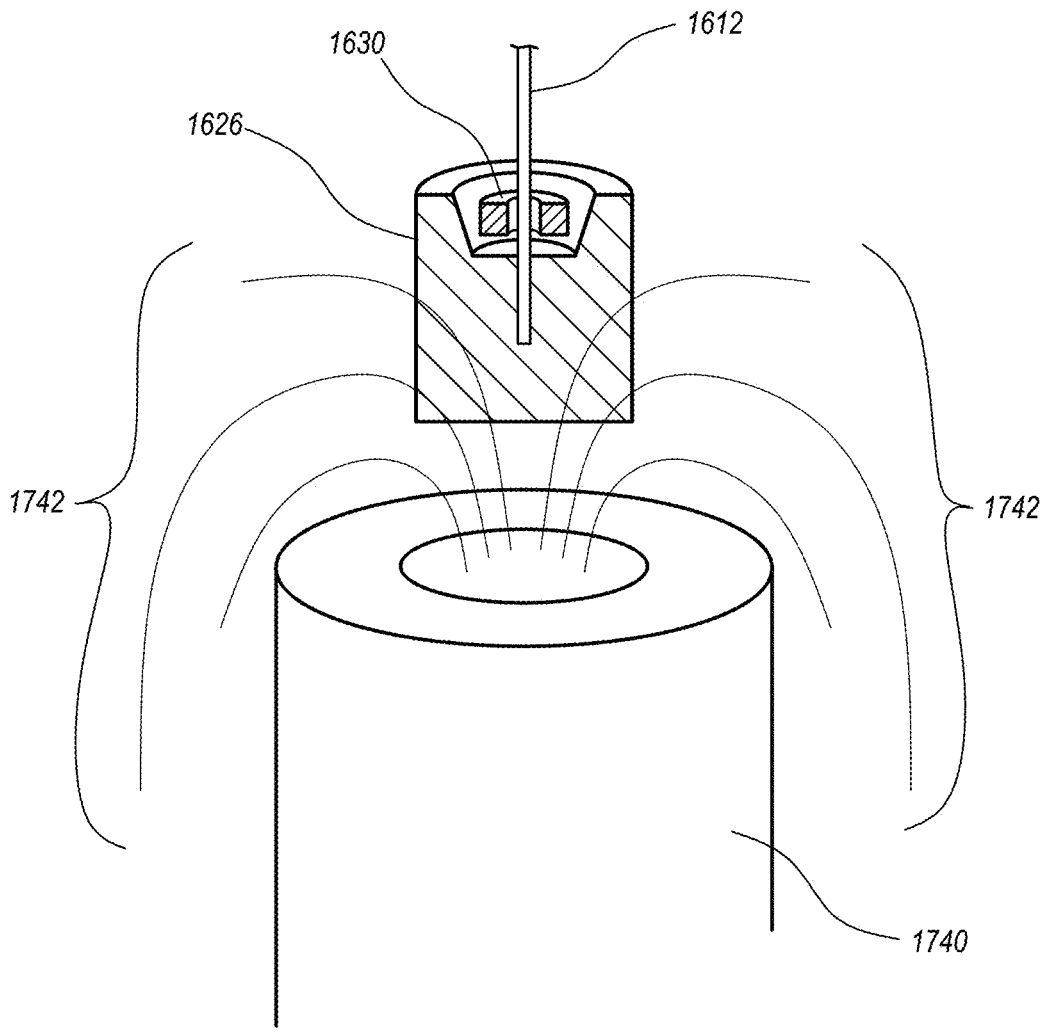
Figures 60A, 60B:
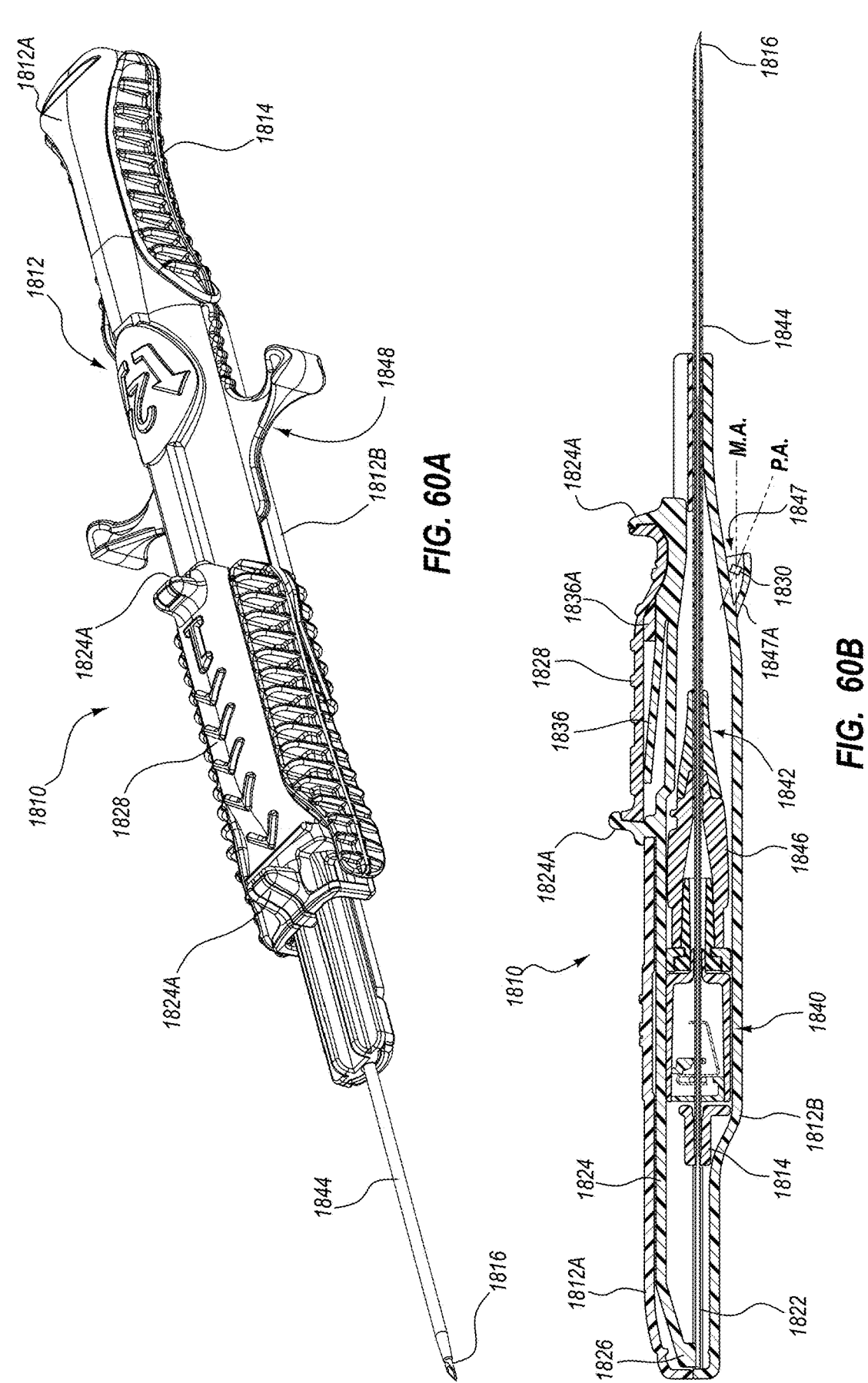
Figures 62, 63, 64:
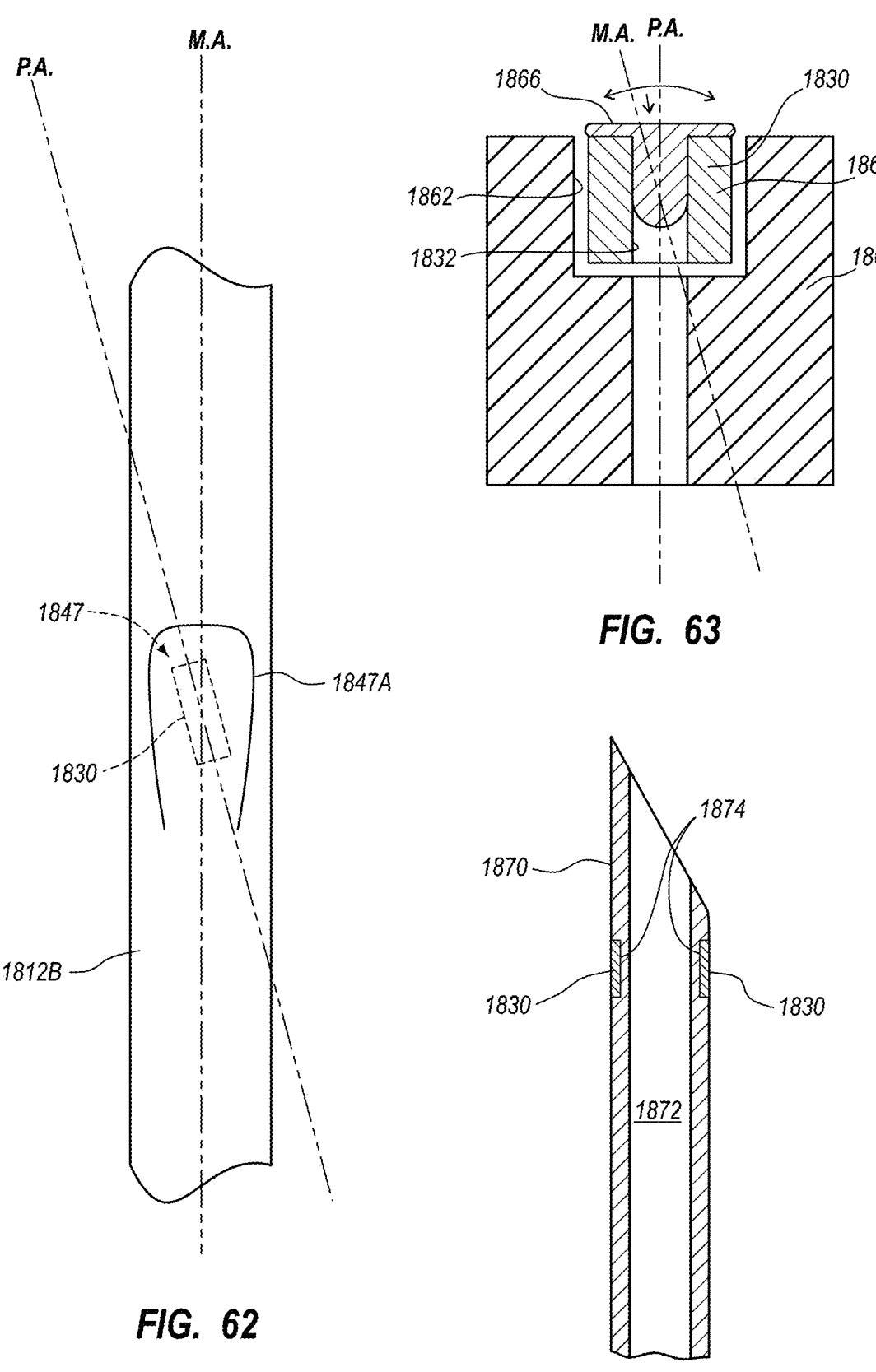
Figure 74A:
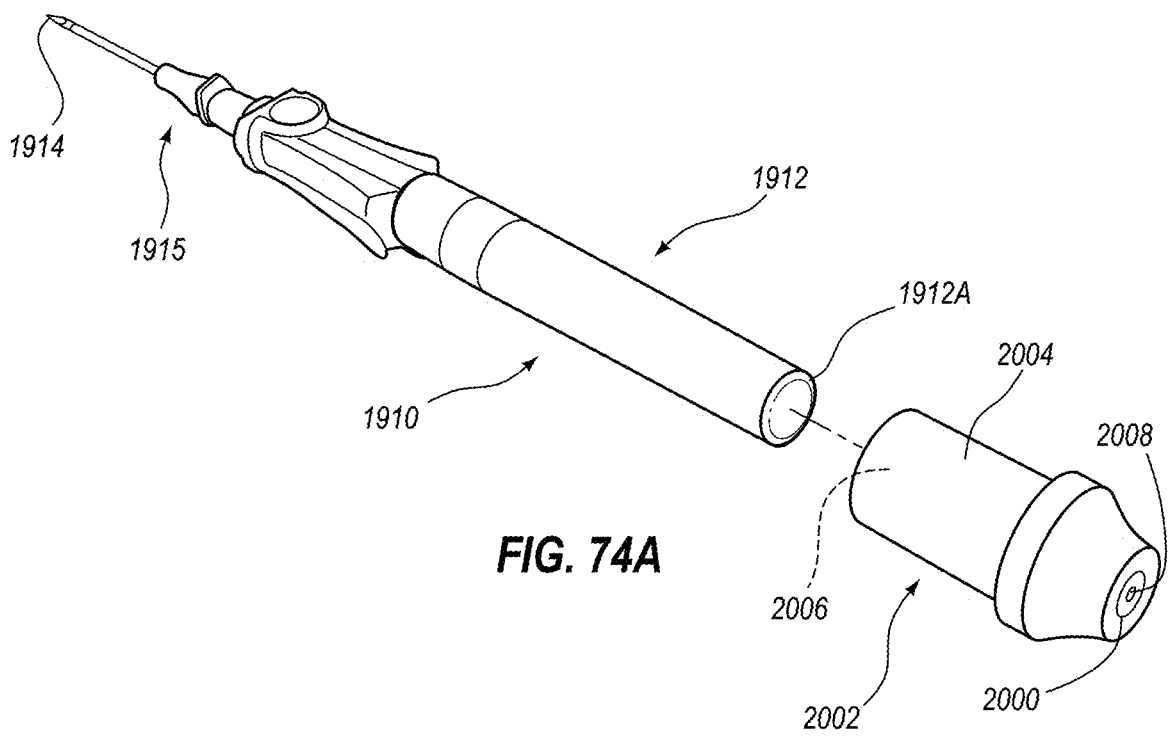
Figure 74B:
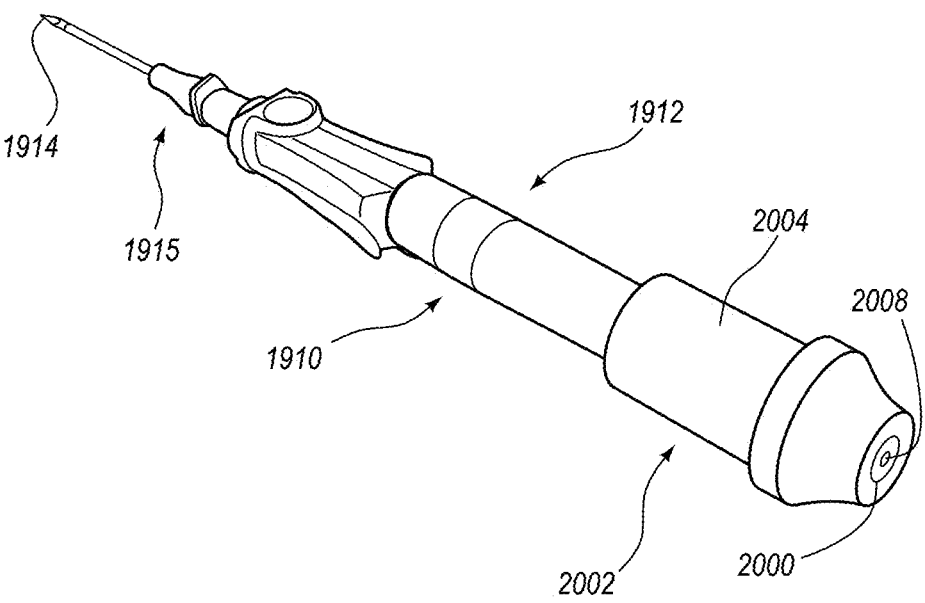
Figure 75:
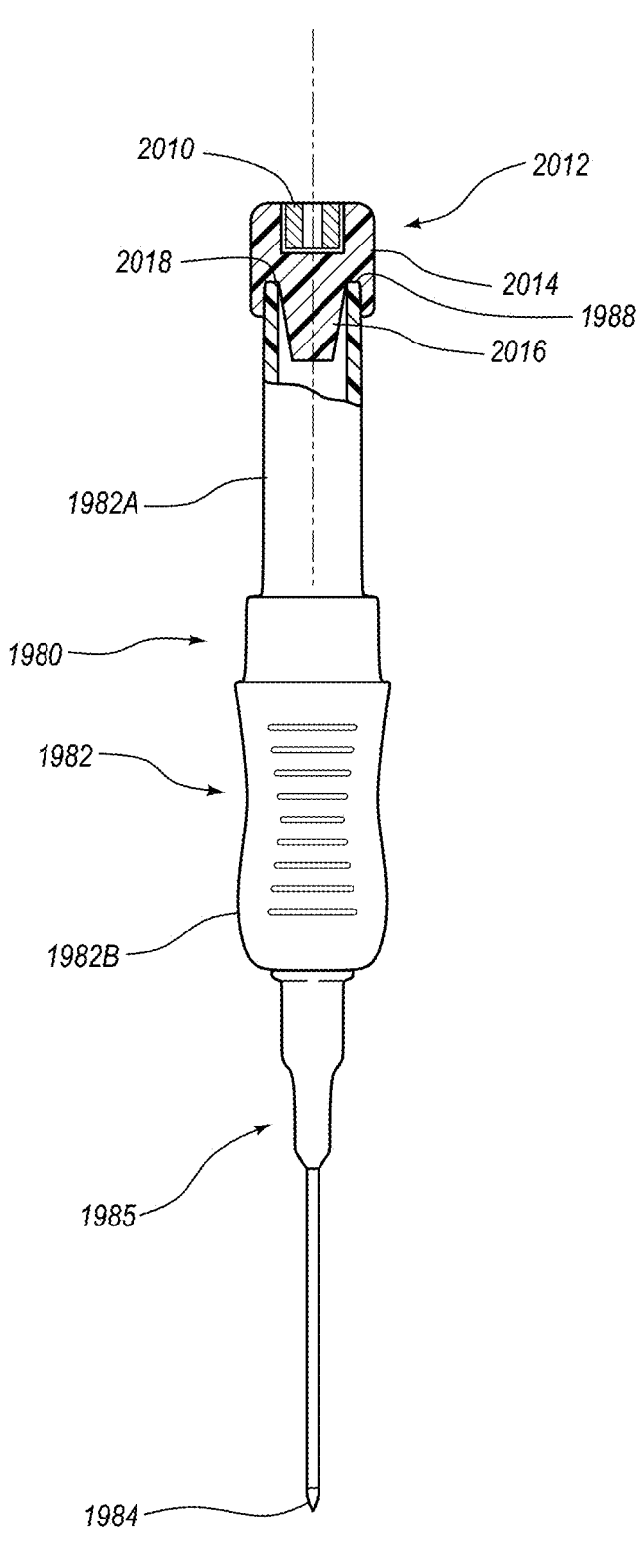

FIGS. 54A-54C shows various details of the fixture of FIGS. 53A and 53B according to one embodiment;

FIGS. 55A-55C shows various views of a magnetic element and cap according to one embodiment;

FIG. 56 shows a cap and magnetic element configuration according to one embodiment;

FIG. 57 shows a cap and magnetic element configuration according to one embodiment;

FIG. 58 shows a cap and magnetic element configuration according to one embodiment;

FIG. 59 shows details of a method for aligning a magnetic element in accordance with one embodiment;

FIGS. 60A and 60B show various views of a catheter insertion tool including a magnetic element according to one embodiment;

FIGS. 61A and 61B show various simplified views of the catheter insertion tool of FIGS. 60A and 60B;

FIG. 62 is a simplified bottom view of the catheter insertion tool of FIGS. 60A and 60B;

FIG. 63 is a cross sectional view of an alignment assembly for a magnetic element according to one embodiment;

FIG. 64 is a cross sectional view of a needle cannula including a magnetic element according to one embodiment;

FIGS. 65-70 show various needle assemblies including magnetic elements according to one embodiment;

FIGS. 71A and 71B show various views of a needle assembly including a magnetic element according to one embodiment;

FIGS. 72A and 72B show various views of a needle assembly including a magnetic element according to one embodiment;

FIGS. 73A and 73B show various views of a needle assembly including a magnetic element according to one embodiment;

FIGS. 74A and 74B show various views of a needle assembly including a cap and magnetic element according to one embodiment; and FIG. 75 is a side view of a needle assembly including a magnetic element according to one embodiment.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle placed within the body of a patient is considered a distal end of the needle, while the needle end remaining outside the body is a proximal end of the needle. Also, the words "including," "has," and "having," as used herein, including the claims, shall have the same meaning as the word "comprising."

I. Assisted Catheter Placement

Embodiments of the present invention are generally directed to a catheter placement system configured for accurately placing a catheter within the vasculature of a patient. In one embodiment, the catheter placement system employs at least two modalities for improving catheter placement accuracy: 1) ultrasound-assisted guidance for introducing the catheter into the patient's vasculature; and 2) a tip location/navigation system ("TLS"), or magnetically-based tracking of the catheter tip during its advancement through the tortuous vasculature path to detect and facilitate correction of any tip malposition during such advancement. The ultrasound guidance and tip location features of the present system according to one embodiment are integrated into a single device for use by a clinician placing the catheter. Integration of these two modalities into a single device simplifies the catheter placement process and results in relatively faster catheter placements. For instance, the integrated catheter placement system enables ultrasound and TLS activities to be viewed from a single display of the integrated system. Also, controls located on an ultrasound probe of the integrated device, which probe is maintained within the sterile field of the patient during catheter placement, can be used to control functionality of the system, thus precluding the need for a clinician to reach out of the sterile field in order to control the system.

In another embodiment, a third modality, i.e., ECG signal-based catheter tip guidance, is included in the integrated system to enable guidance of the catheter tip to a desired position with respect to a node of the patient's heart from which the ECG signals originate. Such ECG-based positional assistance is also referred to herein as "tip confirmation."

Combination of the three modalities above according to one embodiment enables the catheter placement system to facilitate catheter placement within the patient's vasculature with a relatively high level of accuracy, i.e., placement of the distal tip of the catheter in a predetermined and desired position. Moreover, because of the ECG-based guidance of the catheter tip, correct tip placement may be confirmed without the need for a confirmatory X-ray. This, in turn, reduces the patient's exposure to potentially harmful x-rays, the cost and time involved in transporting the patient to and from the x-ray department, costly and inconvenient catheter repositioning procedures, etc.

Figures 1, 2:
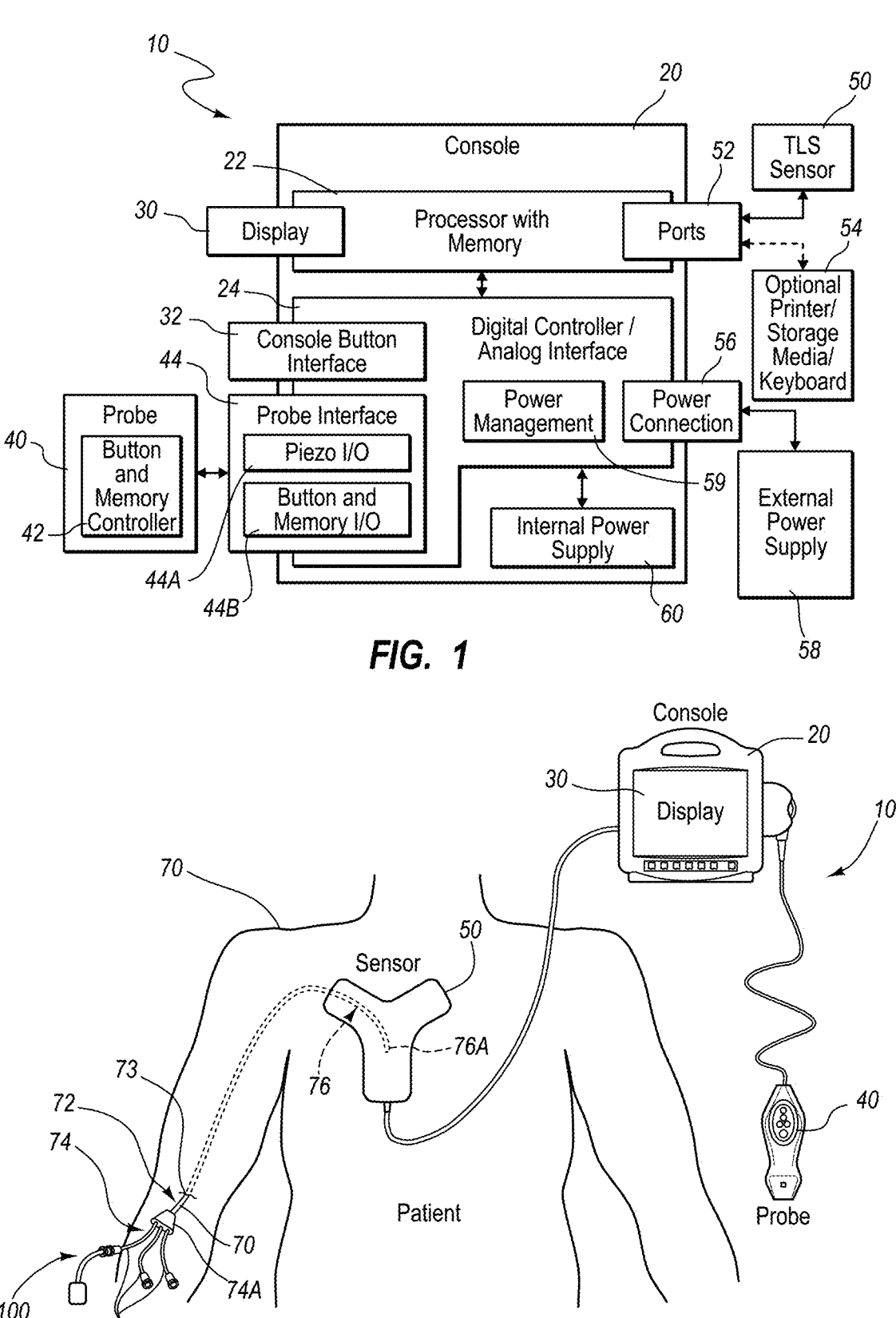
FIG. 1 is a block diagram depicting various elements of an integrated system for intravascular placement of a catheter, according to one example embodiment of the present invention.
FIG. 2 is a simplified view of a patient and a catheter being inserted therein with assistance of the integrated system of FIG. 1.

Reference is first made to FIGS. 1 and 2 which depict various components of a catheter placement system ("system"), generally designated at 10, configured in accordance with one example embodiment of the present invention. As shown, the system 10 generally includes a console 20, display 30, probe 40, and sensor 50, each of which is described in further detail below.

FIG. 2 shows the general relation of these components to a patient 70 during a procedure to place a catheter 72 into the patient vasculature through a skin insertion site 73. FIG. 2 shows that the catheter 72 generally includes a proximal portion 74 that remains exterior to the patient and a distal potion 76 that resides within the patient vasculature after placement is complete. The system 10 is employed to ultimately position a distal tip 76A of the catheter 72 in a desired position within the patient vasculature. In one embodiment, the desired position for the catheter distal tip 76A is proximate the patient's heart, such as in the lower one-third ($\frac{1}{3}^{rd}$) portion of the Superior Vena Cava ("SVC"). Of course, the system 10 can be employed to place the catheter distal tip in other locations. The catheter proximal portion 74 further includes a hub 74A that provides fluid communication between the one or more lumens of the catheter 72 and one or more extension legs 74B extending proximally from the hub.

Figure 8A:
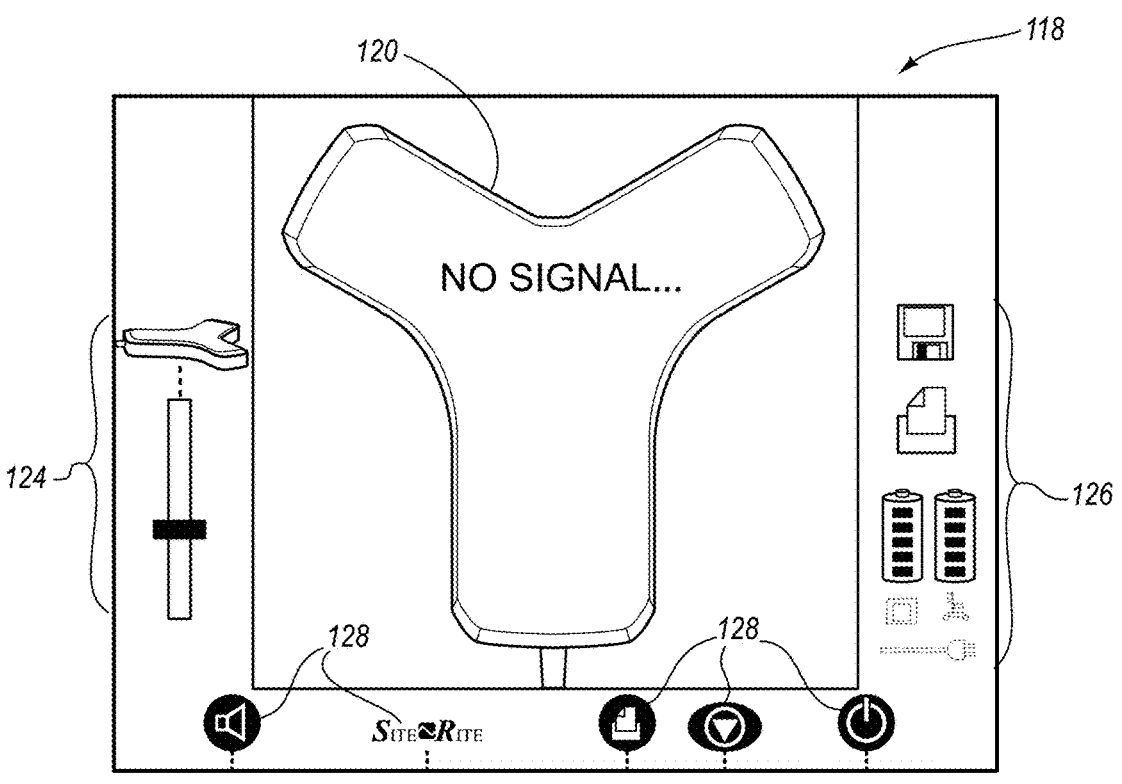
FIGS. 8A-8C are screenshots of images depicted on a display of the integrated system of FIG. 1 during catheter tip placement procedures.
Figure 8B:
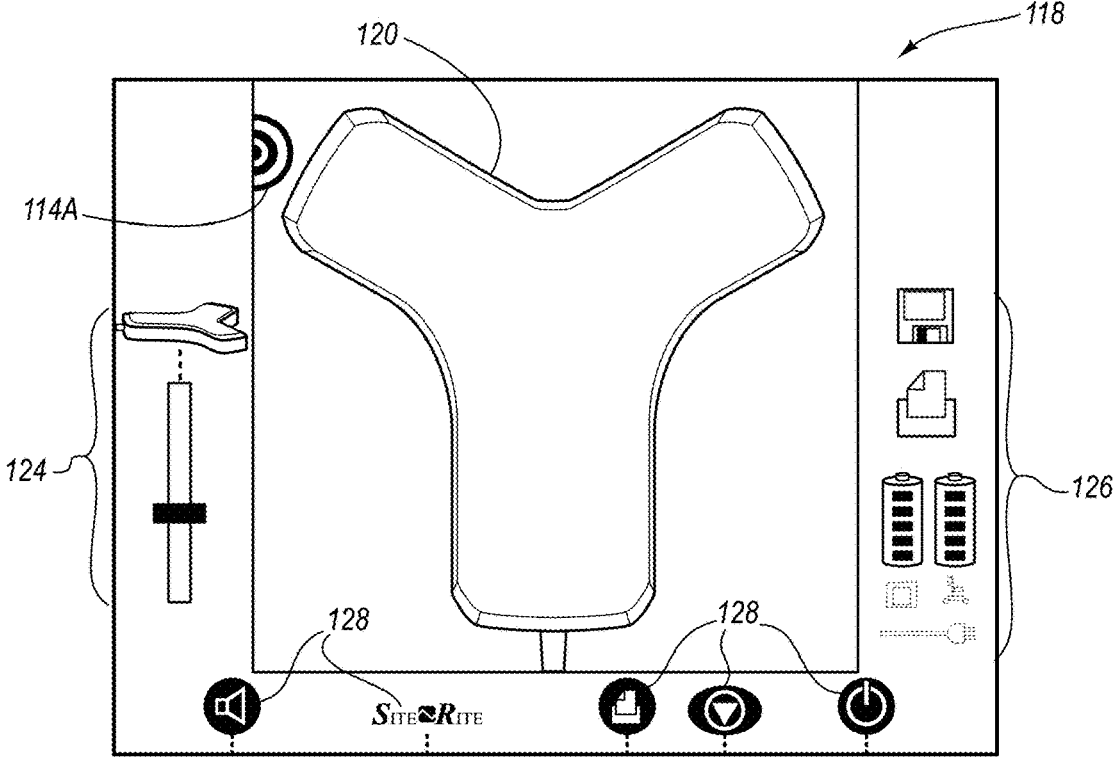
Figures 8C, 9:
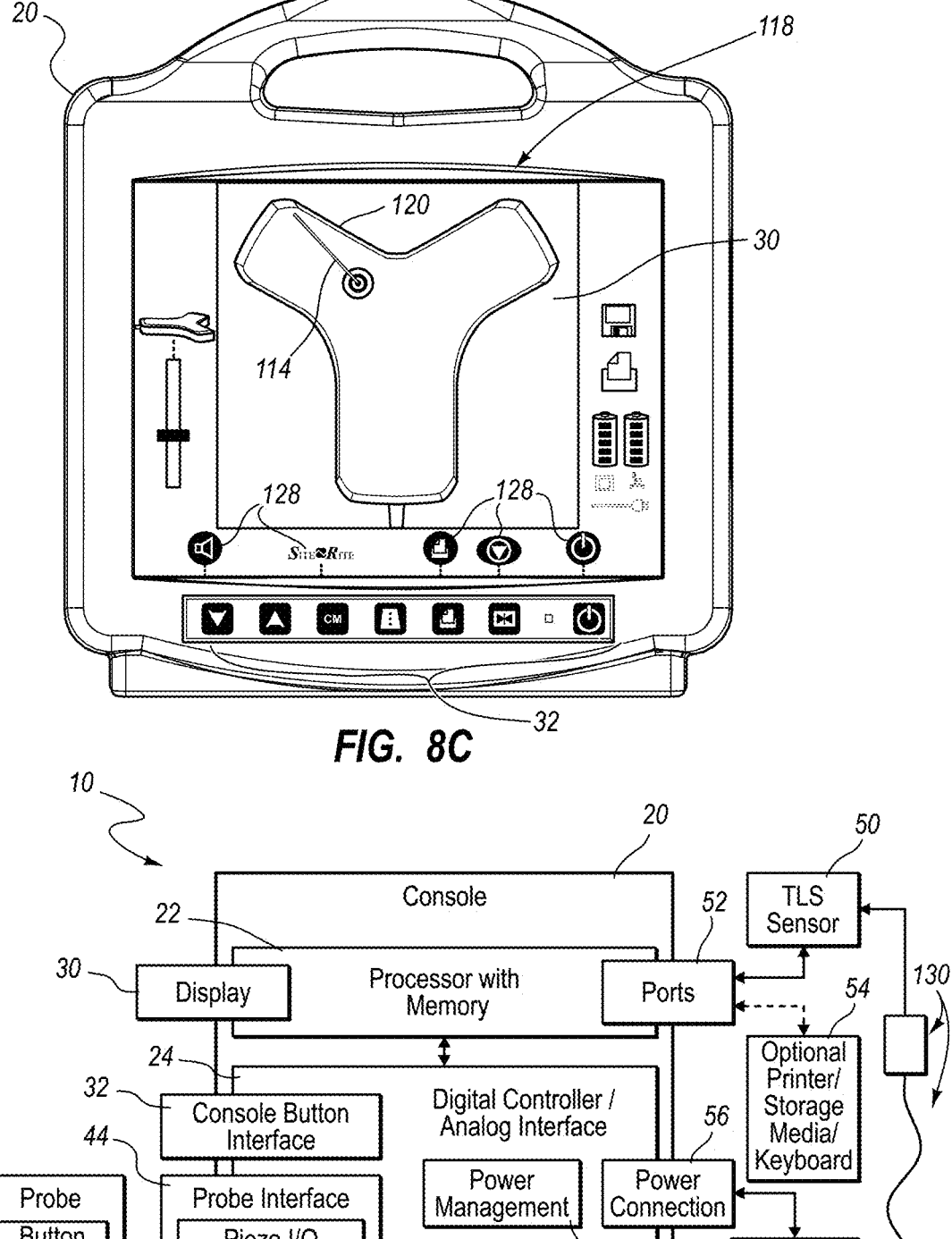
FIG. 9 is a block diagram depicting various elements of an integrated system for intravascular placement of a catheter, according to another example embodiment of the present invention.

An example implementation of the console 20 is shown in FIG. 8C, though it is appreciated that the console can take one of a variety of forms. A processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, sensor 50, and other system components.

The system 10 further includes ports 52 for connection with the sensor 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal battery 60 can also be employed, either with or exclusive of an external power supply. Power management circuitry 59 is included with the digital controller/analog interface 24 of the console to regulate power use and distribution.

The display 30 in the present embodiment is integrated into the console 20 and is used to display information to the clinician during the catheter placement procedure. In another embodiment, the display may be separate from the console. As will be seen, the content depicted by the display 30 changes according to which mode the catheter placement system is in: US, TLS, or in other embodiments, ECG tip confirmation. In one embodiment, a console button interface 32 (see FIGS. 1, 8C) and buttons included on the probe 40 can be used to immediately call up a desired mode to the display 30 by the clinician to assist in the placement procedure. In one embodiment, information from multiple modes, such as TLS and ECG, may be displayed simultaneously, such as in FIG. 17. Thus, the single display 30 of the system console 20 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In one embodiment, the display 30 is an LCD device.

Figure 3A:
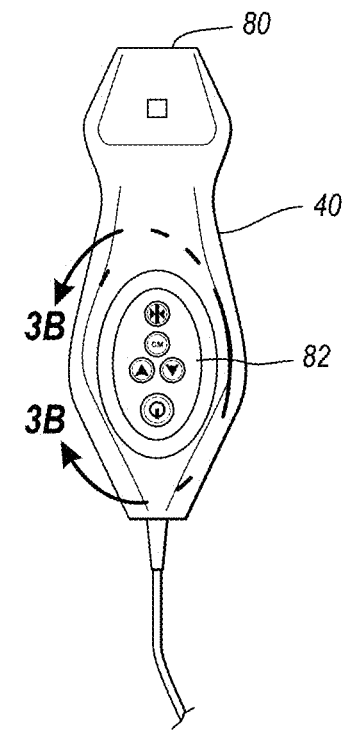
FIGS. 3A and 3B are views of a probe of the integrated system of FIG. 1.
Figure 3B:
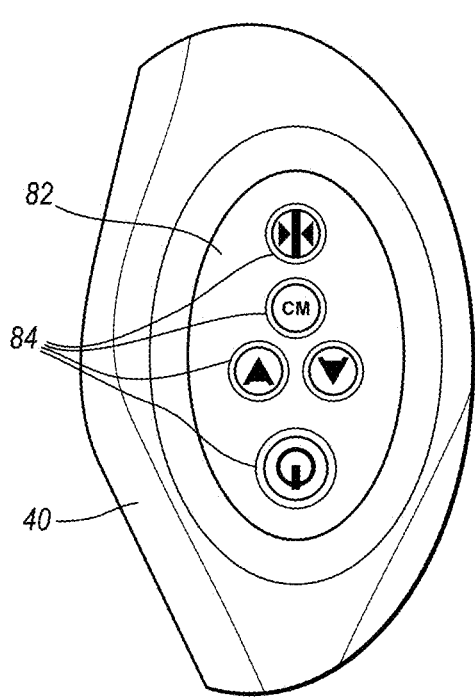

FIGS. 3A and 3B depict features of the probe 40 according to one embodiment. The probe 40 is employed in connection with the first modality mentioned above, i.e., ultrasound ("US")-based visualization of a vessel, such as a vein, in preparation for insertion of the catheter 72 into the vasculature. Such visualization gives real time ultrasound guidance for introducing the catheter into the vasculature of the patient and assists in reducing complications typically associated with such introduction, including inadvertent arterial puncture, hematoma, pneumothorax, etc.

The handheld probe 40 includes a head 80 that houses a piezoelectric array for producing ultrasonic pulses and for receiving echoes thereof after reflection by the patient's body when the head is placed against the patient's skin proximate the prospective insertion site 73 (FIG. 2). The probe 40 further includes a plurality of control buttons 84, which can be included on a button pad 82. In the present embodiment, the modality of the system 10 can be controlled by the control buttons 84, thus eliminating the need for the clinician to reach out of the sterile field, which is established about the patient insertion site prior to catheter placement, to change modes via use of the console button interface 32.

As such, in one embodiment a clinician employs the first (US) modality to determine a suitable insertion site and establish vascular access, such as with a needle or introducer, then with the catheter. The clinician can then seamlessly switch, via button pushes on the probe button pad 82, to the second (TLS) modality without having to reach out of the sterile field. The TLS mode can then be used to assist in advancement of the catheter 72 through the vasculature toward an intended destination.

FIG. 1 shows that the probe 40 further includes button and memory controller 42 for governing button and probe operation. The button and memory controller 42 can include non-volatile memory, such as EEPROM, in one embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

Figure 4:
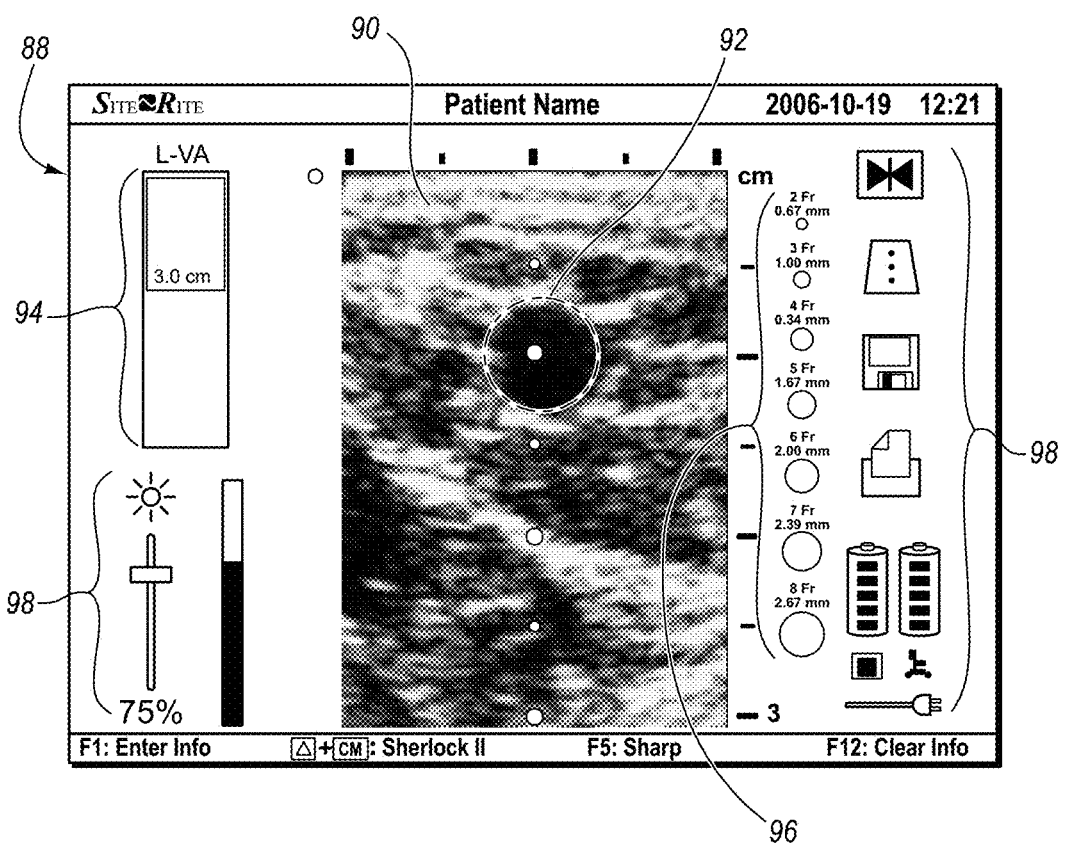
FIG. 4 is a screenshot of an ultrasound image as depicted on a display of the integrated system of FIG. 1.

FIG. 4 shows an example screenshot 88 as depicted on the display 30 while the system 10 is in its first ultrasound modality. An image 90 of a subcutaneous region of the patient 70 is shown, depicting a cross section of a vein 92. The image 90 is produced by operation of the piezoelectric array of the probe 40. also included on the display screenshot 88 is a depth scale indicator 94, providing information regarding the depth of the image 90 below the patient's skin, a lumen size scale 96 that provides information as to the size of the vein 92 relative to standard catheter lumen sizes, and other indicia 98 that provide information regarding status of the system 10 or possible actions to be taken, e.g., freeze frame, image templates, data save, image print, power status, image brightness, etc.

Note that while a vein is depicted in the image 90, other body lumens or portions can be imaged in other embodiments. Note that the US mode shown in FIG. 4 can be simultaneously depicted on the display 30 with other modes, such as the TLS mode, if desired. In addition to the visual display 30, aural information, such as beeps, tones, etc., can also be employed by the system 10 to assist the clinician during catheter placement. Moreover, the buttons included on the probe 40 and the console button interface 32 can be configured in a variety of ways, including the use of user input controls in addition to buttons, such as slide switches, toggle switches, electronic or touch-sensitive pads, etc. Additionally, both US and TLS activities can occur simultaneously or exclusively during use of the system 10.

As just described, the handheld ultrasound probe 40 is employed as part of the integrated catheter placement system 10 to enable US visualization of the peripheral vasculature of a patient in preparation for transcutaneous introduction of the catheter. In the present example embodiment, however, the probe is also employed to control functionality of the TLS portion, or second modality, of the system 10 when navigating the catheter toward its desired destination within the vasculature as described below. Again, as the probe 40 is used within the sterile field of the patient, this feature enables TLS functionality to be controlled entirely from within the sterile field. Thus the probe 40 is a dual-purpose device, enabling convenient control of both US and TLS functionality of the system 10 from the sterile field. In one embodiment, the probe can also be employed to control some or all ECG-related functionality, or third modality, of the catheter placement system 10, as described further below.

The catheter placement system 10 further includes the second modality mentioned above, i.e., the magnetically-based catheter TLS, or tip location system. The TLS enables the clinician to quickly locate and confirm the position and/or orientation of the catheter 72, such as a peripherally-inserted central catheter ("PICC"), central venous catheter ("CVC"), or other suitable catheter, during initial placement into and advancement through the vasculature of the patient 70. Specifically, the TLS modality detects a magnetic field generated by a magnetic element-equipped tip location stylet, which is pre-loaded in one embodiment into a longitudinally defined lumen of the catheter 72, thus enabling the clinician to ascertain the general location and orientation of the catheter tip within the patient body. In one embodiment, the magnetic assembly can be tracked using the teachings of one or more of the following U.S. Pat. Nos. 5,775,322; 5,879,297; 6,129,668; 6,216,028; and 6,263,230. The contents of the afore-mentioned U.S. patents are incorporated herein by reference in their entireties. The TLS also displays the direction in which the catheter tip is pointing, thus further assisting accurate catheter placement. The TLS further assists the clinician in determining when a malposition of the catheter tip has occurred, such as in the case where the tip has deviated from a desired venous path into another vein.

Figure 5:
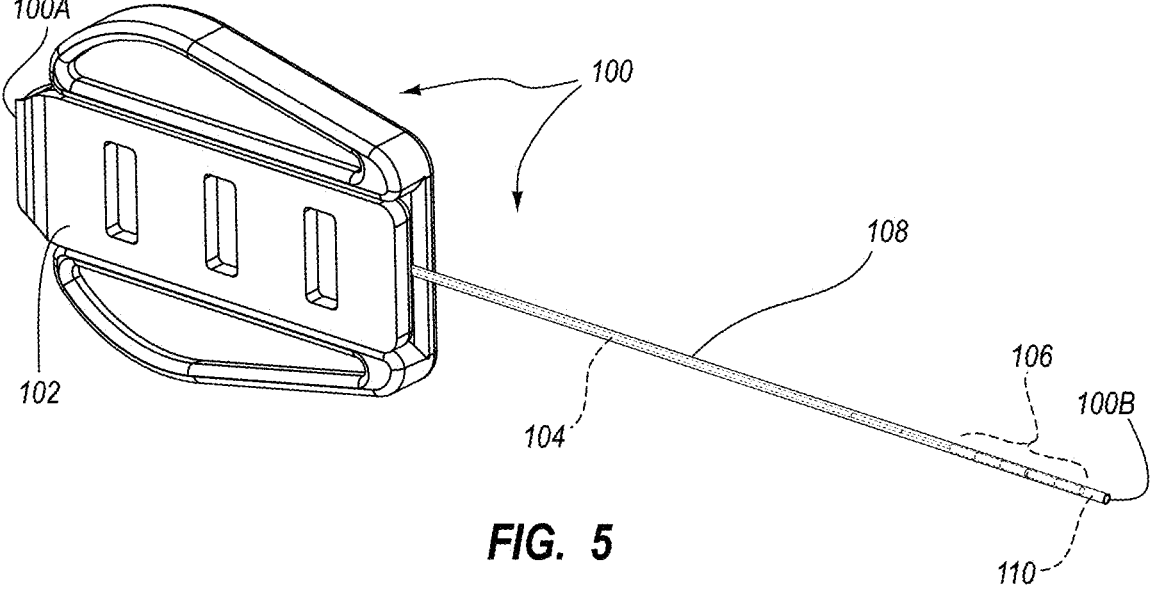
FIG. 5 is a perspective view of a stylet employed in connection with the system of FIG. 1 in placing a catheter within a patient vasculature.

As mentioned, the TLS utilizes a stylet to enable the distal end of the catheter 72 to be tracked during its advancement through the vasculature. FIG. 5 gives an example of such a stylet 100, which includes a proximal end 100A and a distal end 100B. A handle 102 is included at the stylet proximal end 100A, with a core wire 104 extending distally therefrom. A magnetic assembly is disposed distally of the core wire 104. The magnetic assembly includes one or more magnetic elements 106 disposed adjacent one another proximate the stylet distal end 100B and encapsulated by tubing 108. In the present embodiment, a plurality of magnetic elements 106 is included, each element including a solid, cylindrically shaped ferromagnetic stacked end-to-end with the other magnetic elements. An adhesive tip 110 can fill the distal tip of the tubing 108, distally to the magnetic elements 106.

Note that in other embodiments, the magnetic elements may vary from the design in not only shape, but also composition, number, size, magnetic type, and position in the stylet distal segment. For example, in one embodiment, the plurality of ferromagnetic magnetic elements is replaced with an electromagnetic assembly, such as an electromagnetic coil, which produces a magnetic field for detection by the sensor. Another example of an assembly usable here can be found in U.S. Pat. No. 5,099,845, titled "Medical Instrument Location Means," which is incorporated herein by reference in its entirety. Yet other examples of stylets including magnetic elements that can be employed with the TLS modality can be found in U.S. Pat. No. 8,784,336, titled "Stylet Apparatuses and Methods of Manufacture," which is incorporated herein by reference in its entirety. These and other variations are therefore contemplated by embodiments of the present invention. It should appreciated herein that "stylet" as used herein can include any one of a variety of devices configured for removable placement within a lumen of the catheter to assist in placing a distal end of the catheter in a desired location within the patient's vasculature.

FIG. 2 shows disposal of the stylet 100 substantially within a lumen in the catheter 72 such that the proximal portion thereof extends proximally from the catheter lumen, through the hub 74A and out through a selected one of the extension legs 74B. So disposed within a lumen of the catheter, the distal end 100B of the stylet 100 is substantially co-terminal with the distal catheter end 76A such that detection by the TLS of the stylet distal end correspondingly indicates the location of the catheter distal end.

The TLS sensor 50 is employed by the system 10 during TLS operation to detect a magnetic field produced by the magnetic elements 106 of the stylet 100. As seen in FIG. 2, the TLS sensor 50 is placed on the chest of the patient during catheter insertion. The TLS sensor 50 is placed on the chest of the patient in a predetermined location, such as through the use of external body landmarks, to enable the magnetic field of the stylet magnetic elements 106, disposed in the catheter 72 as described above, to be detected during catheter transit through the patient vasculature. Again, as the magnetic elements 106 of the stylet magnetic assembly are co-terminal with the distal end 76A of the catheter 72 (FIG. 2), detection by the TLS sensor 50 of the magnetic field of the magnetic elements provides information to the clinician as to the position and orientation of the catheter distal end during its transit.

In greater detail, the TLS sensor 50 is operably connected to the console 20 of the system 10 via one or more of the ports 52, as shown in FIG. 1. Note that other connection schemes between the TLS sensor and the system console can also be used without limitation. As just described, the magnetic elements 106 are employed in the stylet 100 to enable the position of the catheter distal end 76A (FIG. 2) to be observable relative to the TLS sensor 50 placed on the patient's chest. Detection by the TLS sensor 50 of the stylet magnetic elements 106 is graphically displayed on the display 30 of the console 20 during TLS mode. In this way, a clinician placing the catheter is able to generally determine the location of the catheter distal end 76A within the patient vasculature relative o the TLS sensor 50 and detect when catheter malposition, such as advancement of the catheter along an undesired vein, is occurring.

Figure 6:
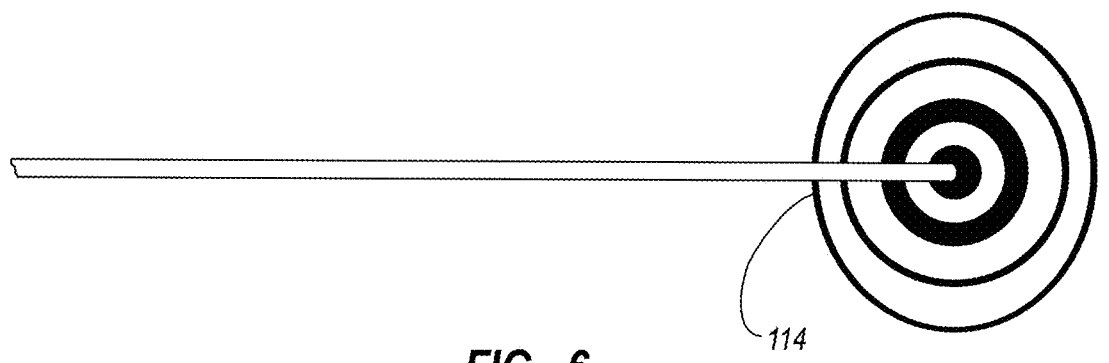
FIG. 6 is an icon as depicted on a display of the integrated system of FIG. 1, indicating a position of a distal end of the stylet of FIG. 5 during catheter tip placement procedures.
Figure 7A:
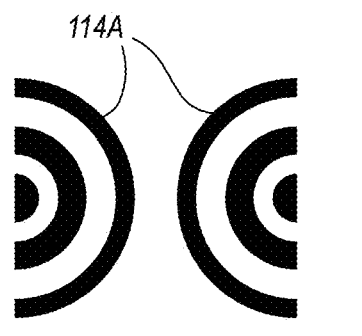
FIGS. 7A-7E depict various example icons that can be depicted on the display of the integrated system of FIG. 1 during catheter tip placement procedures.
Figure 7B:
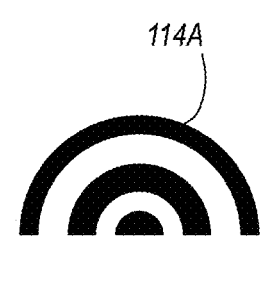
Figure 7C:
Figure 7D:
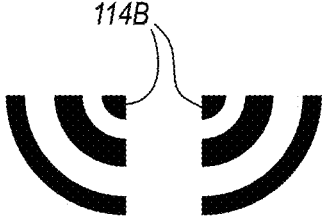
Figure 7E:
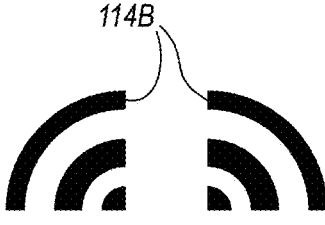

FIGS. 6 and 7A-7E show examples of icons that can be used by the console display 30 to depict detection of the stylet magnetic elements 106 by the TLS sensor 50. In particular, FIG. 6 shows an icon 114 that depicts the distal portion of the stylet 100, including the magnetic elements 106 as detected by the TLS sensor 50 when the magnetic elements are positioned under the TLS sensor. As the stylet distal end 100B is substantially co-terminal with the distal end 76A of the catheter 72, the icon indicates the position and orientation of the catheter distal end. FIGS. 7A-7E show various icons that can be depicted on the on the console display 30 when the magnetic elements 106 of the stylet 100 are not positioned directly under a portion of the TLS sensor 50, but are nonetheless detected nearby. The icons can include half-icons 114A and quarter-icons 114B that are displayed according to the position of the stylet magnetic assembly, i.e., the magnetic elements 106 in the present embodiment, relative to the TLS sensor 50.

FIGS. 8A-8C depict screenshots taken from the display 30 of the system 10 while in TLS mode, showing how the magnetic assembly of the stylet 100 is depicted. The screenshot 118 of FIG. 8A shows a representative image 120 of the TLS sensor 50. Other information is provided on the display screenshot 118, including a depth scale indicator 124, status/action indicia 126, and icons 128 corresponding to the button interface 32 included on the console 20 (FIG. 8C). Though the icons 128 in the present embodiment are simply indicators to guide the user in identifying the purpose of the corresponding buttons of the button interface 32, in another embodiment the display can be made touch-sensitive so that the icons themselves can function as button interfaces and can change according to the mode the system is in.

During initial stages of catheter advancement through the patient's vasculature after insertion therein, the distal end 76A of the catheter 72, having the stylet distal end 100B substantially co-terminal therewith, is relatively distant from the TLS sensor 50. As such, the display screenshot will indicate "no signal," indicating that the magnetic field from the stylet magnetic assembly has not been detected. In FIG. 8B, the magnetic assembly proximate the stylet distal end 100B has advanced sufficiently close to the TLS sensor 50 to be detected thereby, though it is not yet under the sensor. This is indicated by the half-icon 114A shown to the left of the sensor image 120, representing the stylet magnetic assembly being positioned to the right of the TLS sensor 50 from the perspective of the patient.

In FIG. 8C, the magnetic assembly proximate the stylet distal end 100B has advanced under the TLS sensor 50 such that its position and orientation relative thereto is detected by the TLS sensor. This is indicated by the icon 114 on the sensor image 120. Note that the button icons 128 provide indications of the actions that can be performed by pressing the corresponding buttons of the console button interface 32. As such, the button icons 128 can change according to which modality the system 10 is in, thus providing flexibility of use for the button interface 32. Note further that, as the button pad 82 of the probe 40 (FIG. 3A, 3B) includes buttons 84 that mimic several of the buttons of the button interface 32, the button icons 128 on the display 30 provide a guide to the clinician for controlling the system 10 with the probe buttons 84 while remaining in the sterile field. For instance, if the clinician has need to leave TLS mode and return to US (ultrasound) mode, the appropriate control button 84 on the probe button pad 82 can be depressed, and the US mode can be immediately called up, with the display 30 refreshing to accommodate the visual information needed for US functionality, such as that shown in FIG. 4. This is accomplished without a need for the clinician to reach out of the sterile field.

Figure 10:
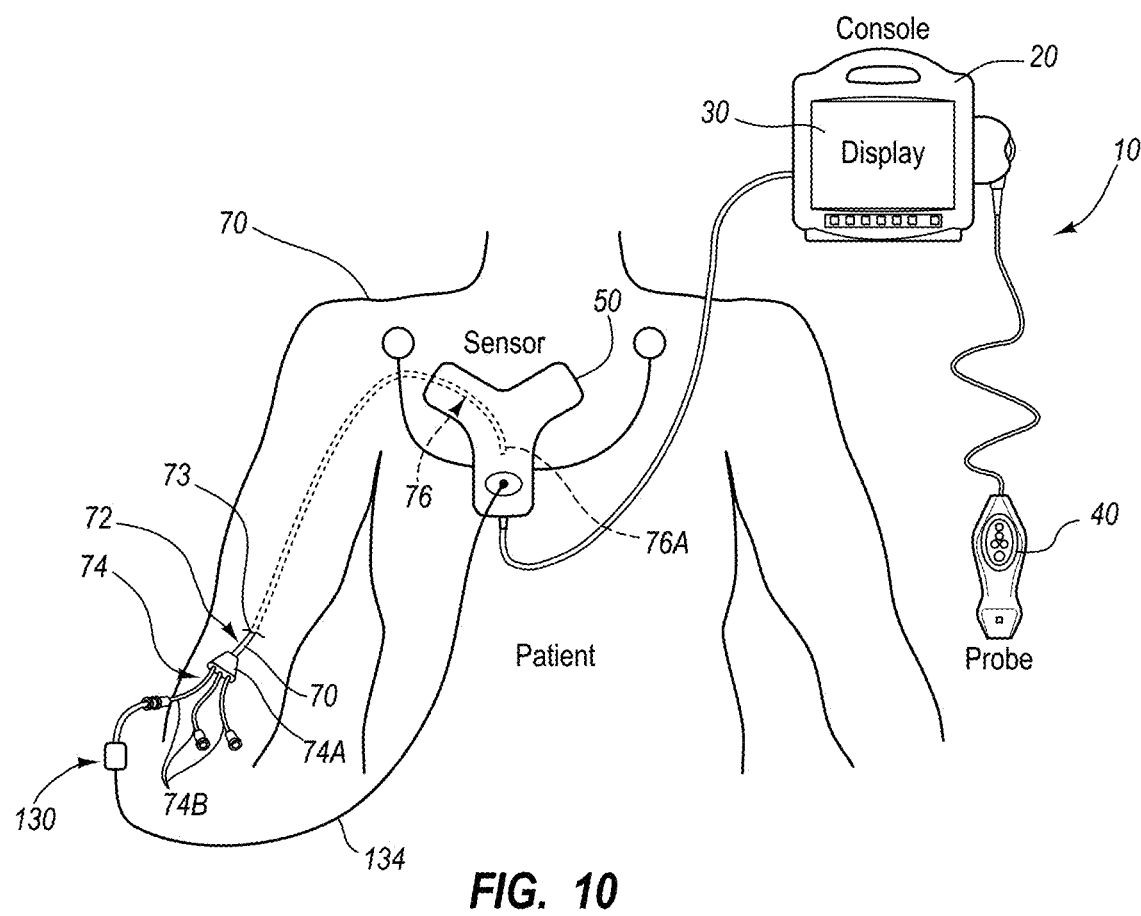
FIG. 10 is a simplified view of a patient and a catheter being inserted therein with assistance of the integrated system of FIG. 9.

Reference is now made to FIGS. 9 and 10 in describing the integrated catheter placement system 10 according to another example embodiment. As before, the integrated system 10 includes the console 20, display 30, probe 40 for US functionality, and the TLS sensor 50 for tip location functionality as described above. Note that the system 10 depicted in FIGS. 9 and 10 is similar in many respects to the system shown in FIGS. 1 and 2. As such, only selected differences will be discussed below. The system 10 of FIGS. 9 and 10 includes additional functionality wherein determination of the proximity of the catheter distal tip 76A relative to a sino-atrial ("SA") or other electrical impulse-emitting node of the heart of the patient 70 can be determined, thus providing enhanced ability to accurately place the catheter distal tip in a desired location proximate the node. Also referred to herein as "ECG" or "ECG-based tip confirmation," this third modality of the system 10 enables detection of ECG signals from the SA node in order to place the catheter distal tip in a desired location within the patient vasculature. Note that the US, TLS, and ECG modalities are seamlessly combined in the present system 10 and can be employed in concert or individually to assist in catheter placement.

FIGS. 9 and 10 show the addition to the system 10 of a stylet 130 configured in accordance with the present embodiment. As an overview, the catheter stylet 130 is removably predisposed within the lumen of the catheter 72 being inserted into the patient 70 via the insertion site 73. The stylet 130, in addition to including a magnetic assembly for the magnetically-based TLS modality, includes an ECG sensor assembly proximate its distal end and including a portion that is co-terminal with the distal end of the catheter tip for sensing ECG signals produced by the SA node. In contrast to the previous embodiment, the stylet 130 includes a tether 134 extending from its proximal end that operably connects to the TLS sensor 50. As will be described in further detail, the stylet tether 134 permits ECG signals detected by the ECG sensor assembly included on a distal portion of the stylet 130 to be conveyed to the TLS sensor 50 during confirmation of the catheter tip location as part of the ECG signal-based tip confirmation modality. Reference and ground ECG lead/electrode pairs 158 attach to the body of the body of the patient 70 and are operably attached to the TLS sensor 50 to enable the system to filter out high level electrical activity unrelated to the electrical activity of the SA node of the heart, thus enabling the ECG-based tip confirmation functionality. Together with the reference and ground signals received from the ECG lead/electrode pairs 158 placed on the patient's skin, the ECG signals sensed by the stylet ECG sensor assembly are received by the TLS sensor 50 positioned on the patient's chest (FIG. 10). The TLS sensor 50 and/or console processor 22 can process the ECG signal data to produce an electrocardiogram waveform on the display 30, as will be described. In the case where the TLS sensor 50 processes the ECG signal data, a processor is included therein to perform the intended functionality. If the console 20 processes the ECG signal data, the processor 22, controller 24, or other processor can be utilized in the console to process the data.

Thus, as it is advanced through the patient vasculature, the catheter 72 equipped with the stylet 130 as described above can advance under the TLS sensor 50, which is positioned on the chest of the patient as shown in FIG. 10. This enables the TLS sensor 50 to detect the position of the magnetic assembly of the stylet 130, which is substantially co-terminal with the distal tip 76A of the catheter as located within the patient's vasculature. The detection by the TLS sensor 50 of the stylet magnetic assembly is depicted on the display 30 during ECG mode. The display 30 further depicts during ECG mode an ECG electrocardiogram waveform produced as a result of patient heart's electrical activity as detected by the ECG sensor assembly of the stylet 130. In greater detail, the ECG electrical activity of the SA node, including the P-wave of the waveform, is detected by the ECG sensor assembly of the stylet (described below) and forwarded to the TLS sensor 50 and console 20. The ECG electrical activity is then processed for depiction on the display 30. The clinician placing the catheter can then observe the ECG data to determine optimum placement of the distal tip 76A of the catheter 72, such as proximate the SA node in one embodiment. In one embodiment, the console 20 which includes the electronic components, such as the processor 22 (FIG. 9) necessary to receive and process the signals detected by the stylet ECG sensor assembly. In another embodiment, the TLS sensor 50 can include the necessary electronic components processing the ECG signals.

As already discussed, the display 30 is used to display information to the clinician during the catheter placement procedure. The content of the display 30 changes according to which mode the catheter placement system is in: US, TLS, or ECG. Any of the three modes can be immediately called up to the display 30 by the clinician, and in some cases information from multiple modes, such as TLS and ECG, may be displayed simultaneously. In one embodiment, as before, the mode the system is in may be controlled by the control buttons 84 included on the handheld probe 40, thus eliminating the need for the clinician to reach out of the sterile field (such as touching the button interface 32 of the console 20) to change modes. Thus, in the present embodiment the probe 40 is employed to also control some or all ECG-related functionality of the system 10. Note that the button interface 32 or other input configurations can also be used to control system functionality. Also, in addition to the visual display 30, aural information, such as beeps, tones, etc., can also be employed by the system to assist the clinician during catheter placement.

Figure 11:
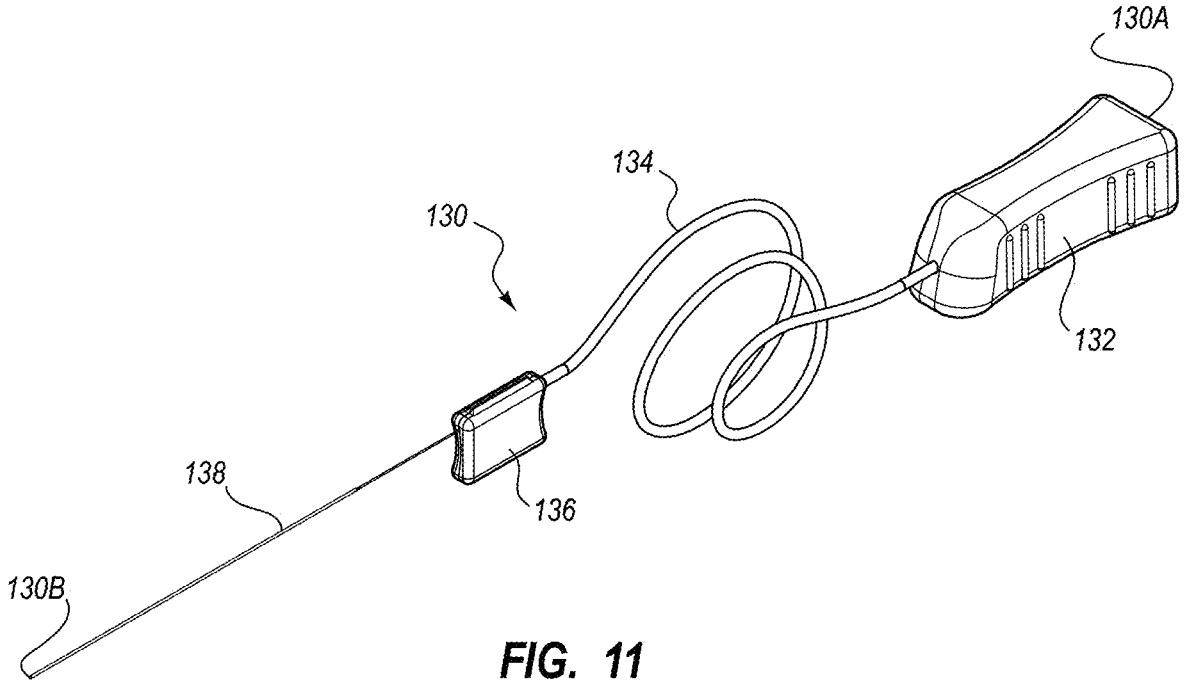
FIG. 11 is a perspective view of a stylet employed in connection with the integrated system of FIG. 9 in placing a catheter within a patient vasculature.

Reference is now made to FIGS. 11-12E in describing various details of one embodiment of the stylet 130 that is removably loaded into the catheter 72 and employed during insertion to position the distal tip 76A of the catheter in a desired location within the patient vasculature. As shown, the stylet 130 as removed from the catheter defines a proximal end 130A and a distal end 130B. A connector 132 is included at the proximal stylet end 130A, and a tether 134 extends distally from the connector and attaches to a handle 136. A core wire 138 extends distally from the handle 136. The stylet 130 is pre-loaded within a lumen of the catheter 72 in one embodiment such that the distal end 130B is substantially flush, or co-terminal, with the catheter opening at the distal end 76A thereof (FIG. 10), and such that a proximal portion of the core wire 138, the handle 136, and the tether 134 extend proximally from a selected one of the extension tubes 74B. Note that, though described herein as a stylet, in other embodiments a guidewire or other catheter guiding apparatus could include the principles of the embodiment described herein.

The core wire 138 defines an elongate shape and is composed of a suitable stylet material including stainless steel or a memory material such as, in one embodiment, a nickel and titanium-containing alloy commonly known by the acronym "nitinol." Though not shown here, manufacture of the core wire 138 from nitinol in one embodiment enables the portion of the core wire corresponding to a distal segment of the stylet to have a pre-shaped bent configuration so as to urge the distal portion of the catheter 72 into a similar bent configuration. In other embodiments, the core wire includes no pre-shaping. Further, the nitinol construction lends torqueability to the core wire 138 to enable a distal segment of the stylet 130 to be manipulated while disposed within the lumen of the catheter 72, which in turn enables the distal portion of the catheter to be navigated through vasculature during catheter insertion.

The handle 136 is provided to enable insertion/removal of the stylet from the catheter 72. In embodiments where the stylet core wire 138 is torqueable, the handle 136 further enables the core wire to be rotated within the lumen of the catheter 72, to assist in navigating the catheter distal portion through the vasculature of the patient 70.

The handle 136 attaches to a distal end of the tether 134. In the present embodiment, the tether 134 is a flexible, shielded cable housing one or more conductive wires electrically connected both to the core wire 138, which acts as the ECG sensor assembly referred to above, and the tether connector 132. As such, the tether 134 provides a conductive pathway from the distal portion of the core wire 138 through to the tether connector 132 at proximal end 130A of the stylet 130. As will be explained, the tether connector 132 is configured for operable connection to the TLS sensor 50 on the patient's chest for assisting in navigation of the catheter distal tip 76A to a desired location within the patient vasculature.

As seen in FIGS. 12B-12D, a distal portion of the core wire 138 is gradually tapered, or reduced in diameter, distally from a junction point 142. A sleeve 140 is slid over the reduced-diameter core wire portion. Though of relatively greater diameter here, the sleeve in another embodiment can be sized to substantially match the diameter of the proximal portion of the stylet core wire. The stylet 130 further includes a magnetic assembly disposed proximate the distal end 130B thereof for use during TLS mode. The magnetic assembly in the illustrated embodiment includes a plurality of magnetic elements 144 interposed between an outer surface of the reduced-diameter core wire 138 and an inner surface of the sleeve 140 proximate the stylet distal end 130B. In the present embodiment, the magnetic elements 144 include 20 ferromagnetic magnets of a solid cylindrical shape stacked end-to-end in a manner similar to the stylet 100 of FIG. 2. In other embodiments, however, the magnetic element(s) may vary from this design in not only shape, but also composition, number, size, magnetic type, and position in the stylet. For example, in one embodiment the plurality of magnets of the magnetic assembly is replaced with an electromagnetic coil that produces a magnetic field for detection by the TLS sensor. These and other variations are therefore contemplated by embodiments of the present invention.

The magnetic elements 144 are employed in the stylet 130 distal portion to enable the position of the stylet distal end 130B to be observable relative to the TLS sensor 50 placed on the patient's chest. As has been mentioned, the TLS sensor 50 is configured to detect the magnetic field of the magnetic elements 144 as the stylet advances with the catheter 72 through the patient vasculature. In this way, a clinician placing the catheter 72 is able to generally determine the location of the catheter distal end 76A within the patient vasculature and detect when catheter malposition is occurring, such as advancement of the catheter along an undesired vein, for instance.

The stylet 130 further includes the afore-mentioned ECG sensor assembly, according to one embodiment. The ECG sensor assembly enables the stylet 130, disposed in a lumen of the catheter 72 during insertion, to be employed in detecting an intra-atrial ECG signal produced by an SA or other node of the patient's heart, thereby allowing for navigation of the distal tip 76A of the catheter 72 to a predetermined location within the vasculature proximate the patient's heart. Thus, the ECG sensor assembly serves as an aide in confirming proper placement of the catheter distal tip 76A.

In the embodiment illustrated in FIGS. 11-12E, the ECG sensor assembly includes a distal portion of the core wire 138 disposed proximate the stylet distal end 130B. The core wire 138, being electrically conductive, enables ECG signals to be detected by the distal end thereof and transmitted proximally along the core wire. A conductive material 146, such as a conductive epoxy, fills a distal portion of the sleeve 140 adjacent the distal termination of the core wire 138 so as to be in conductive communication with the distal end of the core wire. This in turn increases the conductive surface of the distal end 130B of the stylet 130 so as to improve its ability to detect ECG signals.

Before catheter placement, the stylet 130 is loaded into a lumen of the catheter 72. Note that the stylet 130 can come preloaded in the catheter lumen from the manufacturer, or loaded into the catheter by the clinician prior to catheter insertion. The stylet 130 is disposed within the catheter lumen such that the distal end 130B of the stylet 130 is substantially co-terminal with the distal tip 76A of the catheter 72, thus placing the distal tips of both the stylet and the catheter in substantial alignment with one another. The co-terminality of the catheter 72 and stylet 130 enables the magnetic assembly to function with the TLS sensor 50 in TLS mode to track the position of the catheter distal tip 76A as it advances within the patient vasculature, as has been described. Note, however, that for the tip confirmation functionality of the system 10, the distal end 130B of the stylet 130 need not be co-terminal with the catheter distal end 76A. Rather, all that is required is that a conductive path between the vasculature and the ECG sensor assembly, in this case the core wire 138, be established such that electrical impulses of the SA node or other node of the patient's heart can be detected. This conductive path in one embodiment can include various components including saline solution, blood, etc.

In one embodiment, once the catheter 72 has been introduced into the patient vasculature via the insertion site 73 (FIG. 10) the TLS mode of the system 10 can be employed as already described to advance the catheter distal tip 76A toward its intended destination proximate the SA node. Upon approaching the region of the heart, the system 10 can be switched to ECG mode to enable ECG signals emitted by the SA node to be detected. As the stylet-loaded catheter is advanced toward the patient's heart, the electrically conductive ECG sensor assembly, including the distal end of the core wire 138 and the conductive material 146, begins to detect the electrical impulses produced by the SA node. As such, the ECG sensor assembly serves as an electrode for detecting the ECG signals. The elongate core wire 138 proximal to the core wire distal end serves as a conductive pathway to convey the electrical impulses produced by the SA node and received by the ECG sensor assembly to the tether 134.

The tether 134 conveys the ECG signals to the TLS sensor 50 temporarily placed on the patient's chest. The tether 134 is operably connected to the TLS sensor 50 via the tether connector 132 or other suitable direct or indirect connective configuration. As described, the ECG signal can then be process and depicted on the system display 30 (FIG. 9, 10). Monitoring of the ECG signal received by the TLS sensor 50 and displayed by the display 30 enables a clinician to observe and analyze changes in the signal as the catheter distal tip 76A advances toward the SA node. When the received ECG signal matches a desired profile, the clinician can determine that the catheter distal tip 76A has reached a desired position with respect to the SA node. As mentioned, in one embodiment this desired position lies within the lower one-third ($\frac{1}{3}_{rd}$) portion of the SVC.

The ECG sensor assembly and magnetic assembly can work in concert in assisting a clinician in placing a catheter within the vasculature. Generally, the magnetic assembly of the stylet 130 assists the clinician in generally navigating the vasculature from initial catheter insertion so as to place the distal end 76A of the catheter 72 in the general region of the patient's heart. The ECG sensor assembly can then be employed to guide the catheter distal end 76A to the desired location within the SVC by enabling the clinician to observe changes in the ECG signals produced by the heart as the stylet ECG sensor assembly approaches the SA node. Again, once a suitable ECG signal profile is observed, the clinician can determine that the distal ends of both the stylet 130 and the catheter 72 have arrived at the desired location with respect to the patient's heart. Once it has been positioned as desired, the catheter 72 may be secured in place and the stylet 130 removed from the catheter lumen. It is noted here that the stylet may include one of a variety of configurations in addition to what is explicitly described herein. In one embodiment, the stylet can attach directly to the console instead of an indirect attachment via the TLS sensor. In another embodiment, the structure of the stylet 130 that enables its TLS and ECG-related functionalities can be integrated into the catheter structure itself. For instance, the magnetic assembly and/or ECG sensor assembly can, in one embodiment, be incorporated into the wall of the catheter.

FIGS. 13A-15 describe various details relating to the passage of ECG signal data from the stylet tether 134 to the TLS sensor 50 positioned on the patient's chest, according the present embodiment. In particular, this embodiment is concerned with passage of ECG signal data from a sterile field surrounding the catheter 72 and insertion site 73, which includes the stylet 130 and tether 134, and a non-sterile field, such as the patient's chest on which the TLS sensor is positioned. Such passage should not disrupt the sterile field so that the sterility thereof is compromised. A sterile drape that is positioned over the patient 70 during the catheter insertion procedure defines the majority of the sterile field: areas above the drape are sterile, while areas below (excluding the insertion site and immediately surrounding region) are non-sterile. As will be seen, the discussion below includes at least a first communication node associated with the stylet 130, and a second communication node associated with the TLS sensor 50 that operably connect with one another to enable ECG signal data transfer therebetween.

Figure 13A:
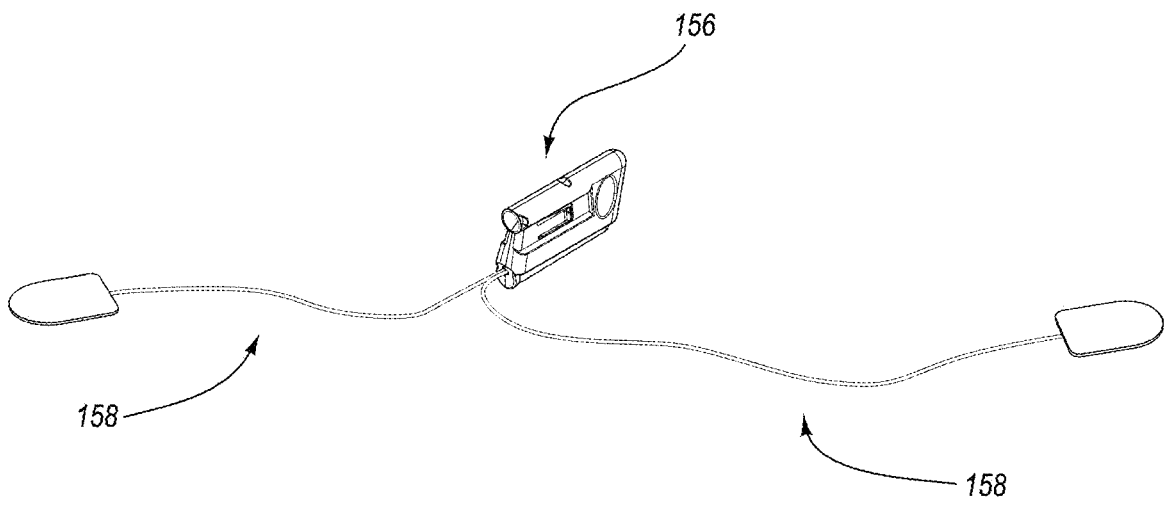
FIGS. 13A-13D are various views of a fin connector assembly for use with the integrated system of FIG. 9.
Figure 13B:
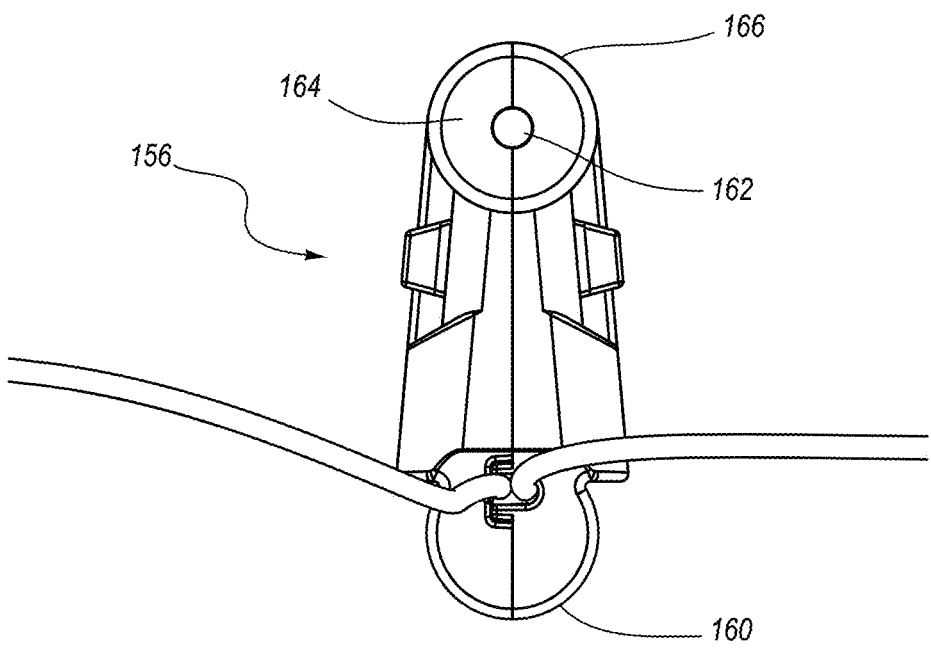
Figure 13C:
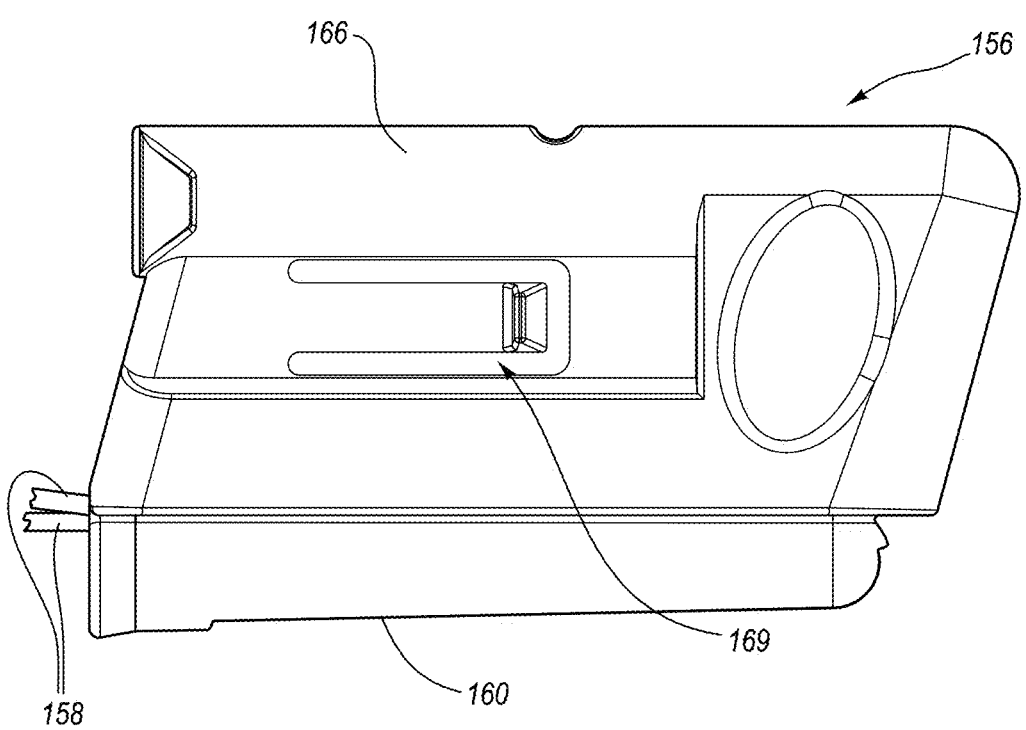
Figure 13D:
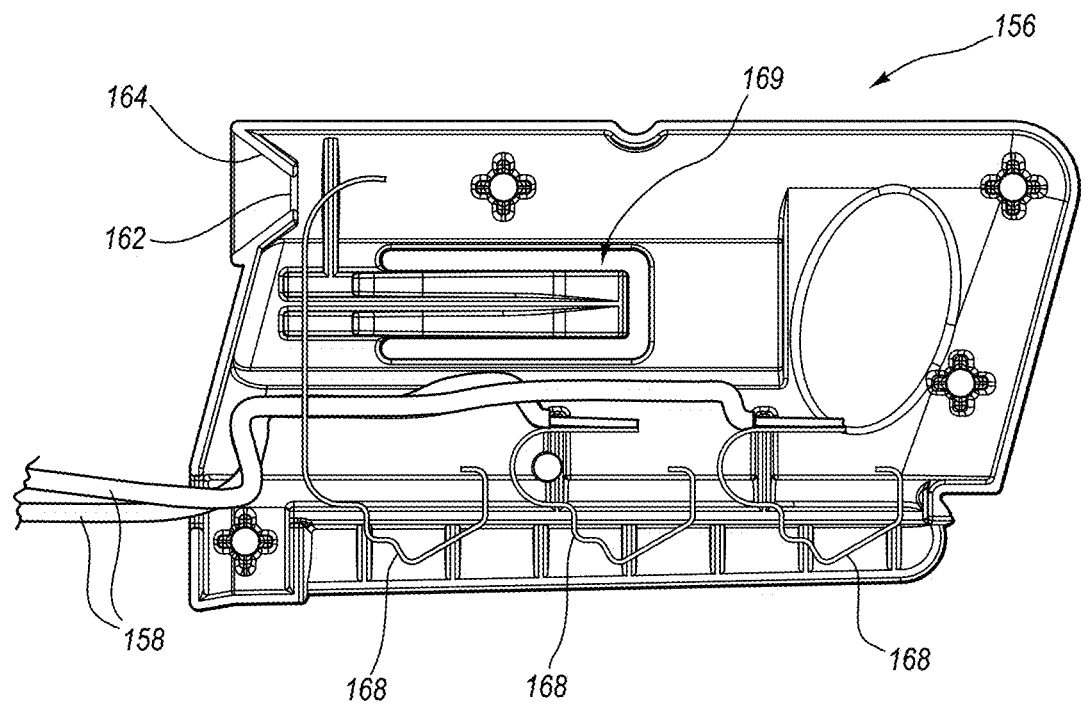
Figure 14A:
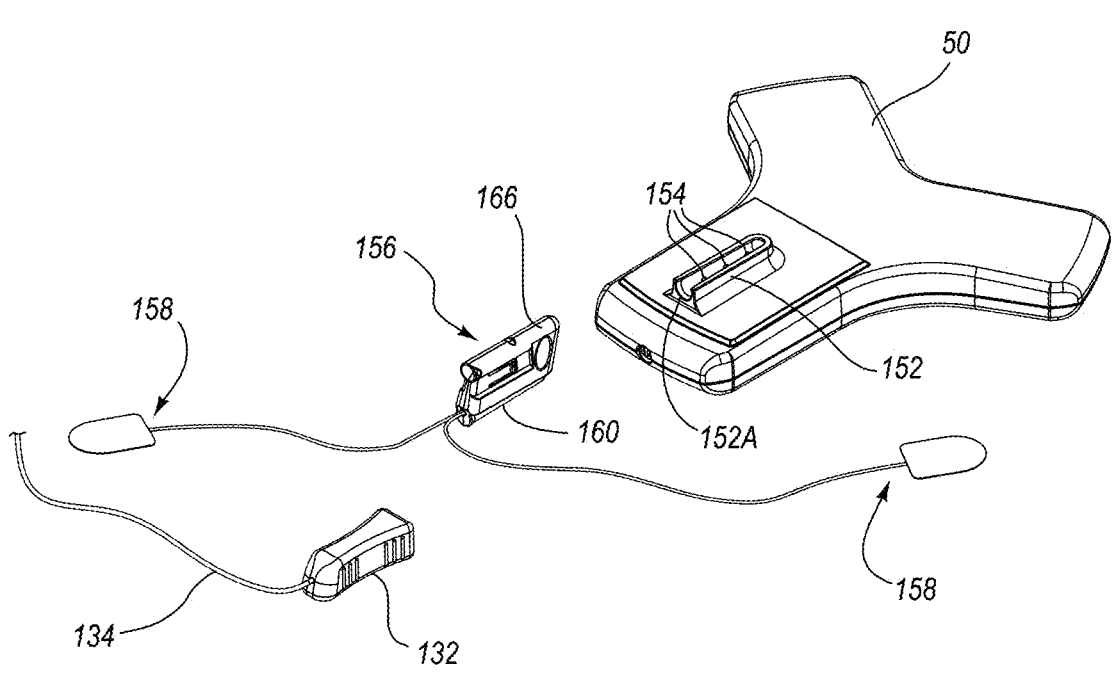
FIGS. 14A-14C are views showing the connection of a stylet tether and fin connector to a sensor of the integrated system of FIG. 9.
Figure 14B:
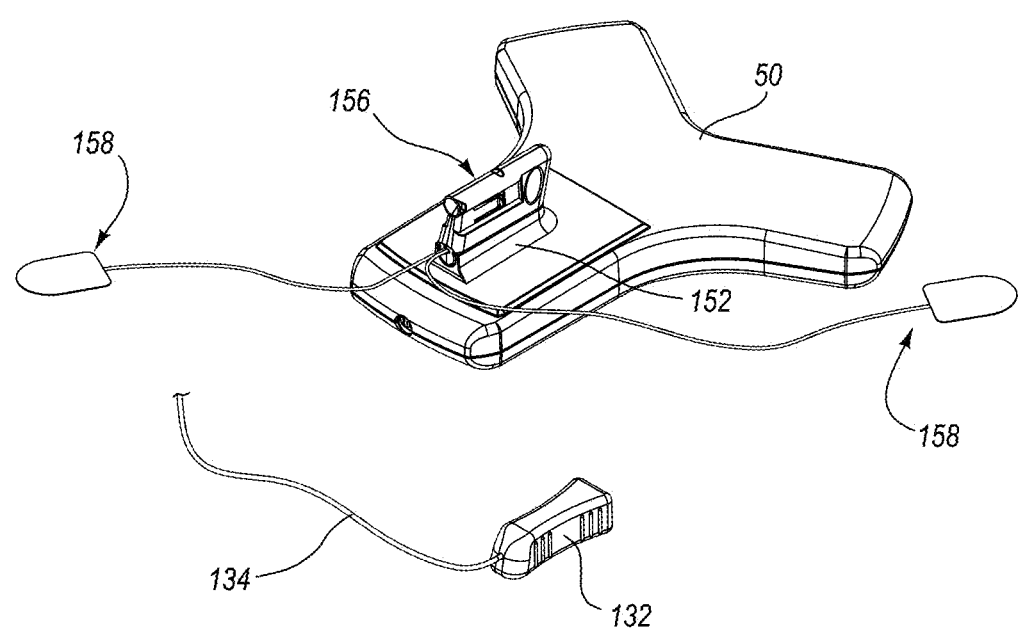
Figure 14C:
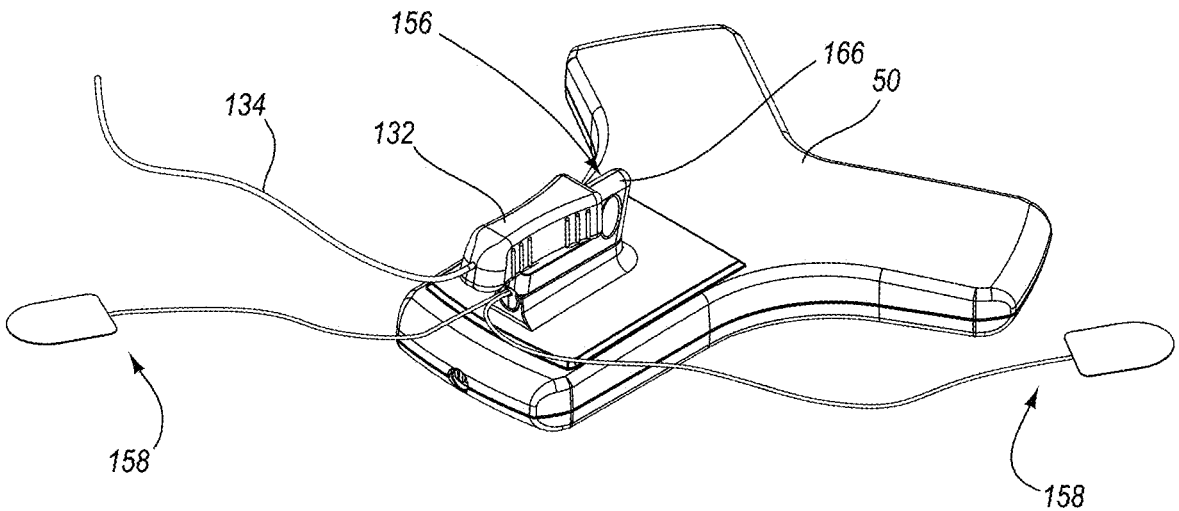
Figure 15:
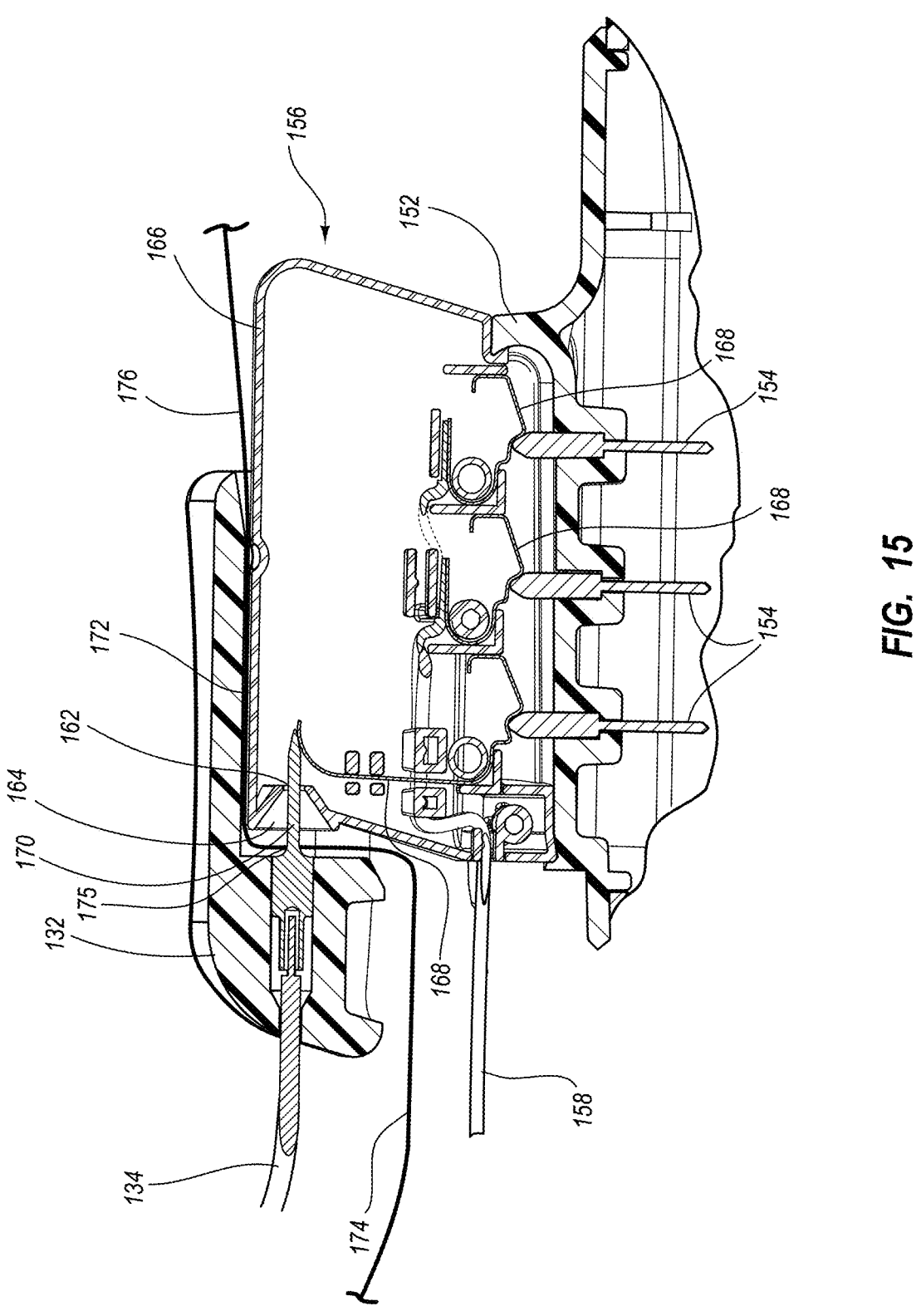
FIG. 15 is a cross sectional view of the connection of the stylet tether, fin connector, and sensor shown in FIG. 14C.

One embodiment addressing the passage of ECG signal data from the sterile field to the non-sterile field without compromising the sterility of the former is depicted in FIGS. 13A-15, which depict a "through-drape" implementation also referred to as a "shark fin" implementation. In particular, FIG. 14A shows the TLS sensor 50 as described above for placement on the chest of the patient during a catheter insertion procedure. The TLS sensor 50 includes on a top surface thereof a connector base 152 defining a channel 152A in which are disposed three electrical base contacts 154. A fin connector 156, also shown in FIGS. 13A-13D, is sized to be slidingly received by the channel 152A of the connector base 152, as shown in FIGS. 14B and 15. Two ECG lead/electrode pairs 158 extend from the fin connector 156 for placement on the shoulder and torso or other suitable external locations on the patient body. The drape-piercing tether connector 132 is configured to slidingly mate with a portion of the fin connector 156, as will be described further below, to complete a conductive pathway from the stylet 120, through the sterile field to the TLS sensor 50.

FIGS. 13A-13D show further aspects of the fin connector 156. In particular, the fin connector 156 defines a lower barrel portion 160 that is sized to be received in the channel 152A of the connector base 152 (FIGS. 14B, 15). A hole 162 surrounded by a centering cone 164 is included on a back end of an upper barrel portion 166. The upper barrel portion 166 is sized to receive the tether connector 132 of the stylet 130 (FIGS. 14C, 15) such that a pin contact 170 extending into a channel 172 of the tether connector 132 (FIG. 15) is guided by the centering hole until it seats within the hole 162 of the fin connector 156, thus interconnecting the tether connector with the fin connector. An engagement feature, such as the engagement feature 169 shown in FIGS. 13C and 13D, can be included on the fin connector 156 to engage with a corresponding feature on the tether connector 132 to assist with maintaining a mating between the two components.

FIG. 13D shows that the fin connector 156 includes a plurality of electrical contacts 168. In the present embodiment, three contacts 168 are included: the two forward-most contact each electrically connecting with a terminal end of one of the ECG leads 158, and the rear contact extending into axial proximity of the hole 162 so as to electrically connect with the pin contact 170 of the tether connector 132 when the latter is mated with the fin connector 156 (FIG. 15). A bottom portion of each contact 168 of the fin connector 156 is positioned to electrically connect with a corresponding one of the base contacts 154 of the TLS sensor connector base 152.

FIG. 14B shows a first connection stage, wherein the fin connector 156 is removably mated with the TLS sensor connector base 152 by the sliding engagement of the lower barrel portion 160 of the fin connector with the connector base channel 152A. This engagement electrically connects the connector base contacts 154 with the corresponding fin contacts 168.

FIG. 14C shows a second connection stage, wherein the tether connector 132 is removably mated with the fin connector 156 by the sliding engagement of the tether connector channel 172 with the upper barrel portion 166 of the fin connector. This engagement electrically connects the tether connector pin contact 170 with the back contact 168 of the fin connector 156, as best seen in FIG. 15. In the present embodiment, the horizontal sliding movement of the tether connector 132 with respect to the fin connector 156 is in the same engagement direction as when the fin connector is slidably mated to the sensor connector base channel 152A (FIG. 14B). In one embodiment, one or both of the stylet 130/tether connector 132 and the fin connector 156 are disposable. Also, the tether connector in one embodiment can be mated to the fin connector after the fin connector has been mated to the TLS sensor, while in another embodiment the tether connector can be first mated to the fin connector through the surgical drape before the fin connector is mated to the TLS sensor.

In the connection scheme shown in FIG. 14C, the stylet 130 is operably connected to the TLS sensor 50 via the tether connector 132, thus enabling the ECG sensor assembly of the stylet to communicate ECG signals to the TLS sensor. In addition, the ECG lead/electrode pairs 158 are operably connected to the TLS sensor 50. In one embodiment, therefore, the tether connector 132 is referred to as a first communication node for the stylet 130, while the fin connector 156 is referred to as a second communication node for the TLS sensor 50.

Note that various other connective schemes and structures can be employed to establish operable communication between the stylet and the TLS sensor. For instance, the tether connector can use a slicing contact instead of a pin contact to pierce the drape. Or, the fin connector can be integrally formed with the TLS sensor. These and other configurations are therefore embraced within the scope of embodiments of the present disclosure.

As seen in FIG. 15, a sterile drape 174 used during catheter placement to establish a sterile field is interposed between the interconnection of the tether connector 132 with the fin connector 156. As just described, the tether connector 132 includes the pin contact 170 that is configured to pierce the drape 174 when the two components are mated. This piercing forms a small hole, or perforation 175, in the sterile drape 174 that is occupied by the pin contact 170, thus minimizing the size of the drape perforation by the pin contact. Moreover, the fit between the tether connector 132 and the fin connector 156 is such that the perforation in sterile drape made by piercing of the pin contact 170 is enclosed by the tether connector channel 172, thus preserving the sterility of the drape and preventing a breach in the drape that could compromise the sterile field established thereby. The tether connector channel 172 is configured so as to fold the sterile drape 174 down prior to piercing by the pin contact 170 such that the pin contact does not pierce the drape until it is disposed proximate the hole 162 of the fin connector 156. It is noted here that the tether connector 132 and fin connector 156 are configured so as to facilitate alignment therebetween blindly through the opaque sterile drape 174, i.e., via palpation absent visualization by the clinician of both components.

Note further that the fin contacts 168 of the fin connector 156 as shown in FIG. 15 are configured to mate with the sensor base contacts 154 in such a way as to assist in retaining the fin connector in engagement with the sensor base channel 152A. This in turn reduces the need for additional apparatus to secure the fin connector 156 to the TLS sensor 50.

Figure 16:
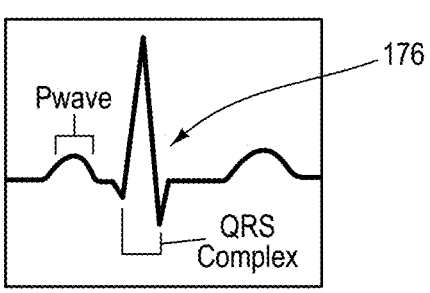
FIG. 16 is simplified view of an ECG trace of a patient.

FIG. 16 shows a typical ECG waveform 176, including a P-wave and a QRS complex. Generally, the amplitude of the P-wave varies as a function of distance of the ECG sensor assembly from the SA node, which produces the waveform 176. A clinician can use this relationship in determining when the catheter tip is properly positioned proximate the heart. For instance, in one implementation the catheter tip is desirably placed within the lower one-third ($\frac{1}{3}_{rd}$) of the superior vena cava, as has been discussed. The ECG data detected by the ECG sensor assembly of the stylet 130 is used to reproduce waveforms such as the waveform 176, for depiction on the display 30 of the system 10 during ECG mode.

Figure 17:
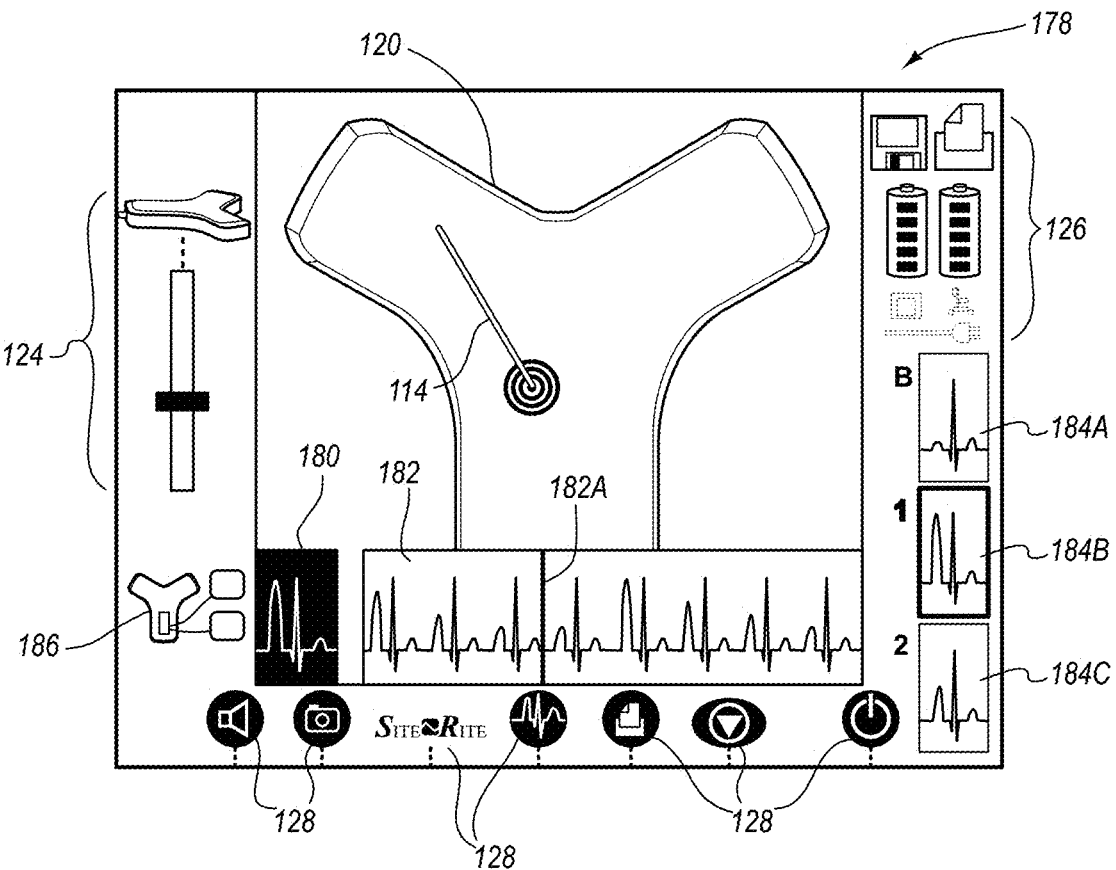
FIG. 17 is a screenshot of an image depicted on a display of the integrated system of FIG. 9 during catheter tip placement procedures.

Reference is now made to FIG. 17 in describing display aspects of ECG signal data on the display 30 when the system 10 is in ECG mode, the third modality described further above, according to one embodiment. The screenshot 178 of the display 30 includes elements of the TLS modality, including a representative image 120 of the TLS sensor 50, and can the icon 114 corresponding to the position of the distal end of the stylet 130 during transit through the patient vasculature. The screenshot 178 further includes a window 180 in which the current ECG waveform captured by the ECG sensor assembly of the stylet 130 and processed by the system 10 is displayed. The window 180 is continually refreshed as new waveforms are detected.

Window 182 includes a successive depiction of the most recent detected ECG waveforms, and includes a refresh bar 182A, which moves laterally to refresh the waveforms as they are detected. Window 184A is used to display a baseline ECG waveform, captured before the ECG sensor assembly is brought into proximity with the SA node, for comparison purposes to assist the clinician in determining when the desired catheter tip location has been achieved. Windows 184B and 184C can be filed by user-selected detected ECG waveforms when the user pushes a predetermined button on the probe 40 or the console button interface 32. The waveforms in the windows 184B and 184C remain until overwritten by new waveforms as a result of user selection via button pushes or other input. As in previous modes, the depth scale 124, status/action indicia 126, and button icons 128 are included on the display 30. An integrity indicator 186 is also included on the display 30 to give an indication of whether the ECG lead/electrode pairs 158 are operably connected to the TLS sensor 50.

As seen above, therefore, the display 30 depicts in one embodiment elements of both the TLS and ECG modalities simultaneously on a single screen, thus offering the clinician ample data to assist in placing the catheter distal tip in a desired position. Note further that in one embodiment a printout of the screenshot or selected ECG or TLS data can be saved, printed, or otherwise preserved by the system 10 to enable documentation of proper catheter placement.

Although the embodiments described herein relate to a particular configuration of a catheter, such as a PICC or CVC, such embodiments are merely exemplary. Accordingly, the principles of the present invention can be extended to catheters of many different configurations and designs.

II. Assisted Guidance for Needle/Medical Component

Embodiments of the present invention described herein are generally directed to a guidance system for locating and guiding a needle or other medical component during ultrasound-based or other suitable procedures for accessing with the needle a subcutaneous vessel of a patient, for instance. In one embodiment, the guidance system enables the position, orientation, and advancement of the needle to be superimposed in real-time atop the ultrasound image of the vessel, thus enabling a clinician to accurately guide the needle to the intended target. Furthermore, in one embodiment, the guidance system tracks the needle's position in five degrees of motion: x, y, and z spatial coordinate space, needle pitch, and needle yaw. Such tracking enables the needle to be guided and placed with relatively high accuracy.

Figures 18, 19:
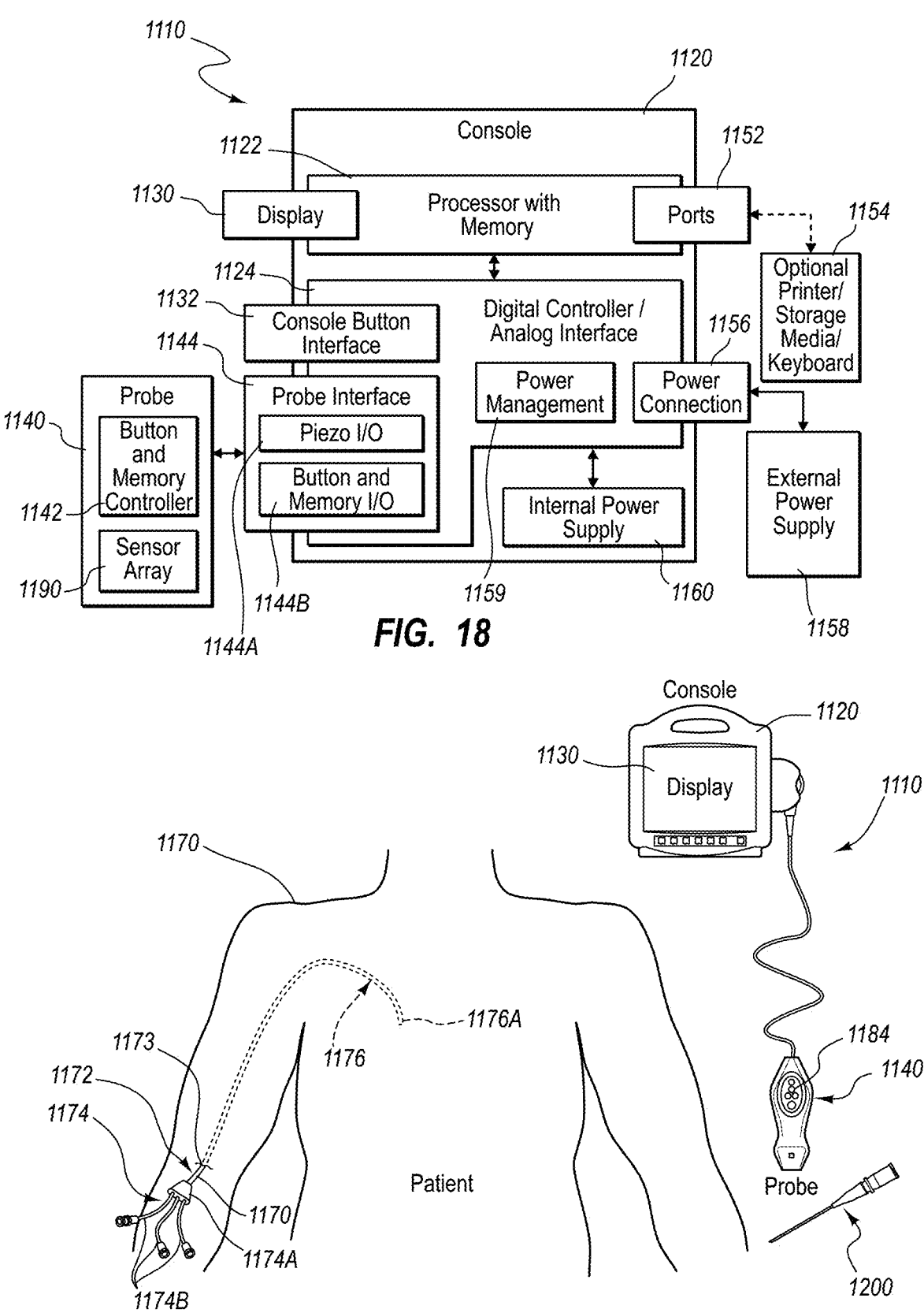
FIG. 18 is a block diagram depicting various elements of an ultrasound-based guidance system for needles and other medical components, according to one embodiment.
FIG. 19 is a simplified view of a patient and a catheter being inserted therein, showing one possible environment in which the guidance system of FIG. 18 can be practiced.

Reference is first made to FIGS. 18 and 19, which depict various components of an ultrasound-based needle guidance system ("system"), generally designated at 1110, configured in accordance with one embodiment of the present invention. As shown, the system 1110 generally includes an ultrasound ("US") imaging portion including a console 1120, display 1130, and probe 1140, each of which is described in further detail below. Note that the system 1110 bears similarity to the system 10 shown in FIG. 1 with respect to some components, in one embodiment. It should be noted, however, that the ultrasound imaging portion can be configured in one of a variety of ways in addition to what is shown and described herein.

The ultrasound imaging portion of the system 1110 is employed to image a targeted internal portion of a body of a patient prior to percutaneous insertion of a needle or other device to access the target. As described below, in one embodiment insertion of the needle is performed prior to the subsequent insertion of a catheter into a vein or other portion of the vasculature of the patient. It is appreciated, however, that insertion of a needle into the body of a patient can be performed for a variety of medical purposes.

FIG. 19 shows the general relation of the above-described components to a patient 1170 during a procedure to ultimately place a catheter 1172 into the patient vasculature through a skin insertion site 1173, according to one embodiment. FIG. 19 shows that the catheter 1172 generally includes a proximal portion 1174 that remains exterior to the patient and a distal potion 1176 that resides within the patient vasculature after placement is complete. The system 1110 is employed to ultimately position a distal tip 1176A of the catheter 1172 in a desired position within the patient vasculature. In one embodiment, the desired position for the catheter distal tip 1176A is proximate the patient's heart, such as in the lower one-third ($\frac{1}{3}^{rd}$) portion of the Superior Vena Cava ("SVC"). Of course, the system 1110 can be employed to place the catheter distal tip in other locations.

The catheter proximal portion 1174 further includes a hub 1174A that provides fluid communication between the one or more lumens of the catheter 1172 and one or more extension legs 1174B extending proximally from the hub. As mentioned, placement of a needle into the patient vasculature at the insertion site 1173 is typically performed prior to insertion of the catheter, though it is appreciated that other placement methods can be employed. Further, it is appreciated that the above discussion is only one example for use of the system 1110; indeed it can be employed for a variety of uses, such as the placement of needles preparatory to insertion of a catheter as above, the insertion of a needle for other uses, or for the insertion of other medical components into the body of a patient, including x-ray or ultrasound markers, biopsy sheaths, ablation components, bladder scanning components, vena cava filters, etc.

In greater detail, the console 1120 houses a variety of components of the system 1110 and it is appreciated that the console can take one of a variety of forms. A processor 1122, including non-volatile memory such as EEPROM for instance, is included in the console 1120 for controlling system function and executing various algorithms during operation of the system 1110, thus acting as a control processor. A digital controller/analog interface 1124 is also included with the console 1120 and is in communication with both the processor 1122 and other system components to govern interfacing between the probe 1140 and other system components.

The system 1110 further includes ports 1152 for connection with additional components such as optional components 1154 including a printer, storage media, keyboard, etc. The ports in one embodiment are USB ports, though other port types or a combination of port types can be used for this and the other interfaces connections described herein. A power connection 1156 is included with the console 1120 to enable operable connection to an external power supply 1158. An internal battery 1160 can also be employed, either with or exclusive of an external power supply. Power management circuitry 1159 is included with the digital controller/analog interface 1124 of the console to regulate power use and distribution.

The display 1130 in the present embodiment is integrated into the console 1120 and is used to display information to the clinician during the placement procedure, such as an ultrasound image of the targeted internal body portion attained by the probe 1140. In another embodiment, the display may be separate from the console. In one embodiment, a console button interface 1132 and control buttons 1184 (FIG. 19) included on the probe 1140 can be used to immediately call up a desired mode to the display 1130 by the clinician to assist in the placement procedure. In one embodiment, the display 1130 is an LCD device.

FIG. 19 further depicts a needle 1200 used to gain initial access to the patient vasculature via the insertion site 1173. As will be described in further detail below, the needle 1200 is configured to cooperate with the system 1110 in enabling the system to detect the position, orientation, and advancement of the needle during an ultrasound-based placement procedure.

Figure 20:
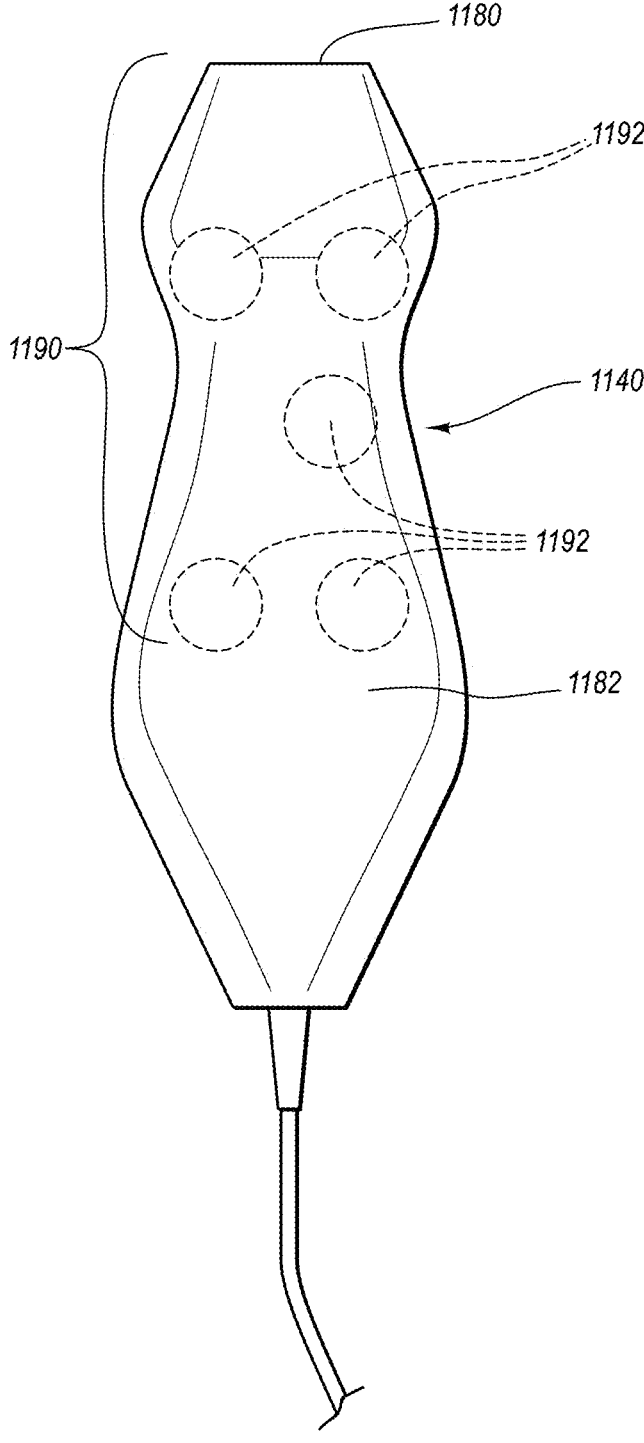
FIG. 20 is a top view of the ultrasound probe of the guidance system of FIG. 18.

FIG. 20 depicts features of the probe 1140 according to one embodiment. The probe 1140 is employed in connection with ultrasound-based visualization of a vessel, such as a vein, in preparation for insertion of the needle 1200 and/or catheter 1172 into the vasculature. Such visualization gives real time ultrasound guidance and assists in reducing complications typically associated with such introduction, including inadvertent arterial puncture, hematoma, pneumothorax, etc.

The handheld probe 1140 includes a head 1180 that houses a piezoelectric array for producing ultrasonic pulses and for receiving echoes thereof after reflection by the patient's body when the head is placed against the patient's skin proximate the prospective insertion site 1173 (FIG. 19). The probe 1140 further includes a plurality of control buttons 1184 (FIG. 19) for controlling the system, thus eliminating the need for the clinician to reach out of the sterile field, which is established about the patient insertion site prior to establishment of the insertion site, to control the system 1110.

As such, in one embodiment a clinician employs the ultrasound imaging portion of the system 1110 to determine a suitable insertion site and establish vascular access, such as with the needle 1200, prior to introduction of the catheter 1172 for ultimate advancement thereof through the vasculature toward an intended destination.

FIG. 18 shows that the probe 1140 further includes a button and memory controller 1142 for governing button and probe operation. The button and memory controller 1142 can include non-volatile memory, such as EEPROM, in one embodiment. The button and memory controller 1142 is in operable communication with a probe interface 1144 of the console 1120, which includes a piezo input/output component 1144A for interfacing with the probe piezoelectric array and a button and memory input/output component 1144B for interfacing with the button and memory controller 1142.

As seen in FIG. 20, the probe 1140 includes a sensor array 1190 for detecting the position, orientation, and movement of the needle 1200 during ultrasound imaging procedures, such as those described above. As will be described in further detail below, the sensor array includes a plurality of magnetic sensors 1192 embedded within the housing of the probe. The sensors 1192 are configured to detect a magnetic field associated with the needle 1200 and enable the system 1110 to track the needle. Though configured here as magnetic sensors, it is appreciated that the sensors 1192 can be sensors of other types and configurations, as will be described. Also, though they are shown in FIG. 20 as included with the probe 1140, the sensors 1192 of the sensor array 1190 can be included in a component separate from the probe, such as a separate handheld device. In the present embodiment, the sensors 1192 are disposed in a planar configuration below a top face 1182 of the probe 1140, though it is appreciated that the sensors can be arranged in other configurations, such as in an arched or semi-circular arrangement.

In the present embodiment, each of the sensors 1192 includes three orthogonal sensor coils for enabling detection of a magnetic field in three spatial dimensions. Such three dimensional ("3-D") magnetic sensors can be purchased, for example, from Honeywell Sensing and Control of Morristown, NJ Further, the sensors 1192 of the present embodiment are configured as Hall-effect sensors, though other types of magnetic sensors could be employed. Further, instead of 3-D sensors, a plurality of one dimensional magnetic sensors can be included and arranged as desired to achieve 1-, 2-, or 3-D detection capability.

In the present embodiment, five sensors 1192 are included in the sensor array 1190 so as to enable detection of the needle 1200 in not only the three spatial dimensions (i.e., X, Y, Z coordinate space), but also the pitch and yaw orientation of the needle itself. Note that in one embodiment, orthogonal sensing components of two or more of the sensors 1192 enable the pitch and yaw attitude of the magnetic element 1210, and thus the needle 1200, to be determined.

In other embodiments, fewer or more sensors can be employed in the sensor array. More generally, it is appreciated that the number, size, type, and placement of the sensors of the sensor array can vary from what is explicitly shown here.

Figure 21A:
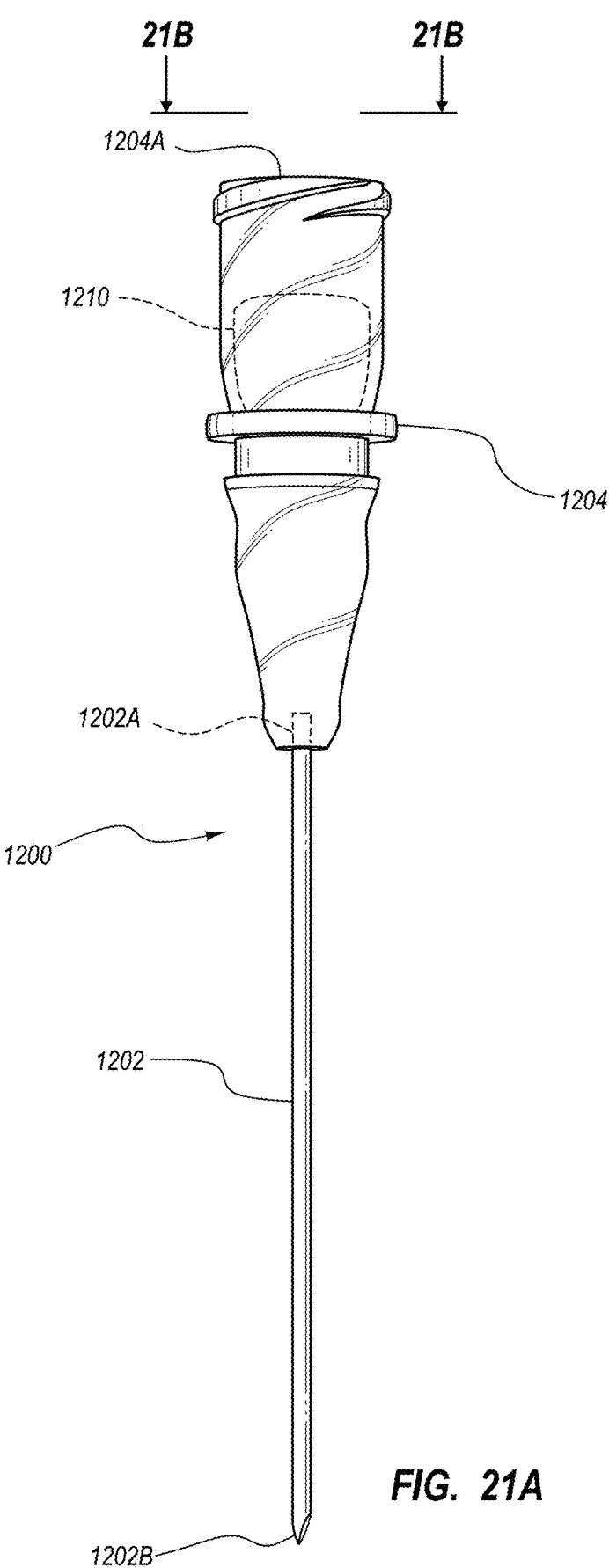
FIG. 21A is a side view of a needle for use with the guidance system of FIG. 18, according to one embodiment.
Figure 21B:
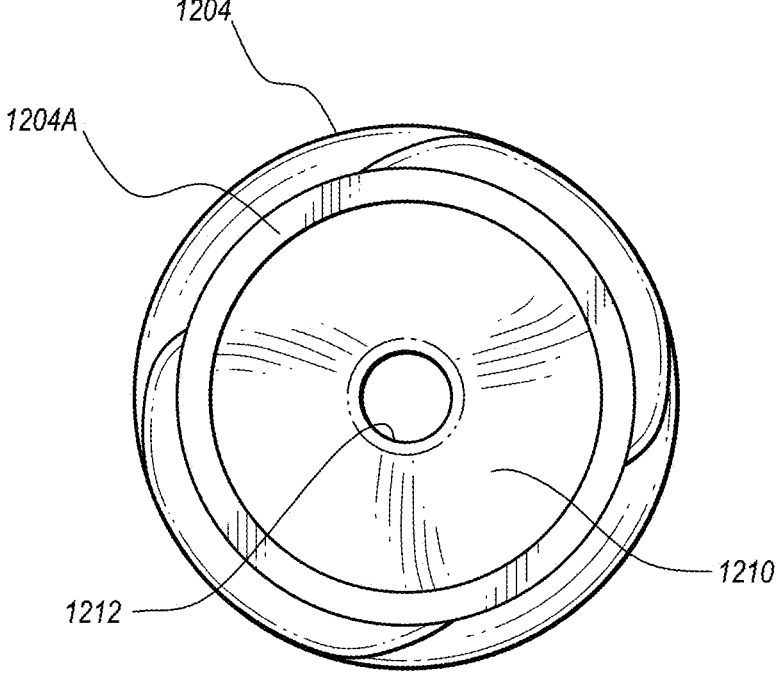
FIG. 21B is an end view of the needle of FIG. 21A.

FIGS. 21A and 21B show details of one example of the needle 1200 that can be used in connection with the guidance system 1110 in accessing a targeted internal body portion of the patient, as shown in FIG. 19, according to one embodiment. In particular, the needle 1200 includes a hollow cannula 1202, which defines a proximal end 1202A and a distal end 1202B. A hub 1204 is attached to the proximal end 1202A of the cannula 1202 and includes an open end 1204A that is configured as a connector for connecting with various devices, in the present embodiment. Indeed, the open end 1204A of the hub 1204 is in communication with the hollow cannula 1202 such that a guide wire, stylet, or other component may be passed through the hub into the cannula.

As shown in FIGS. 21A and 21B, a magnetic element 1210 is included with the hub 1204. As best seen in FIG. 21B, the magnetic element 1210 in the present embodiment is a permanent magnet, including a ferromagnetic substance for instance, and is ring-shaped so as to define hole 1212 that is aligned with the hollow cannula 1202. So configured, the magnetic element 1210 produces a magnetic field that is detectable by the sensor array 1190 of the ultrasound probe 1140 so as to enable the location, orientation, and movement of the needle 1200 to be tracked by the system 1110, as described further below.

In other embodiments, it is appreciated that many other types, numbers, and sizes of magnetic elements can be employed with the needle 1200 or other medical component to enable tracking thereof by the present guidance system.

Figures 22A, 22B:
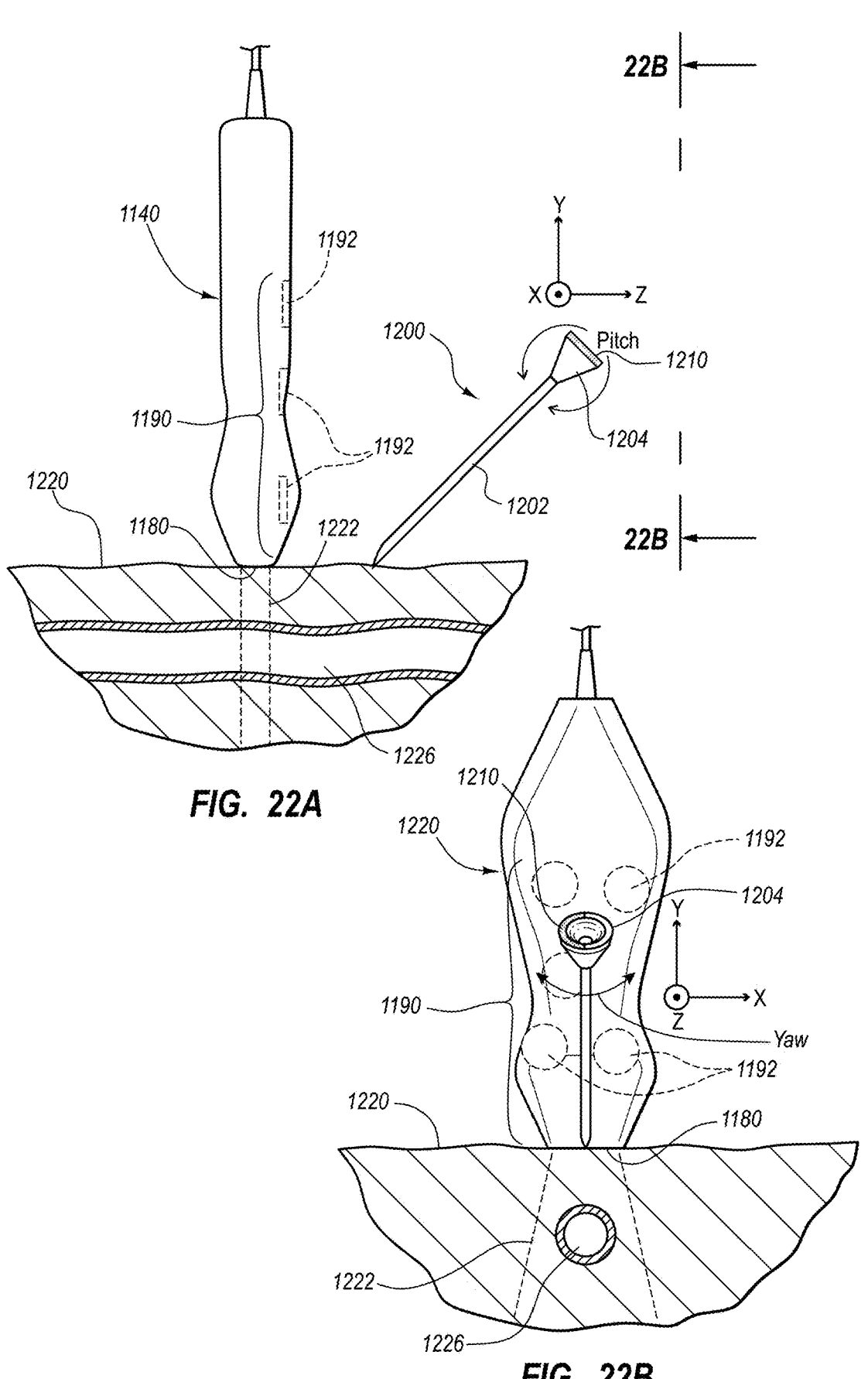
FIGS. 22A and 22B are simplified views of the ultrasound probe of the guidance system being used to guide a needle toward a vessel within the body of a patient.

Reference is now made to FIGS. 22A and 22B, which show the ultrasound probe 1140 of the system 1110 and the needle 1200 in position and ready for insertion thereof through a skin surface 1220 of a patient to access a targeted internal body portion. In particular, the probe 1140 is shown with its head 1180 placed against the patient skin and producing an ultrasound beam 1222 so as to ultrasonically image a portion of a vessel 1226 beneath the patient skin surface 1220. The ultrasonic image of the vessel 1226 can be depicted on the display 1130 of the system 1110 (FIG. 19).

As mentioned above, the system 1110 in the present embodiment is configured to detect the position, orientation, and movement of the needle 1200 described above. In particular, the sensor array 1190 of the probe 1140 is configured to detect a magnetic field of the magnetic element 1210 included with the needle 1200. Each of the sensors 1192 of the sensor array 1190 is configured to spatially detect the magnetic element 1210 in three dimensional space. Thus during operation of the system 1110, magnetic field strength data of the needle's magnetic element 1210 sensed by each of the sensors 1192 is forwarded to a processor, such as the processor 1122 of the console 1120 (FIG. 18), which computes in real-time the position and/or orientation of the magnetic element 1210.

Specifically, and as shown in FIGS. 22A and 22B, the position of the magnetic element 1210 in X, Y, and Z coordinate space with respect to the sensor array 1190 can be determined by the system 1110 using the magnetic field strength data sensed by the sensors 1192. Moreover, FIG. 22A shows that the pitch of the magnetic element 1210 can also be determined, while FIG. 22B shows that the yaw of the magnetic element can be determined. Suitable circuitry of the probe 1140, the console 1120, or other component of the system can provide the calculations necessary for such position/orientation. In one embodiment, the magnetic element 210 can be tracked using the teachings of one or more of the following U.S. Pat. Nos. 5,775,322; 5,879,297; 6,129, 668; 6,216,028; and 6,263,230. The contents of the aforementioned U.S. patents are incorporated herein by reference in their entireties.

Figure 23A:
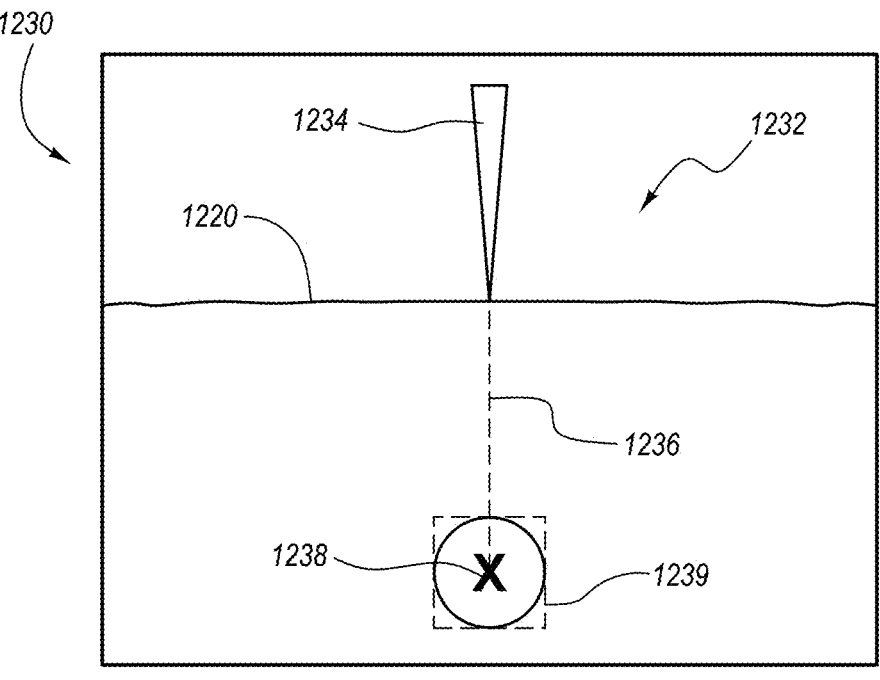
FIGS. 23A and 23B show possible screenshots for depiction on the display of the guidance system, showing the position and orientation of a needle according to one embodiment.
Figure 23B:
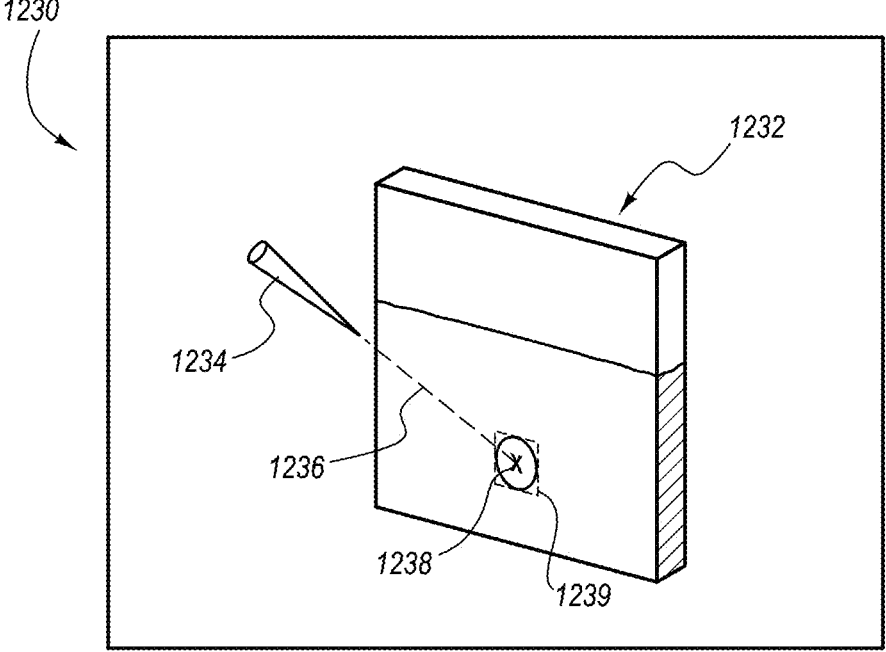

The above position and orientation information determined by the system 1110, together with the length of the cannula 1202 and position of the magnetic element 1210 with respect to the distal needle tip as known by or input into the system, enable the system to accurately determine the location and orientation of the entire length of the needle 1200 with respect to the sensor array 1190. Optionally, the distance between the magnetic element 1210 and the distal needle tip is known by or input into the system 1110. This in turn enables the system 1110 to superimpose an image of the needle 1200 on to an image produced by the ultrasound beam 1222 of the probe 1140. FIGS. 23A and 23B show examples of such a superimposition of the needle onto an ultrasound image. Specifically, FIGS. 23A and 23B each show a screenshot 1230 that can be depicted on the display 1130 (FIG. 19), for instance. In FIG. 23A, an ultrasound image 1232 is shown, including depiction of the patient skin surface 1220, and the subcutaneous vessel 1226. The ultrasound image 1232 corresponds to an image acquired by the ultrasound beam 1222 shown in FIGS. 22A and 22B, for instance.

The screenshot 1230 further shows a needle image 1234 representing the position and orientation of the actual needle 1200 as determined by the system 1110 as described above. Because the system is able to determine the location and orientation of the needle 1200 with respect to the sensor array 1190, the system is able to accurately determine the position and orientation of the needle 1200 with respect to the ultrasound image 1232 and superimpose it thereon for depiction as the needle image 1234 on the display 1130. Coordination of the positioning of the needle image 1234 on the ultrasound image 1232 is performed by suitable algorithms executed by the processor 1122 or other suitable component of the system 1110.

The sensors 1192 are configured to continuously detect the magnetic field of the magnetic element 1210 of the needle 1200 during operation of the system 1110. This enables the system 1110 to continuously update the position and orientation of the needle image 1234 for depiction on the display 1130. Thus, advancement or other movement of the needle 1200 is depicted in real-time by the needle image 1234 on the display 1130. Note that the system 1110 is capable of continuously updating both the ultrasound image 1232 and the needle image 1234 on the display 1130 as movements of the probe 1140 and the needle 1200 occur during a placement procedure or other activity.

FIG. 23A further shows that in one embodiment the system 1110 can depict a projected path 1236 based on the current position and orientation of the needle 1200 as depicted by the needle image 1234. The projected path 1236 assists a clinician in determining whether the current orientation of the needle 1200, as depicted by the needle image 1234 on the display 1130, will result in arriving at the desired internal body portion target, such as the vessel 1226 shown here. Again, as the orientation and/or position of the needle image 1234 changes, the projected path 1236 is correspondingly modified by the system 1110. A target 1238, indicating the point where the projected path 1236 crosses the plane of the ultrasound image 1232, can also be depicted on the display 1130 by the system 1110. As shown in FIG. 23A, in the present example the target 1238 is located within the vessel 1226 depicted in the ultrasound image 1232. Note that the position of the target 1238 on the display 1130 can also be modified as the needle 1200 and/or the ultrasound image 1232 are adjusted. The screenshot 1230 also includes an area of probability 1239, here depicted as a box, which indicates any possible margin of error of the system due to needle length, needle rigidity and flex, field strength of the magnetic element, magnetic interference, possible discrepancy in alignment of the magnetic axis of the magnetic element with the longitudinal axis of the needle, orientation of the sensor array with respect to the ultrasound imaging plane, etc.

FIG. 23B shows that, in one embodiment, the screenshot 1230 can be configured such that the ultrasound image 1232 and the needle image 1234 are oriented so as to be displayed in a three dimensional aspect. This enables the angle and orientation of the needle 1200, as depicted by the needle image 1234, to be ascertained and compared with the intended target imaged by the ultrasound image 1232. It should be noted that the screenshots 1230 are merely examples of possible depictions produced by the system 1110 for display; indeed, other visual depictions can be used. Note further that the particular area of the body being imaged is merely an example; the system can be used to ultrasonically image a variety of body portions, and should not be limited to what is explicitly depicted in the accompanying figures. Further, the system as depicted and described herein can be included as a component of a larger system, if desired, or can be configured as a stand-alone device. Also, it is appreciated that, in addition to the visual display 1130, aural information, such as beeps, tones, etc., can also be employed by the system 1110 to assist the clinician during positioning and insertion of the needle into the patient.

As mentioned above, in one embodiment it is necessary for the system 1110 to know the total length of the needle 1200 and the location of the magnetic element 1210 thereon in order to enable an accurate depiction of the needle image 1234 and other features of the screenshots 1230 of FIGS. 23A and 23B to be made. The system 1110 can be informed these and/or other pertinent parameters in various ways, including scanning by the system of a barcode included on or with the needle, the inclusion of a radiofrequency identification ("RFID") chip with the needle for scanning by the system, color coding of the needle, manual entry of the parameters by the clinician into the system, etc. For instance, an RFID chip 1354 is included on the needle 1200 shown in FIG. 33A. The probe 1140 or other component of the system 1110 can include an RFID reader to read the information included on the RFID chip 1354, such as the type or length of the needle 1200, etc. These and other means for inputting the needle parameters into the system 1110 or detecting the parameters are therefore contemplated.

In one embodiment, a length of the needle (or other aspect of a medical component) can be determined by measurement by the probe/system of a characteristic of the magnetic element, such as its field strength. For instance, in one embodiment the magnetic element of the needle can be positioned at a predetermined distance from the probe or at a predetermined location with respect to the probe. With the magnetic element so positioned, the sensor array of the probe detects and measures the field strength of the magnetic element. The system can compare the measured field strength with a stored list of possible field strengths corresponding to different lengths of needles. The system can match the two strengths and determine the needle length. The needle location and subsequent needle insertion can then proceed as described herein. In another embodiment, instead of holding the magnetic element stationary at a predetermined location, the magnetic element can be moved about the probe such that multiple field strength readings are taken by the probe. Aspects that can be modified so as to impart different field strengths to a set of magnetic element include size, shape, and composition of the magnetic element, etc.

Further details are given here regarding use of the system 1110 in guiding a needle or other medical device in connection with ultrasonic imaging of a targeted internal body portion ("target") of a patient, according to one embodiment. With the magnetic element-equipped needle 1200 positioned a suitable distance (e.g., two or more feet) away from the ultrasound probe 1140 including the sensor array 1190, the probe is employed to ultrasonically image, for depiction on the display 1130 of the system 1110, the target within the patient that the needle is intended to intersect via percutaneous insertion. A calibration of the system 1110 is then initiated, in which algorithms are executed by the processor 1122 of the console 1120 to determine a baseline for any ambient magnetic fields in the vicinity of where the procedure will be performed. The system 1110 is also informed of the total length of the needle 1200, and/or position of the magnetic element with respect to the distal needle tip such as by user input, automatic detection, or in another suitable manner, as has been discussed above.

The needle 1200 is then brought into the range of the sensors 1192 of the sensor array 1190 of the probe 1140. Each of the sensors 1192 detects the magnetic field strength associated with the magnetic element 1210 of the needle 1200, which data is forwarded to the processor 1122. In one embodiment, such data can be stored in memory until needed by the processor. As the sensors 1192 detect the magnetic field, suitable algorithms are performed by the processor 1122 to calculate a magnetic field strength of the magnetic element 1210 of the needle 1200 at predicted points in space in relationship to the probe. The processor 1122 then compares the actual magnetic field strength data detected by the sensors 1192 to the calculated field strength values. Note that this process is further described by the U.S. patents identified above. This process can be iteratively performed until the calculated value for a predicted point matches the measured data. Once this match occurs, the magnetic element 1210 has been positionally located in three dimensional space. Using the magnetic field strength data as detected by the sensors 1192, the pitch and yaw (i.e., orientation) of the magnetic element 1210 can also be determined. Together with the known length of the needle 1200 and the position of the distal tip of the needle with respect to the magnetic element, this enables an accurate representation of the position and orientation of the needle can be made by the system 1110 and depicted as a virtual model, i.e., the needle image 1234, on the display 1130. Note that the predicted and actual detected values must match within a predetermined tolerance or confidence level in one embodiment for the system 1110 to enable needle depiction to occur.

Depiction of the virtual needle image 1234 of the needle 1200 as described above is performed in the present embodiment by overlaying the needle image on the ultrasound image 1232 of the display 1130 (FIGS. 23A, 23B). Suitable algorithms of the system 1110 as executed by the processor 1122 or other suitable component further enable the projected path 1236, the target 1238, and area of probability 1239 (FIGS. 23A, 23B) to be determined and depicted on the display 1130 atop the ultrasound image 1232 of the target. The above prediction, detection, comparison, and depiction process is iteratively performed to continue tracking the movement of the needle 1200 in real-time.

Figure 24:
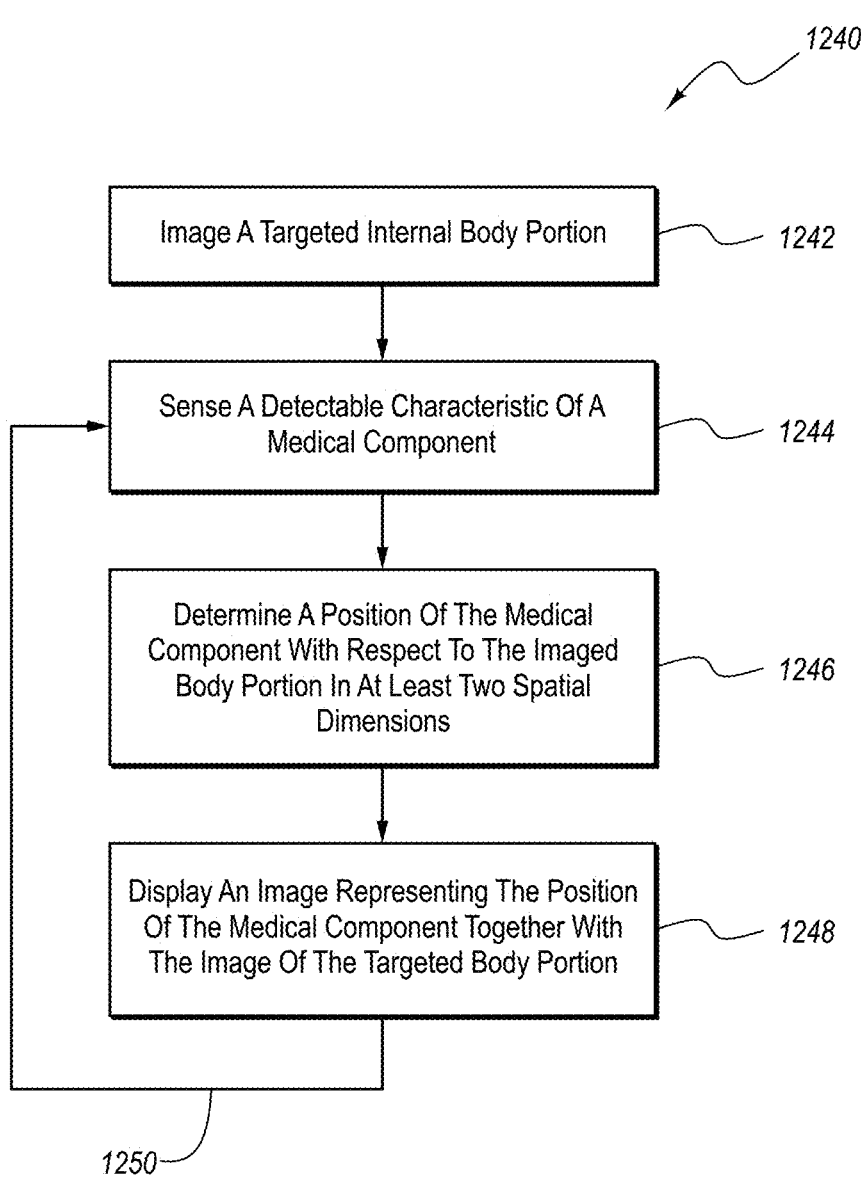
FIG. 24 shows various stages of a method for guiding a needle to a desired target within the body of a patient according to one embodiment.

In light of the foregoing and with reference to FIG. 24, it is appreciated that in one embodiment a method 1240 for guiding a needle or other medical component includes various stages. At stage 1242, a targeted internal body portion of a patient is imaged by an imaging system, such as an ultrasound imaging device for instance.

At stage 1244, a detectable characteristic of a medical component such as a needle is sensed by one or more sensors included with the imaging system. In the present embodiment, the detectable characteristic of the needle is a magnetic field of the magnetic element 1210 included with the needle 1200 and the sensors are magnetic sensors included in the sensor array 1190 included with the ultrasound probe 1140.

At stage 1246, a position of the medical component with respect to the targeted internal body portion is determined in at least two spatial dimensions via sensing of the detectable characteristic. As described above, such determination is made in the present embodiment by the processor 1122 of the console 1120.

At stage 1248, an image representing the position of the medical component is combined with the image of the targeted internal body portion for depiction on a display. Stage 1250 shows that stages 1244-1248 can be iteratively repeated to depict advancement or other movement of the medical component with respect to the imaged target, such as percutaneous insertion of the needle 1200 toward the vessel 1226 (FIGS. 23A, 23B), for instance.

It is appreciated that the processor 1122 or other suitable component can calculate additional aspects, including the area of probability 1239 and the target 1238 (FIGS. 23A, 23B) for depiction on the display 1130.

Figure 25:
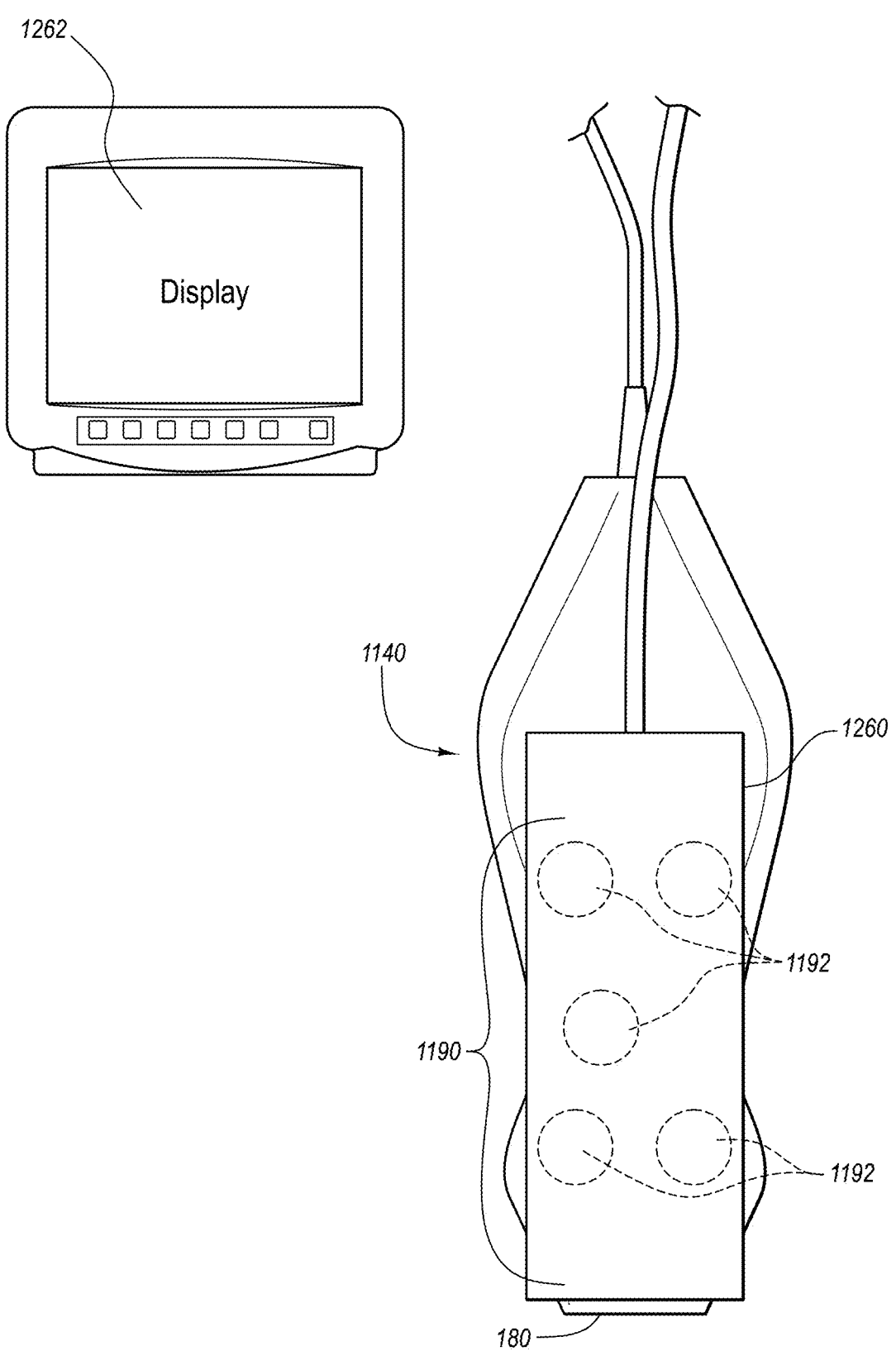
FIG. 25 shows a sensor array for attachment to an ultrasound probe and associated display, according to one embodiment.

It is appreciated that in one embodiment the sensor array need not be incorporated natively into the ultrasound imaging device, but can be included therewith in other ways. FIG. 25 shows one example of this, wherein an attachable sensor module 1260 including the sensors 1192 of the sensor array 1190 is shown attached to the ultrasound probe 1140. Such a configuration enables needle guidance as described herein to be achieved in connection with a standard ultrasound imaging device, i.e., a device not including a sensor array integrated into the ultrasound probe or a processor and algorithms configured to locate and track a needle as described above. As such, the sensor module 1260 in one embodiment includes a processor and algorithms suitable for locating and tracking the needle or other medical component and for depicting on a display the virtual image of the needle for overlay on to the ultrasound image. In one embodiment, the sensor module 1260 can be included with a module display 1262 for depiction of the needle tracking. These and other configurations of the guidance system are therefore contemplated.

Figures 26, 27:
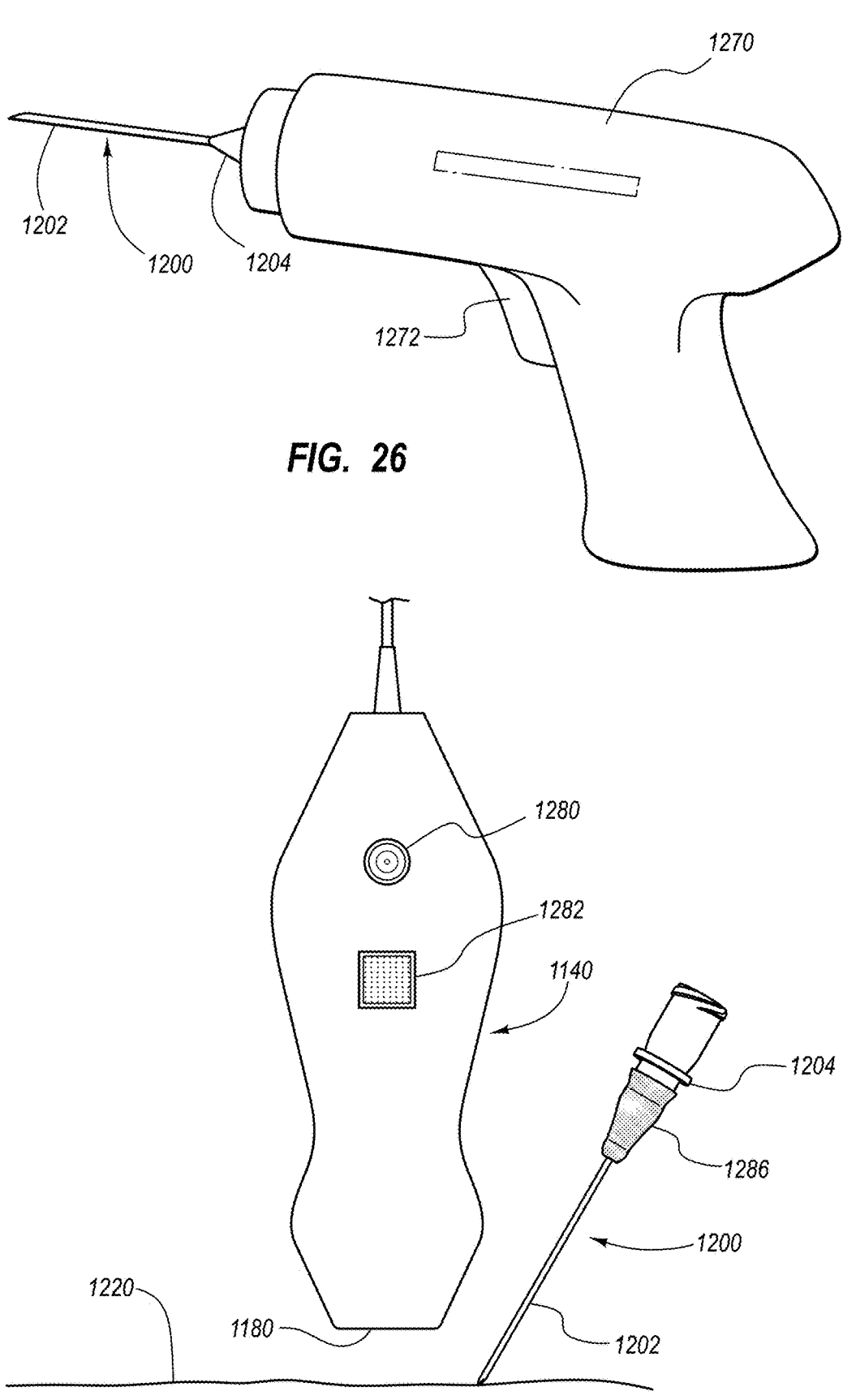
FIG. 26 is a simplified view of a needle holder gun for use with the guidance system of FIG. 18, according to one embodiment.
FIG. 27 is a simplified view of an ultrasound probe and needle including elements of an optical guidance system, according to one embodiment.

FIG. 26 shows that in one embodiment, a needle holder can be employed to hold and advance the needle 1200 during the ultrasound imaging and needle guidance procedure performed by the system 1110 as has been described. As shown, the needle holder 1270 is pistol-shaped and includes a trigger 1272 for selectively advancing the needle 1200 or other suitable medical component by moving the needle longitudinally away from the barrel of the holder upon pressing of the trigger. So configured, the needle holder 1270 facilitates ease of needle handling with one hand of the clinician while the other hand is grasping and manipulating the ultrasound probe 1140. In addition, the needle holder 1270 can provide needle movement/rotation assistance such as via a motor, ratcheting, hydraulic/pneumatic drivers, etc. Moreover, a clocking feature can be included on the needle holder 1270 to assist with determining the orientation of the distal tip of the needle 1200 and for facilitating rotation of the needle.

In one embodiment, the needle holder 1270 can be operably connected to the system 1110 such that advancement by the needle holder is automatically stopped when the distal end 1202B of the needle cannula 1202 reaches the targeted internal body portion or the needle intercepts the ultrasound plane. In yet another embodiment the magnetic element can be included with the needle holder instead of the needle itself. The needle, when temporarily attached to the needle holder, can thus be located and guided by the guidance system without the need for a magnetic element to be attached directly to the needle.

Note that other sensor configurations can also be employed. In one embodiment, an annular sensor can be configured to receive through a hole defined thereby the cannula of the needle. So disposed, a magnetic element of the needle is positioned proximate the annular sensor, which enables ready detection of the magnetic element and location of the needle by the system. The annular sensor can be attached to a surface of the probe, in one embodiment.

Figures 28, 29:
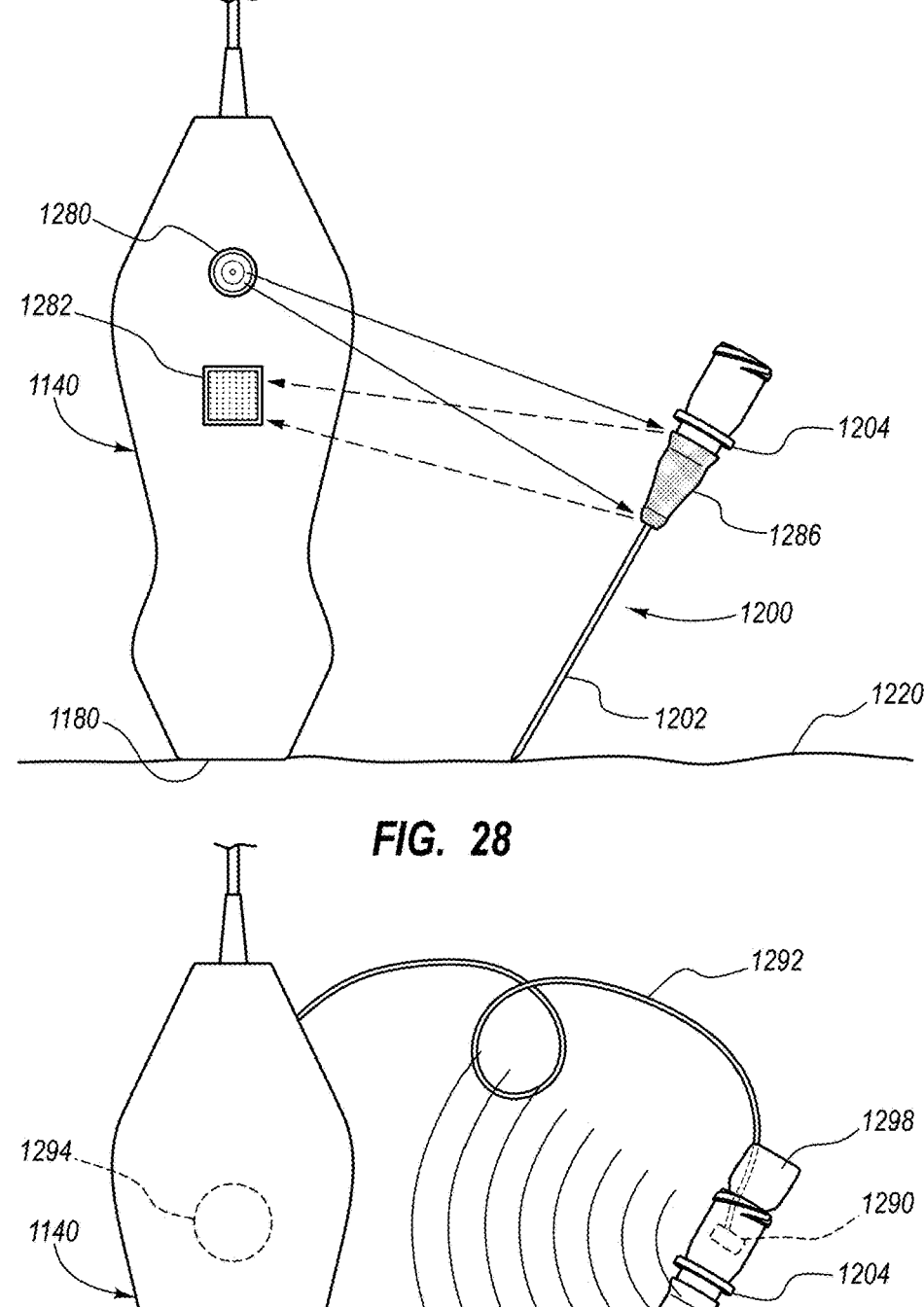
FIG. 28 shows operation of the ultrasound probe and needle of FIG. 27, according to one embodiment.
FIG. 29 is a simplified view of an ultrasound probe and needle including elements of an electromagnetic signal-based guidance system, according to one embodiment.

FIGS. 27 and 28 depict components of the guidance system 1110 according to another embodiment, wherein an optical-based interaction between the probe 1140 and the needle 1200 is employed to enable tracking and guidance of the needle. In particular, the probe 1140 includes an optical/light source, such as an LED 1280, and a photodetector 1282 positioned on the probe surface. It is appreciated that the light source and detector can be configured to produce and detect light signals of a variety of ranges including visible, infrared, etc.

The needle hub 1204 includes a reflective surface 1286 capable of reflecting light produced by the LED 1280 and incident thereon. As shown in FIG. 28, light emitted by the LED 1280 is reflected by the reflective surface 1286 of the needle 1200, a portion of which is received and sensed by the photodetector 1282. As in previous embodiments, the processor 1122 of the system console 1120 can be employed to receive the sensed data of the photodetector 1282 and compute the position and or orientation of the needle 1200. As before, the length of the needle 1200 and/or the position of the reflective surface with respect to the distal end of the needle 1200 are input into or otherwise detectable or known by the system 1110. Note that the reflective surface can be included at other locations on the needle.

In light of the above, it is appreciated that in the present embodiment the detectable characteristic of the needle 1200 includes the reflectivity of the reflective surface 1286, in contrast to the magnetic field characteristic of the magnetic element 1210 of previous embodiments, and the sensor includes the photodetector 1282, in contrast to the magnetic sensors 1192 of previous embodiments. It should be appreciated that in one embodiment, the above-described configuration can be reversed, wherein an optical source is included with the needle or medical component. In this case, light is emitted from the needle and detected by the photodetector 1282 included with the probe 1140 so as to enable location and tracking of the needle. A power source can be included with the needle, such as a watch battery or the like, in order to power the light source of the needle.

More generally, it is appreciated that the needle or medical component can include one or more of these or other detectable characteristics to enable the needle to be tracked and guided toward a target within the body of the patient. Non-limiting examples of other detectable characteristic modalities include electromagnetic or radiofrequency ("RF") (see, e.g., FIGS. 29-30 below), and radioactivity. With respect to RF modalities, it is appreciated that one or more synchronously or asynchronously pulsed frequency sources can be included with the needle as to enable detection thereof by a suitable sensor(s). Or, an RF first source can be coupled with a passive magnet as a second source.

Figure 30:
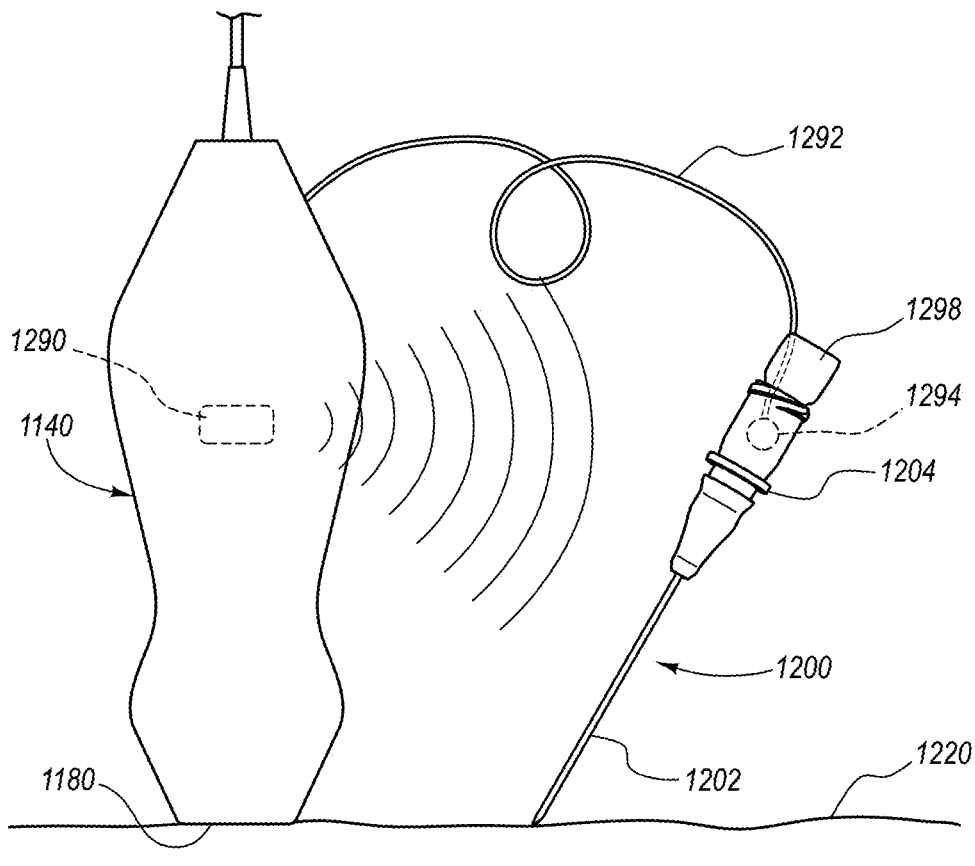
FIG. 30 is a simplified view of an ultrasound probe and needle including elements of an electromagnetic signal-based guidance system, according to another embodiment.
Figures 31A, 31B:
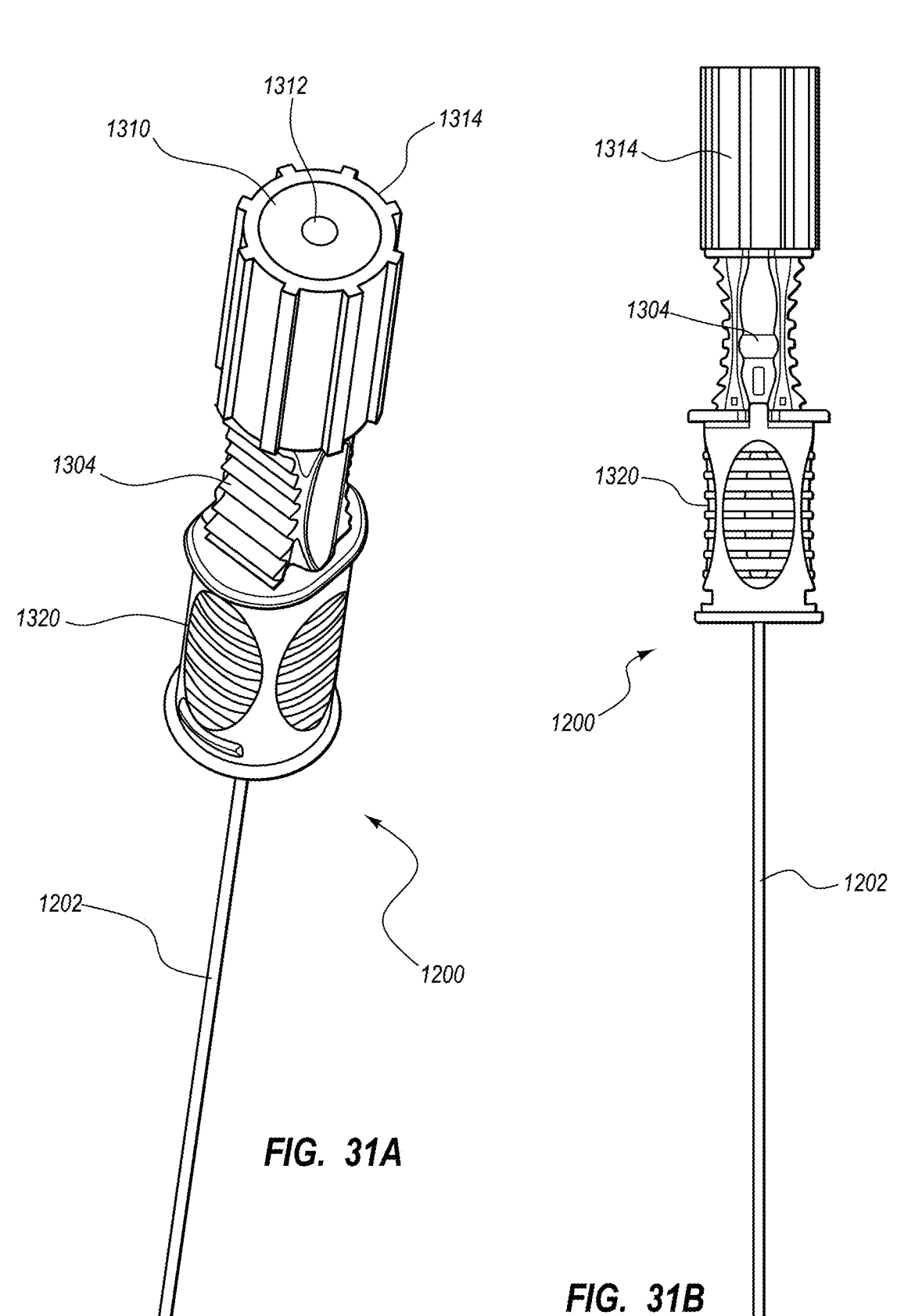
FIGS. 31A-31D are various views of a needle and associated components for use with a needle guidance system, according to one embodiment.
Figure 31C:
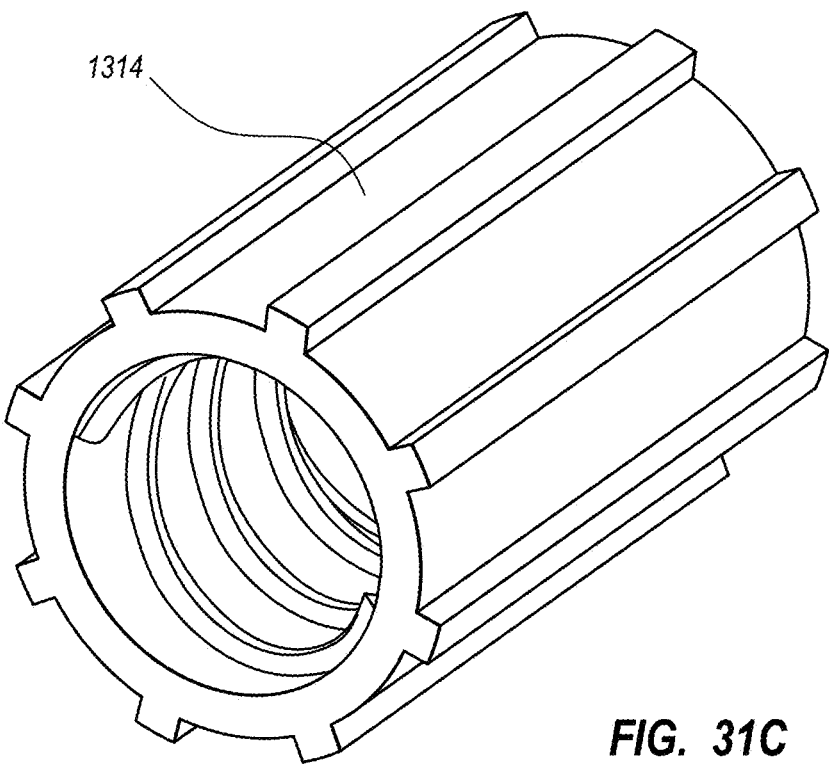
Figure 31D:
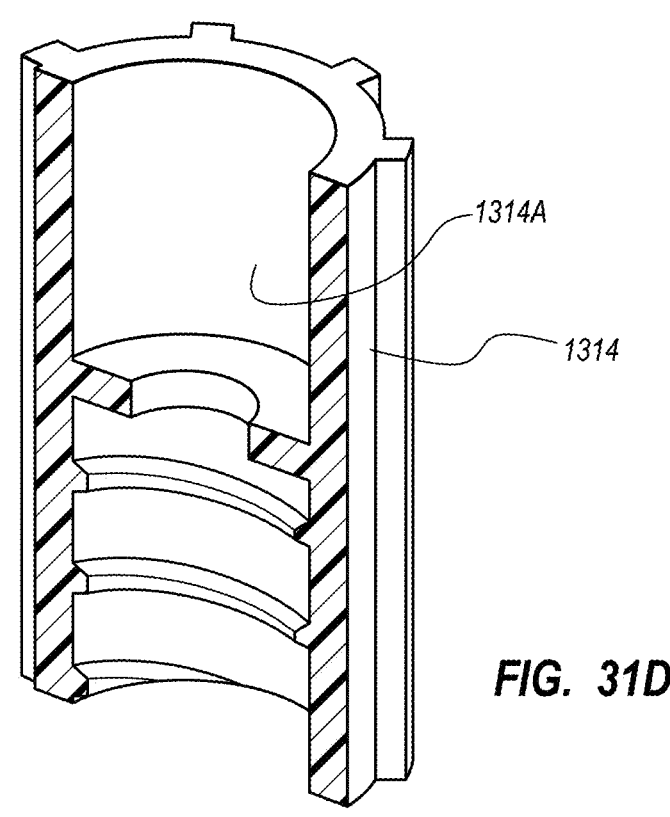

FIGS. 29 and 30 depict components of a guidance system according to one embodiment, wherein EM signal interaction between the probe 1140 and the needle 1200 is employed to enable tracking and guidance of the needle. In particular, in FIG. 29 the needle 1200 includes a stylet 1298 disposed therein. The stylet 1298 includes an EM coil 1290 that is operably connected to the probe 1140 via a tether 1292. In this way, the EM coil 1290 can be driven by suitable components included in the probe 1140 or system console 1120 such that the EM coil emits an EM signal during operation.

A sensor 1294 suitable for detecting EM signals emitted by the EM coil 1290 of the stylet 1298 is included in the probe 1140. In the present embodiment, the sensor 1294 is a three-axis sensor for detecting corresponding orthogonal components of the EM signal, though other coil and sensor configurations can also be employed. So configured, the position and orientation of the needle 1200 can be determined, by EM signal triangulation or other suitable process, and displayed by the system in a manner similar to that already described above. As in previous embodiments, the processor 1122 of the system console 1120 (FIG. 18) can be employed to receive the sensed data of the EM sensor 1294 and compute the position and/or orientation of the needle 1200. As before, the length of the needle 1200 and/or the position of the EM coil 1290 with respect to the distal end of the needle 1200 are input into or otherwise detectable or known by the system.

FIG. 30 shows a variation of the EM configuration of FIG. 29, wherein the respective positions of the EM components is reversed: the EM coil 1290 is included in the probe 1140 and the EM sensor 1294 is included with the stylet 1298 disposed in the needle 1200. Note that in the embodiments of FIGS. 29 and 30, the operable connection between the EM coil 1290 and the EM sensor 1294 via the tether 1292 enables the component disposed in the stylet 1298 to be driven by the system 1110. This also enables correspondence of the particular EM frequency/frequencies emitted by the EM coil 1290 and detected by the EM sensor 1294 to be made. In one embodiment, the configuration shown in FIG. 29 can be varied, wherein no tether operably connects the EM coil and the EM sensor; rather, the EM coil of the stylet operates as a separate component from the probe and its EM sensor and is powered by an independent power source, such as a battery. In this case, the probe/system includes suitable signal processing components configured to detect the EM signal emitted by the EM coil and to process it as necessary in order to locate the needle.

Note that the EM coil and EM sensors can be included at other locations than what is depicted herein. For instance, the EM coil can be included on the needle itself, or on a connector that is attachable to the proximal end of the needle.

FIGS. 31A-31D give further details of the needle 1200 configured according to one embodiment, wherein the needle includes a hub 1304 from which extends the cannula 1202. A magnetic element 1310 defining a hole 1312 is included in a cavity 1314A of a housing 1314. The housing 1314 includes threads so as to threadably engage the needle hub 1304 or other suitable component of the needle or medical component. In this way, the magnetic element 1310 is removably attachable to the needle 1200 via the housing 1314. Thus, the magnetic element 1310 need not be permanently affixed or included with the needle 1200, but rather can be removed therefrom when magnetic-based needle guidance is no longer needed. In addition, this enables the magnetic element to be attached to many different types and sizes of needles. Note that in the present embodiment the needle 1200 further includes a distally slidable needle safety component 1320 for safely isolating the distal tip of the needle upon removal of the needle from the patient. Note further that other removable magnetic elements can be employed in addition to what is explicitly shown and described herein.

Figures 32, 33A, 33B:
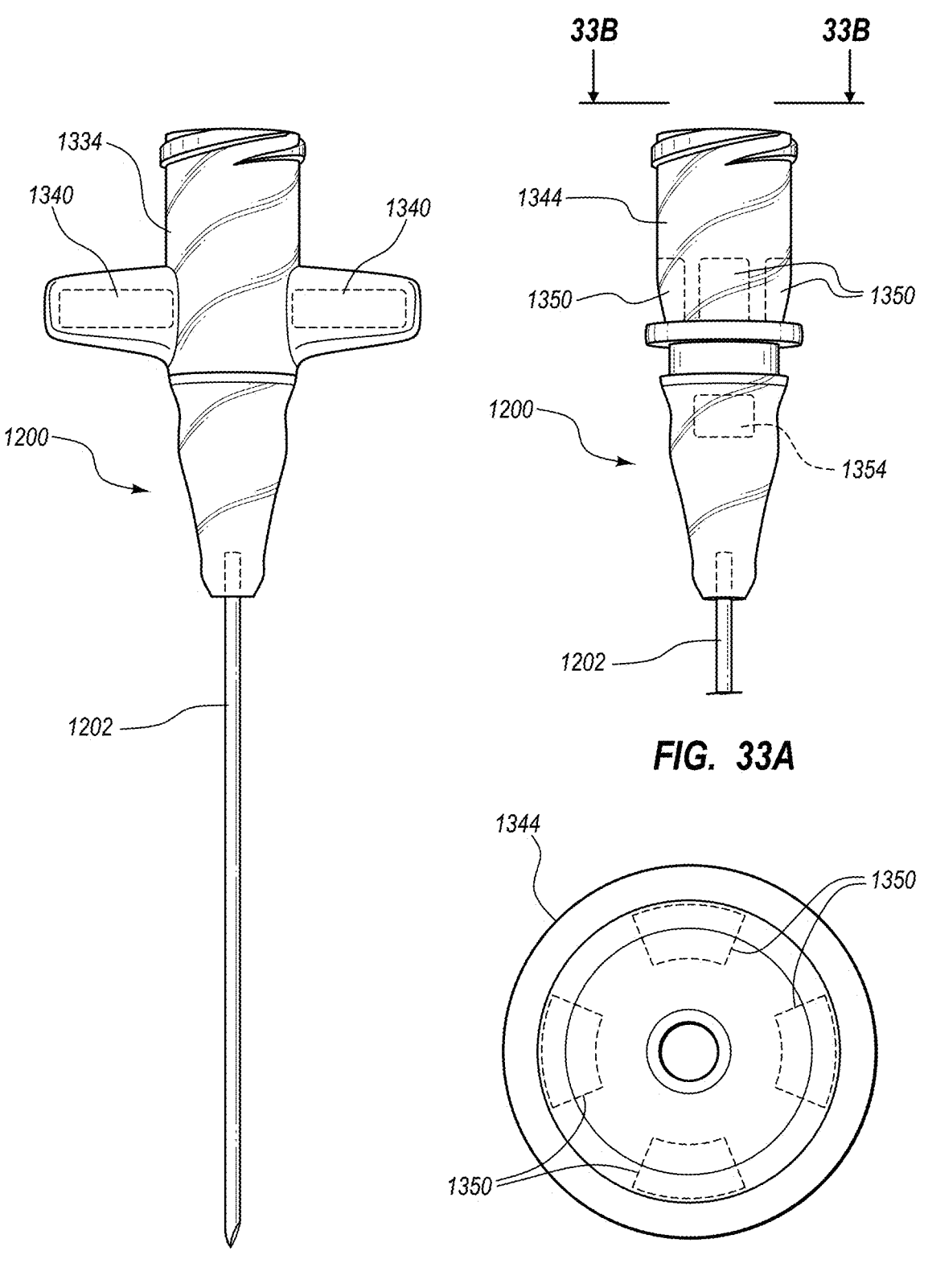
FIG. 32 is a side view of a needle for use with a needle guidance system, according to one embodiment.
FIGS. 33A and 33B are various views of a needle for use with a needle guidance system, according to one embodiment.

FIGS. 32-33B give further examples of the needle 1200 including a magnetic element. In FIG. 32, two bar-like magnetic elements 1340 are disposed so as to orthogonally extend from a hub 1334 of the needle 1200, illustrating that the magnetic element need not be oriented parallel to the longitudinal axis of the needle. In FIGS. 33A-33B, four magnetic elements 1350 are included in the needle hub 1344, showing that more than one magnetic element can be included with the needle. Such a configuration may be employed, for example, where limited space prevents one magnetic element from being used. Note the number, shape, and placement of the magnetic elements here is only one example of many possible configurations.

Figure 34A:
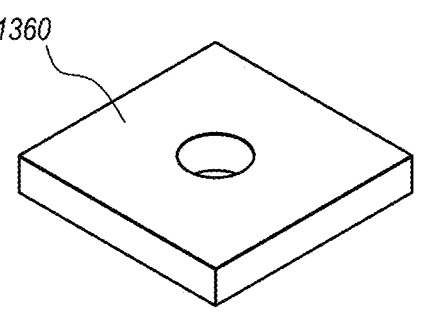
FIGS. 34A-34G are views of variously shaped magnetic elements for use with a needle guidance system according to one embodiment.
Figure 34B:
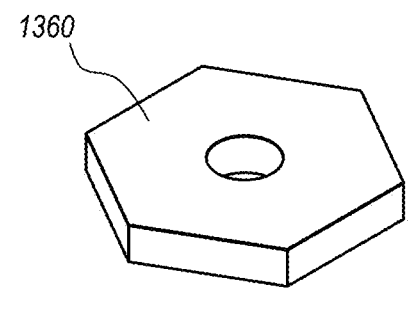
Figure 34C:
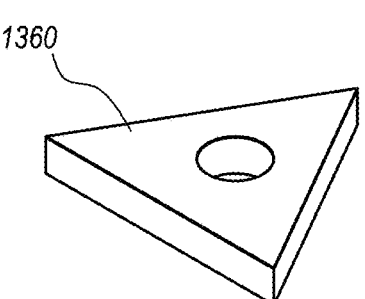
Figure 34D:
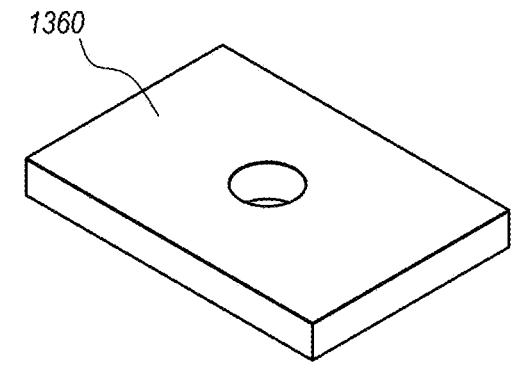
Figure 34E:
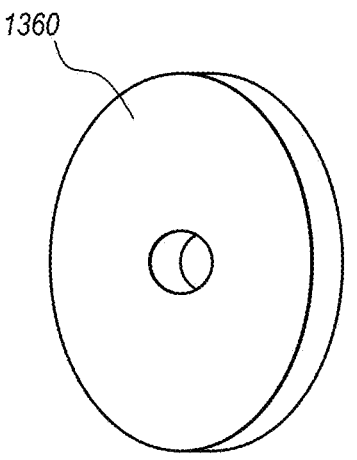
Figure 34F:
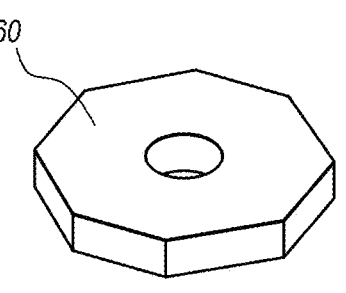
Figure 34G:
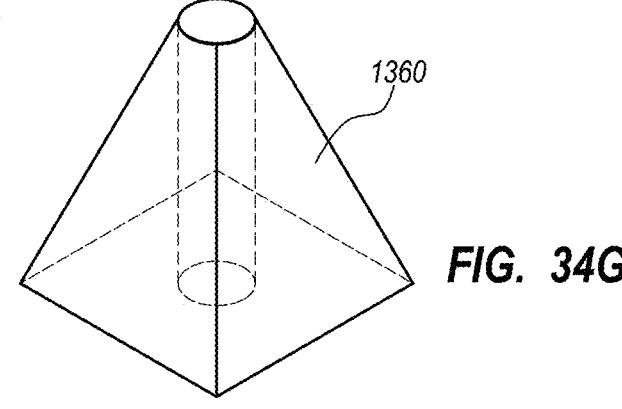

FIGS. 34A-34G give various example configurations of a magnetic element 1360 that defines a hole for receiving the cannula of the needle therethrough. Various shape configurations for the magnetic element 1360 are shown, including a square (FIG. 34A), a hexagon (FIG. 34B), a triangle (FIG. 34C), a rectangle (FIG. 34D), an oval (FIG. 34E), an octagon (FIG. 34F), and a four-sided pyramid (FIG. 34G). The magnetic elements shown in the accompanying figures are merely examples of the broad number of geometric and other shapes that can be used to define the magnetic element; indeed other shapes not shown explicitly herein are also contemplated.

Figures 35, 36:
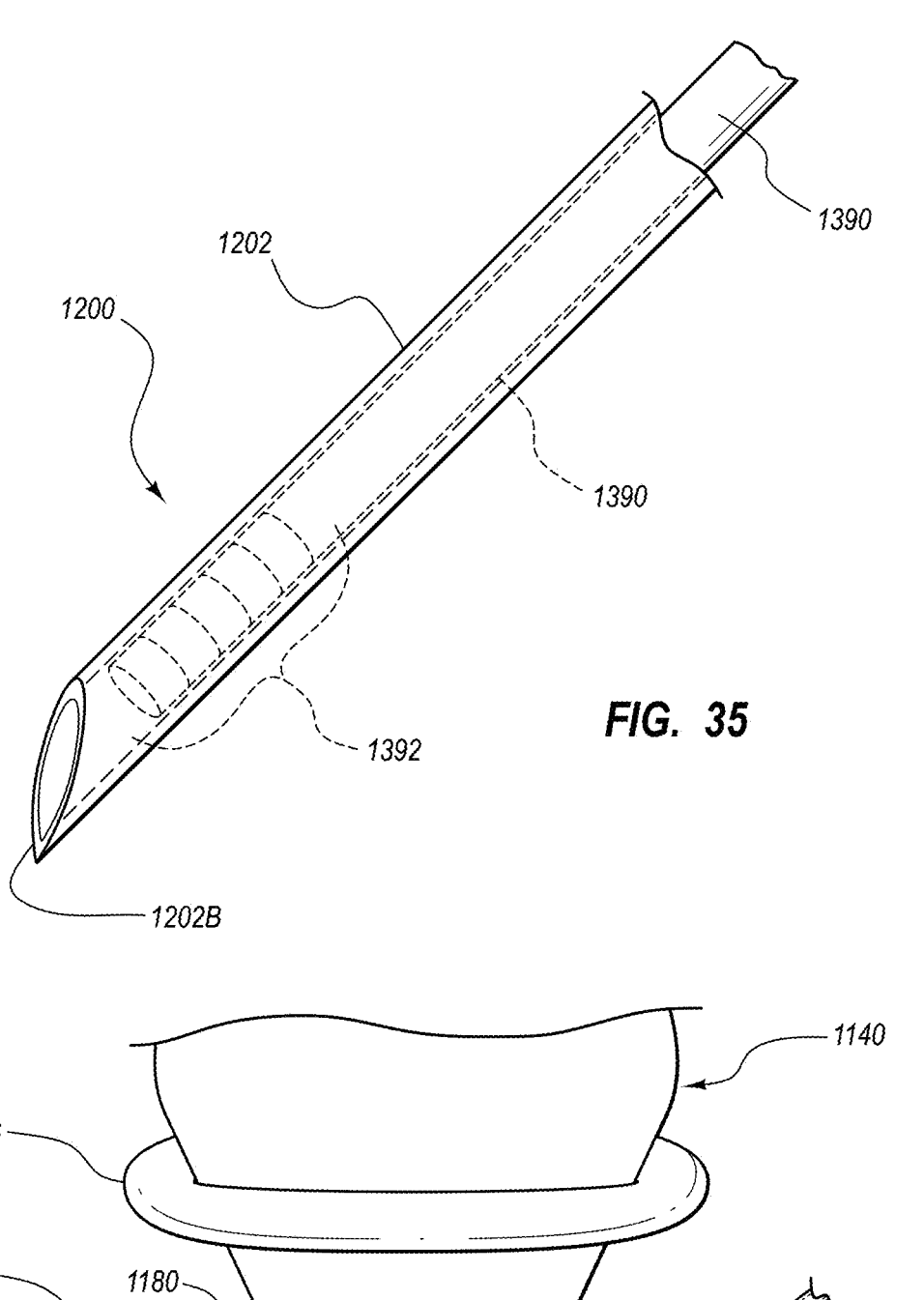
FIG. 35 is a perspective view of a distal portion of a needle cannula including a magnet-bearing stylet disposed therein, according to one embodiment.
FIG. 36 shows the needle of FIG. 35 in use with an ultrasound probe including a ring sensor, according to one embodiment.

FIGS. 35 and 36 depict yet another embodiment, wherein a stylet 1390 is included for removable insertion into the hollow cannula 1202 of the needle 1200. A plurality of permanent magnets 1392, such as solid, cylindrically shaped ferromagnets stacked end-to-end with each other, is included at a distal end of the stylet 1390. As shown in FIG. 36, the stylet 1390 is received within the needle cannula 1202 during insertion of the needle 1200 into the patient. A sensor ring 1396 or other suitable magnetic sensor can be included with or in proximity to the probe 1140 to enable detection of the magnetic field of the magnets 1392, thus enabling the guidance system to detect the position and orientation of the needle 1200 and superimpose an image thereof atop the ultrasound image produced by the probe 1140 in a manner similar to that described in connection with FIGS. 5A-7.

FIGS. 35 and 36 thus illustrate that the magnetic element(s) can be configured in any one of a variety of ways. In one embodiment, for example, the magnetic elements can be disposed more proximally along the stylet length. In another embodiment, the stylet itself can be magnetized or composed of magnetic materials. It is appreciated that the stylet can be configured in one of many different ways, analogous examples of which can be found in U.S. Pat. No. 5,099,845, titled "Medical Instrument Location Means," and U.S. Pat. No. 8,784,336, titled "Stylet Apparatuses and Methods of Manufacture," both of which are incorporated herein by reference in their entireties. These and other variations are therefore contemplated.

It should be appreciated herein that "stylet" as used herein can include any one of a variety of devices, including guidewires, configured for removable placement within a lumen of the needle to assist in the placement thereof within the patient. In one embodiment, the stylet can include a sharp end that distally extends past a blunt distal end of the needle cannula so as to enable a blunt needle to be inserted into a patient. Note that the stylet in one embodiment stiffens the needle so as to minimize unintended bending thereof during insertion.

Figure 37:
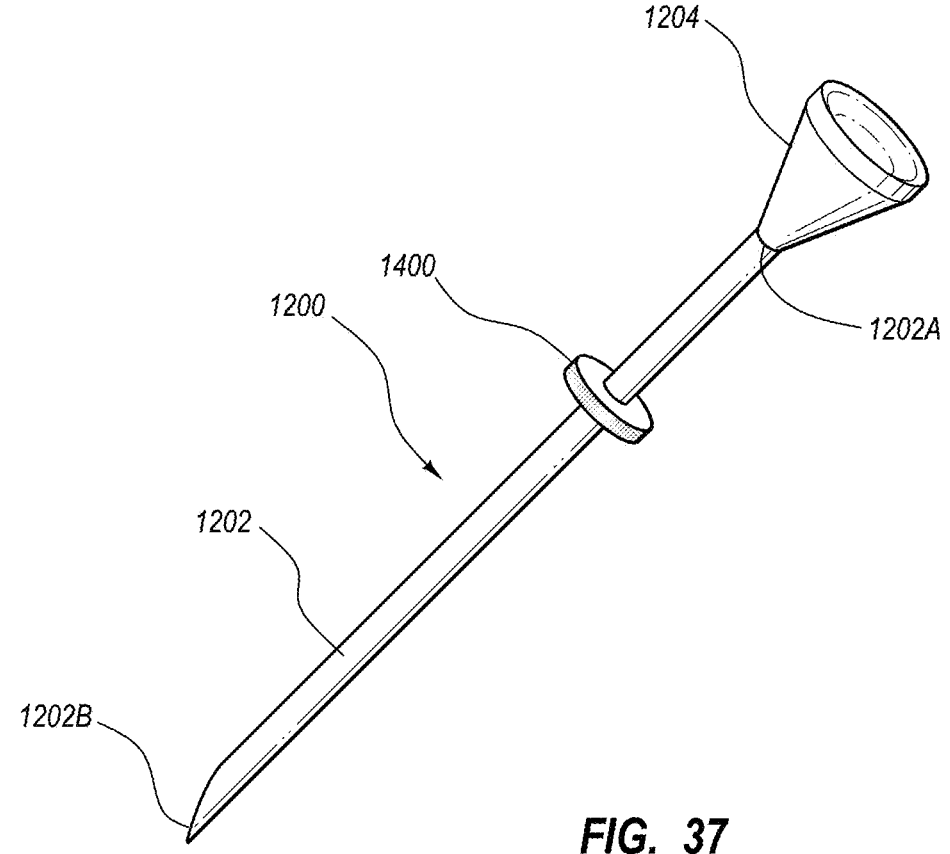
FIG. 37 is a perspective view of a needle including a donut magnet disposed on the cannula, according to one embodiment.

FIG. 37 depicts yet another possible embodiment, wherein the needle 1200 includes an annular or donut-shaped magnet 1400 disposed distal to a proximal end 1202A of the needle cannula 1202. Note that the magnet 1400 can be positioned in one of several positions along the length of the cannula 1202, in other embodiments. Positioning of the magnet 1400 relatively closer to the distal needle tip reduces the effects that unintended bending of the needle has on determining and displaying the position of the needle. In yet another embodiment, the needle itself can be magnetized. Note further that the relative places of the sensor and source (e.g., magnet) of the system can be reversed. These and other configurations are also contemplated. Further, note that the discussion herein can be applied to other imaging modalities in addition to ultrasound, including MRI, x-ray and CT scanning, etc.

Figure 38:
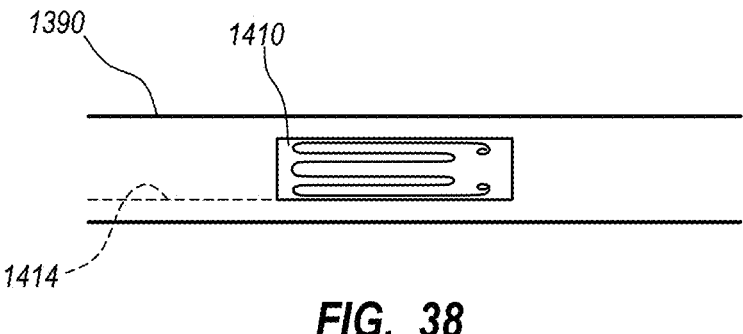
FIG. 38 is a side view of a stylet including a strain gauge according to one embodiment.

FIG. 38 depicts a strain gauge 1410 included on a stylet, such as the stylet 1390 shown in FIGS. 35 and 36 for instance. The strain gauge 1410 can be operably connected to the probe 1140, console 1120 (FIG. 18), or other component of the system 1110 via a conductive path 1414. One example of the conductive path 1414 includes one or more conductive wires disposed in or along the stylet 1390, for instance. So connected, the strain gauge 1410 acts as a transducer and can provide data relating to bending of the needle in which the stylet 1390 is disposed during needle insertion procedures, given that bending of the needle 1200 will cause similar bending to occur in the stylet 1390.

Figure 39A:
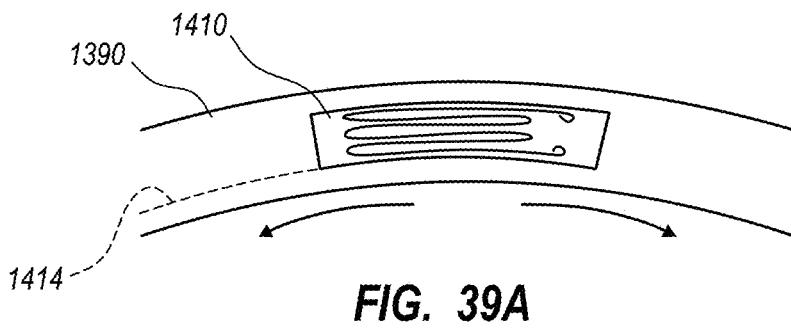
FIGS. 39A-39B show the stylet and strain gauge of FIG. 38 under bending stress.
Figure 39B:
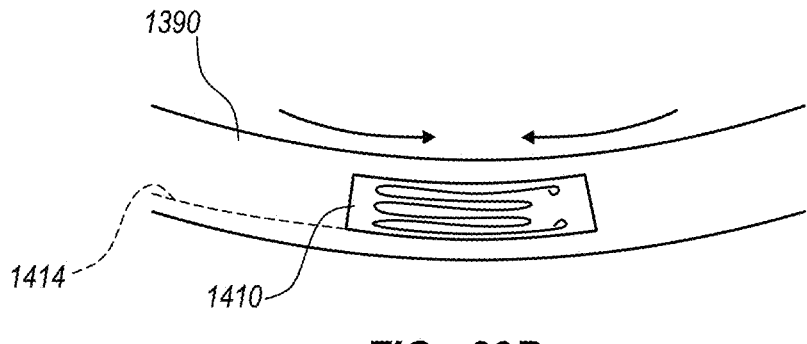
Figure 40:
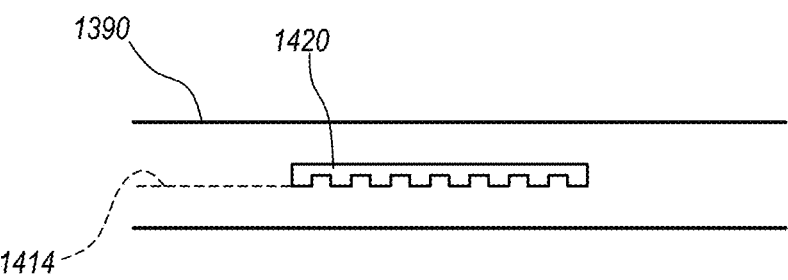
FIG. 40 is a side view of a stylet including a flex sensor according to one embodiment.

These data sensed via bending of the strain gauge 1410 can be forwarded to and interpreted by the processor 1122 (FIG. 18) or other suitable component of the system 1110 so as to include such bending together with detection of the magnetic element by the probe sensors 1192 (FIG. 20) in computing the position of the needle 1200, especially the distal tip thereof. This results in enhanced accuracy for locating and depicting the position of the needle distal tip. Indeed, FIG. 39A shows flexure of the strain gauge 1410 in one direction as caused by bending of the stylet 1390, wherein FIG. 39B shows flexure of the strain gauge in another direction. Such stylet bending is thus detected by the strain gauge 1410 (via changes in electrical resistance within the strain gauge in one embodiment) and forwarded to the system 1110 for use in computing needle position. Note that other suitable sensors and gauges can optionally be used for measuring needle/stylet bending, including a flex sensor 1420, as shown in FIG. 40 for instance, and capacitance and fiber optic-based strain gauges/sensors. Also, the sensor/gauge may be placed directly on the needle/medical component, in one embodiment.

FIGS. 41-59 depict various embodiments generally directed to the inclusion of a magnetic element, such as a permanent magnet with a needle, needle-related component, or other medical device. In particular, embodiments are disclosed for providing a needle assembly with a magnetic element whose magnetic axis is coaxially aligned with the longitudinal axis of the needle cannula. Such a magnetic element-equipped needle assembly can be spatially tracked by a suitable magnetic-based needle insertion guidance tracking system, in preparation for insertion of the needle into the body of a patient, for instance, as already described above.

Figures 41A, 41B:
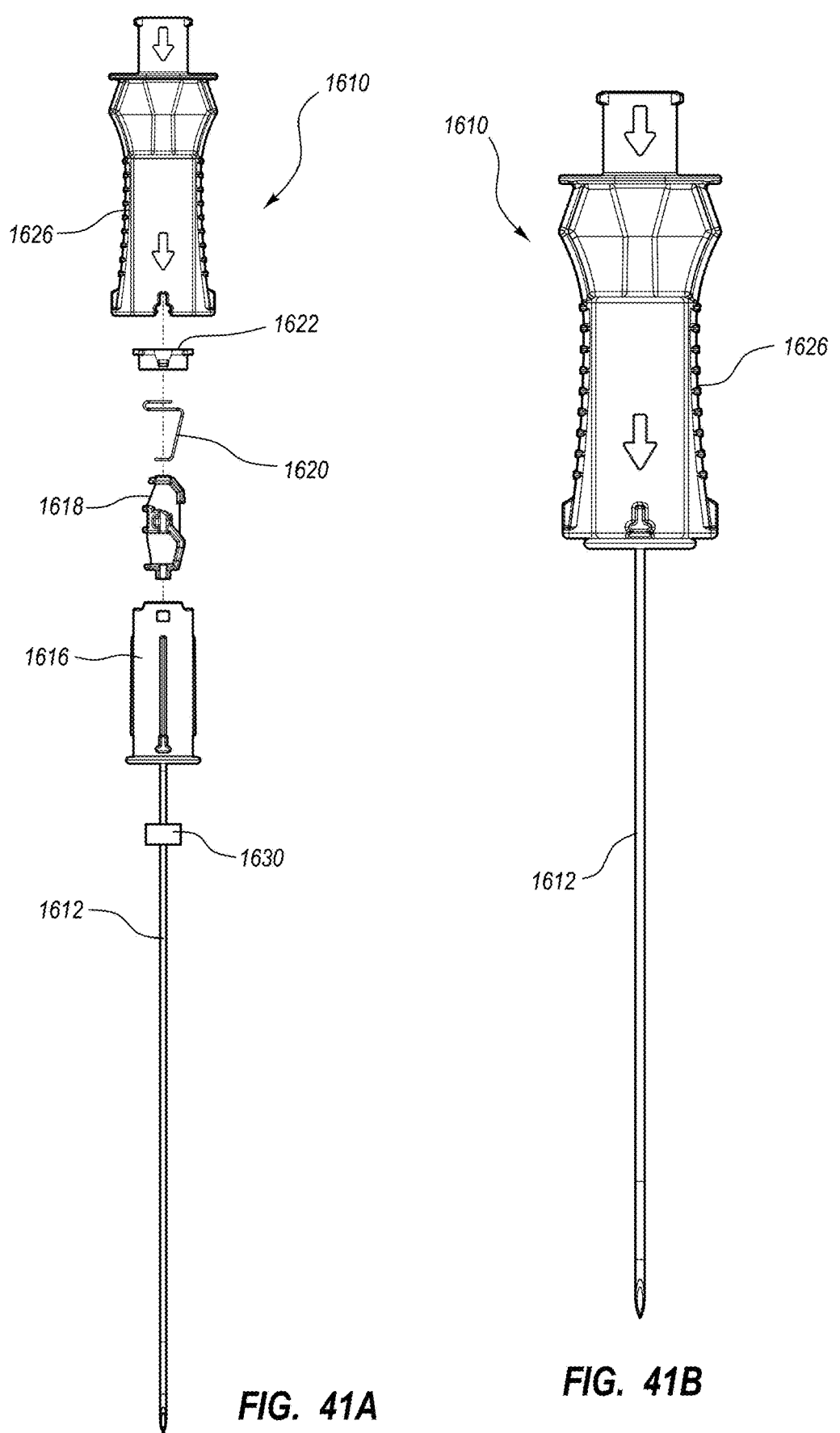
FIGS. 41A-41C are various views of a needle assembly according to one embodiment.
Figure 41C:
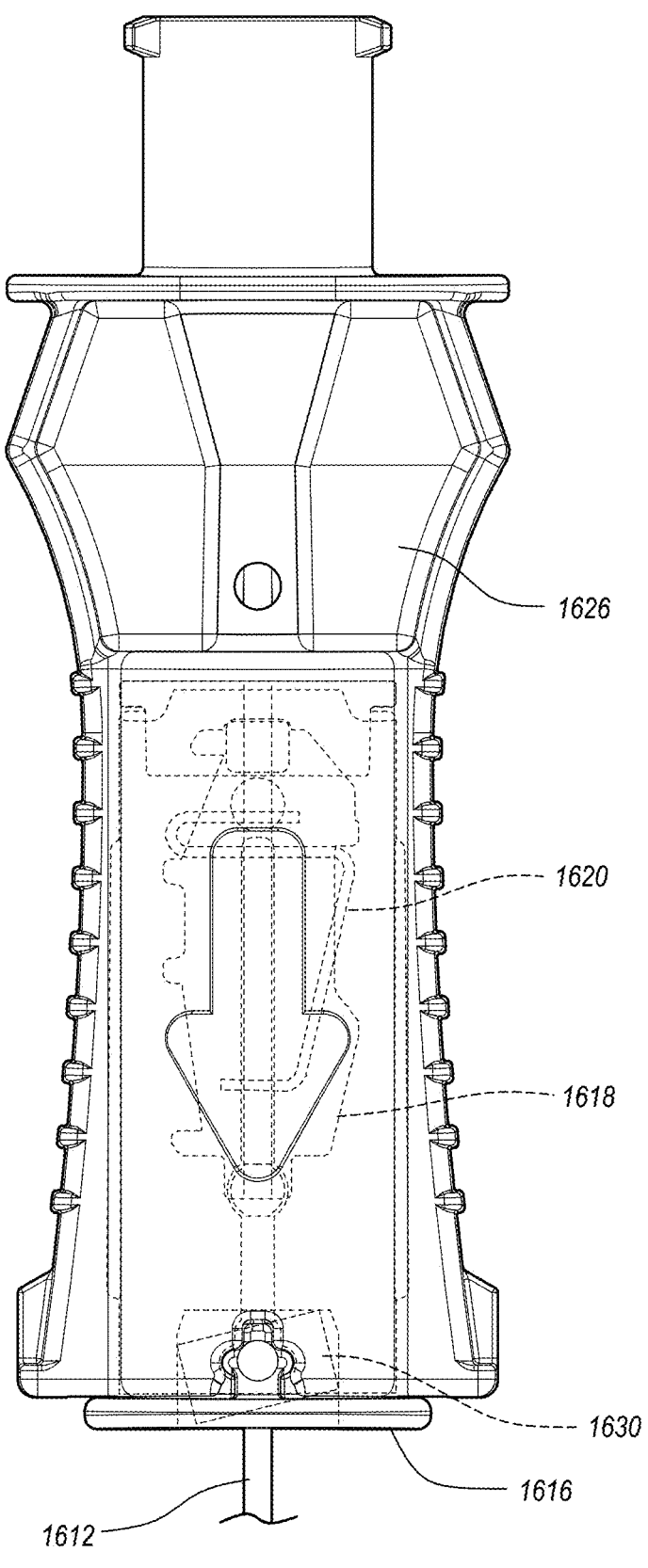

FIGS. 41A-41C show various details regarding a needle assembly 1610 that serves as one example of a medical device or component that can be guided by the above-described guidance system, in accordance with one embodiment. As shown, the needle assembly 1610 includes a hollow cannula 1612 and a safety can 1616 disposed at a proximal end of the cannula. A carriage 1618 and binding element 1620 of a needle safety component are shown for disposal within the safety can 1616. A cap 1622 covers a proximal end of the safety can 1616, and the safety can is sized for insertion into and affixation within a needle hub 1626.

A magnetic element 1630, such as a permanent magnet, is also included and is sized such that the cannula 1612 can pass through a hole 1632 defined therein and such that the magnetic element is securely disposed within a recess defined in the safety can 1616. So configured, the magnetic element 1630 in the present embodiment is cylindrically shaped with the hole 1632 defined along its central axis. Further, in accordance with present embodiments and as best seen in FIG. 41C, the magnetic element 1630 is oriented within the recess of the safety can 1616 such that its magnetic axis, which may not align with its central axis, is coaxially aligned with the longitudinal axis of the cannula 12. For example, the permanent magnet serving as the magnetic element 1630 shown in FIGS. 41A-41C is shown in FIG. 41C as tilted with respect to the needle assembly cannula 1612 such that its magnetic axis is substantially coaxially aligned with the longitudinal axis of the cannula. This alignment enables the needle insertion guidance system described further above to accurately track the distal needle tip.

Note that, though explicitly described in connection with the needle assembly shown in FIGS. 41A-41C and in the other accompanying figures, the present embodiments regarding magnetic element alignment can be applied to needle assemblies/medical devices of varying configurations, designs, etc. As such, the discussion to follow should not be considered limiting in any way. In particular, though described herein as disposed in a safety can of a needle assembly hub, the magnetic element can be disposed/positioned in other ways as well. Further, "safety can" as used herein can be understood to refer to a hub, housing, or any other object in which or with which a magnetic element can be disposed.

In one embodiment, the cannula 1612 includes a material of low magnetic permeability. Specifically, in one embodiment the cannula 1612 includes an austenitic alloy including nickel and chromium, such as the material marketed under the name INCONEL® 625, by Special Metals Corporation, New Hartford, NY, U.S.A. Such material shows a reduced tendency to become temporarily magnetized and attracted by the magnetic material, thus preserving the integrity of the magnetic field and leading to more accurate results when the needle is tracked using a magnetic-based guidance system. Other possible materials include low magnetic-permeability stainless steel, other variations of stainless steel, etc.

In one embodiment, the magnetic element 1630 is a permanent magnet including neodynium-iron-boron. In one embodiment, such a permanent magnet may further include dysprosium and other rare-earth elements. In one embodiment, the permanent magnet is formed from a powder, which is first oriented by an applied magnetic field, then compressed at high pressure before being sintered in a furnace. It is appreciated that a permanent magnet can be composed of other materials, including samarium-cobalt, and manufactured in ways other than pressed and sintered powders. As such, it is appreciated that the examples of magnetic elements given herein are not considered limiting. In another embodiment, an N52 MGOe rare-earth neodynium magnet is employed.

Note that, in one embodiment the needle 10 or other medical device to be tracked by a magnetic-based guidance system referred to herein includes an RFID chip that can be read by an RFID reader included with a probe or other component of the guidance system. The RFID chip of the needle can include information of the needle including the needle name, type, distance from the needle magnetic element to the needle distal tip, the strength and/or size of the magnetic element, and other useful information. Such information can be used by the guidance system to adjust its operating parameters to match the type of needle being used. In another embodiment, the information regarding the needle is manually input into the guidance system. In yet another embodiment, a barcode can be included on or with the needle to enable the guidance system to determine pertinent information regarding the needle. In one embodiment, the system includes a memory location for storing a database of characteristics of needles that may be used with the guidance system.

FIG. 42 shows a permanent magnet as the magnetic element 1630 including a hole 1632 and is similar to the magnetic element shown in FIGS. 41A-41C. As shown, the magnetic element 1630 includes a physical axis, indicated by P.A., which extends through the body of the magnetic element. As the magnetic element 1630 is defined as a cylinder, the physical axis P.A. corresponds with the central axis of the cylindrical magnetic element. Also shown is a magnetic axis, indicated by M.A., which extends through the cylindrical body of the magnetic element 1630 at an angle with respect to the physical axis P.A., and thus is not coaxial with the physical axis.

As many permanent magnets include non-coaxial, angularly-deviated physical and magnetic axes as just described, it is desirable in such cases to position a magnet in a needle assembly for use with the above-described needle insertion guidance system such that its magnetic axis—and not necessarily its physical axis—is substantially coaxially aligned with the longitudinal axis of the needle assembly cannula so that the needle insertion guidance system can accurately indicate the position of the needle distal tip, given its detection of the properly oriented magnet. When this is done, the magnetic element may be physically oriented at an angle with respect to the needle cannula in cases where the magnetic element receives the cannula through a hole defined therein. This instance is shown in FIG. 43, where the magnetic element 1630 is shown with the needle assembly cannula 1612 disposed through the magnetic element hole 1632 and the magnetic element angularly skewed so that the magnetic axis of the magnetic element is substantially coaxially aligned with the longitudinal axis of the cannula. Note that the hole 1632 is of sufficient diameter to enable such orienting of the magnetic element 1630 on the cannula 1612. Suitable measurements can be made to determine the angular offset of the magnetic axis, if any, so as to determine the amount of skewing/tilting necessary for each magnetic element.

Figure 45:
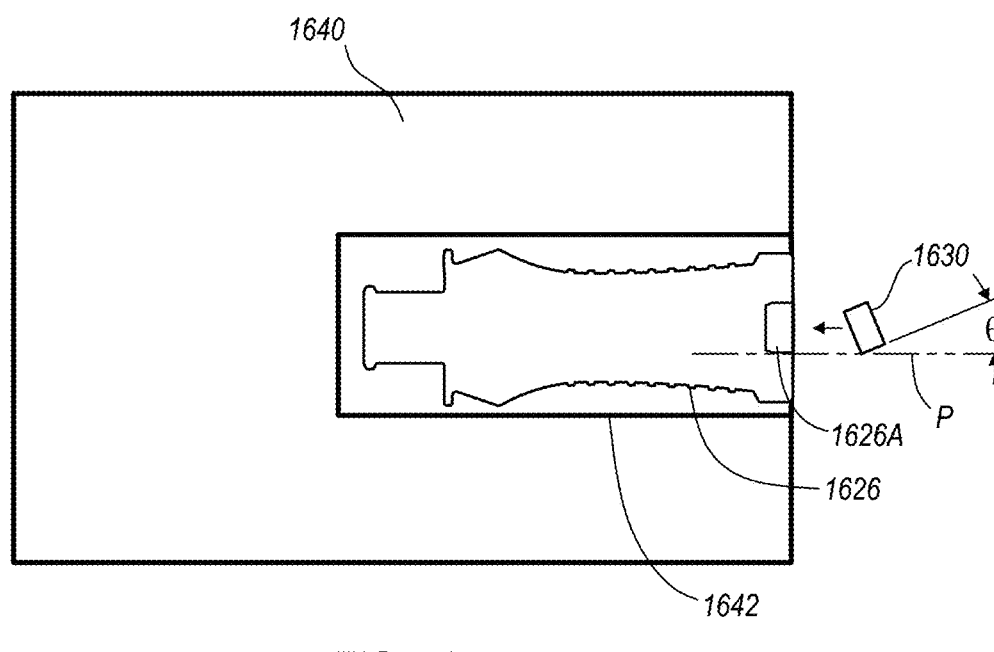
FIG. 45 is a top view of a jig, needle hub, and magnetic element according to one embodiment.

FIGS. 44 and 45 show orientation of the magnetic element 1630 with respect to a portion of a needle assembly according to one embodiment. In particular, FIG. 44 shows a jig 1640 that includes a cavity 1642 that is angularly offset at an angle θ from parallel P, as shown. The magnitude of the offset angle θ corresponds with the deviation of the magnetic axis of the magnetic element from its physical axis. The needle assembly hub 1626, including a recess 1626A, is disposed in the angled cavity 1642. The magnetic element 1630 is then inserted into the hub recess 1626A in a direction parallel to P such that it seats within the hub recess in an angled orientation. The magnetic element 1630 is affixed within the hub recess 1626A in this orientation. Later, when the proximal end of the cannula is received into the hub recess 1626A and the hole of the magnetic element 1630, its longitudinal axis will be substantially coaxially aligned with the magnetic axis of the magnetic element, as desired.

The configuration of the jig 1640 in FIG. 45 differs from that in FIG. 44 in that the cavity 1642 is parallel to P while the magnetic element 1630 is inserted into the hub recess 1626A at the offset angle θ that corresponds to its angle of magnetic axis deviation from its physical axis. The magnetic axis 1630 can be affixed within the hub recess 1626A in this orientation. Note that, though shown in FIGS. 44 and 45 as being inserted into a recess directly defined in the needle assembly hub, the magnetic element can be inserted in this manner into a safety can or other component of the needle assembly or suitable medical device.

Figure 46:
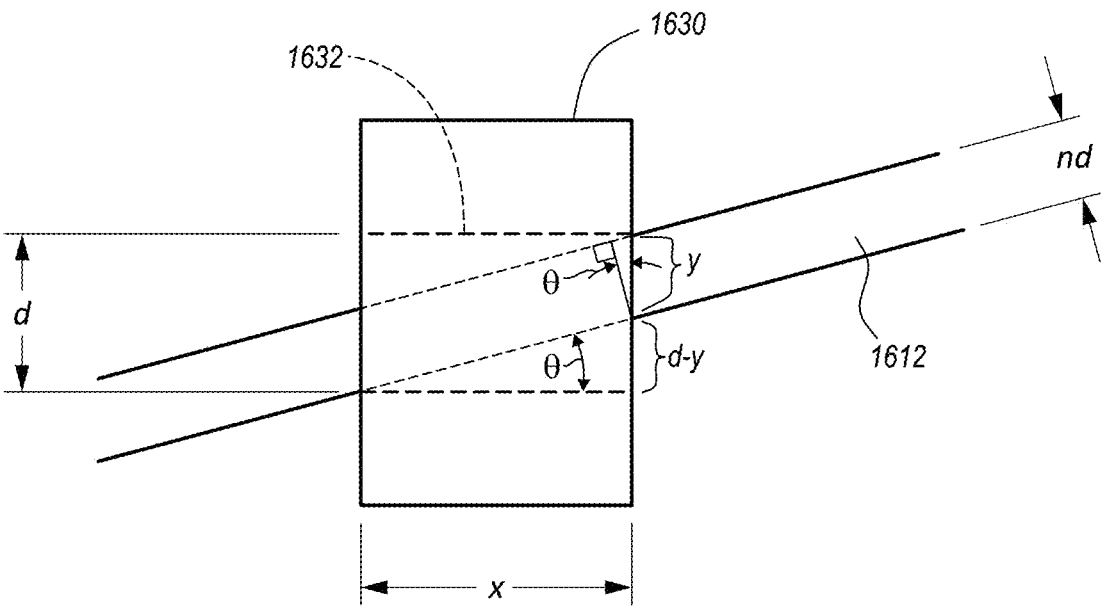
FIG. 46 is a simplified view of a magnetic element and cannula according to one embodiment.

FIG. 46 geometrically shows the extent of possible angular deviation between the magnetic element 1630 and the needle cannula 1612 when the cannula is received through the magnetic element hole 1632. In particular, the offset angle θ of deviation between the cannula 1612 and the magnetic element 1630 is shown, together with the diameter d of the hole 1632. The needle cannula diameter, nd, is also shown. A right triangle is formed, including the offset angle θ, the adjacent side length x, hypotenuse h, and opposite side d-y, where y is measured at an angle θcross the cannula 1612, as shown.

The following trigonometric functions can be used to find the maximum offset angle the magnetic element of a given dimension can be deviated while still allowing a sized needle cannula to be suitably received therethrough:

$$\text{Sin } \theta = d - y/h \tag{1}$$

$$\text{Cos } \theta = nd/y \tag{2}$$

$$\text{Tan } \theta = \text{Sin } \theta / \text{Cos } \theta = d - y/x \tag{3}$$

$$h = x^2 + [(d-y)^2]^{1/2} \tag{4}$$

$$\theta = \cos^{-1} * nd/y \tag{5}$$

In one embodiment, the offset angle θ can be determined by using the known values for d, nd, and x to solve for y, then substitute y back into the equations to determine θ. Knowledge of the maximum offset angle θ for a given size of magnetic element enables a specification for the magnetic element to be made, which specification details the maximum variance possible between the physical axis and the magnetic axis of the magnetic element.

Figure 47A:
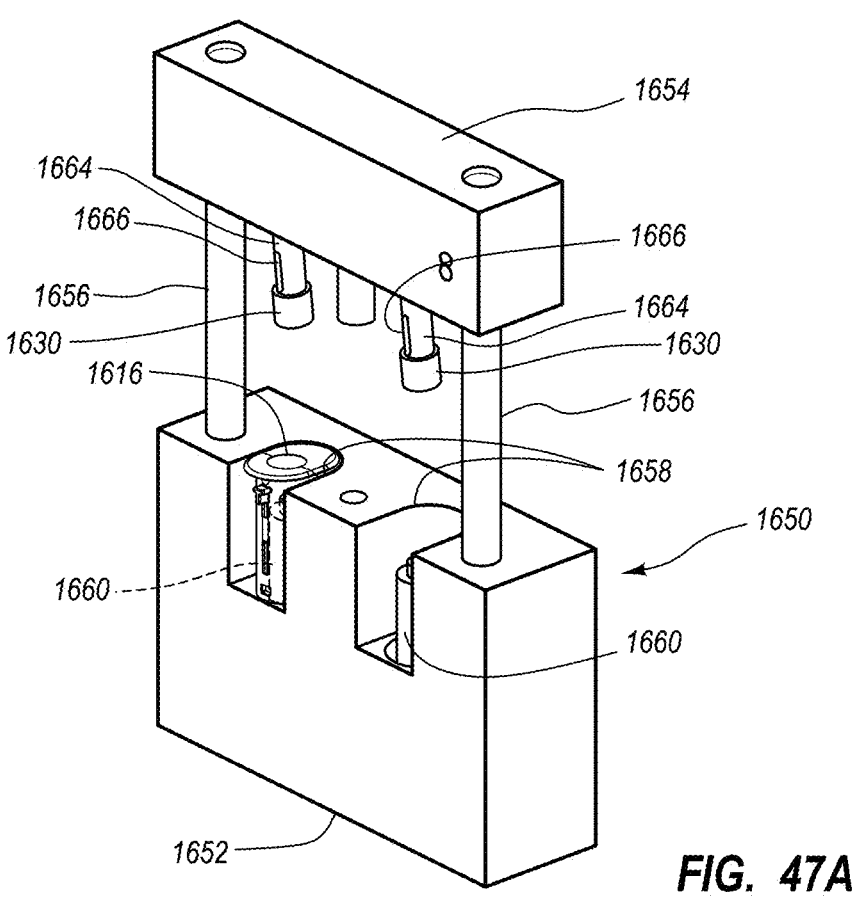
FIGS. 47A-48B are various views of a fixture for mating a magnetic element to a portion of a needle assembly according to one embodiment.
Figure 47B:
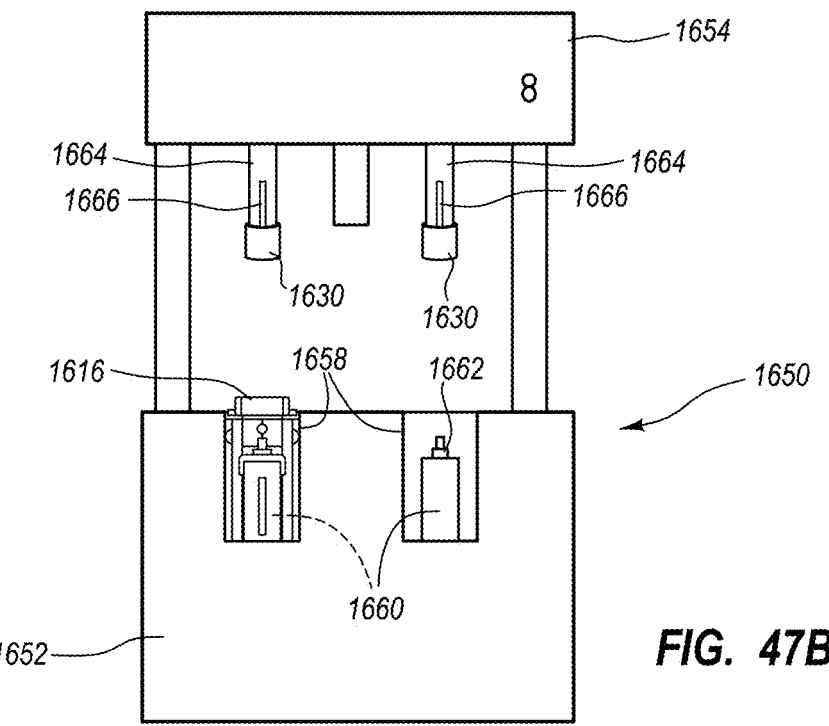

FIGS. 47A-47B show details of a magnetic element insertion fixture 1650 for inserting magnetic elements into the safety can 1616 (FIGS. 41A-41C), according to one embodiment. The fixture 1650 includes a base 1652 that has a slide portion 1654 slidably attached thereto via two slide posts 1656. Two cavities 1658 are defined in the base 1652. A post 1660 is included in each cavity 1658 that is sized to accept thereon the safety can 1616. A guide pin 1662 upwardly extends from each post 1660.

The slide portion 1654 includes two downwardly extending, angled insertion posts 1664 that are each configured to releasably hold a corresponding one of the magnetic elements 1630. Notches 1666 are included on each angled insertion post 1664 to enable orientation of the magnetic elements. The insertion posts 1664 are angled to match the angle of deviation of the magnetic axis of the magnetic element placed thereon from its physical axis. In one embodiment, the deviation between the physical axis and the magnetic axis of the magnetic element 1630 is known so as to enable it to be matched with a properly angled insertion post 1664. Indeed, in a batch of magnetic elements, initial sorting of the magnetic elements according to the magnitude of deviation between the physical and magnetic axes can be performed in one embodiment. In one embodiment, the angle of the insertion posts 1664 can be adjusted to suit the magnetic axis deviation in the magnetic elements. If needed, the notches 1666 can be used as reference features to properly orient the magnetic elements on the angled insertion posts 1664.

Figure 48A:
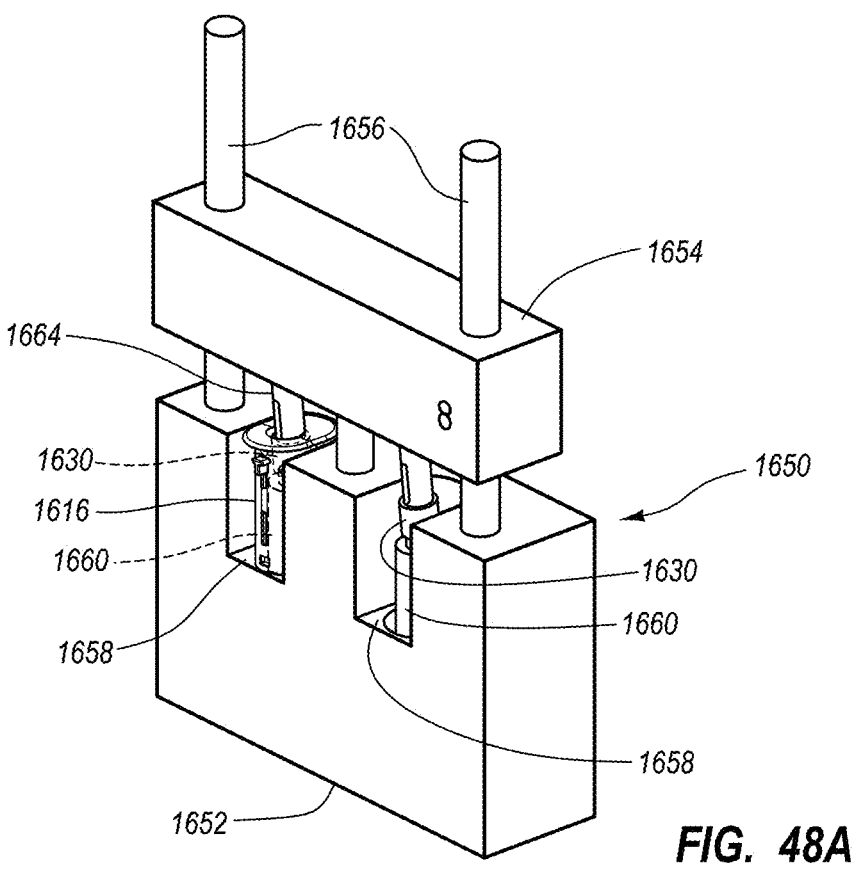
Figure 48B:
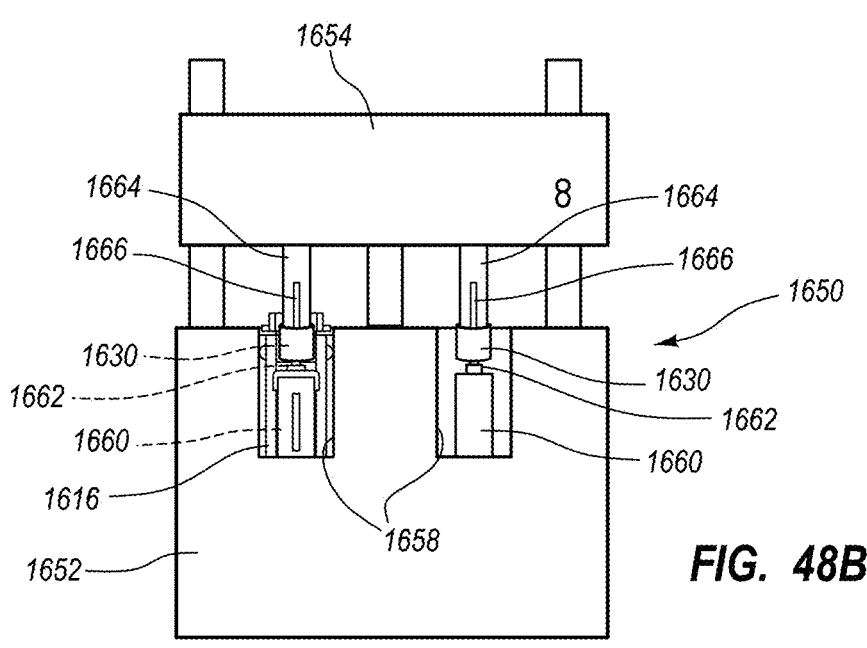

FIGS. 48A and 48B show use of the insertion fixture 1650 in inserting magnetic elements 1630 into corresponding safety cans 1616. As shown, with the magnetic elements 1630 included on each angled insertion post 1664, the slide portion 1654 is lowered via the slide posts 1656 until the magnetic element is received into a recess of the safety can 1616. As the safety can is held by the posts 1660 at an upwardly erect orientation, the magnetic element is inserted into the safety can recess at the desired angled orientation so that its magnetic axis is properly aligned with the safety can and the longitudinal axis of a cannula that will be subsequently attached with the safety can. Adhesive or other fixation medium can be used to affix the magnetic element 1630 in place at its angled orientation. The slide portion 1654 can then be raised so as to release the angled insertion post 1664 from engagement with the magnetic element 1630 and safety can 1616. Note that the number of insertion posts and cavities on the insertion fixture can be varied in one embodiment so as to simultaneously perform a desired number of magnetic element insertion procedures.

Figures 49, 50, 51:
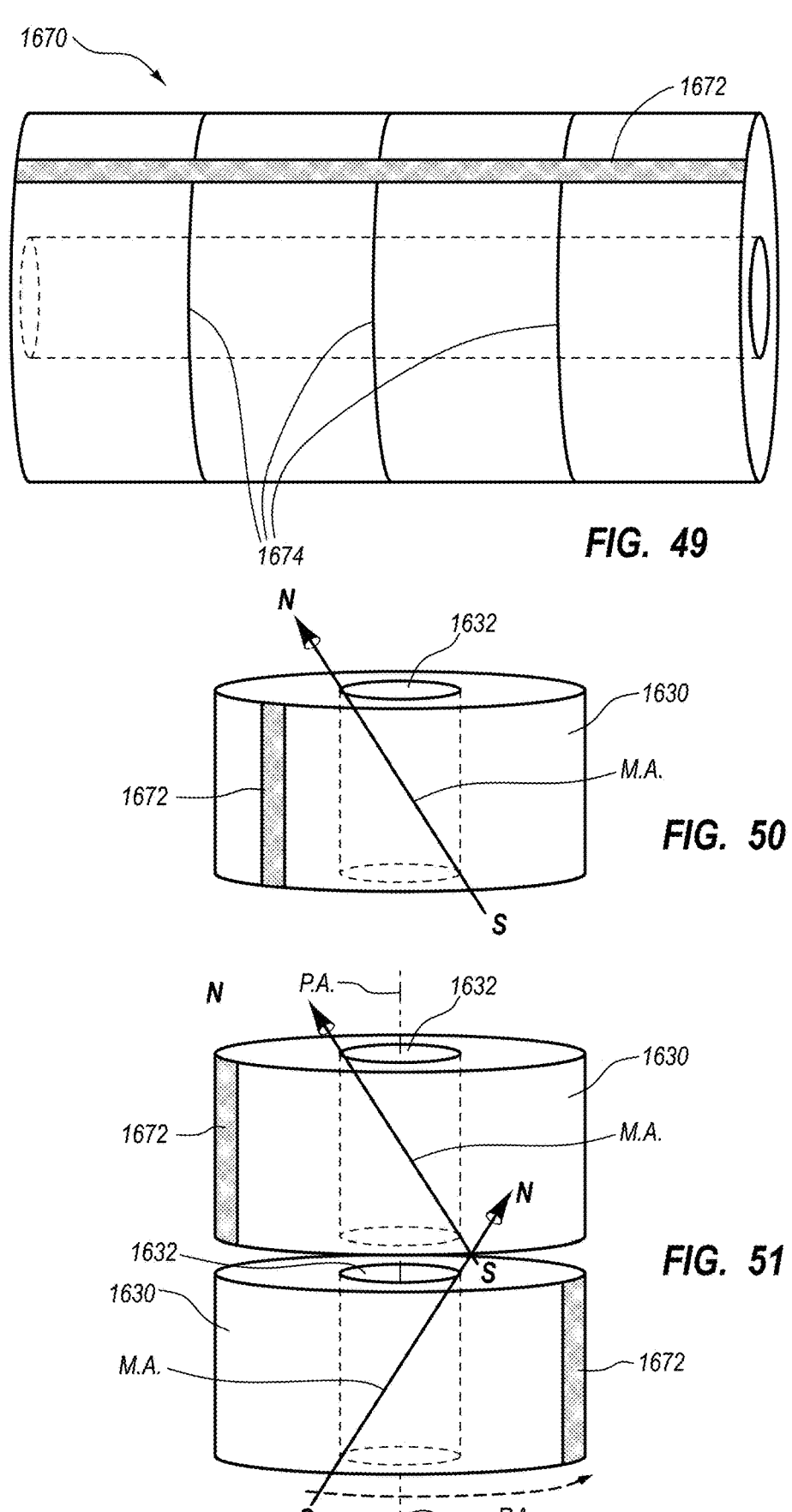
FIG. 49 is a side view of a bar of magnetic material used in forming a magnetic element according to one embodiment.
FIG. 50 shows a portion of the bar of magnetic material of FIG. 49.
FIG. 51 shows formation of a magnetic element according to one embodiment.

FIGS. 49-51 depict a manner for substantially aligning a magnetic axis of a magnetic element with its physical axis, according to one embodiment. FIG. 49 shows a bored cylindrical magnetic rod 1670 including a magnetic material. An orientation mark 1672 is included along the length of the rod 1670. The rod 1670 is sliced orthogonally to its central axis along cut lines 1674 to yield a plurality of magnetic elements 1630 including a hole 1632, one of which is shown in FIG. 50. The magnetic axis M.A. of the magnetic element 1630 is shown.

As shown in FIG. 51, two magnetic elements 1630 cut from the rod 1670 are rotated 180 degrees with respect to one another such that their respective orientation marks 1672 are opposed to one another. The two magnetic elements are mated to one another, such as via adhesive. This rotation results in placing the magnetic axes M.A. of the magnetic elements 1630 opposite one another such that the opposing components of their magnetic axes cancel out one another. This results in a net magnetic axis for the joined magnetic elements 1630 that is substantially coaxially aligned with the central physical axis P.A. of the joined magnetic elements, as desired. Note that more than two magnetic elements can be joined, and that other symmetrically shaped rods/masses could be used to achieve the results described here. Also, discrete magnetic elements that are not cut from the same bar of magnetic material but have similar magnetic axis-to-physical axis deviations can be grouped together to be joined in the manner just described, in one embodiment.

Figure 52A:
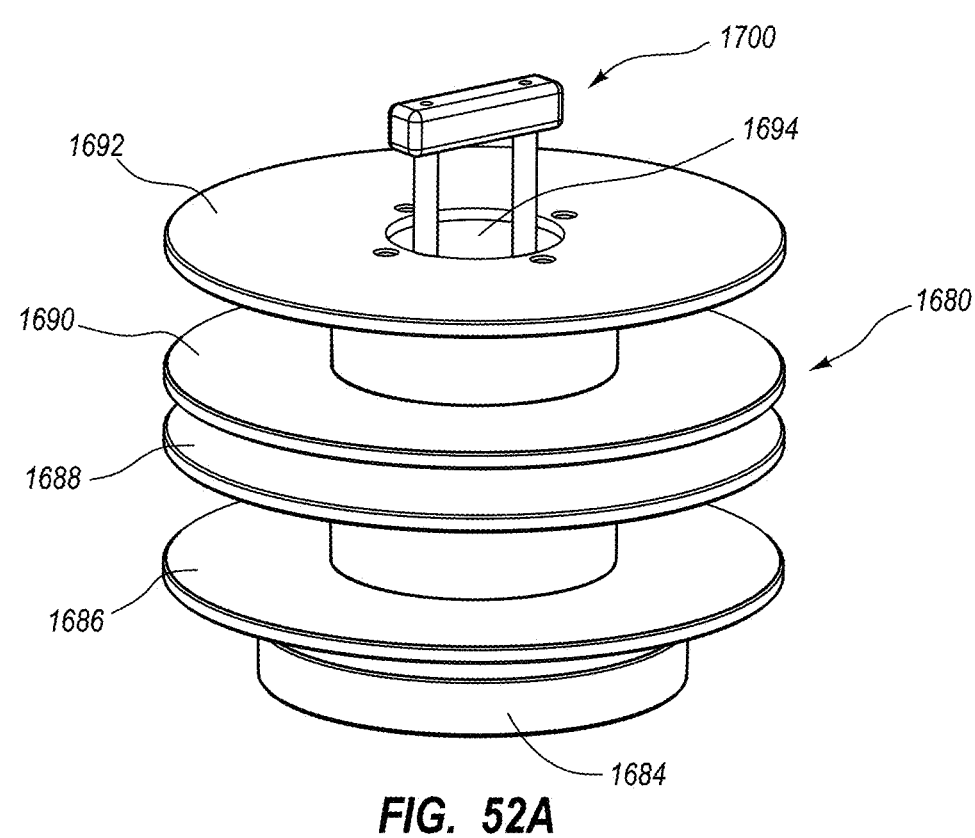
FIGS. 52A and 52B shows various views of an alignment coil assembly according to one embodiment.

FIGS. 52A-54C depict various details regarding an alignment coil assembly 1680 that can be used in orienting magnetic elements for inclusion with a needle assembly, such as the needle assembly 1610 shown in FIGS. 41A-41C, according to one embodiment. As shown in FIGS. 52A and 52B, the alignment coil assembly 1680 includes a base 1682 (FIG. 52B) on which a plurality of components are attached together in a stacked configuration, including a mount 1684, a lower coil bobbin 1686, a centerplate 1688, an upper coil bobbin 1690, and a top plate 1692. These components in one embodiment include a non-magnetically conductive material, such as aluminum and/or brass, and cooperate to define a central bore 1694 of the assembly 1680.

Each of the lower coil bobbin 1686 and the upper coil bobbin 1690 includes windings 1696 that, when electrically energized, produce an electromagnetic field in an around the alignment coil assembly 1680. The windings 1696 in one embodiment are secured in place with an adhesive, such as epoxy. The electromagnetic field produced by the windings 1696 is substantially parallel to the longitudinal axis of the central bore 1694 within the volume of the central bore. Operation of the alignment coil assembly 1680 is thus similar in some respects to a single-axis Helmholtz coil. The upper coil bobbin 1690 further defines a plurality of access holes 1698 for providing access to the central bore 1694 from outside the alignment coil assembly 1680.

FIGS. 52A, 53A, and 53B show that the alignment coil assembly 1680 further includes a fixture 1700 for holding the safety can 1616 from the needle assembly 1610 (FIGS. 41A-41C) and for inserting the safety can into and withdrawing it from the central bore 1694 of the assembly via manual handling of the fixture, though an automated process is also contemplated. As shown, the fixture 1700 includes a handle 1702 and two extension posts that extend from the handle to a base 1706. FIG. 54A shows that the base 1706 in turn includes a post 1708 for releasably holding the safety can 1616, as seen in FIG. 53A, and a guide pin 1710 upwardly extending from the post. FIG. 53B shows the manner in which the fixture 1700 is seated within the central bore 1694 of the alignment coil assembly 1680, where the centerplate 1688 and the upper coil bobbin 1690 have been removed for clarity. Note that the particular configuration of the alignment coil assembly 1680 and the fixture 1700 can be modified to accommodate needle assembly components of different sizes, designs, etc. In one embodiment, the fixture 1700 includes a suitable non-magnetically conductive material, such as aluminum or brass.

FIG. 54B shows the manner of placement of the safety can 1616 on the post 1708 of the base 1706. So positioned, the guide pin 1710 extends through a cannula conduit 1714 (FIG. 54C) and into a recess 1712 defined by the safety can 1616 to assist in eventual placement of a magnetic element in the recess. Note that the safety can 1616 includes additional features, including orientation features 1718 for enabling the safety can to be oriented as desired in the alignment coil assembly and/or needle assembly, and an adhesive insertion hole for enabling adhesive to be injected into the safety can recess 1712 either before or after the magnetic axis of the magnetic element has been aligned.

During a procedure to place a magnetic element, such as the magnetic element 1630 shown in FIGS. 41A and 41B, into the safety can 1616 via use of the alignment coil assembly 1680, the safety can is first placed on the post 1708 of the fixture 1700, as shown in FIG. 54B. The magnetic element 1630 is placed in the safety can recess 1712 and is left unsecured therein. Note that the safety can recess 1712 includes a concavely rounded feature 1699 on the bottom surface of the recess to facilitate movement/orientation of the magnetic element 1630 during the alignment procedure described here.

With the safety can in place on the post 1708 of the fixture base 1706, the fixture 1700 is then manually inserted into the central bore 1694 of the alignment coil assembly 1680, similar to that shown in FIG. 53B. The windings 1696 of the alignment coil assembly 1680 are then energized, which produces a uniform magnetic field within the central bore 1694 of the alignment coil assembly 1680. The direction of the uniform magnetic field runs parallel to the longitudinal axis of the central bore 1694, which direction is the same as the longitudinal axis of the needle cannula 1612 (FIGS. 41A and 41B) that will be passed through the safety can when assembly is complete, and which direction is the desired direction for the magnetic axis of the magnetic element to be aligned with. This field causes the magnetic element 1630 to orient itself such that its magnetic axis aligns itself with the uniform magnetic field present in the central bore 1694. Such alignment may cause the magnetic element to skew with respect to the guide pin 1710, which guide pin is present to preserve the ability of the needle cannula 1612 (FIGS. 41A and 41B) to pass through the hole 1632 of the magnetic element when needle assembly is complete. Note the skewing of the magnetic element 1630 within the safety can recess 1712 in FIG. 54C. Again, the rounded feature 1699 within the recess 1712 assists with orientation of the magnetic element 1630 by the uniform magnetic field present in the central bore 1694.

Figure 52B:
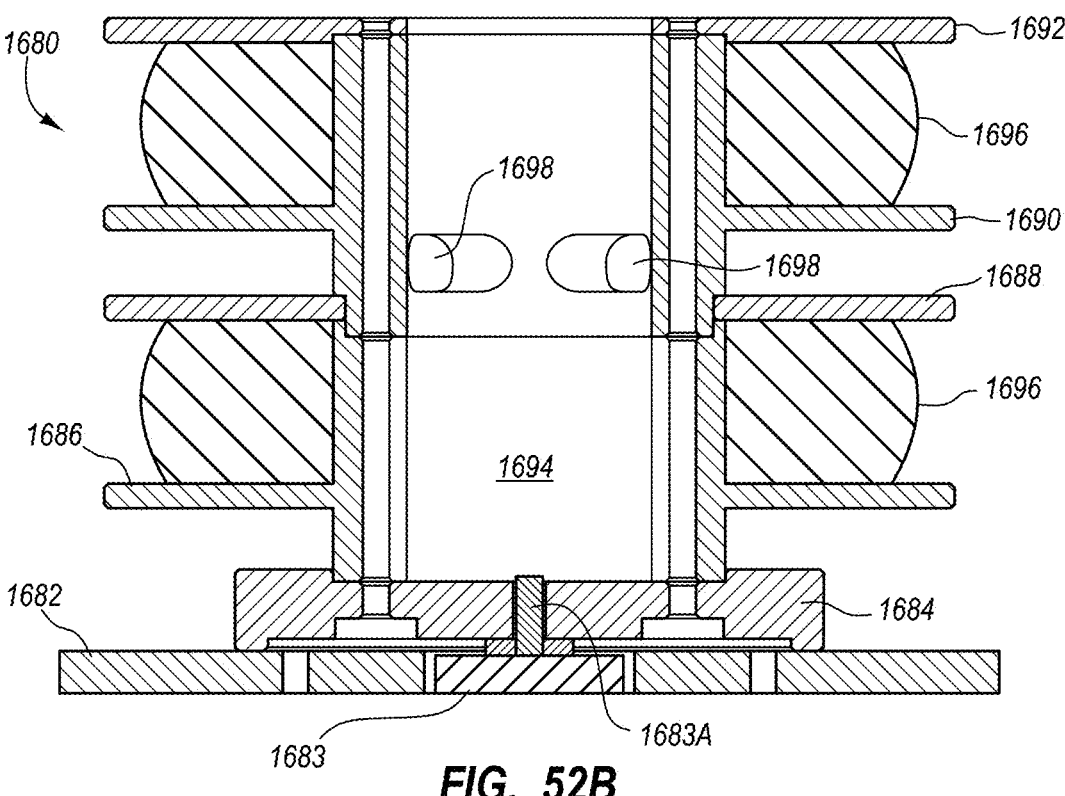

Also, in the present embodiment a vibrating component, such as a vibratory motor 1683 that includes a projection 1683A to contact a portion of the fixture base 1706, is included with the alignment coil assembly 1680 as shown in FIG. 52B to provide vibration to the fixture 1700 and safety can 1616 disposed thereon. This enables the magnetic element 1630 to more freely orient itself to the uniform magnetic field while disposed within the recess 1712 and prevent the magnetic element from physically binding up within the recess.

Once the magnetic axis of the magnetic element 1630 has been properly aligned, a quick-set, UV light-activated epoxy—which was previously introduced into the safety can recess 1712 via the adhesive insertion hole 1716 defined in the housing of the safety can 1616 can be set by exposure to a UV light source introduced into the safety can region within the central bore 1694. Note that access to the adhesive insertion hole 1716 of the safety can 1616 can be made via the access holes 1698 of the upper coil bobbin 1690 of the alignment coil assembly 1680. The use of such a light-cured epoxy enables relatively quick fixation of the magnetic element 1630 within the safety can 1616 in the magnetically aligned orientation.

After or during securement of the magnetic element 1630 within the recess 1712 of the safety can 1616, the cannula 1612 can be passed through the safety can, which can be joined to the needle hub 1626, and the rest of the elements can be incorporated to define the needle assembly 1610 as shown in FIGS. 41A-41C. As a result of the above alignment process, the magnetic axis of the magnetic element 1630 will be substantially coaxially aligned with the longitudinal axis of the needle cannula 1612, as desired. Note that the configuration of the safety can, needle, hub, magnetic element, etc. can vary from what is shown and described herein while still residing within the principles of the present disclosure. For instance, the magnetic element can be incorporated directly into the needle hub or cannula without the presence of a safety can. Note also that other winding configurations are also possible, including square windings and windings of other shapes, three or more windings instead of two, and other configurations that can produce a uniform magnetic field in the central bore of the alignment coil assembly.

FIGS. 55A-55C show alignment of the magnetic element 1630 according to one embodiment, wherein an orientation mark 1724 is placed on the magnetic element to indicate the orientation of its magnetic axis M.A. A cap 1720 also includes an orientation mark 1724, and further defines a recess 1722 into which the magnetic element 1630 is to be secured. Alignment of the two orientation marks 1724 can enable an observer to suitably manipulate the magnetic element 1630 within the recess 1722 before affixation of the element into place such that the magnetic axis thereof is directed in the desired direction.

FIGS. 56-58 show additional features for enabling manipulation of the magnetic element 1630 within a recess of the cap 1720, which cap is representative of a variety of recesses for receiving the magnetic element in a needle assembly or other suitable medical device, for use with a needle tracking system such as is described further above. In FIG. 56, the magnetic element 1630 includes a pointed end that enables the element to be more easily manipulated during procedures to orient its magnetic axis. Similarly, FIG. 57 shows the cap 1720 including a pointed feature on the base of the recess 1732 to ease manipulation of the magnetic element. Further, FIG. 58 includes a convexly-rounded feature on the base of the recess to ease magnetic element manipulation. In another embodiment, a concavely-rounded feature can be employed. These and other features can be included in the recess in which the magnetic element is disposed to ease its manipulation during magnetic axis orienting procedures.

FIG. 59 shows alignment of a magnetic axis of the magnetic element 1630 according to another embodiment, wherein the magnetic element 1630 the needle hub 1626 or other suitable component is positioned directly above an electromagnetic or other suitable magnetic coil 1740 such that the magnetic element is positioned within a symmetrical magnetic field as represented by magnetic field lines 1742 of FIG. 59. Such positioning enables the magnetic element to align its magnetic axis with the magnetic field of the coil 1740, thus enabling the magnetic axis of the magnetic element to substantially and coaxially align with the longitudinal axis of the needle cannula 1612, as desired. This process does not require placement of the magnetic element 1630 into an internal magnetic field such as is found in the bore of the alignment coil assembly 1680 described in connection with FIGS. 52A-54C, but rather utilizes a potentially more convenient external magnetic field.

Note that, in addition to coaxially aligning the magnetic axis of the magnetic element with the longitudinal axis of the needle cannula, it is possible in other embodiments to align the magnetic axis along other desired directions, such as perpendicular to the cannula longitudinal axis, for instance. These and other variations are therefore contemplated.

FIGS. 60A and 60B show various details regarding a catheter insertion tool 1810 including a magnetic element according to one embodiment. As shown, the insertion tool 1810 includes a housing 1812 that in turn includes a top housing portion 1812A separably mated with a bottom housing portion 1812B. A needle hub 1814 supporting a hollow needle 1816, also referred to herein as a cannula, is interposed between the housing portions 1812A and 1812B. The needle 1816 extends distally from the needle hub 1814 so as to extend through the body of the insertion tool 1810 and out a distal end of the housing 1812. In another embodiment, the needle is at least partially hollow while still enabling the functionality described herein.

The insertion tool 1810 further includes a guidewire advancement assembly for advancing a guidewire 1822 through the needle 1816 and into the vasculature of the patient once access by the needle has been achieved. The guidewire 1822 is pre-disposed within the lumen of the needle 1816, with a proximal end of the guidewire positioned proximate the proximal end of the needle hub 1814, as best seen in FIG. 60B. The guidewire advancement assembly includes a guidewire lever 1824 that selectively advances the guidewire 1822 in a distal direction during use of the insertion tool 1810 such that the distal portion of the guidewire extends beyond the distal end of the needle 1816. The guidewire lever 1824 includes a lever tab 1826 that engages the proximal end of the guidewire 1822 so as to push the guidewire through the lumen of the needle 1816.

The guidewire advancement assembly further includes a slide 1828 that is slidably attached to the top housing portion 1812A. Two tabs 1824A of the guidewire lever 1824 operably attach to the slide 1828 so that selective movement by a user of the slide results in corresponding movement of the lever 1824, and by extension, the guidewire 1822. Engagement of the lever tabs 1824A with the slide 1828 also maintains attachment of the slide to the housing 1812. Of course, other engagement schemes to translate user input to guidewire movement could also be employed. Suitable tracks are included in the top housing portion 1812A to enable sliding movement of the slide 1828 and the lever 1824, including a track extending to the distal end of the housing 1812.

The guidewire lever 1824 includes a locking arm 1836 resiliently disposed so as to spring up and engage an extension 1836A defined in the interior of the top housing portion 1812A when the slide 1828 has been fully slid distally. This prevents inadvertent retraction of the guidewire 1822 once distally extended, which could otherwise cause unintended severing of a distal portion of the guidewire by the distal tip of the needle 1816 during insertion procedures. Note that engagement of the locking arm 1836 with the extension 1836A can provide tactile and/or audible feedback to the user in one embodiment so as to indicate full distal extension of the guidewire 1822.

The insertion tool 1810 further includes a catheter advancement assembly 1840 for selectively advancing in a distal direction a catheter 1842, pre-disposed in the housing 1812, and including a catheter tube 1844 and a hub 1846 at a proximal end thereof. As seen in FIGS. 60A and 60B, the catheter 1842 is partially and initially pre-disposed within a volume defined by the housing 1812 such that the lumen of the catheter tube 1844 is disposed over the needle 1816, which in turn is disposed over the guidewire 1822, as mentioned.

Further details regarding the catheter insertion tool 1810 can be found in U.S. Pat. No. 8,932,258, titled "Catheter Placement Device and Method," which is incorporated herein by reference in its entirety.

As best seen in FIG. 60B, the insertion tool 1810 in the present embodiment further includes a pocket wall 1847A that is defined as a part of the bottom portion 1812B of the housing 1812. The pocket wall 1847A defines a pocket 1847 in which a magnetic element 1830, such as a permanent magnet, is disposed. The inclusion of the magnetic element 1830 enables the insertion tool 1810 to be tracked and guided by the needle insertion guidance system as described further above.

It is appreciated that the magnetic element 1830 can include both a physical axis P.A. and a magnetic axis M.A. that may not be in alignment with one another. In accordance with one embodiment, the magnetic element 1830 is oriented within the pocket such that its magnetic axis M.A. is in a desired orientation with respect to the longitudinal axis of the needle 1816. In one embodiment this desired orientation includes the magnetic axis of the magnetic element 1830 and the longitudinal axis of the insertion tool needle 1816 being both parallel to and coplanar with one another. Such orientation enables the needle insertion guidance system described further above to accurately track the position and orientation of the insertion tool needle 1816. Of course, in other embodiments other respective orientations between the needle and the magnetic element are possible, including a coaxial orientation relationship as described in earlier embodiments. It is also appreciated that the placement of the magnetic element with the insertion tool can vary from what is shown and described herein. In one embodiment, the magnetic element is placed proximate the distal end of the insertion tool housing so as to be relatively close to the distal end of the needle. In one embodiment, the needle insertion guidance system described further above will be programmed as to the location of the magnetic element on/in the insertion tool relative to the distal tip of the needle such that accurate tracking of the distal tip is possible.

FIGS. 61A-61C depict simplified views of the housing 1812 of the insertion tool 1810 and its relationship to the magnetic element 1830 according to the present embodiment. In particular, FIG. 61A shows the magnetic element 1830 disposed within the pocket 1847 before magnetic axis orientation. As such, the magnetic axis M.A. is shown in a non-aligned orientation with respect to the housing 1812 and the longitudinal axis of the needle 1816 (FIGS. 60A, 60B). The teachings regarding orienting a magnetic element as described in connection with FIGS. 41A-59 can be employed with the present insertion tool/magnetic element combination to orient the magnetic element 1830 as desired. In accordance with such teachings, the magnetic axis M.A. of the magnetic element 1830 can be orientated to be parallel to and coplanar with the insertion tool needle 1816 and its longitudinal axis, as discussed earlier. This oriented relationship is shown in FIGS. 61B and 61C wherein, though the physical axis P.A. is non-aligned, the magnetic axis M.A. is desirably aligned with the insertion tool needle 1816. Such alignment of the magnetic element 1830 within the pocket 1847 can be secured via various suitable methods, including in one embodiment, the use of a light-cured adhesive.

FIG. 63 shows one manner for orientating the magnetic element 1830 within a recess 1862 of a safety can 1860 such that its magnetic axis is oriented as desired, as further relating to the discussion above with respect to FIGS. 41A-59. As shown, an alignment plate 1866 includes a projection 1868 that is received within a hole 1832 defined in the magnetic element 1830. The alignment plate 1866 can then be manipulated as shown so as to orient the magnetic axis M.A. of the magnetic element 1830 as desired. Light-cured adhesive or other suitable fixation method can be used to fix the magnetic element 1830 in position within the recess 1862 once proper magnetic element orientation has been achieved. The alignment plate 1866 in one embodiment can be controlled by a motor and governing software.

FIG. 64 shows a magnetic element-equipped needle according to one embodiment. A needle cannula 1870 is shown, defining a lumen 1872 extending to the distal end of the cannula. A notch 1874 is defined in the wall of the cannula and sized to receive therein one or more magnetic elements 1830. In one embodiment, the notch 1874 is disposed proximate the distal end of the cannula 1870 and is sized to receive two U-shaped magnetic elements that form a cylindrical magnet when disposed in the notch, though any number and suitable shapes of magnetic elements can be employed. Adhesive or other suitable fixation can be used to secure the magnetic elements 1830 in place.

In the present embodiment, the magnetic elements 1830 are manufactured and arranged such that the magnetic axis of each is substantially oriented with respect to the longitudinal axis of the needle, as desired. Further, such positioning of the magnetic elements enables the magnetic axis of the magnetic element 1830 and the longitudinal axis of the needle cannula 1870 to be substantially coaxial with respect to one another. Note that more than one notch can be defined on the cannula and that the size and shape of the notch(es) and corresponding magnetic elements can vary from what is shown and described herein.

Figures 65, 66, 67, 68, 69, 70:
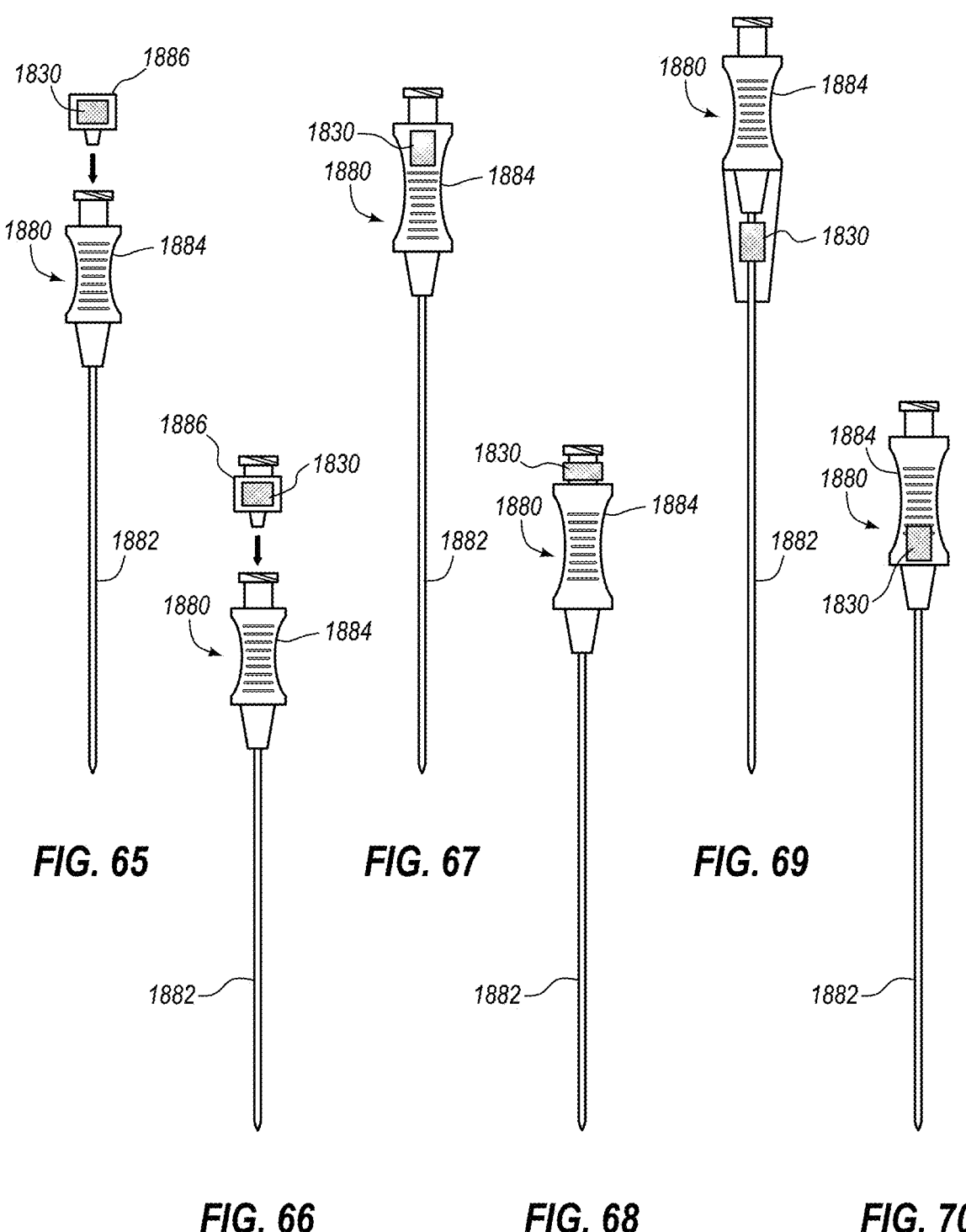

FIGS. 65-70 show various possible placement locations for the magnetic element 1830 both in and proximate to a hub 1884 of a needle assembly 1880 according to possible embodiments. The needle assembly further includes a cannula 1882 extending from the hub 1884. In FIG. 65, the magnetic element 1830 is included in an insert 1886 that attaches to a proximal portion of the needle hub 1884, such as into a luer fitting. In FIG. 66, the magnetic element-containing insert 1886 includes a luer fitting and is attachable to a second luer fitting included on the needle hub 1884. A bore can be defined through the inserts 1886 of FIGS. 65 and 66 so as to provide for fluid passage therethrough.

In FIG. 67, the magnetic element 1830 is included in a more proximal portion of the interior of the hub 1884, while in FIG. 68 the magnetic element is externally disposed about a portion of a luer fitting of the hub. FIG. 69 shows the magnetic element 1830 disposed about a portion of the cannula 1882 within a needle safety housing, and in FIG. 70 the magnetic element is disposed in a more distal portion of the interior of the hub 1884. These and other possible magnetic element placements with a needle assembly are therefore contemplated.

Reference is now made to FIGS. 71A and 71B, which depict various details of a needle assembly 1910 configured in accordance with one embodiment. As shown, the needle assembly 1910 includes a housing 1912 defining a proximal end 1912A and a distal end 1912B. A needle cannula 1914 extends distally from the housing distal end 1912B. A catheter 1915, such as a peripheral I.V. catheter, is coaxially disposed over the needle cannula 1914. A needle safety mechanism can be disposed within the housing 1912 to safety the needle cannula 1914 after use thereof. An opening 1918 is included at the proximal end 1912A of the housing 1912. Note that the needle assembly shown in FIGS. 71A and 71B is manufactured in one embodiment under the name INSYTE™ AUTOGUARD™ by BD Medical, Sandy, Utah. Note further, however, that the principles described herein can be applied to needles and medical devices of a variety of types and configurations.

A magnetic element 1930, implemented here as a donut-shaped permanent magnet, is also included with the needle assembly 1910. Inclusion of the magnetic element 1930 with the needle assembly 1910 enables the needle assembly to be guided by a needle insertion guidance system in connection with an ultrasound imaging system or other imaging system, as described further above and as disclosed in U.S. Pat. No. 9,521,961, titled "Systems And Methods For Guiding A Medical Instrument," which is incorporated herein by reference in its entirety.

The magnetic element 1930 is operably attached to the needle assembly 1910 by a retention component. In the present embodiment, the retention component includes an end plug 1932, which in turn includes a base 1934 from which extends a projection 1926 that is sized for being received into the housing opening 1918 and maintained in place via a friction fit, adhesive, mechanical fit, etc. In one embodiment, for instance, deformable barbs can be included on the base or projection of the retention component to hold the magnetic element in place within the opening 1918. The end plug 1932 in the present embodiment includes plastic, though other suitable materials can be employed. The magnetic element 1930 can be secured to the base 1934 of the end plug via suitable schemes, including a friction or mechanical fit including the use of barbs, adhesive, welding, etc.

FIG. 71B shows the magnetic element-equipped end plug 1932 seated in the housing opening 1918 so as to secure the end plug to the housing 1912 of the needle assembly 1910. So configured, the magnetic element 1930 is positioned at a static, predetermined location with respect to the needle cannula 1914 in its extended state, i.e., prior to the cannula being retracted into the housing 1912 by the needle safety mechanism after needle use. This enables a needle insertion guidance system, such as those described further above, to continuously track the position and/or orientation of the needle cannula 1914 during procedures to insert the needle into a vessel or other subcutaneous feature of the patient's body. Knowledge by the needle insertion guidance system of the location of the magnetic element 1930 with respect to the distal end of the needle cannula 1914 enables such accurate tracking to occur, thus assisting a clinician using the system in guiding the needle to an intended destination. Note that, as the needle assembly in this and other embodiments herein is a premanufactured needle assembly, the magnetic element-equipped retention component can be separately manufactured then attached to the needle assembly prior to its use in a procedure. In such a case, the attachment should be such so as to ensure that the magnetic axis of the magnetic element is oriented as desired, such as with respect to the longitudinal axis of the needle, so as to ensure accurate needle tracking by a needle insertion tracking system. In another embodiment, the retention component and/or magnetic element can be included on the needle assembly at the time of manufacture.

FIGS. 72A and 72B depict a needle assembly 1950 including a magnetic element and retention component according to another embodiment. As shown, the needle assembly 1950 includes a housing 1952 defining a proximal end 1952A and a distal end 1952B. A needle cannula 1954 extends distally from the housing distal end 1952B. A catheter 1955 is coaxially disposed over the needle cannula 1954. A needle safety mechanism is disposed within a portion of the catheter 1955 to safety the needle cannula 1954 after use thereof. An opening 1958 is included at the proximal end 1952A of the housing 1952. Note that the needle assembly shown in FIGS. 72A and 72B is manufactured in one embodiment under the name INTROCAN SAFETY® IV Catheter by B. Braun, Bethlehem, Pennsylvania.

A magnetic element 1960, implemented here as a donut-shaped permanent magnet, is also included with the needle assembly 1950. Inclusion of the magnetic element 1960 with the needle assembly 1950 enables the needle assembly to be guided by a needle insertion guidance system in connection with an ultrasound imaging system or other imaging system, as described further above.

In further detail, the magnetic element 1960 is operably attached to the needle assembly 1950 by a retention component. In the present embodiment, the retention component includes a filter plug 1962 that is included as a native component of the needle assembly 1950. The filter plug 1962 includes a base 1964 from which extends a projection 1966 that is sized for being received into the housing opening 1958 and maintained in place via a friction fit, though other attachment schemes can be employed, as before with other retention components disclosed herein. The filter plug 1962 in the present embodiment includes plastic, though other suitable materials can be employed. The magnetic element 1960 can be secured to the base 1964 of the filter plug 1962 via suitable schemes, including friction or mechanical fit, adhesive, welding, etc. In another embodiment, the magnetic element, such as a donut-type permanent magnet, can be disposed within an interior portion of the filter plug. In yet another embodiment, the magnetic element can be insert-molded into the housing, a luer connector of the needle assembly or other portion of the needle assembly to provide a secure attachment for the magnetic element.

FIG. 72B shows the magnetic element-equipped filter plug 1962 seated in the housing opening 1958 so as to secure the retention component to the housing 1952 of the needle assembly 1950. So configured, the magnetic element 1960 is positioned at a static, predetermined location with respect to the needle 1954. This enables a needle insertion guidance system, such as those described above, to continuously track the position and/or orientation of the needle 1954 during procedures to insert the needle into a vessel or other subcutaneous feature of the patient's body, as already discussed. In this and other embodiments, a filter can be included in the filter plug 1962 to enable air passage through the filter plug and into/out of the needle assembly housing 1952.

FIGS. 73A and 73B depict a needle assembly 1980 including a magnetic element and retention component according to another embodiment. As shown, the needle assembly 1980 includes a housing 1982 defining a proximal end 1982A and a distal end 1982B. A needle cannula 1984 extends distally from the housing distal end 1982B. An opening 1988 is included at the proximal end 1982A of the housing 1982. Note that the needle assembly shown in FIGS. 73A and 73B is manufactured in one embodiment under the name PROTECTIV® Safety IV Catheter by Smiths Medical, Dublin, Ohio.

A magnetic element 1990, implemented here as a donut-shaped permanent magnet, is also included with the needle assembly 1980. Inclusion of the magnetic element 1990 with the needle assembly 1980 enables the needle assembly to be guided by a needle insertion guidance system in connection with an ultrasound imaging system or other imaging system, as described further above.

In further detail, the magnetic element 1990 is operably attached to the needle assembly 1980 by a retention component. In the present embodiment, the retention component includes an annular ring 1992 in which the magnetic element 1990 is disposed. The ring 1992 is sized for sliding over the proximal portion of the needle assembly housing 1982 and seating in place via a friction fit as shown in FIG. 73B, though other attachment schemes can also be employed. The ring 1992 in the present embodiment includes plastic, though other suitable materials can be employed, including metal, glass, etc. The magnetic element 1990 can be secured to the ring 1992 via insert molding, friction or mechanical fit, adhesive, welding, etc.

With the magnetic element-equipped ring 1992 seated on the needle assembly housing 1982 as shown in FIG. 73B, the magnetic element 1992 is positioned at a static, predetermined location with respect to the needle cannula 1984 before the cannula is placed in a needle-safe position. This enables a needle insertion guidance system, such as those described further above, to continuously track the position and/or orientation of the needle cannula 1984 during procedures to insert the needle into a vessel or other subcutaneous feature of the patient's body, as already discussed.

FIGS. 74A and 74B depict the needle assembly 1910, previously shown in FIGS. 71A and 71B, with a magnetic element and retention component according to another embodiment. As shown, the needle assembly 1910 in the present embodiment includes a magnetic element 2000, implemented here as a donut-shaped permanent magnet, which is housed in a retention component. The retention component in the present embodiment includes an end cap 2002, which in turn includes a body 2004 formed of plastic or other suitable material that defines a cavity 2006 into which the proximal end 1912A of the needle assembly housing 1912 can be received in a friction or other suitable fit so as to be removably retained. This places the magnetic element 2000 at a fixed location with respect to the needle cannula 1914, enabling it to be tracked by a magnetic-based guidance system. Note that the body 2004 of the end cap 2002 defines a bore 2008 that cooperates with the hole of the magnetic element 2000 to provide a passage through the end cap. This passage enables air to pass from the interior of the needle assembly housing 1912 (via the proximal end opening 1918) to the exterior of the needle assembly. This assists in some embodiments to equalize the air pressure in the interior of the needle assembly. It is noted that the body 2004 of the end cap 2002 can be formed in any number of shapes to provide convenience during use or otherwise improve use of the needle assembly.

Note that various aspects of the magnetic element and retention component embodiments described herein can be varied, including the number, shape, type, composition and placement of the magnet(s) and retention component, the size and type of needle assembly, etc.

FIG. 75 depicts the needle assembly 1980, previously shown in FIGS. 73A and 73B, including a magnetic element and retention component according to another embodiment. As shown, the needle assembly 1980 in the present embodiment includes a donut-type magnetic element 2010 disposed in an end cap 2012 that serves as a retention component. The end cap 2012 includes a base 2014 and a projection 2016 extending from the base. The projection 2016 is received into the proximal opening 1988 in the needle assembly housing 1982. The annular ridge about the proximal opening 1988 is received into an annular groove 2018 of the end cap 2012. A bore can be defined through the end cap 2012 and communicate with the hole of the magnetic element 2010 so as to provide communication into the interior of the housing 1982, in one embodiment. It is thus seen that various configurations for including a magnetic element with a needle assembly or other medical device are possible within the principles of the present disclosures.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A needle assembly for use with a handheld ultrasound probe, the handheld ultrasound probe including a plurality of magnetic sensors configured to detect a magnetic field, the needle assembly comprising:
a hub;
a needle distally extending from the hub along a longitudinal axis, the needle including an outer wall circumscribing a lumen and a distal needle tip; and
a cylindrical permanent magnet positioned in a cylindrical notch defined in the outer wall of the needle proximate the distal needle tip, the cylindrical permanent magnet producing a magnetic field strength capable of detection by the plurality of magnetic sensors of the handheld ultrasound probe,
further comprising the handheld ultrasound probe, wherein the plurality of magnetic sensors of the handheld ultrasound probe are embedded in a housing of the handheld ultrasound probe, and wherein the plurality of magnetic sensors consist of five magnetic sensors.

2. The needle assembly as defined in claim 1, wherein the cylindrical permanent magnet includes a magnetic axis that is substantially aligned with the longitudinal axis of the needle.

3. The needle assembly as defined in claim 1, wherein the cylindrical permanent magnet includes a first permanent magnet and a second permanent magnet that together form the cylindrical permanent magnet.

4. The needle assembly as defined in claim 3, wherein the first permanent magnet and the second permanent magnet are each substantially U-shaped.

5. The needle assembly as defined in claim 1, further comprising a needle holder configured to enable a user to hold and advance the needle during an ultrasound imaging and needle guidance procedure.

6. The needle assembly as defined in claim 5, wherein the needle holder is pistol-shaped and includes a trigger.

7. The needle assembly as defined in claim 6, wherein the trigger is configured to selectively advance the needle by moving the needle longitudinally away from a barrel of the needle holder upon actuation of the trigger.

8. The needle assembly as defined in claim 1, wherein the plurality of magnetic sensors are disposed in a planar configuration below a top face of the handheld ultrasound probe.

9. The needle assembly as defined in claim 1, wherein each of the plurality of magnetic sensors comprise three orthogonal sensor coils for enabling detection of the magnetic field in three spatial dimensions.

* * * * *